United States Patent
Washko, Jr. et al.

(10) Patent No.: US 11,869,187 B2
(45) Date of Patent: Jan. 9, 2024

(54) SYSTEM AND METHOD FOR PREDICTING THE RISK OF FUTURE LUNG CANCER

(71) Applicant: Johnson & Johnson Enterprise Innovation Inc., New Brunswick, NJ (US)

(72) Inventors: George R. Washko, Jr., West Roxbury, MA (US); Christopher Scott Stevenson, West Sussex (GB); Samuel Yoffe Ash, Newton, MA (US); Raul San Jose Estepar, Wellesley, MA (US); Matthew David Mailman, New Hope, PA (US)

(73) Assignee: Johnson & Johnson Enterprise Innovation Inc., New Brunswick, NJ (US)

( * ) Notice: Subject to any disclaimer, the term of this patent is extended or adjusted under 35 U.S.C. 154(b) by 0 days.

(21) Appl. No.: 18/181,764

(22) Filed: Mar. 10, 2023

(65) Prior Publication Data
US 2023/0215004 A1  Jul. 6, 2023

Related U.S. Application Data

(63) Continuation of application No. 17/150,063, filed on Jan. 15, 2021, now Pat. No. 11,640,661.
(Continued)

(51) Int. Cl.
*G06K 9/00* (2022.01)
*G06T 7/00* (2017.01)
(Continued)

(52) U.S. Cl.
CPC ............ *G06T 7/0012* (2013.01); *A61B 6/032* (2013.01); *A61B 6/50* (2013.01); *A61B 6/5217* (2013.01);
(Continued)

(58) Field of Classification Search
CPC .............................. G06T 7/0012–0016; G06T 2207/10064–10136;
(Continued)

(56) References Cited

U.S. PATENT DOCUMENTS

| 2017/0035381 A1 | 2/2017 | Madabhushi et al. |
| 2018/0068083 A1 | 3/2018 | Cohen et al. |

(Continued)

FOREIGN PATENT DOCUMENTS

| WO | 2015/127355 A1 | 8/2015 |
| WO | 2021/049729 A1 | 3/2021 |

OTHER PUBLICATIONS

Bin Zheng, Yuchen Qiu, Faranak Aghaei, "Developing global image feature analysis models to predict cancer risk and prognosis", Visual Computing for Industry, Biomedicine, and Art (2019) 2:17; pp. 1-14 (Year: 2019).*

(Continued)

*Primary Examiner* — Atiba O Fitzpatrick
(74) *Attorney, Agent, or Firm* — Goodwin Procter LLP

(57) ABSTRACT

Risk prediction models are trained and deployed to analyze images, such as computed tomography scans, for predicting future risk of lung cancer for one or more subjects. Individual risk prediction models are separately trained on nodule-specific and non-nodule specific features such that each risk prediction model can predict future risk of lung cancer across different time periods (e.g., 1 year, 3 years, or 5 years). Such risk prediction models are useful for developing preventive therapies for lung cancer by enabling clinical trial enrichment.

20 Claims, 36 Drawing Sheets

Related U.S. Application Data

(60) Provisional application No. 62/962,614, filed on Jan. 17, 2020.

(51) Int. Cl.

| | | |
|---|---|---|
| *A61B 6/03* | (2006.01) | |
| *A61B 6/00* | (2006.01) | |
| *G06V 10/40* | (2022.01) | |
| *G16H 50/50* | (2018.01) | |
| *G16H 50/30* | (2018.01) | |
| *G16H 30/40* | (2018.01) | |

(52) U.S. Cl.
CPC ............ *G06T 7/0014* (2013.01); *G06V 10/40* (2022.01); *G16H 30/40* (2018.01); *G16H 50/30* (2018.01); *G16H 50/50* (2018.01); *G06T 2207/10081* (2013.01); *G06T 2207/10116* (2013.01); *G06T 2207/20076* (2013.01); *G06T 2207/30061* (2013.01); *G06T 2207/30096* (2013.01); *G06V 2201/032* (2022.01)

(58) Field of Classification Search
CPC ...................... G06T 2207/30004–30104; G06T 2207/30061; G06T 2207/20081; G06T 2207/20084; G06T 2207/30096; G06V 2201/03–034; G06V 10/70; G06V 10/82; G06V 10/774–7796; A61B 2017/00809; G06K 9/6256; G06K 9/6257; G06K 9/6259; G06N 3/02–126; G06N 20/00–20
See application file for complete search history.

(56) References Cited

U.S. PATENT DOCUMENTS

| | | | | |
|---|---|---|---|---|
| 2018/0242905 | A1* | 8/2018 | Madabhushi | ......... G06F 18/241 |
| 2020/0160980 | A1 | 5/2020 | Lyman et al. | |
| 2020/0211710 | A1* | 7/2020 | Do | ............ G16H 50/30 |
| 2020/0320692 | A1* | 10/2020 | Fleming | ................ G16H 50/50 |
| 2021/0110540 | A1* | 4/2021 | Vaidya | ................... G06N 20/20 |
| 2021/0118130 | A1* | 4/2021 | Zhang | ................. A61B 5/4887 |
| 2021/0169349 | A1* | 6/2021 | Madabhushi | ............ A61B 5/08 |
| 2021/0225511 | A1* | 7/2021 | Kiraly | ........................ G06N 3/08 |
| 2022/0240881 | A1* | 8/2022 | Huang | ................. A61B 6/5229 |
| 2022/0301714 | A1* | 9/2022 | Kim | ..................... A61B 6/5217 |

OTHER PUBLICATIONS

Rahul Paul, Samuel H. Hawkins, Matthew B. Schabath, "Predicting malignant nodules by fusing deep features with classical radiomics features", Journal of Medical Imaging 5(1), 011021 (Jan.-Mar. 2018), pp. 1-11 (Year: 2018).*

Ardila et al., "End-to-End Lung Cancer Screening with Three-Dimensional Deep Learning on Low-Ose Chest Computed Tomography," Nature Medicine, vol. 25, Jun. 2019, pp. 954-961.

Baldwin et al., "External Validation of a Convolutional Neural Network Artificial Intelligence Tool to Predict Malginancy in Pulmonary Nodules," Thorax 2020; 0:1-7.

Cherezov et al., "Delta Radiomic Features Improve Prediction for Lung Cancer Incidence: A Nested Case-Control Analysis of the Naitonal Lung Screening Trial," Cancer Medicine, published by John Wiley & Sons Ltd. Cancer Medicine. 2018;7:6340-6356 (2018).

Dilger et al., "Improved Pulmonary Nodule Classification Utilizing Lung Parenchyma Texture Features," Progress in Biomedical Optics and Imaging, SPIE—International Society for Optical Engineering, Bellingham, WA, US, vol. 9414, Mar. 20, 2015, p. 94142T.

Gould et al., "Evaluation of Individuals with Pulmonary Nodules: When is it Lung Cancer?—Diagnosis and Management of Lung Cancer, 3rd Edition: American College of Chest Physicians Evidence-Based Clinical Practice Guidelines," Chest, vol. 143, No. 5, May 1, 2013, pp. e93s-e120s.

Huang et al., "Prediction of Lung Cancer Risk at Follow-Up Screening with Low-Dose CT: A Traininig and Validation Study of a Deep Learning Methods," The Lancet, Digitial Health, vol. 1, Nov. 2019, e353-e362.

International Search Report and Written Opinion dated Apr. 7, 2021, PCT Application No. PCT/US2021/013571, 14 pages.

Jia et al., "Computer-Aided Diagnosis of Pulmonary Nodules on CT Scan Images," 2018 10th International Conference on Modelling, Identification and Control, IEEE, Jul. 2, 2018, pp. 1-6.

Jirapatnakul, "Characterization of Solid Pulmonary Nodules Using Three-Dimensional Features," SPIE, P.O. Box 10, Bellingham WA 98227-0010, Dec. 31, 2007.

Kalpathy-Cramer et al., "Radiomics of Lung Nodules: A Multi-Institutional Study of Robustness and Agreement of Quantitative Imaging Features," Tomography.org, vol. 2, No. 4, Dec. 2016, pp. 430-437.

Lambin et al., "Radiomics: Extracting More Information from Medical Images Using Advanced Feature Analysis," Eur J Cancer, Mar. 2012, 48(4) 441-446.

Paul et al., "Predicting Malignant Nodules by Fusing Deep Features with Classical Radiomics Features," Journal of Medical Imaging 5(1), 011021 (Jan.-Mar. 2018), pp. 1-11 (2018).

Uthoff et al., "Machine Learning Approach for Distinguishing Malignant and Benign Lung Nodules Utilizing Standarized Perinodular Parenchymal Features from CT," Medica Physics, AIP, Melville, NY, vol. 46, No. 7, pp. 3207-3216.

Van Griethuysen et al., "Computational Radiomics System to Decode the Radiographic Phenotype," Cancer Res; 77 (21) Nov. 1, 2017, pp. e104-e108.

Zheng et al., "Developing Global Image Feature Analysis Models to Predict Cancer Risk and Prognosis," Visual Computing for Industry, Biomedicine, and Art (2019) 2:17; pp. 1-14 (2019).

* cited by examiner

SYSTEM AND METHOD FOR PREDICTING THE RISK OF FUTURE LUNG CANCER

CROSS REFERENCE

This application is a continuation of U.S. application Ser. No. 17/150,063 filed on Jan. 15, 2021, which claims the benefit of and priority to U.S. Provisional Patent Application No. 62/962,614 filed on Jan. 17, 2020, the entire disclosure of each of which is hereby incorporated by reference in its entirety for all purposes.

BACKGROUND

Lung cancer most commonly begins with the development of a lung nodule. A nodule may be cancerous or may be a benign overgrowth of tissue that subsequently undergoes malignant transformation. The radiologic community recognizes this process and, in an attempt to standardize medical management, developed a scoring system to stage nodules discovered on CT scan to assess their likelihood of being cancer. This staging system is called Lung CT screening, Reporting and Data System (Lung-RADS) and is based upon the size of the nodule, the rate of growth of the nodule and the appearance of the nodule. Generally, the larger the nodule, the more rapid its growth or the more irregular it is in appearance, the more likely it is to be cancer.

However, in many scenarios, lung nodules in patients remain undetected for periods of time or, even if detected, can already indicate an advanced stage of cancer. Therefore, there is a need for early prediction of lung cancer risk in patients even prior to the development of one or more lung nodules.

SUMMARY

Embodiments of the invention disclosed herein involve implementing risk predictions models to analyze images (e.g., CT scans) for predicting future risk of lung cancer. Risk prediction models analyze features extracted from images, such as nodule specific features and non-nodule specific features. In various embodiments, inclusion of non-nodule specific features in the risk prediction model has the benefit of enabling the risk prediction models to generate future risk of cancer predictions for subjects that do not yet have a lung nodule. For example, by analyzing non-nodule specific features, examples of which include lung parenchyma features and/or body composition features, risk prediction models can be implemented for the early detection of lung cancer prior to the development of a lung nodule. In various embodiments, risk prediction models can be implemented to predict whether a subject is likely to develop cancer in the next year. In various embodiments, risk prediction models can be implemented to predict whether a subject is likely to develop cancer in the next 3 years. In various embodiments, risk prediction models can be implemented to predict whether a subject is likely to develop cancer in the next 5 years. In various embodiments, risk prediction models can be implemented to predict whether a subject is likely to develop cancer within a M time period. In various embodiments, M is any of 6 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years.

Risk prediction models are useful for developing preventive therapies for lung cancer by enabling clinical trial enrichment and ultimately clinical care. For example, clinical trials will be more efficient and feasible because the event rate (future lung cancer) will be above background thereby enabling the enrollment of smaller cohort sizes and reducing the numbers of patients that need to be treated to show that a therapy prevents lung cancer. As another example, knowing future risk of cancer for subjects enables the tailoring of clinical care for the subjects. Subjects at high risk of cancer can be monitored and/or screened at an increased rate of frequency. Additionally, subjects a high risk of cancer can be informed and/or counseled to lower their risk (e.g., counseled to change lifestyle such as smoking cessation). As another example, since cancer treatments involve some degree of risk, knowing who is most likely to develop lung cancer will influence the risk/benefit decision analysis and reimbursement around the implementation of therapy in the individual.

Disclosed herein is a method for predicting one or more future risks of lung cancer for a subject, the method comprising: obtaining one or more images captured from the subject at a single timepoint; extracting features from the one or more obtained images, the extracted features comprising at least non-nodule specific features, wherein the non-nodule specific features comprise one or both of lung parenchyma features or body composition features; predicting one or more future risks of lung cancer for the subject by applying one or more trained risk prediction models to analyze the extracted features from the one or more obtained images. In various embodiments, predicting the one or more future risks of lung cancer for the subject comprises applying a M year risk prediction model to predict whether the subject is likely to develop lung cancer within M years, wherein the M year risk prediction model comprises nodule specific features and non-nodule specific features, wherein greater than 50% of the top 3 extracted features with the highest feature importance values are non-nodule specific features, wherein lung parenchyma features comprise one or more of percentage of low attenuation area of the lung, percentage of high attenuation area of the lung, ratio of low attenuation or high attenuation area in an upper lung zone in comparison to a lower lung zone, percentage(s) of lung occupied by any of normal tissue, centrilobular emphysema, centrilobular nodule, ground glass, honeycombing, linear scar, nodular, reticular, subpleural line, other emphysema, or cyst, and wherein body composition features comprise one or more of pectoralis cross-sectional area, pectoralis lean cross-sectional area, or sub-cutaneous fat cross-sectional area.

In various embodiments, the lung parenchyma features comprise one or more of densitometric measures of the lung parenchyma or local histogram measures of the lung parenchyma. In various embodiments, the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone. In various embodiments, the local histogram measures of the lung parenchyma comprise one or more percentage(s) of lung occupied by any of normal tissue, centrilobular emphysema, centrilobular nodule, ground glass, honeycombing, linear scar, nodular, reticular, subpleural line, other emphysema, or cyst. In various embodiments, body composition features comprise one or more of pectoralis cross-sectional area, pectoralis lean cross-sectional area, or sub-cutaneous fat cross-sectional area.

In various embodiments, the extracted features further comprise nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, radiomic features comprise one or more of first order statistics, 3D shape based features, 2D shape based features, gray level cooccurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level cooccurrence matrix, gray level run length matrix, gray level size zone matrix, neighboring gray tone difference matrix, and gray level dependence matrix can be extracted from a wavelet transformed image or a gaussian transformed image. In various embodiments, the nodule specific features are extracted from a radiologist report. In various embodiments, the nodule specific features are computationally extracted by implementing an image analysis algorithm.

In various embodiments, predicting the one or more future risks of lung cancer for the subject comprises applying a 5 year risk prediction model to predict whether the subject is likely to develop lung cancer within 5 years. In various embodiments, the 5 year risk prediction model comprises nodule specific features and non-nodule specific features, wherein the non-nodule specific features have higher feature importance values than the nodule specific features. In various embodiments, greater than 50% of the top 3 extracted features with the highest feature importance values are non-nodule specific features. In various embodiments, greater than 50% of the top 5 extracted features with the highest feature importance values are non-nodule specific features. In various embodiments, greater than 50% of the top 10 extracted features with the highest feature importance values are non-nodule specific features. In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 5 year risk prediction model exhibits an area under the curve (AUC) value of at least 0.74. In various embodiments, the 5 year risk prediction model achieves at least a 5.1-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 5 year risk prediction model exhibits an area under the curve (AUC) value of at least 0.72. In various embodiments, the 5 year risk prediction model achieves at least a 3.9-fold increase in cumulative incidence in comparison to a background rate.

In various embodiments, determining that the subject is a candidate further comprises determining that the subject is classified in any of Lung-RADS 1, Lung-RADS 2, or Lung-RADS 3. In various embodiments, the 5 year risk prediction model exhibits an area under the curve (AUC) value of at least 0.67. In various embodiments, the 5 year risk prediction model achieves at least a 3.7-fold increase in cumulative incidence in comparison to a background rate.

In various embodiments, determining that the subject is a candidate further comprises determining that the subject is classified in any of Lung-RADS 1 or Lung-RADS 2. In various embodiments, the 5 year risk prediction model exhibits an area under the curve (AUC) value of at least 0.65. In various embodiments, the 5 year risk prediction model achieves at least a 1.9-fold increase in cumulative incidence in comparison to a background rate.

In various embodiments, determining that the subject is a candidate further comprises determining that the subject is classified in Lung-RADS 1. In various embodiments, the 5 year risk prediction model exhibits an area under the curve (AUC) value of at least 0.57. In various embodiments, the 5 year risk prediction model achieves at least a 1.9-fold increase in cumulative incidence in comparison to a background rate.

In various embodiments, predicting the one or more future risks of lung cancer for the subject comprises applying a 3 year risk prediction model to predict whether the subject is likely to develop lung cancer within 3 years. In various embodiments, the 3 year risk prediction model comprises nodule specific features and non-nodule specific features, wherein the non-nodule specific features have higher feature importance values than the nodule-specific features. In various embodiments, greater than 50% of the top 5 extracted features with the highest feature importance values are non-nodule specific features. In various embodiments, greater than 50% of the top 10 extracted features with the highest feature importance values are non-nodule specific features.

In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 3 year risk prediction model exhibits an area under the curve (AUC) value of at least 0.79. In various embodiments, the 3 year risk prediction model achieves at least a 6.3-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 3 year risk prediction model exhibits an area under the curve (AUC) value of at least 0.72. In various embodiments, the 3 year risk prediction model achieves at least a 5.1-fold increase in cumulative incidence in comparison to a background rate.

In various embodiments, determining that the subject is a candidate further comprises determining that the subject is classified in any of Lung-RADS 1, Lung-RADS 2, or Lung-RADS 3. In various embodiments, the 3 year risk prediction model exhibits an area under the curve (AUC) value of at least 0.72. In various embodiments, the 3 year risk prediction model achieves at least a 5.7-fold increase in cumulative incidence in comparison to a background rate. In various embodiments, the 3 year risk prediction model exhibits an area under the curve (AUC) value of at least 0.676.

In various embodiments, determining that the subject is a candidate further comprises determining that the subject is classified in any of Lung-RADS 1 or Lung-RADS 2. In various embodiments, the 3 year risk prediction model exhibits an area under the curve (AUC) value of at least 0.65. In various embodiments, the 3 year risk prediction model achieves at least a 3-fold increase in cumulative incidence in comparison to a background rate. In various embodiments, determining that the subject is a candidate further comprises determining that the subject is classified in Lung-RADS 1. In various embodiments, the 3 year risk prediction model exhibits an area under the curve (AUC) value of at least 0.60. In various embodiments, the 3 year risk prediction model achieves at least a 2.3-fold increase in cumulative incidence in comparison to a background rate.

In various embodiments, predicting the one or more future risks of lung cancer for the subject comprises applying a 1 year risk prediction model to predict whether the subject is likely to develop lung cancer within 1 year. In various embodiments, the 1 year risk prediction model comprises nodule specific features and non-nodule specific features, wherein the non-nodule specific features have higher feature importance values than the nodule-specific features. In various embodiments, determining that the subject is a candidate further comprises determining that the subject is classified in any of Lung-RADS 1 or Lung-RADS 2. In various embodiments, the 1 year risk prediction model exhibits an area under the curve (AUC) value of at least 0.72. In various embodiments, the 1 year risk prediction model achieves at least a 5.5-fold increase in cumulative incidence in comparison to a background rate. In various embodiments, determining that the subject is a candidate further comprises determining that the subject is classified in Lung-RADS 1. In various embodiments, the 1 year risk prediction model exhibits an area under the curve (AUC) value of at least 0.57.

In various embodiments, the 1 year risk prediction model comprises nodule specific features and non-nodule specific features, wherein the nodule specific features have higher feature importance values than the non-nodule specific features. In various embodiments, greater than 50% of the top 3 extracted features with the highest feature importance values are nodule specific features. In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 1 year risk prediction model exhibits an area under the curve (AUC) value of at least 0.90. In various embodiments, the 1 year risk prediction model achieves at least a 11-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 1 year risk prediction model exhibits an area under the curve (AUC) value of at least 0.81. In various embodiments, the 1 year risk prediction model achieves at least a 7.6-fold increase in cumulative incidence in comparison to a background rate.

In various embodiments, greater than 50% of the top 5 extracted features with the highest feature importance values are nodule specific features. In various embodiments, determining that the subject is a candidate further comprises determining that the subject is classified in any of Lung-RADS 1, Lung-RADS 2, or Lung-RADS 3. In various embodiments, the 1 year risk prediction model exhibits an area under the curve (AUC) value of at least 0.82. In various embodiments, the 1 year risk prediction model achieves at least a 8.6-fold increase in cumulative incidence in comparison to a background rate.

In various embodiments, predicting the one or more future risks of lung cancer for the subject comprises applying multiple risk prediction models to predict whether the subject is likely to develop lung cancer within N different time periods. In various embodiments, at least one of the N different time periods is any one of 6 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, N is 1, 2, 3, 4, 5, 6, 7, 8, 9, 10, 11, 12, 13, 14, 15, 16, 17, 18, 19, or 20 different time periods.

In various embodiments, one of the one or more risk prediction models is a Lung-RADS 1-4B prediction model that is trained to predict the future risk of lung cancer using training images captured from a training cohort of training individuals classified in any of Lung-RADS 1-4B. In various embodiments, one of the one or more risk prediction models is a Lung-RADS 1-4A model trained to predict the future risk of lung cancer using training images captured from a training cohort of training individuals classified in any of Lung-RADS 1-4A. In various embodiments, one of the one or more risk prediction models is a Lung-RADS 1-3 model to predict the future risk of lung cancer using training images captured from a training cohort of training individuals classified in any of Lung-RADS 1-3. In various embodiments, one of the one or more risk prediction models is a Lung-RADS 1-2 model trained to predict the future risk of lung cancer using training images captured from a training cohort of training individuals classified in either Lung-RADS 1 or 2. In various embodiments, one of the one or more risk prediction models is a Lung-RADS 1 model trained to predict the future risk of lung cancer using training images captured from a training cohort of training individuals classified in Lung-RADS 1. In various embodiments, a majority of training individuals in the training cohort are previously classified in Lung-RADS 1.

In various embodiments, the one or more images are computed tomography (CT) images or X-ray images. In various embodiments, the one or more images comprises are thoracic CT images or chest X-ray images. In various embodiments, the risk prediction model is trained using training images of the National Lung Screening Trial (NLST). In various embodiments, methods disclosed herein further comprise: prior to predicting one or more future risks of lung cancer for the subject: obtaining nodule-specific features corresponding to the subject; determining that the subject is a candidate for future risk prediction based on the nodule-specific features.

In various embodiments, determining that the subject is a candidate comprises determining that the subject does not have lung cancer or is at low-risk of developing lung cancer. In various embodiments, determining that the subject is at low-risk of developing lung cancer comprises determining that the subject does not have a nodule based on the nodule-specific features.

In various embodiments, the lung cancer is either non-small cell lung cancer or small cell lung cancer. In various embodiments, the lung cancer is either adenocarcinoma or squamous cell carcinoma. In various embodiments, methods disclosed herein further comprise selecting a clinical response for the subject based on the predicted future risk of lung cancer. In various embodiments, selecting a clinical response for the subject comprises selecting an intervention for treating the subject. In various embodiments, selecting an intervention comprises selecting a therapeutic for administration to the subject. In various embodiments, the selected therapeutic is prophylactically administered to the subject to delay or prevent the development of the lung cancer. In various embodiments, the clinical response comprises providing counseling to the subject to modify behavior of the subject. In various embodiments, the clinical response comprises increasing a frequency of follow up for the subject. In various embodiments, the clinical response comprises performing or scheduling to be performed an additional risk prediction test to confirm the predicted future risk of lung cancer. In various embodiments, one or more of the trained risk prediction models are one of a random forest model or gradient boosted model.

Additionally disclosed herein is a non-transitory computer readable medium for predicting one or more future risks of lung cancer for a subject, the non-transitory computer readable medium comprising instructions that, when executed by a processor, cause the processor to: obtain one or more images captured from the subject at a single timepoint; extract features from the one or more obtained images, the extracted features comprising at least non-nodule specific features, wherein the non-nodule specific features comprise one or both of lung parenchyma features or body composition features; predict one or more future risks of lung cancer for the subject by applying one or more trained risk prediction models to analyze the extracted features from the one or more obtained images. In various embodiments, the instructions that cause the processor to predict the one or more future risks of lung cancer for the subject further comprises instructions that, when executed by the processor, cause the processor to apply a M year risk prediction model to predict whether the subject is likely to develop lung cancer within M years, wherein the M year risk prediction model comprises nodule specific features and non-nodule specific features, wherein greater than 50% of the top 3 extracted features with the highest feature importance values are non-nodule specific features, wherein lung parenchyma features comprise one or more of percentage of low attenuation area of the lung, percentage of high attenuation area of the lung, ratio of low attenuation or high attenuation area in an upper lung zone in comparison to a lower lung zone, percentage(s) of lung occupied by any of normal tissue, centrilobular emphysema, centrilobular nodule, ground glass, honeycombing, linear scar, nodular, reticular, subpleural line, other emphysema, or cyst, and wherein body composition features comprise one or more of pectoralis cross-sectional area, pectoralis lean cross-sectional area, or sub-cutaneous fat cross-sectional area.

In various embodiments, the lung parenchyma features comprise one or more of densitometric measures of the lung parenchyma or local histogram measures of the lung parenchyma. In various embodiments, the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone. In various embodiments, the local histogram measures of the lung parenchyma comprise one or more percentage(s) of lung occupied by any of normal tissue, centrilobular emphysema, centrilobular nodule, ground glass, honeycombing, linear scar, nodular, reticular, subpleural line, other emphysema, or cyst. In various embodiments, body composition features comprise one or more of pectoralis cross-sectional area, pectoralis lean cross-sectional area, or sub-cutaneous fat cross-sectional area.

In various embodiments, the extracted features further comprise nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, radiomic features comprise one or more of first order statistics, 3D shape based features, 2D shape based features, gray level cooccurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level cooccurrence matrix, gray level run length matrix, gray level size zone matrix, neighboring gray tone difference matrix, and gray level dependence matrix can be extracted from a wavelet transformed image or a gaussian transformed image. In various embodiments, the nodule specific features are extracted from a radiologist report. In various embodiments, the nodule specific features are computationally extracted by implementing an image analysis algorithm.

In various embodiments, the instructions that cause the processor to predict the one or more future risks of lung cancer for the subject further comprises instructions that, when executed by the processor, cause the processor to apply a 5 year risk prediction model to predict whether the subject is likely to develop lung cancer within 5 years. In various embodiments, the 5 year risk prediction model comprises nodule specific features and non-nodule specific features, wherein the non-nodule specific features have higher feature importance values than the nodule specific features. In various embodiments, greater than 50% of the top 3 extracted features with the highest feature importance values are non-nodule specific features. In various embodiments, greater than 50% of the top 5 extracted features with the highest feature importance values are non-nodule specific features. In various embodiments, greater than 50% of the top 10 extracted features with the highest feature importance values are non-nodule specific features.

In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 5 year risk prediction model exhibits an area under the curve (AUC) value of at least 0.74. In various embodiments, the 5 year risk prediction model achieves at least a 5.1-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 5 year risk prediction model exhibits an area under the curve (AUC) value of at least 0.72. In various embodiments, the 5 year risk prediction model achieves at least a 3.9-fold increase in cumulative incidence in comparison to a background rate.

In various embodiments, determining that the subject is a candidate further comprises determining that the subject is classified in any of Lung-RADS 1, Lung-RADS 2, or Lung-RADS 3. In various embodiments, the 5 year risk prediction model exhibits an area under the curve (AUC) value of at least 0.67. In various embodiments, the 5 year risk prediction model achieves at least a 3.7-fold increase in cumulative incidence in comparison to a background rate.

In various embodiments, determining that the subject is a candidate further comprises determining that the subject is classified in any of Lung-RADS 1 or Lung-RADS 2. In various embodiments, the 5 year risk prediction model exhibits an area under the curve (AUC) value of at least 0.65. In various embodiments, the 5 year risk prediction model achieves at least a 1.9-fold increase in cumulative incidence in comparison to a background rate.

In various embodiments, determining that the subject is a candidate further comprises determining that the subject is classified in Lung-RADS 1. In various embodiments, the 5 year risk prediction model exhibits an area under the curve (AUC) value of at least 0.57. In various embodiments, the 5 year risk prediction model achieves at least a 1.9-fold increase in cumulative incidence in comparison to a background rate.

In various embodiments, the instructions that cause the processor to predict the one or more future risks of lung cancer for the subject further comprises instructions that, when executed by the processor, cause the processor to apply a 3 year risk prediction model to predict whether the subject is likely to develop lung cancer within 3 years. In various embodiments, the 3 year risk prediction model comprises nodule specific features and non-nodule specific features, wherein the non-nodule specific features have higher feature importance values than the nodule-specific features. In various embodiments, greater than 50% of the top 5 extracted features with the highest feature importance values are non-nodule specific features. In various embodiments, greater than 50% of the top 10 extracted features with the highest feature importance values are non-nodule specific features.

In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 3 year risk prediction model exhibits an area under the curve (AUC) value of at least 0.79. In various embodiments, the 3 year risk prediction model achieves at least a 6.3-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 3 year risk prediction model exhibits an area under the curve (AUC) value of at least 0.72. In various embodiments, the 3 year risk prediction model achieves at least a 5.1-fold increase in cumulative incidence in comparison to a background rate.

In various embodiments, determining that the subject is a candidate further comprises determining that the subject is classified in any of Lung-RADS 1, Lung-RADS 2, or Lung-RADS 3. In various embodiments, the 3 year risk prediction model exhibits an area under the curve (AUC) value of at least 0.72. In various embodiments, the 3 year risk prediction model achieves at least a 5.7-fold increase in cumulative incidence in comparison to a background rate. In various embodiments, the 3 year risk prediction model exhibits an area under the curve (AUC) value of at least 0.676.

In various embodiments, determining that the subject is a candidate further comprises determining that the subject is classified in any of Lung-RADS 1 or Lung-RADS 2. In various embodiments, the 3 year risk prediction model exhibits an area under the curve (AUC) value of at least 0.65. In various embodiments, the 3 year risk prediction model achieves at least a 3-fold increase in cumulative incidence in comparison to a background rate.

In various embodiments, determining that the subject is a candidate further comprises determining that the subject is classified in Lung-RADS 1. In various embodiments, the 3 year risk prediction model exhibits an area under the curve (AUC) value of at least 0.60. In various embodiments, the 3 year risk prediction model achieves at least a 2.3-fold increase in cumulative incidence in comparison to a background rate.

In various embodiments, the instructions that cause the processor to predict the one or more future risks of lung cancer for the subject further comprises instructions that, when executed by the processor, cause the processor to apply a 1 year risk prediction model to predict whether the subject is likely to develop lung cancer within 1 year. In various embodiments, the 1 year risk prediction model comprises nodule specific features and non-nodule specific features, wherein the non-nodule specific features have higher feature importance values than the nodule-specific features. In various embodiments, determining that the subject is a candidate further comprises determining that the subject is classified in any of Lung-RADS 1 or Lung-RADS 2. In various embodiments, the 1 year risk prediction model exhibits an area under the curve (AUC) value of at least 0.72. In various embodiments, the 1 year risk prediction model achieves at least a 5.5-fold increase in cumulative incidence in comparison to a background rate.

In various embodiments, determining that the subject is a candidate further comprises determining that the subject is classified in Lung-RADS 1. In various embodiments, the 1 year risk prediction model exhibits an area under the curve (AUC) value of at least 0.57.

In various embodiments, the 1 year risk prediction model comprises nodule specific features and non-nodule specific features, wherein the nodule specific features have higher feature importance values than the non-nodule specific features. In various embodiments, greater than 50% of the top 3 extracted features with the highest feature importance values are non-nodule specific features. In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 1 year risk prediction model exhibits an area under the curve (AUC) value of at least 0.90. In various embodiments, the 1 year risk prediction model achieves at least a 11-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 1 year risk prediction model exhibits an area under the curve (AUC) value of at least 0.81. In various embodiments, the 1 year risk prediction model achieves at least a 7.6-fold increase in cumulative incidence in comparison to a background rate. In various embodiments, greater than 50% of the top 5 extracted features with the highest feature importance values are non-nodule specific features.

In various embodiments, determining that the subject is a candidate further comprises determining that the subject is classified in any of Lung-RADS 1, Lung-RADS 2, or Lung-RADS 3. In various embodiments, the 1 year risk prediction model exhibits an area under the curve (AUC) value of at least 0.82. In various embodiments, the 1 year risk prediction model achieves at least a 8.6-fold increase in cumulative incidence in comparison to a background rate.

In various embodiments, the instructions that cause the processor to predict the one or more future risks of lung cancer for the subject further comprises instructions that, when executed by the processor, cause the processor to apply multiple risk prediction models to predict whether the subject is likely to develop lung cancer within N different time periods. In various embodiments, at least one of the N different time periods is any one of 6 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, N is 1, 2, 3, 4, 5, 6, 7, 8, 9, 10, 11, 12, 13, 14, 15, 16, 17, 18, 19, or 20 different time periods.

In various embodiments, one of the one or more risk prediction models is a Lung-RADS 1-4B prediction model that is trained to predict the future risk of lung cancer using training images captured from a training cohort of training individuals classified in any of Lung-RADS 1-4B. In various embodiments, one of the one or more risk prediction models is a Lung-RADS 1-4A model trained to predict the future risk of lung cancer using training images captured from a training cohort of training individuals classified in any of Lung-RADS 1-4A. In various embodiments, one of the one or more risk prediction models is a Lung-RADS 1-3 model to predict the future risk of lung cancer using training images captured from a training cohort of training individuals classified in any of Lung-RADS 1-3. In various embodiments, one of the one or more risk prediction models is a Lung-RADS 1-2 model trained to predict the future risk of lung cancer using training images captured from a training cohort of training individuals classified in either Lung-RADS 1 or 2. In various embodiments, one of the one or more risk prediction models is a Lung-RADS 1 model trained to predict the future risk of lung cancer using training images captured from a training cohort of training individuals classified in Lung-RADS 1. In various embodiments, a majority of training individuals in the training cohort are previously classified in Lung-RADS 1

In various embodiments, the one or more images are computed tomography (CT) images or X-ray images. In various embodiments, the one or more images comprises are thoracic CT images or chest X-ray images. In various embodiments, the risk prediction model is trained using training images of the National Lung Screening Trial (NLST).

In various embodiments, the non-transitory computer readable medium further comprises instructions that, when executed by the processor, cause the processor to: prior to predicting one or more future risks of lung cancer for the subject: obtain nodule-specific features corresponding to the subject; determine that the subject is a candidate for future risk prediction based on the nodule-specific features.

In various embodiments, the instructions that cause the processor to determine that the subject is a candidate further comprises instructions that, when executed by the processor, cause the processor to determine that the subject does not have lung cancer or is at low-risk of developing lung cancer. In various embodiments, the instructions that cause the processor to determine that the subject is at low-risk of developing lung cancer further comprises instructions that, when executed by the processor, cause the processor to determine that the subject does not have a nodule based on the nodule-specific features.

In various embodiments, the lung cancer is either non-small cell lung cancer or small cell lung cancer. In various embodiments, the lung cancer is either adenocarcinoma or squamous cell carcinoma. In various embodiments, a non-transitory computer readable medium disclosed herein further comprises instructions that, when executed by the processor, cause the processor to select an intervention for treating the subject based on the predicted future risk of lung cancer. In various embodiments, the instructions that cause the processor to select an intervention further comprises instructions that, when executed by the processor, cause the processor to select a therapeutic for administration to the subject. In various embodiments, the selected therapeutic is a prophylactic for delaying or preventing the development of the lung cancer. In various embodiments, one or more of the trained risk prediction models are one of a random forest model or gradient boosted model.

Additionally disclosed herein is a system for predicting one or more future risks of lung cancer for a subject, the system comprising: an imaging device configured to capture one or more images of the subject at a single timepoint; and a computing device configured to perform the steps of: obtaining one or more images captured from the subject at the single timepoint; extracting features from the one or more obtained images, the extracted features comprising at least non-nodule specific features, wherein the non-nodule specific features comprise one or both of lung parenchyma features or body composition features; predicting one or more future risks of lung cancer for the subject by applying one or more trained risk prediction models to analyze the extracted features from the one or more obtained images. In various embodiments, predicting the one or more future risks of lung cancer for the subject comprises applying a M year risk prediction model to predict whether the subject is likely to develop lung cancer within M years, wherein the M year risk prediction model comprises nodule specific features and non-nodule specific features, wherein greater than 50% of the top 3 extracted features with the highest feature importance values are non-nodule specific features, wherein lung parenchyma features comprise one or more of percentage of low attenuation area of the lung, percentage of high attenuation area of the lung, ratio of low attenuation or high attenuation area in an upper lung zone in comparison to a lower lung zone, percentage(s) of lung occupied by any of normal tissue, centrilobular emphysema, centrilobular nodule, ground glass, honeycombing, linear scar, nodular, reticular, subpleural line, other emphysema, or cyst, and wherein body composition features comprise one or more of pectoralis cross-sectional area, pectoralis lean cross-sectional area, or sub-cutaneous fat cross-sectional area.

In various embodiments, the lung parenchyma features comprise one or more of densitometric measures of the lung parenchyma or local histogram measures of the lung parenchyma. In various embodiments, the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone. In various embodiments, the local histogram measures of the lung parenchyma comprise one or more percentage(s) of lung occupied by any of normal tissue, centrilobular emphysema, centrilobular nodule, ground glass, honeycombing, linear scar, nodular, reticular, subpleural line, other emphysema, or cyst. In various embodiments, body composition features comprise one or more of pectoralis cross-sectional area, pectoralis lean cross-sectional area, or sub-cutaneous fat cross-sectional area.

In various embodiments, the extracted features further comprise nodule specific features. In various embodiments, the nodule specific features comprise one or more of nodule specific attenuation, nodule margin description, nodule size, nodule shape, nodule texture, nodule diameter, Lung-RADS score, or radiomic features. In various embodiments, radiomic features comprise one or more of first order statistics, 3D shape based features, 2D shape based features, gray level cooccurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level cooccurrence matrix, gray level run length matrix, gray level size zone matrix, neighboring gray tone difference matrix, and gray level dependence matrix can be extracted from a wavelet transformed image or a gaussian transformed image. In various embodiments, the nodule specific features are extracted from a radiologist report. In various embodiments, the nodule specific features are computationally extracted by implementing an image analysis algorithm.

In various embodiments, predicting the one or more future risks of lung cancer for the subject comprises applying a 5 year risk prediction model to predict whether the subject is likely to develop lung cancer within 5 years. In various embodiments, the 5 year risk prediction model comprises nodule specific features and non-nodule specific features, wherein the non-nodule specific features have higher feature importance values than the nodule specific features. In various embodiments, greater than 50% of the top 3 extracted features with the highest feature importance values are non-nodule specific features. In various embodiments, greater than 50% of the top 5 extracted features with the highest feature importance values are non-nodule specific features. In various embodiments, greater than 50% of the top 10 extracted features with the highest feature importance values are non-nodule specific features.

In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 5 year risk prediction model exhibits an area under the curve (AUC) value of at least 0.74. In various embodiments, the 5 year risk prediction model achieves at least a 5.1-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 5 year risk prediction model exhibits an area under the curve (AUC) value of at least 0.72. In various embodiments, the 5 year risk prediction model achieves at least a 3.9-fold increase in cumulative incidence in comparison to a background rate.

In various embodiments, determining that the subject is a candidate further comprises determining that the subject is classified in any of Lung-RADS 1, Lung-RADS 2, or Lung-RADS 3. In various embodiments, the 5 year risk prediction model exhibits an area under the curve (AUC) value of at least 0.67. In various embodiments, the 5 year risk prediction model achieves at least a 3.7-fold increase in cumulative incidence in comparison to a background rate.

In various embodiments, determining that the subject is a candidate further comprises determining that the subject is classified in any of Lung-RADS 1 or Lung-RADS 2. In various embodiments, the 5 year risk prediction model exhibits an area under the curve (AUC) value of at least 0.65. In various embodiments, the 5 year risk prediction model achieves at least a 1.9-fold increase in cumulative incidence in comparison to a background rate.

In various embodiments, determining that the subject is a candidate further comprises determining that the subject is classified in Lung-RADS 1. In various embodiments, the 5 year risk prediction model exhibits an area under the curve (AUC) value of at least 0.57. In various embodiments, the 5 year risk prediction model achieves at least a 1.9-fold increase in cumulative incidence in comparison to a background rate.

In various embodiments, predicting the one or more future risks of lung cancer for the subject comprises applying a 3 year risk prediction model to predict whether the subject is likely to develop lung cancer within 3 years. In various embodiments, the 3 year risk prediction model comprises nodule specific features and non-nodule specific features, wherein the non-nodule specific features have higher feature importance values than the nodule-specific features. In various embodiments, greater than 50% of the top 5 extracted features with the highest feature importance values are non-nodule specific features. In various embodiments, greater than 50% of the top 10 extracted features with the highest feature importance values are non-nodule specific features.

In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 3 year risk prediction model exhibits an area under the curve (AUC) value of at least 0.79. In various embodiments, the 3 year risk prediction model achieves at least a 6.3-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 3 year risk prediction model exhibits an area under the curve (AUC) value of at least 0.72. In various embodiments, the 3 year risk prediction model achieves at least a 5.1-fold increase in cumulative incidence in comparison to a background rate.

In various embodiments, determining that the subject is a candidate further comprises determining that the subject is classified in any of Lung-RADS 1, Lung-RADS 2, or Lung-RADS 3. In various embodiments, the 3 year risk prediction model exhibits an area under the curve (AUC) value of at least 0.72. In various embodiments, the 3 year risk prediction model achieves at least a 5.7-fold increase in cumulative incidence in comparison to a background rate. In various embodiments, the 3 year risk prediction model exhibits an area under the curve (AUC) value of at least 0.676.

In various embodiments, determining that the subject is a candidate further comprises determining that the subject is classified in any of Lung-RADS 1 or Lung-RADS 2. In various embodiments, the 3 year risk prediction model exhibits an area under the curve (AUC) value of at least 0.65. In various embodiments, the 3 year risk prediction model achieves at least a 3-fold increase in cumulative incidence in comparison to a background rate.

In various embodiments, determining that the subject is a candidate further comprises determining that the subject is classified in Lung-RADS 1. In various embodiments, the 3 year risk prediction model exhibits an area under the curve (AUC) value of at least 0.60. In various embodiments, the 3 year risk prediction model achieves at least a 2.3-fold increase in cumulative incidence in comparison to a background rate.

In various embodiments, predicting the one or more future risks of lung cancer for the subject comprises applying a 1 year risk prediction model to predict whether the subject is likely to develop lung cancer within 1 year. In various embodiments, the 1 year risk prediction model comprises nodule specific features and non-nodule specific features, wherein the non-nodule specific features have higher feature importance values than the nodule-specific features.

In various embodiments, determining that the subject is a candidate further comprises determining that the subject is classified in any of Lung-RADS 1 or Lung-RADS 2. In various embodiments, the 1 year risk prediction model exhibits an area under the curve (AUC) value of at least 0.72. In various embodiments, the 1 year risk prediction model achieves at least a 5.5-fold increase in cumulative incidence in comparison to a background rate. In various embodiments, determining that the subject is a candidate further comprises determining that the subject is classified in Lung-RADS 1. In various embodiments, the 1 year risk prediction model exhibits an area under the curve (AUC) value of at least 0.57. In various embodiments, the 1 year risk prediction model comprises nodule specific features and non-nodule specific features, wherein the nodule specific features have higher feature importance values than the non-nodule specific features. In various embodiments, greater than 50% of the top 3 extracted features with the highest feature importance values are non-nodule specific features.

In various embodiments, determining that the subject is a candidate comprises obtaining a classification of the subject in one of Lung-RADS 1, Lung-RADS 2, Lung-RADS 3, Lung-RADS 4A, or Lung-RADS 4B. In various embodiments, the 1 year risk prediction model exhibits an area under the curve (AUC) value of at least 0.90. In various embodiments, the 1 year risk prediction model achieves at least a 11-fold increase in cumulative incidence in comparison to a background rate.

In various embodiments, determining that the subject is a candidate further comprises determining that the subject is classified in any of Lung-RADS 1, Lung-RADS 2, Lung-RADS 3, or Lung-RADS 4A. In various embodiments, the 1 year risk prediction model exhibits an area under the curve (AUC) value of at least 0.81. In various embodiments, the 1 year risk prediction model achieves at least a 7.6-fold increase in cumulative incidence in comparison to a background rate. In various embodiments, greater than 50% of the top 5 extracted features with the highest feature importance values are non-nodule specific features.

In various embodiments, determining that the subject is a candidate further comprises determining that the subject is classified in any of Lung-RADS 1, Lung-RADS 2, or Lung-RADS 3. In various embodiments, the 1 year risk prediction model exhibits an area under the curve (AUC) value of at least 0.82. In various embodiments, the 1 year risk prediction model achieves at least a 8.6-fold increase in cumulative incidence in comparison to a background rate.

In various embodiments, predicting the one or more future risks of lung cancer for the subject comprises applying multiple risk prediction models to predict whether the subject is likely to develop lung cancer within N different time periods. In various embodiments, at least one of the N different time periods is any one of 6 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, N is 1, 2, 3, 4, 5, 6, 7, 8, 9, 10, 11, 12, 13, 14, 15, 16, 17, 18, 19, or 20 different time periods.

In various embodiments, one of the one or more risk prediction models is a Lung-RADS 1-4B prediction model that is trained to predict the future risk of lung cancer using training images captured from a training cohort of training individuals classified in any of Lung-RADS 1-4B. In various embodiments, one of the one or more risk prediction models is a Lung-RADS 1-4A model trained to predict the future risk of lung cancer using training images captured from a training cohort of training individuals classified in any of Lung-RADS 1-4A. In various embodiments, one of the one or more risk prediction models is a Lung-RADS 1-3 model to predict the future risk of lung cancer using training images captured from a training cohort of training individuals classified in any of Lung-RADS 1-3. In various embodiments, one of the one or more risk prediction models is a Lung-RADS 1-2 model trained to predict the future risk of lung cancer using training images captured from a training cohort of training individuals classified in either Lung-RADS 1 or 2. In various embodiments, one of the one or more risk prediction models is a Lung-RADS 1 model trained to predict the future risk of lung cancer using training images captured from a training cohort of training individuals classified in Lung-RADS 1. In various embodiments, a majority of training individuals in the training cohort are previously classified in Lung-RADS 1.

In various embodiments, the one or more images are computed tomography (CT) images or X-ray images. In various embodiments, the one or more images comprises are thoracic CT images or chest X-ray images. In various embodiments, the risk prediction model is trained using training images of the National Lung Screening Trial (NLST).

In various embodiments, the computational device is further configured to: prior to predicting one or more future risks of lung cancer for the subject: obtaining nodule-specific features corresponding to the subject; determining that the subject is a candidate for future risk prediction based on the nodule-specific features. In various embodiments, determining that the subject is a candidate comprises determining that the subject does not have lung cancer or is at low-risk of developing lung cancer. In various embodiments, determining that the subject is at low-risk of developing lung cancer comprises determining that the subject does not have a nodule based on the nodule-specific features.

In various embodiments, the lung cancer is either non-small cell lung cancer or small cell lung cancer. In various embodiments, the lung cancer is either adenocarcinoma or squamous cell carcinoma. In various embodiments, the computing device is further configured to perform the step of selecting an intervention for treating the subject based on the predicted future risk of lung cancer. In various embodiments, selecting an intervention for treating the subject comprises selecting a therapeutic for administration to the subject. In various embodiments, the selected therapeutic is a prophylactic for delaying or preventing the development of the lung cancer. In various embodiments, one or more of the trained risk prediction models are one of a random forest model or gradient boosted model.

BRIEF DESCRIPTION OF THE DRAWINGS

These and other features, aspects, and advantages of the present invention will become better understood with regard to the following description and accompanying drawings.

DETAILED DESCRIPTION

I. Definitions

Figure 1A:
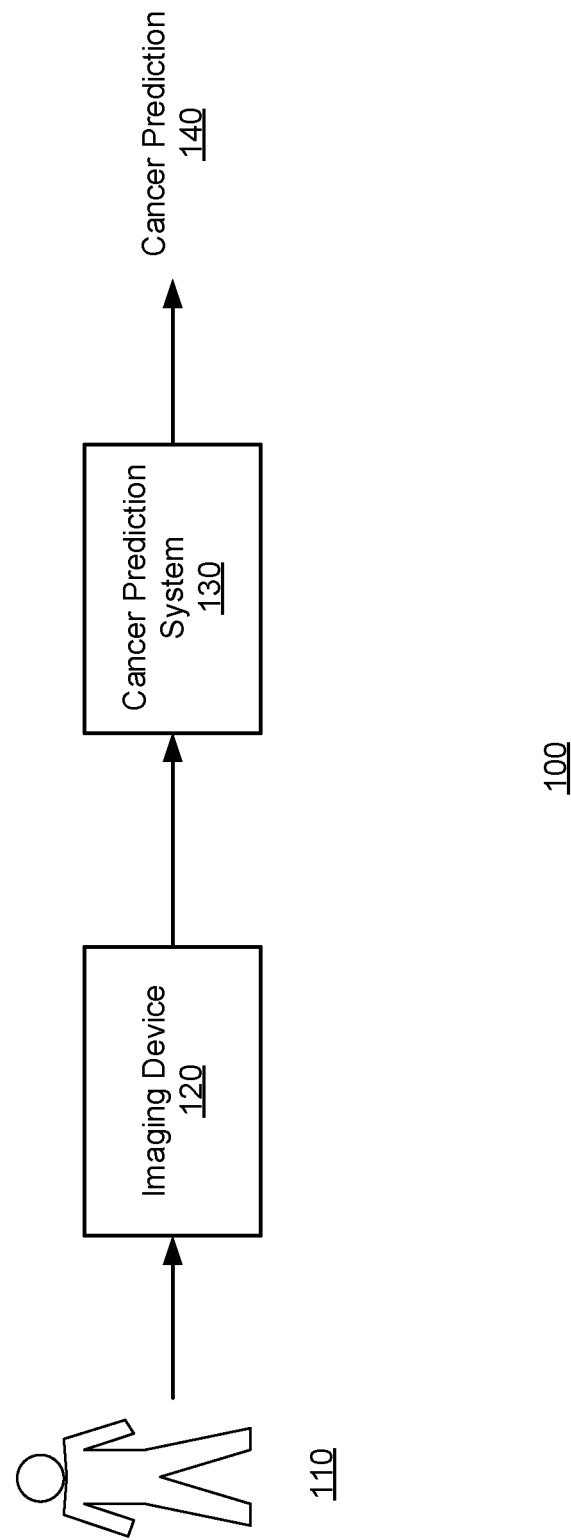
FIG. 1A depicts a system environment overview for determining a cancer prediction for a subject, in accordance with an embodiment.

Terms used in the claims and specification are defined as set forth below unless otherwise specified.

The terms "subject" or "patient" are used interchangeably and encompass a cell, tissue, or organism, human or non-human, whether in vivo, ex vivo, or in vitro, male or female.

The term "mammal" encompasses both humans and non-humans and includes but is not limited to humans, non-human primates, canines, felines, murines, bovines, equines, and porcines.

The term "sample" or "test sample" can include a single cell or multiple cells or fragments of cells or an aliquot of body fluid, such as a blood sample, taken from a subject, by means including venipuncture, excretion, ejaculation, massage, biopsy, needle aspirate, lavage sample, scraping, surgical incision, or intervention or other means known in the art. Examples of an aliquot of body fluid include amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In various embodiments, a sample can be a biopsy of a tissue, such as a lung tumor or a lung nodule.

The term "obtaining one or more images" encompasses obtaining one or more images captured from a subject or obtaining one or more images captured from a sample obtained from a subject. Obtaining one or more images can encompass performing steps of capturing the one or more images from the subject or from a sample obtained from the subject. The phrase can also encompass receiving one or more images, e.g., from a third party that has performed the steps of capturing the one or more images from the subject or from a sample obtained from the subject. The one or more images can be obtained by one of skill in the art via a variety of known ways including stored on a storage memory. In various embodiments, "obtaining one or more images" refers to obtaining one or more images that are each captured from a subject at a single timepoint (e.g., a single patient visit).

The term "training image" refers to an image (e.g., CT image or X-ray image) captured from an individual that is used to train a risk prediction model, e.g., a lung cancer risk prediction model such as a model described herein. In various embodiments, a training image is a computed tomography (CT) image from a cohort that is built from routine clinical care of patients (e.g., from patients that were routinely screened). In various embodiments, a training image is a computed tomography (CT) image from a cohort built from research investigations (e.g., federally/industry sponsored research investigations). In various embodiments, a training image is a computed tomography (CT) image from the National Lung Cancer Screening Trial (NLST) cohort. In various embodiments, a training image is a computed tomography (CT) image included in a custom dataset. For example, the training image can be captured from a training individual. The term "training individual" refers to an individual from whom a training image is captured or otherwise obtained for use in training a risk prediction model.

The term "nodule specific features" refers to features of a lung nodule, examples of which include nodule specific attenuation, nodule margin description, nodule size, nodule shape, nodule texture (e.g., smooth, spiculated, etc.), nodule diameter, and Lung-RADS score. In various embodiments, nodule-specific features are computationally extracted from images (e.g., by implementing an image analysis algorithm). For example, nodule specific features can be radiomic features that are extracted using an image processing algorithm, such as PyRadiomics. Example radiomic features can include first order statistics, 3D shape based features, 2D shape based features, gray level cooccurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level cooccurrence matrix, gray level run length matrix, gray level size zone matrix, neighboring gray tone difference matrix, and gray level dependence matrix can be extracted from a wavelet transformed image or a gaussian transformed image. As used herein, "nodule-specific features" are also referred to as "subjective features." In various embodiments, nodule-specific features are extracted from a report prepared by a trained professional (e.g., a radiologist) who analyzes images of a subject, such as CT scans of the subject.

The term "non-nodule specific features" refers to any of lung parenchyma features or body composition features. Non-nodule specific features can include features from a subject that are not nodules. Non-nodule specific features can include features from a subject that are not associated with nodules. Lung parenchyma features can include densitometric measures of the lung parenchyma which may include, for example, the percentage of the lung occupied by (i) low attenuation area (LAA), which is defined as the area/volume having an attenuation less than −950 Hounsfield Units (HU) and (ii) high attenuation area (HAA), which is defined as the area/volume of lung having attenuation between −600 HU and −250 HU, and the ratio between LAA in the upper lung zone to that in the lower lung zone (Ratio LAA). Lung parenchyma features can further include measures of interstitial changes in the lung parenchyma such as local histogram measures of the lung parenchyma, the percentage of lung occupied by, for example, normal tissue, centrilobular emphysema, centrilobular nodule, ground glass, honeycombing, linear scar, nodular, reticular, subpleural line, other emphysema and/or cyst. Body composition features include, for example, pectoralis major cross-sectional area, pectoralis minor cross-sectional area, pectoralis major lean cross-sectional area, pectoralis minor lean cross-sectional area, aggregate cross-sectional area of the left or right pectoralis major or minor muscles, and subcutaneous fat cross-sectional area. As used herein, "non-nodule specific features" are also referred to as "objective features." In various embodiments, "non-nodule specific features" are computationally extracted from images, such as images captured from a subject. In various embodiments, non-nodule features that are computationally extracted from features can be used to construct a report, such as a radiologist report that includes the non-nodule features. In various embodiments, "non-nodule specific features" do not include a duration of emphysema or a duration of cardiovascular disease.

The phrase "Lung-RADS X-Y" is meant to include individuals classified as Lung-RADS X, Lung-RADS Y, and any value in between numerical variables "X" and "Y." For example, Lung-RADS 1-3 is indicative of individuals classified as Lung-RADS 1, Lung-RADS 2, and Lung-RADS 3.

The phrase "Lung-RADS X-Y prediction model" refers to a risk prediction model that is trained using training images captured from training individuals that are classified in any one of Lung-RADS X-Y.

The phrase "M year prediction model" refers to a risk prediction model that is trained to predict a future risk of cancer within a "M" time period. In various embodiments, "M" is any of 6 months, 1 year, 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. In various embodiments, "M" is measured from the time of acquisition of one or more images from a subject. Therefore, a 1 year prediction model refers to a risk prediction model that is trained to predict a future risk of cancer within 1 year from the time of acquisition of one or more images from a subject.

The phrase "M year, Lung-RADS X-Y prediction model" refers to a risk prediction model that 1) is trained using training images captured from training individuals that are classified in any one of Lung-RADS X-Y and 2) is trained to predict a future risk of cancer within "M" years.

The phrase "future risk of cancer" refers to a risk that subject will develop cancer within a given period of time, e.g., 1 year or 3 years from T0. In various embodiments, the future risk of cancer refers to a likelihood that a subject will develop cancer within a given period of time from time zero (T0). In various embodiments, the future risk of cancer refers to a likelihood that a subject will develop cancer within 1 year. In various embodiments, the future risk of cancer refers to a likelihood that a subject will develop cancer within 3 years. In various embodiments, the future risk of cancer refers to a likelihood that a subject will develop cancer within 5 years. In various embodiments, the future risk of cancer refers to a likelihood that a subject will develop cancer within at least 1 year, at least 2 years, at least 3 years, at least 4 years, at least 5 years, at least 6 years, at least 7 years, at least 8 years, at least 9 years, at least 10 years, at least 11 years, at least 12 years, at least 13 years, at least 14 years, at least 15 years, at least 16 years, at least 17 years, at least 18 years, at least 19 years, or at least 20 years. In various embodiments, the "future risk of cancer" is a binary value (e.g., 0 or 1, where 0 indicates unlikely to develop cancer in the period of time and 1 indicates likely to develop cancer in the period of time). In various embodiments, the "future risk of cancer" is a continuous value (e.g., between 0 and 1, where a value closer to 1 indicates higher likelihood of developing cancer in the period of time).

The terms "treating," "treatment," or "therapy" of lung cancer shall mean slowing, stopping or reversing a cancer's progression by administration of treatment. In some embodiments, treating lung cancer means reversing the cancer's progression, ideally to the point of eliminating the cancer itself. In various embodiments, "treating," "treatment," or "therapy" of lung cancer includes administering a therapeutic agent or pharmaceutical composition to the subject. Additionally, as used herein, "treating," "treatment," or "therapy" of lung cancer further includes administering a therapeutic agent or pharmaceutical composition for prophylactic purposes. Prophylaxis of a cancer refers to the administration of a composition or therapeutic agent to prevent the occurrence, development, onset, progression, or recurrence of cancer or some or all of the symptoms of lung cancer or to lessen the likelihood of the onset of lung cancer.

It must be noted that, as used in the specification, the singular forms "a," "an" and "the" include plural referents unless the context clearly dictates otherwise.

II. System Environment Overview

FIG. 1A depicts a system environment overview for determining a cancer prediction for a subject, in accordance with an embodiment. The system environment 100 provides context in order to introduce a subject 110, an imaging device 120, and a cancer prediction system 130 for determining a cancer prediction 140 for the subject 110. Although FIG. 1A depicts one subject 110 for whom a cancer prediction 140 is generated, in various embodiments, the system environment 100 includes two or more subjects such that that cancer prediction system 130 generates cancer predictions 140 for the two or more subjects (e.g., a cancer prediction for each subject).

In various embodiments, the subject 110 is healthy. For example, the subject is not previously diagnosed with cancer or is not suspected of having cancer. Thus, the methods for future risk prediction of cancer described herein can be beneficial for early detection of cancer in the healthy subject.

In particular embodiments, the type of cancer in the subject is a lung cancer. Thus, the methods described herein can be beneficial for early detection of lung cancer. In various embodiments, the subject was previously diagnosed with a cancer. In such embodiments, the subject can be in remission and therefore, the methods for future risk prediction of cancer can be beneficial for determining whether the subject is likely to experience a recurrence of cancer within a time period.

In various embodiments, subjects predicted to develop cancer or experience a cancer recurrence within a time period can be administered treatments, such as prophylactic treatments that slow or prevent the onset or recurrence of the cancer. In various embodiments, subjects predicted to develop cancer or experience a cancer recurrence within a time period are selected to be enrolled in a clinical trial.

Referring to FIG. 1A, the imaging device 120 captures an image from the subject 110. In various embodiments, the imaging device 120 captures an image from a test sample obtained from the subject 110. In various embodiments, the image and/or the sample can be obtained by a third party, e.g., a medical professional. Examples of medical professionals include physicians, emergency medical technicians, nurses, first responders, psychologists, phlebotomist, medical physics personnel, nurse practitioners, surgeons, dentists, and any other obvious medical professional as would be known to one skilled in the art. In various embodiments, the image and/or the sample can be obtained in a hospital setting or a medical clinic. In various embodiments, the image and/or the sample can be captured using an imaging device, such as a mobile imaging device.

In some embodiments, the imaging device 120 captures an image of an anatomical location of the subject 110. Example anatomical locations of a subject can include lungs, thoracic cavity, kidney, liver, pancreas, brain, stomach, intestines, hip, knees, legs, arms, and face. In various embodiments, the imaging device 120 captures an image of the thoracic cavity of the subject 110. In various embodiments, the imaging device 120 captures an image of the subject's lungs. In various embodiments, the imaging device 120 captures an image of the subject's chest (e.g., chest wall including the pectoralis muscle). In various embodiments, the imaging device 120 captures an image of the thoracic cavity including the subject's lungs. In various embodiments, the imaging device 120 captures an image of the thoracic cavity including the subject's chest (e.g., chest wall including the pectoralis muscle). In various embodiments, the imaging device 120 captures an image of the thoracic cavity including both the subject's lungs and the subject's chest (e.g., chest wall including the pectoralis muscle).

In various embodiments, the imaging device 120 is one of a computed tomography (CT) scanner, magnetic resonance imaging (MRI) scanner, positron emission tomography (PET) scanner, x-ray scanner, or an ultrasound imaging device. In particular embodiments, the imaging device 120 is a CT scanner that captures one or more images of the subject 110. In particular embodiments, the imaging device 120 is a CT scanner that captures one or more CT images of the thoracic cavity including both the subject's lungs and the subject's chest (e.g., chest wall including the pectoralis muscle). In particular embodiments, the imaging device 120 is an X-ray scanner that captures one or more X-ray images of the chest including both the subject's lungs and the subject's chest (e.g., chest wall including the pectoralis muscle).

Generally, the cancer prediction system 130 analyzes one or more images captured from the subject 110 (e.g., images captured by the imaging device 120) and generates the cancer prediction 140 for the subject 110. In various embodiments, the cancer prediction 140 determined by the cancer prediction system 130 is a predicted future risk of cancer for the subject 110. For example, the cancer prediction 140 is a value indicating whether the subject 110 is predicted to develop cancer within a time period (e.g., within 1 year, within 3 years, or within 5 years) from a date that the images were captured from the subject 110.

In various embodiments, to generate the cancer prediction 140, the cancer prediction system 130 extracts features from the one or more images and applies one or more trained risk prediction models to analyze the features of the one or more images. A trained risk prediction model predicts a future risk of cancer for the subject 110 within a time period. For example, the cancer prediction system 130 can apply a risk prediction model that is trained to predict a future risk of cancer within 3 years. In various embodiments, the cancer prediction system 130 determines multiple future risks of cancer across different time periods for the subject 110 by applying multiple trained risk prediction models. For example, in addition to applying a risk prediction model that is trained to predict a future risk of cancer within 3 years, the cancer prediction system 130 further applies a second risk prediction model that is trained to predict a future risk of cancer within 5 years. The cancer prediction system 130 can apply more trained risk prediction models that are trained for additional time periods (e.g., 1 year, 10 years, 15 years, 20 years, etc). Generally, risk prediction models are trained independently and not additive (e.g., cannot subtract cancers predicted in 1 year from cancers predicted in 3 years to obtain cancers predicted to develop 1 year but before 3 years).

In various embodiments, the cancer prediction 140 is an indication derived from the predicted future risk of cancer for the subject, the indication identifying whether the subject 110 is to be included or excluded from a patient cohort for enrollment in a clinical trial. The indication is useful for clinical trial enrichment purposes. For example, if the subject 110 is predicted to develop cancer within a time period, the indication identifies that the subject 110 is to be included in a patient cohort for enrollment in a clinical trial. As another example, if the subject 110 is not predicted to develop cancer within a time period, the indication identifies that the subject 110 is to be excluded from the patient cohort for enrollment in a clinical trial.

In various embodiments, the cancer prediction 140 can include a recommended intervention for the subject 110 based on the predicted future risk of cancer. For example, if the cancer prediction system 130 determines that the subject 110 is likely to develop cancer within 1 year, the cancer prediction 140 can include a recommended intervention to delay or prevent the rapid onset of the cancer over the next year.

The cancer prediction system 130 can include one or more computers, embodied as a computer system 400 as discussed below with respect to FIG. 4. Therefore, in various embodiments, the steps described in reference to the cancer prediction system 130 are performed in silico.

In various embodiments, the imaging device 120 and the cancer prediction system 130 are employed by different parties. For example, a first party operates the imaging device 120 to capture one or more images from the subject 110 and then provides the captured one or more images to a second party which implements the cancer prediction system 130 to determine a cancer prediction 140. In some embodiments, the imaging device 120 and the cancer prediction system 130 are employed by the same party.

Figure 1B:
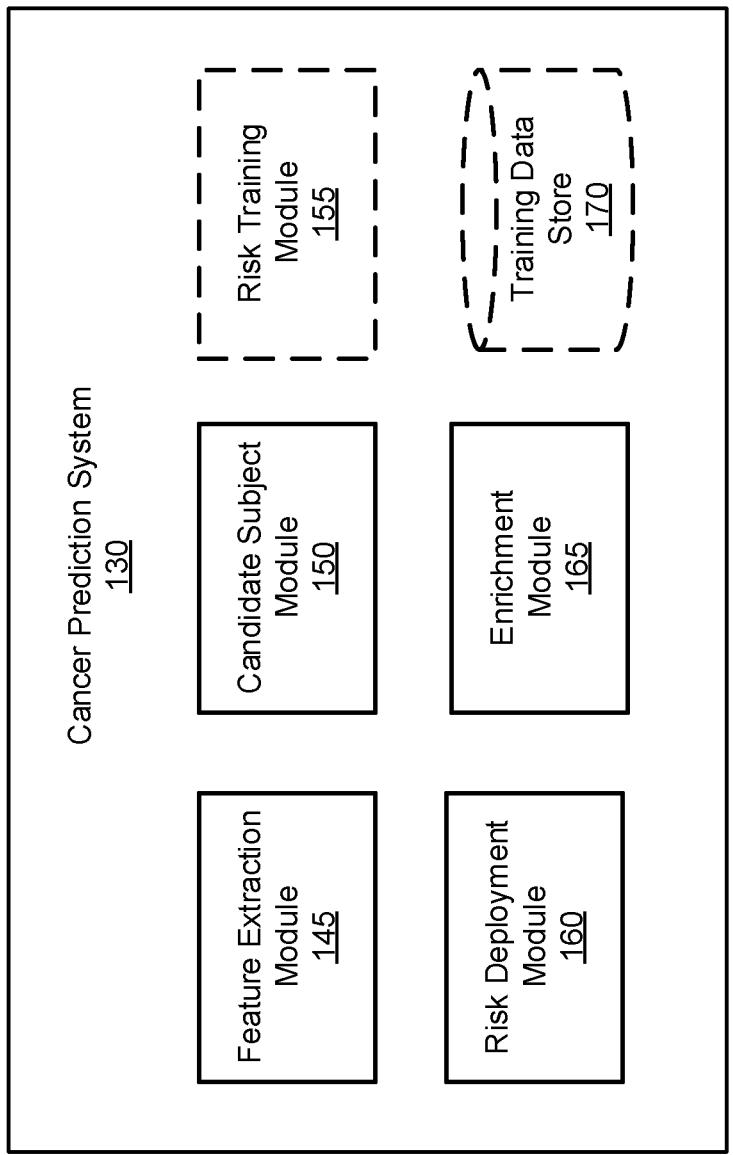
FIG. 1B depicts a block diagram of the cancer prediction system, in accordance with an embodiment.

Reference is now made to FIG. 1B which depicts a block diagram illustrating the computer logic components of the cancer prediction system 130, in accordance with an embodiment. Here, the cancer prediction system 130 includes a feature extraction module 145, a candidate subject module 150, a risk training module 155, a risk deployment module 160, an enrichment module 165, and a training data store 170. In various embodiments, the cancer prediction system 130 can be configured differently with additional or fewer modules. For example, a cancer prediction system 130 need not include the candidate subject module 150. As another example, the cancer prediction system 130 need not include the risk training module 155 or the training data store 170 (as indicated by their dotted lines in FIG. 1), and instead, the risk training module 155 and training data store 170 are employed by a different system and/or party.

Generally, the feature extraction module 145 extracts features from images captured from subjects or training images captured from training individuals. In various embodiments, the feature extraction module 145 extracts non-nodule specific features from images or training images. In various embodiments, the feature extraction module 145 extracts nodule specific features from images or training images. In various embodiments, the feature extraction module 145 extracts nodule specific features and non-nodule specific features from images or training images. The feature extraction module 145 provides features extracted from training images to the risk training module 155 for training risk prediction models. In various embodiments, the feature extraction module 145 provides features extracted from images captured from subjects to the risk to the candidate subject module 150 for identifying candidate subjects. In various embodiments, the feature extraction module 145 provides features extracted from images captured from subjects to the risk deployment module 160 for deploying one or more trained risk prediction models.

The candidate subject module 150 analyzes features extracted from one or more images captured from a subject and determines whether the subject is a candidate subject for undergoing future risk prediction. This is useful for identifying a subset of patients who are to undergo future risk prediction. For example, it may be preferable to predict future risk of cancer for low risk cancer patients (e.g., patients who currently do not have cancer and/or do not currently have a lung nodule indicative of cancer). Therefore, the candidate subject module 150 can identify a subset of low risk cancer patients for subsequent future risk prediction. In various embodiments, the candidate subject module 150 analyzes both nodule specific features and non-nodule specific features to determine whether a subject is a candidate subject. In various embodiments, the candidate subject module 150 only analyzes nodule specific features to determine whether a subject is a candidate subject. In various embodiments, the candidate subject module 150 need not be implemented by the cancer staging system 140. For example, in a scenario where all subjects are to be analyzed for future risk of cancer, then all subjects are candidate subjects who are to undergo future risk prediction.

The risk training module 155 trains risk prediction models using training data derived from training individuals. For example, the training data includes extracted features from one or more training images captured from the training individuals. In various embodiments, the risk training module 155 trains a risk prediction model comprising both nodule specific features and non-nodule specific features. In such embodiments, the risk deployment module 160 implements a risk prediction model to analyze both nodule specific features and non-nodule specific features extracted from images obtained from a subject (e.g., subject 110 in FIG. 1A) to determine a future risk of cancer. In various embodiments, the risk training module 155 trains a risk prediction model comprising only non-nodule specific features. In such embodiments, the risk deployment module 160 implements a risk prediction model to analyze only non-nodule specific features extracted from images obtained from a subject (e.g., subject 110 in FIG. 1A) to determine a future risk of cancer.

The risk deployment module 160 implements risk prediction models to analyze features extracted from images obtained from a subject (e.g., subject 110 in FIG. 1A) to determine a cancer prediction, such as a prediction of future risk of cancer, for the subject 110. Training risk prediction models and deploying risk prediction models are described in further detail below.

The enrichment module 165 selects for subjects for inclusion in a patient cohort. In various embodiments, the patient cohort is generated for enrollment in a clinical trial. For example, the enrichment module 165 generates a patient cohort (e.g., an enriched patient cohort) including a higher percentage of patients who will develop cancer within a period of time. This enriched patient cohort enables the enrolling of fewer patients in clinical trials, and/or identifies people that may benefit from therapies that intercept and prevent lung cancer.

The components of the cancer prediction system 130 are hereafter described in reference to two phases: 1) a training phase and 2) a deployment phase. More specifically, the training phase refers to the building and training of one or more risk prediction models by the risk training module 155 based on training data, such as training images captured from training individuals (e.g., individuals who are known to develop or not develop cancer within a period of time). Therefore, the models are trained using the training data such that during the deployment phase, implementation of the models by the risk deployment module 160 enables the prediction of a future risk of cancer for a subject (e.g., subject 110 in FIG. 1A).

In some embodiments, the components of the cancer prediction system 130 are applied during one of the training phase and the deployment phase. For example, the risk training module 155 and training data store 170 are applied during the training phase to train a risk model. Additionally, the risk deployment module 160 is applied during the deployment phase. In various embodiments, the components of the cancer prediction system 130 can be performed by different parties depending on whether the components are applied during the training phase or the deployment phase. In such scenarios, the training and deployment of the prediction model are performed by different parties. For example, the risk training module 155 and training data store 170 applied during the training phase can be employed by a first party (e.g., to train a risk prediction model) and the risk deployment module 160 applied during the deployment phase can be performed by a second party (e.g., to deploy the risk prediction model).

III. Methods for Predicting Future Risk of Cancer

Figure 2A:
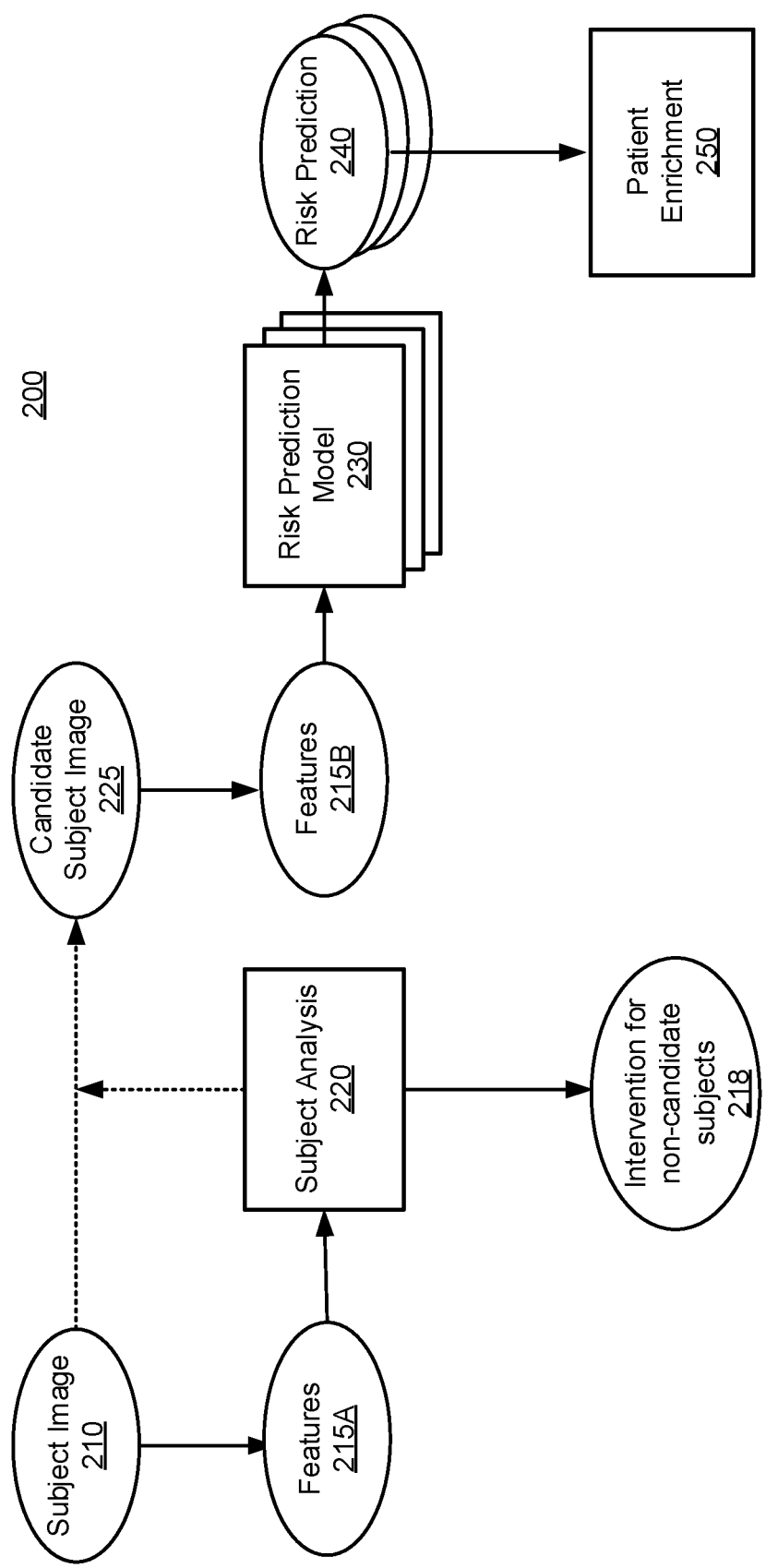
FIG. 2A depicts an example flow diagram for determining a future risk of cancer for a subject for uses such as patient enrichment, in accordance with a first embodiment.

Embodiments described herein include methods for determining a future risk of cancer for a subject by applying one or more trained risk prediction models. Such methods can be performed by the cancer prediction system 130 described in FIG. 1B. Reference will further be made to FIG. 2A, which depicts an example flow diagram 200 for determining a future risk of cancer for a subject for uses such as patient enrichment, in accordance with an embodiment.

As shown in FIG. 2A, a subject image 210 captured from a subject (e.g., subject 110 in FIG. 1A) is obtained. In various embodiments, the subject image 210 is a CT image captured by performing a CT scan of the subject. In various embodiments, the subject image 210 is an X-ray image captured by performing an X-ray scan of the subject. In various embodiments, more than one subject image 210 is captured from the subject.

In various embodiments, the feature extract module 145 extracts features 215A of a subject. In various embodiments, features 215A of the subject include clinical data corresponding to the subject such as age, sex, ethnicity, smoking history, geographical location, pollution exposure, and/or family history of lung cancer. In various embodiments, the feature extraction module 145 (FIG. 1B) extracts features 215A from the subject image 210. In various embodiments, the feature extraction module 145 implements an image analysis algorithm to extract features 215A from the subject image 210. In various embodiments, the feature extraction module 145 implements an image analysis algorithm including a machine learning model that is trained to analyze and extract features from an image. Methods for extraction radiomic features are further described in Radiomics of Lung Nodules: A multi-institutional study of robustness and agreement of quantitative imaging features. Tomography. 2016; 2(4):430-437 and Radiomics: extracting more information from medical images using advanced feature analysis. Eur J Cancer 2012; 48(4):441-446, each of which is hereby incorporated by reference in its entirety.

In various embodiments, the feature extraction module 145 extracts at least 2 features from subject image 210. In various embodiments, the feature extraction module 145 extracts at least 3, at least 4, at least 5, at least 6, at least 7, at least 8, at least 9, or at least 10 features from subject image 210. In various embodiments, the feature extraction module 145 extracts at least 15, at least 20, at least 25, at least 30, at least 35, at least 40, or at least 45 features from subject image 210. In various embodiments, the feature extraction module 145 extracts at least 50 features from subject image 210. In various embodiments, the feature extraction module 145 extracts at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from a subject image 210. In various embodiments, the feature extraction module 145 extracts between 100 features and 1000 features. In various embodiments, the feature extraction module 145 extracts between 300 features and 900 features. In various embodiments, the feature extraction module 145 extracts between 500 features and 1000 features.

In various embodiments, the feature extraction module 145 extracts features 215A including nodule specific features. Nodule specific features refer to features of a lung nodule (e.g., a lung nodule that is present or absent in the subject image 210). Example nodule specific features include nodule specific attenuation, nodule margin description, nodule size, nodule shape, nodule texture (e.g., smooth, spiculated, etc.), nodule diameter, and Lung-RADS score. In various embodiments, nodule specific features can be radiomic features that are extracted using an image processing algorithm, such as PyRadiomics. Example radiomic features can include first order statistics, 3D shape based features, 2D shape based features, Gray level cooccurrence matrix, gray level run length matrix, gray level size zone matrix, neighboring gray tone difference matrix, and gray level dependence matrix. In various embodiments, radiomic features are extracted from an image that has been transformed by applying a filter, such as a wavelet filter or a gaussian filter. Thus, any of first order statistics, 3D shape based features, 2D shape based features, gray level cooccurrence matrix, gray level run length matrix, gray level size zone matrix, neighboring gray tone difference matrix, and gray level dependence matrix can be extracted from a wavelet transformed image or a gaussian transformed image.

In particular embodiments, the feature extraction module 145 analyzes the subject image 210 and assigns a Lung-RADS score to the subject image 210 based on one or more of the extracted nodule-specific features. For example, based on one or more extracted nodule specific features (e.g., such as radiomics features), the feature extraction module 145 determines that the subject image 210 does not include a lung nodule. In such scenarios, the feature extraction module 145 can assign the subject image 210 a Lung-RADS score of 1. As another example, the feature extraction module 145 analyzes the subject image 210 and determines that the subject image 210 includes a nodule based on one or more of the extracted nodule-specific features. Then, based on the nodule-specific features, the feature extraction module 145 can assign a corresponding Lung-RADS score (e.g., Lung-RADS 2, Lung-RADS 3, Lung-RADS 4A, Lung-RADS 4B, or Lung-RADS 4X) according to Lung-RADS criteria, such as current Lung-RADS criteria shown in Table 1 or future Lung-RADS criteria.

In various embodiments, the feature extraction module 145 extracts features 215A including non-nodule specific features. Non-nodule specific features refer to any of lung parenchyma features (e.g., densitometric measures of the lung parenchyma and measures of interstitial changes in the lung parenchyma) and body composition measures of the musculature/chest wall. Densitometric measures of the lung parenchyma may include, for example, the percentage of the lung occupied by (i) low attenuation area (LAA), which is defined as the area/volume having an attenuation less than −950 Hounsfield Units (HU) and (ii) high attenuation area (HAA), which is defined as the area/volume of lung having attenuation between −600 HU and −250 HU, and the ratio between LAA in the upper lung zone to that in the lower lung zone. Measures of interstitial changes in the lung parenchyma include local histogram measures of the lung parenchyma, the percentage of lung occupied by, for example, normal tissue, centrilobular emphysema, centrilobular nodule, ground glass, honeycombing, linear scar, nodular, reticular, subpleural line, other emphysema and/or cyst. Body composition measures of the musculature/chest wall may include, for example, pectoralis major cross-sectional area, pectoralis minor cross-sectional area, pectoralis major lean cross-sectional area, pectoralis minor lean cross-sectional area, aggregate cross-sectional area of the left or right pectoralis major or minor muscles, and subcutaneous fat cross-sectional area.

In various embodiments, the feature extraction module 145 extracts features 215A that include nodule specific features and non-nodule specific features. In various embodiments, the feature extraction module 145 extracts features 215A that include only non-nodule specific features.

In particular embodiments, the feature extraction module 145 extracts features 215A that include only nodule specific features. In various embodiments, the feature extraction module 145 obtains nodule specific features that are determined by a third party. For example, the nodule specific features may have been determined by a trained professional (e.g., a radiologist) that analyzes the subject image 210. In various embodiments, the feature extraction module 145 extracts nodule specific features from a report generated by a third party. For example, the feature extraction module 145 extracts nodule specific features from a report generated by a trained professional (e.g., a radiologist) that analyzes the subject image 210.

The candidate subject module 150 (FIG. 1B) performs subject analysis 220 (shown in FIG. 2A) by analyzing the features 215A of the subject image 210. Based on the analysis, the candidate subject module 150 determines whether the subject is a candidate subject who is to undergo a future risk prediction. Put another way, the subject analysis 220 is a screening process to identify candidate subjects who are eligible for a future risk of cancer prediction. For example, subjects undergoing lung cancer screening that are determined not to have prevalent lung cancer are subsequently evaluated for their risk of developing future incident lung cancer As one example, the candidate subject module 150 determines that a subject is a candidate subject for undergoing future risk prediction if the subject's features 215A, such as clinical data of the subject, meets one or more criterion. For example, if the subject's features 215A indicate that the subject smokes above a threshold amount, the subject is deemed a candidate subject for undergoing future risk prediction. As another example, the candidate subject module 150 determines that a subject is a candidate subject for undergoing future risk prediction if the subject is a low risk cancer patient (e.g., a patient who does not currently have lung cancer and/or does not currently have a lung nodule indicative of cancer). In various embodiments, the candidate subject module 150 determines that a subject is a non-candidate subject for undergoing future risk prediction if the subject is a high risk cancer patient (e.g., a patient currently with lung cancer and/or a patient with a lung nodule that indicates high risk of developing lung cancer). As shown in FIG. 2A, if the subject analysis 220 determines that the subject is a candidate subject, then the subject image 210 is taken as the candidate subject image 225 (shown by the dotted lines) for subsequent future risk prediction analysis. Alternatively, if the subject analysis 220 determines that the subject is a non-candidate subject, the patient does not further undergo future risk prediction analysis. As an example, an intervention for non-candidate subjects 218 can be provided to the subject. For example, a non-candidate subject may be a subject already with lung cancer or with a lung nodule that indicates that the subject has advanced lung cancer. Thus, the non-candidate subject need undergo a future risk of cancer prediction and instead, can be provided an intervention for non-candidate subjects 218 can include a cancer biopsy and/or administration of a therapeutic agent (e.g., chemotherapy, radiation) to treat the non-candidate subject's lung cancer.

In various embodiments, the candidate subject module 150 determines that a subject is a candidate subject based on features 215A that include nodule specific features. As an example, the nodule-specific features can include a Lung-RADS score, such as Lung-RADS 0, Lung-RADS 1, Lung-RADS 2, Lung-RADS 3, Lung-RADS 4A, Lung-RADS 4B, or Lung-RADS 4X. A summary of Lung-RADS score classifications and corresponding characteristics of lung nodules is described in Table 1. In various embodiments, the candidate subject module 150 determines a Lung-RADS score for the subject based on the features 215A, such as nodule specific features. For example, the nodule specific features can include one or more of nodule specific attenuation, nodule margin description, nodule size, nodule shape, nodule texture (e.g., smooth, spiculated, etc.), nodule diameter, Lung-RADS score, and/or radiomic features such as first order statistics, 3D shape based features, 2D shape based features, gray level cooccurrence matrix, gray level run length matrix, gray level size zone matrix, neighboring gray tone difference matrix, and gray level dependence matrix. Thus, if the nodule attenuation feature indicates that the lung nodule is a solid nodule and the nodule margin and/or nodule diameter features indicate that the lung nodule is 5 mm, the candidate subject module 150 can assign a Lung-RADS score of 2 based on criteria specified in Table 1.

In various embodiments, the candidate subject module 150 determines that a subject is a candidate subject if the subject is assigned a Lung-RADS score of 0. In various embodiments, the candidate subject module 150 determines that a subject is a candidate subject if the subject is assigned a Lung-RADS score of 1. In various embodiments, the candidate subject module 150 determines that a subject is a candidate subject if the subject is assigned a Lung-RADS score of 2. In various embodiments, the candidate subject module 150 determines that a subject is a candidate subject if the subject is assigned a Lung-RADS score of 3. In various embodiments, the candidate subject module 150 determines that a subject is a candidate subject if the subject is assigned a Lung-RADS score of 4A. In various embodiments, the candidate subject module 150 determines that a subject is a candidate subject if the subject is assigned a Lung-RADS score of 0 or 1. In various embodiments, the candidate subject module 150 determines that a subject is a candidate subject if the subject is assigned a Lung-RADS score of 0, 1, or 2. In various embodiments, the candidate subject module 150 determines that a subject is a candidate subject if the subject is assigned a Lung-RADS score of 0, 1, 2, or 3. In various embodiments, the candidate subject module 150 determines that a subject is a candidate subject if the subject is assigned a Lung-RADS score of 1, 2, or 3.

In various embodiments, the candidate subject module 150 determines that a subject is a non-candidate subject if the subject is assigned a Lung-RADS score of 3. In various embodiments, the candidate subject module 150 determines that a subject is a non-candidate subject if the subject is assigned a Lung-RADS score of 4A. In various embodiments, the candidate subject module 150 determines that a subject is a non-candidate subject if the subject is assigned a Lung-RADS score of 4B. In various embodiments, the candidate subject module 150 determines that a subject is a non-candidate subject if the subject is assigned a Lung-RADS score of 4A or 4B. In various embodiments, the candidate subject module 150 determines that a subject is a non-candidate subject if the subject is assigned a Lung-RADS score of 3, 4A, or 4B.

In various embodiments, the candidate subject module 150 determines that a subject is a candidate subject if the nodule specific features indicate that the subject does not have a lung nodule. For example, the nodule specific features can include one or more of nodule attenuation, nodule margin description, or nodule diameter. Thus, if the nodule specific features indicates that the subject image 210 does not include a nodule (e.g., lack of attenuation, lack of margins, or near-zero or zero diameter), then the candidate subject module 150 determines that the subject is a candidate subject.

In various embodiments, the candidate subject module 150 determines that a subject is a candidate subject even if the subject has a lung nodule. For example, if the nodule specific features indicate that the subject has a lung nodule, the candidate subject module 150 can further analyze the nodule specific features to classify the nodule as a higher risk nodule or a lower risk nodule. In various embodiments, the candidate subject module 150 can classify a nodule based on whether the nodule is a solid nodule, a semi-solid nodule, or a non-solid nodule. For example, the candidate subject module 150 can classify a nodule as a higher risk nodule if it is a solid nodule or a semi-solid nodule and can classify a nodule as a lower risk nodule if it is a non-solid nodule. In various embodiments, the candidate subject module 150 determines that a subject is a candidate subject if the subject has a lower risk nodule. The candidate subject module 150 can determine that a subject is a non-candidate subject if the subject has a higher risk nodule.

Returning to FIG. 2A, following subject analysis 220, a subject image 210 from a candidate subject is now deemed a candidate subject image 225. The feature extraction module 145 extracts features 215B from the candidate subject image 225. In various embodiments, the feature extraction module 145 extracts features 215B including one or both of nodule specific features and non-nodule specific features from the candidate subject image 225. In various embodiments, the feature extraction module 145 extracts features 215A that include only non-nodule specific features. In various embodiments, the feature extraction module 145 extracts features 215A that include only nodule specific features. In various embodiments, the feature extraction module 145 obtains nodule specific features of candidate subject image 225 that are determined by a third party. For example, the nodule specific features may have been determined by a trained professional (e.g., a radiologist) that analyzes the candidate subject image 225. In various embodiments, the feature extraction module 145 extracts nodule specific features from a report generated by a third party. For example, the feature extraction module 145 extracts nodule specific features from a report generated by a trained professional (e.g., a radiologist) that analyzes the subject image 225.

In various embodiments, one or more of features 215B are the same as one or more of features 215A. Therefore, the same features need not be extracted again and can be reused. For example, nodule specific features that were previously extracted from subject image 210 as features 215A can be the same nodule specific features that are included in features 215B. In various embodiments, all of the features 215B were previously extracted from the subject image 210 and therefore, the previously extracted features can be reused here as features 215B. For example, the feature extraction module 145 may extract features 215A and features 215B prior to subject analysis 220. Thus, features 215B need not be further extracted from candidate subject image 225 and can be reused here.

In various embodiments, features 215B includes additional features that were not included in features 215A. For example, features 215B includes non-nodule specific features that were not previously included in features 215A. Thus, the feature extraction module 145 extracts these additional features that were not previously included in features 215A.

In various embodiments, the feature extraction module 145 extracts at least 2 features from candidate subject image 225. In various embodiments, the feature extraction module 145 extracts at least 3, at least 4, at least 5, at least 6, at least 7, at least 8, at least 9, or at least 10 features from candidate subject image 225. In various embodiments, the feature extraction module 145 extracts at least 15, at least 20, at least 25, at least 30, at least 35, at least 40, or at least 45 features from candidate subject image 225. In various embodiments, the feature extraction module 145 extracts at least 50 features from candidate subject image 225. In various embodiments, the feature extraction module 145 extracts at least 100 features, at least 150 features, at least 200 features, at least 250 features, at least 300 features, at least 350 features, at least 400 features, at least 450 features, at least 500 features, at least 550 features, at least 600 features, at least 650 features, at least 700 features, at least 750 features, at least 800 features, at least 850 features, at least 900 features, at least 950 features, or at least 1000 features from candidate subject image 225. In various embodiments, the feature extraction module 145 extracts between 100 features and 1000 features from candidate subject image 225. In various embodiments, the feature extraction module 145 extracts between 300 features and 900 features from candidate subject image 225. In various embodiments, the feature extraction module 145 extracts between 500 features and 1000 features from candidate subject image 225.

The risk deployment module 160 (FIG. 1B) provides the extracted features 215B to trained risk prediction models 230 (shown in FIG. 2A) to generate a risk prediction 240. In various embodiments, as shown in FIG. 2A, the risk deployment module 160 provides the extracted features 215 to multiple trained risk prediction models 230 to generate multiple risk predictions 240. In various embodiments, a risk prediction model is trained to generate a future risk of cancer prediction within a time period (e.g., future risk of cancer within 1 year, within 3 years, or within 5 years). Therefore, to generate a prediction for multiple time periods, the risk deployment module 160 selects and deploys different risk prediction models to analyze the extracted features 215B. For example, the risk deployment module 160 can deploy a first risk prediction model trained to predict future risk of cancer within a first time period and can further deploy a second risk prediction model trained to predict future risk of cancer within a second time period.

In various embodiments, the risk deployment module 160 deploys 1, 2, 3, 4, 5, 6, 7, 8, 9, 10, 11, 12, 13, 14, 15, 16, 17, 18, 19, or 20 different risk prediction models to generate future risk of cancer over 1, 2, 3, 4, 5, 6, 7, 8, 9, 10, 11, 12, 13, 14, 15, 16, 17, 18, 19, or 20 different time periods, respectively. In various embodiments, the risk deployment module 160 deploys 5 different risk prediction models to generate future risk of cancer over 5 different time periods. In various embodiments, the risk deployment module 160 deploys 3 different risk prediction models to generate future risk of cancer over 3 different time periods. For example, the risk deployment module 160 deploys a 1 year risk prediction model, a 3 year risk prediction model, and a 5 year risk prediction model to generate predictions of future risk of cancer within 1 year, 3 years, and 5 years, respectively.

In various embodiments, each of the one or more risk prediction models 230 that are deployed to analyze the features 215B were previously trained on training images that were separated into different regions (e.g., different lung regions). For example, a first risk prediction model 230 may be trained to predict presence of cancer within a first region of the lung, a second risk prediction model 230 may be trained to predict presence of cancer within a second region of the lung, and a third risk prediction model 230 may be trained to predict presence of cancer within a third region of the lung. As an example, different lung regions can include the upper, middle, and lower third of the lungs by volume or separate lobes of the lungs. Thus, the risk predictions 240 generated for the subject may be future risk of cancer within particular regions (e.g., lung regions).

In various embodiments, each of the one or more risk prediction models 230 that are deployed to analyze the features 215B were previously trained using a cohort of training individuals that aligns with the cohort of candidate subjects that were determined as a result of the subject analysis 220. Put another way, the risk prediction models 230 were previously trained using training individuals that would qualify as candidate subjects if they were to undergo the subject analysis 220.

In various embodiments, one or more of the training individuals used to train the risk prediction models 230 share at least one feature with the candidate subject. As an example, if the candidate subject is classified as Lung-RADS 1, one or more of the training individuals used to train the risk prediction models 230 were also classified as Lung-RADS 1. In various embodiments, the risk prediction models 230 may be trained using training images captured from training individuals that were classified as Lung-RADS 1 (referred to as a Lung-RADS 1 risk prediction model). In various embodiments, the risk prediction models 230 may be trained using training images captured from training individuals that were classified as Lung-RADS 1 or Lung-RADS 2 (referred to as a Lung-RADS 1-2 risk prediction model). In various embodiments, the risk prediction models 230 may be trained using training images captured from training individuals that were classified as Lung-RADS 1, Lung-RADS 2, or Lung-RADS 3 (referred to as a Lung-RADS 1-3 risk prediction model). In various embodiments, the risk prediction models 230 may be trained using training images captured from training individuals that were classified as Lung-RADS 1, Lung-RADS 2, Lung-RADS 3, or Lung-RADS 4A (referred to as a Lung-RADS 1-4A risk prediction model). In various embodiments, the risk prediction models 230 may be trained using training images captured from training individuals that were classified as Lung-RADS 1, Lung-RADS 2, Lung-RADS 3, Lung-RADS 4A, or Lung-RADS 4B (referred to as a Lung-RADS 1-4B risk prediction model). In various embodiments, the risk prediction models 230 may be trained using training images captured from training individuals that were classified as Lung-RADS 1, Lung-RADS 2, Lung-RADS 3, Lung-RADS 4A, Lung-RADS 4B, or Lung-RADS 4X (referred to as a Lung-RADS 1-4X risk prediction model).

In a scenario in which a candidate subject is classified as Lung-RADS 1 (e.g., classified either through subject analysis 220 or previously classified by a third party), then the risk deployment module 160 deploys one or more risk prediction models 230 that were trained using training images captured from at least one training individual that was also previously classified as Lung-RADS 1. Thus, the risk deployment module 160 can deploy one or more risk prediction models 230 that each are any of a Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model. In particular embodiments, the risk deployment module 160 deploys a Lung-RADS 1 prediction model for a Lung-RADS 1 candidate subject. In particular embodiments, the risk deployment module 160 deploys a Lung-RADS 1-2 prediction model for a Lung-RADS 1 candidate subject. In particular embodiments, the risk deployment module 160 deploys a Lung-RADS 1-3 prediction model for a Lung-RADS 1 candidate subject.

In a scenario in which a candidate subject is classified as Lung-RADS 2 (e.g., classified either through subject analysis 220 or previously classified by a third party), then the risk deployment module 160 deploys one or more risk prediction models 230 that were trained using training images captured from at least one training individual that was also previously classified as Lung-RADS 2. Thus, the risk deployment module 160 can deploy one or more risk prediction models 230 that each are any of Lung-RADS 1-2 prediction model, Lung-RADS 1-3 prediction model, Lung-RADS 1-4A prediction model, Lung-RADS 1-4B prediction model, or Lung-RADS 1-4X prediction model. In particular embodiments, the risk deployment module 160 deploys a Lung-RADS 1-2 prediction model for a Lung-RADS 2 candidate subject. In particular embodiments, the risk deployment module 160 deploys a Lung-RADS 1-3 prediction model for a Lung-RADS 2 candidate subject.

In a scenario in which a candidate subject is classified as Lung-RADS 3 (e.g., classified either through subject analysis 220 or previously classified by a third party), then the risk deployment module 160 deploys one or more risk prediction models 230 that were trained using training images captured from at least one training individual that was also previously classified as Lung-RADS 3. Thus, the risk deployment module 160 can deploy one or more risk prediction models 230 that each are any of a Lung-RADS 1-3 prediction model, Lung-RADS 1-4A prediction model, Lung-RADS 1-4B prediction model, or Lung-RADS 1-4X prediction model.

In a scenario in which a candidate subject is classified as Lung-RADS 4A (e.g., classified either through subject analysis 220 or previously classified by a third party), then the risk deployment module 160 deploys one or more risk prediction models 230 that were trained using training images captured from at least one training individual that was also previously classified as Lung-RADS 4A. Thus, the risk deployment module 160 can deploy one or more risk prediction models 230 that each are any of a Lung-RADS 1-4A prediction model, Lung-RADS 1-4B prediction model, or Lung-RADS 1-4X prediction model.

In a scenario in which a candidate subject is classified as Lung-RADS 4B (e.g., classified either through subject analysis 220 or previously classified by a third party), then the risk deployment module 160 deploys one or more risk prediction models 230 that were trained using training images captured from at least one training individual that was also previously classified as Lung-RADS 4B. Thus, the risk deployment module 160 can deploy one or more risk prediction models 230 that each are any of a Lung-RADS 1-4B prediction model, or Lung-RADS 1-4X prediction model.

In a scenario in which a candidate subject is classified as Lung-RADS 4X (e.g., classified either through subject analysis 220 or previously classified by a third party), then the risk deployment module 160 deploys one or more risk prediction models 230 that were trained using training images captured from at least one training individual that was also previously classified as Lung-RADS 4X. Thus, the risk deployment module 160 can deploy one or more risk prediction models 230 that each are a Lung-RADS 1-4X prediction model.

In various embodiments, risk prediction models are 1) trained using a cohort of training individuals that aligns with the cohort of candidate subjects that were determined as a result of the subject analysis 220 and 2) trained to generate a future risk of cancer prediction within a time period (e.g., future risk of cancer within 1 year, within 3 years, or within 5 years). For example, to generate risk predictions 240 for a candidate subject, the risk deployment module 160 applies one or more risk prediction models 230 that 1) are trained using one or more training individuals that share at least one feature with the candidate subject and 2) are trained to predict future risk of cancer within different time periods.

In a scenario in which a candidate subject is classified as Lung-RADS "Z" (e.g., classified either through subject analysis 220 or previously classified by a third party), the risk deployment module 160 deploys one or more risk prediction models 230 that 1) were trained using training images captured from at least one training individual that was also previously classified as Lung-RADS "Z" and 2) predicts future risk of cancer within different time periods. As used herein, these risk prediction models are referred to as a "M year, Lung-RADS X-Y prediction model" where "M" refers to the time period and "X-Y" refer to the range of Lung-RADS scores of the training individuals. For example, a 1 year, Lung-RADS 1-3 prediction model refers to a risk prediction model trained using training individuals previously classified in Lung-RADS 1-3, and trained to predict a future risk of cancer within 1 year.

In various embodiments, for a candidate subject classified as Lung-RADS 1, the risk deployment module 160 deploys one or more M year, Lung-RADS X-Y prediction models where the "M" is variable, but the "X" and "Y" are fixed. For example, for a candidate subject classified as Lung-RADS 1, "M" can range from 1-5 years, whereas X=1 and Y=any value from 1 to 4B. As one example, Y=3 and therefore, the risk deployment module 160 can deploy a 1 year, Lung-RADS 1-3 prediction model, a 2 year, Lung-RADS 1-3 prediction model, a 3 year, Lung-RADS 1-3 prediction model, a 4 year, Lung-RADS 1-3 prediction model, and a 5 year, Lung-RADS 1-3 prediction model. In other embodiments, the risk deployment module 160 can deploy additional risk prediction models than described here (e.g., range of M is 1-10, 1-15, or 1-20 years e.g., X and Y are differently selected to provide different ranges of Lung-RADS scores).

In particular embodiments where a candidate subject is classified as Lung-RADS 1, the risk deployment module 160 deploys 1) a first risk prediction model 230 that predicts a future risk of cancer within 1 year (e.g., a 1 year, Lung-RADS 1-3 prediction model), 2) a second risk prediction model 230 that predicts a future of cancer within 3 years (e.g., a 3 year, Lung-RADS 1-3 prediction model), and 3) a third risk prediction model 230 that predicts a future of cancer within 5 years (e.g., a 5 year, Lung-RADS 1-3 prediction model).

In particular embodiments where a candidate subject is classified as Lung-RADS 2, the risk deployment module 160 deploys 1) a first risk prediction model 230 that predicts a future risk of cancer within 1 year (e.g., a 1 year, Lung-RADS 1-3 prediction model), 2) a second risk prediction model 230 that predicts a future of cancer within 3 years (e.g., a 3 year, Lung-RADS 1-3 prediction model), and 3) a third risk prediction model 230 that predicts a future of cancer within 5 years (e.g., a 5 year, Lung-RADS 1-3 prediction model).

In particular embodiments where a candidate subject is classified as Lung-RADS 3, the risk deployment module 160 deploys 1) a first risk prediction model 230 that predicts a future risk of cancer within 1 year (e.g., a 1 year, Lung-RADS 1-3 prediction model), 2) a second risk prediction model 230 that predicts a future of cancer within 3 years (e.g., a 3 year, Lung-RADS 1-3 prediction model), and 3) a third risk prediction model 230 that predicts a future of cancer within 5 years (e.g., a 5 year, Lung-RADS 1-3 prediction model).

In particular embodiments where a candidate subject is classified as Lung-RADS 4A, the risk deployment module 160 deploys 1) a first risk prediction model 230 that predicts a future risk of cancer within 1 year (e.g., a 1 year, Lung-RADS 1-4A prediction model), 2) a second risk prediction model 230 that predicts a future of cancer within 3 years (e.g., a 3 year, Lung-RADS 1-4A prediction model), and 3) a third risk prediction model 230 that predicts a future of cancer within 5 years (e.g., a 5 year, Lung-RADS 1-4A prediction model).

In particular embodiments where a candidate subject is classified as Lung-RADS 4B, the risk deployment module 160 deploys 1) a first risk prediction model 230 that predicts a future risk of cancer within 1 year (e.g., a 1 year, Lung-RADS 1-4B prediction model), 2) a second risk prediction model 230 that predicts a future of cancer within 3 years (e.g., a 3 year, Lung-RADS 1-4B prediction model), and 3) a third risk prediction model 230 that predicts a future of cancer within 5 years (e.g., a 5 year, Lung-RADS 1-4B prediction model).

In particular embodiments where a candidate subject is classified as Lung-RADS 4X, the risk deployment module 160 deploys 1) a first risk prediction model 230 that predicts a future risk of cancer within 1 year (e.g., a 1 year, Lung-RADS 1-4X prediction model), 2) a second risk prediction model 230 that predicts a future of cancer within 3 years (e.g., a 3 year, Lung-RADS 1-4X prediction model), and 3) a third risk prediction model 230 that predicts a future of cancer within 5 years (e.g., a 5 year, Lung-RADS 1-4X prediction model).

As shown in FIG. 2A, the risk predictions 240 can be used for patient enrichment 250. For example, the subject can be included in one or more patient cohorts that are to be enrolled in a clinical study. Methods for patient enrichment are described in further detail below.

Figure 2B:
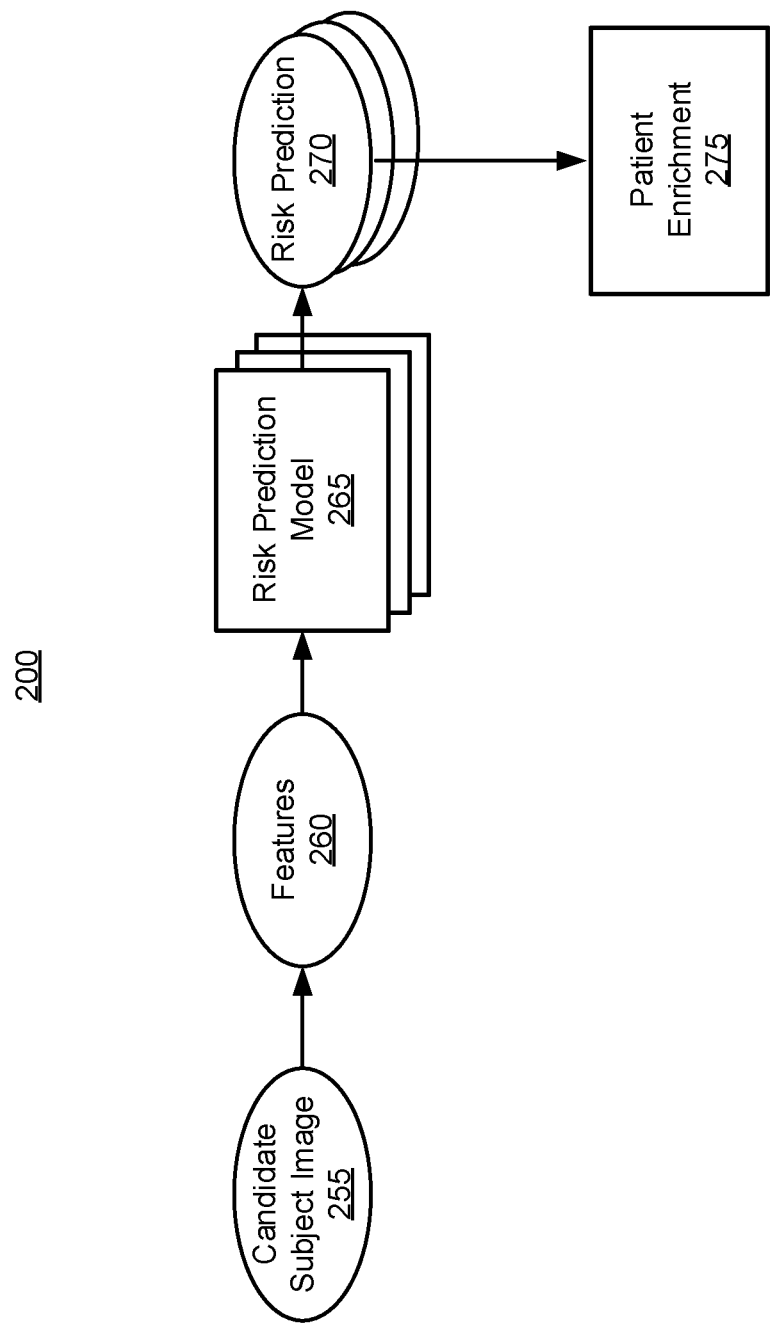
FIG. 2B depicts an example flow diagram for determining a future risk of cancer for a subject for uses such as patient enrichment, in accordance with a second embodiment.

Reference is now made to FIG. 2B, which depicts an example flow diagram for determining a future risk of cancer for a subject for uses such as patient enrichment, in accordance with a second embodiment. Here, FIG. 2B differs from FIG. 2A in that FIG. 2B does not include a subject analysis step (e.g., step 220 shown in FIG. 2A). Thus, FIG. 2B depicts an embodiment where subjects do not undergo a screening. Instead, all subjects are candidate subjects who subsequently undergo future risk prediction. In various embodiments, subjects either have or do not have a lung nodule. In various embodiments, subjects can be previously classified in any one of Lung-RADS 1, Lung-RADS 2, Lung-RADS 3, Lung-RADS 4A, Lung-RADS 4B, or Lung-RADS 4X. Thus, in such embodiments, all subjects, regardless of their lung nodule staging and/or Lung-RADS score, undergo future risk prediction.

As shown in FIG. 2B, the candidate subject image 255 undergoes feature extraction to obtain features 260. In various embodiments, features 260 include one or both of nodule specific features and non-nodule specific features of the candidate subject image 225. In various embodiments, features 260 include only non-nodule specific features. In various embodiments, features 260 include only nodule specific features. In various embodiments, the feature extraction module 140 extracts nodule specific features by implementing an image analysis algorithm, such as an image analysis algorithm that involves implementing a trained machine learning model. In various embodiments, the feature extraction module 140 extracts nodule specific features by implementing PyRadiomics. PyRadiomics is described in further detail in "Computational radiomics system to decode the radiographic phenotype." Cancer Research; 77(21): e104-e107, which is hereby incorporated by reference in its entirety.

In various embodiments, nodule specific features of candidate subject image 255 are determined by a third party. For example, the nodule specific features may have been determined by a trained professional (e.g., a radiologist) that analyzes the candidate subject image 255. In various embodiments, the feature extraction module 145 extracts nodule specific features from a report generated by a third party. For example, the feature extraction module 145 extracts nodule specific features from a report generated by a trained professional (e.g., a radiologist) that analyzes the subject image 225.

The risk deployment module 260 applies one or more risk prediction models 265 to analyze the features 260 to generate the risk prediction 270. Thus, the risk prediction 270 can be used for patient enrichment 275. In various embodiments, the deployment of the risk prediction models 265 to generate the risk prediction 270 as shown in FIG. 2B is the same process as deploying risk prediction models 230 to generate risk predictions 240 as shown in FIG. 2A.

Here, the one or more risk prediction models 265 are trained on training images obtained from training individuals that span the full range of possible subjects. For example, the risk prediction models 265 are trained using training images captured from training individuals either having a lung nodule or not having a lung nodule. As another example, the risk prediction models 265 are trained using training images captured from training individuals of any of Lung-RADS 1, Lung-RADS 2, Lung-RADS 3, Lung-RADS 4A, Lung-RADS 4B, or Lung-RADS 4X (e.g., Lung-RADS 1-4X risk prediction models).

In various embodiments, the risk deployment module 260 deploys multiple future risk models 265 to predict multiple risk predictions 270. For example, the risk deployment module 260 deploys multiple M year, Lung-RADS 1-4X risk prediction models, where "M" refers to the time period in which cancer risk is being evaluated. In various embodiments, "M" is at least 1 year, at least 2 years, at least 3 years, at least 4 years, at least 5 years, at least 6 years, at least 7 years, at least 8 years, at least 9 years, at least 10 years, at least 11 years, at least 12 years, at least 13 years, at least 14 years, at least 15 years, at least 16 years, at least 17 years, at least 18 years, at least 19 years, and/or at least 20 years. In particular embodiments, the risk deployment module 260 deploys 1) a 1 year, Lung-RADS 1-4X risk prediction model, 2) a 3 year, Lung-RADS 1-4X risk prediction model, and 3) a 5 year, Lung-RADS 1-4X risk prediction model, thereby generating future risk of cancer predictions for 1 year, 3 year, and 5 year time periods.

In various embodiments, upon being deployed, a risk prediction model analyzes the extracted image features and generates a predicted score that can be indicative of whether the subject is likely to develop cancer within a time period. For example, the risk prediction model can be a regression model (e.g., a logistic regression or linear regression model) that calculates a predicted score by combining a set of trained parameters with values of the extracted image features. As another example, the risk prediction model can be a neural network model that calculates a predicted score by combining a set of trained parameters associated with nodes and layers of the neural network with values of the extracted image features. As another example, the risk prediction model can be a random forest model that calculates a predicted score by combining a set of trained parameters associated with decision tree nodes with values of the extracted image features. As another example, the risk prediction model can be a gradient boosted machine model that calculates a predicted score by combining a set of trained parameters associated with decision tree nodes with values of the extracted image features.

In various embodiments, the risk prediction model compares the predicted score to one or more reference scores. In various embodiments, the one or more reference scores are threshold cutoff values. For example, a threshold cutoff value can be between 0 and 1, such as 0.1, 0.2, 0.3, 0.4, 0.5, 0.6, 0.7, 0.8, or 0.9. In particular embodiments, a threshold value is 0.1. In particular embodiments, a threshold value is 0.3. Therefore, if the predicted score is above the threshold reference score, the subject is classified into one category (e.g., likely to develop cancer). If the predicted score is below the threshold reference score, the subject is classified into a different category (e.g., unlikely to develop cancer).

In various embodiments, multiple reference threshold scores can be implemented to create multiple classification groups. For example, a first threshold value is 0.1 and a second threshold value is 0.3. Therefore, if the predicted score is below the first threshold value, the subject is classified into a first category (e.g., unlikely to develop cancer. If the predicted score is between the first and second threshold values, the subject is classified into a second category (e.g., low risk of developing cancer). If the predicted score is greater than the second threshold value, the subject is classified into a third category (e.g., high risk of developing cancer).

As one example, a reference score corresponds to one or more training individuals. For example, a reference score can correspond to training individuals that were known to develop cancer within the time period. As another example, a reference score can correspond to training individuals that were known to not develop cancer within the time period. Thus, if the predicted score for the subject is not significantly different (e.g., p-value>0.05) in comparison to the reference score corresponding to training individuals that were known to develop cancer within the time period, then the risk prediction model can classify the subject as likely to develop cancer within the time period. If the predicted score for the subject is significantly different (e.g., p-value<0.05) in comparison to the reference score corresponding to training individuals that were known to develop cancer within the time period, then the risk prediction model can classify the subject as not likely to develop cancer within the time period. If the predicted score for the subject is not significantly different (e.g., p-value>0.05) in comparison to the reference score corresponding to training individuals that were known to not develop cancer within the time period, then the risk prediction model can classify the subject as not likely to develop cancer within the time period. If the predicted score for the subject is significantly different (e.g., p-value<0.05) in comparison to the reference score corresponding to training individuals that were known to not develop cancer within the time period, then the risk prediction model can classify the subject as likely to develop cancer within the time period.

In various embodiments, during training, a risk of future cancer threshold is defined that demarcates high from low risk subjects. Then, only the high risk subjects are included in any given model. In various embodiments, each risk prediction model has a unique future cancer threshold used to demarcate subjects into high or low risk. Once those thresholds are defined for each risk prediction model, the risk prediction model is deployed for a subject to predict a future risk of cancer. If that risk is above the threshold defined in training, the subject can be classified as having a high future risk of cancer.

As shown in FIG. 2B, the risk predictions 270 can be used for patient enrichment 275. For example, the subject can be included in one or more patient cohorts that are to be enrolled in a clinical. Methods for patient enrichment are described in further detail below.

In various embodiments, the risk predictions 270 for the subject can be displayed to a user e.g., a clinician user. Thus, the clinician user can inform the subject of the future risk of cancer that is predicted for the subject. In various embodiments, additional/other information can be displayed to a user e.g., a clinician user. For example, if a future risk of cancer prediction for a subject indicates that the subject is likely to develop cancer within a time period, information such as the features that most heavily contributed to the future risk of cancer prediction can be displayed to the user e.g., clinician user. For example, a subject predicted to have a future risk of cancer can be largely due to a percentage of the subject's lung occupied by centrilobular emphysema. Thus, the identification of the feature and/or the value of the feature (e.g., percentage of the subject's lung occupied by centrilobular emphysema) can be displayed to a user e.g., clinician user. In various embodiments, the top 1, top 2, top 3, top 4, top 5, top 6, top 7, top 8, top 9, or top 10 features that most heavily contributed to the future risk of cancer prediction for the subject can be displayed to a user e.g., clinician user. The display of the heavily contributing features can provide context to the clinician user in understanding the features that resulted in the future risk of cancer prediction.

IV. Methods of Patient Enrichment

Generally, future risk of cancer predictions from the risk prediction models are used for patient enrichment. For example, the future risk of cancer predictions provide insight as to whether a subject is likely to develop cancer within time periods (e.g., within 1 year, within 3 years, or within 5 years). Thus, for subjects that are predicted to develop cancer within a particular time period, the subjects can be selected for inclusion in a patient cohort that is to be enrolled in a clinical trial. Given the insight provided by the future risk of cancer predictions, this enables the enrollment of fewer subjects in patient cohorts for clinical trials. Thus, fewer resources are needed conducting the clinical trial and tracking the subjects in the patient cohort. Additionally, subjects that are not included in the patient cohort (e.g., subjects that are predicted to not develop cancer within a time period) can be used for other purposes (e.g., enrolled in other clinical trials).

In various embodiments, a subject is selected for inclusion in a patient cohort based on one or more of the multiple risk predictions generated for the patient. For example, the subject may have a first risk prediction indicating that the subject will not develop cancer within 1 year, will not develop cancer within 3 years, but is likely to develop cancer within 5 years. Therefore, the subject is selected for inclusion in a patient cohort for enrollment in a cancer clinical trial involving administration of a prophylactic therapeutic agent.

As another example, the subject may have a first risk prediction indicating that the subject is likely to develop cancer within 1 year and therefore, is also likely to develop cancer within 3 years and 5 years. Thus, the subject is selected for inclusion in a patient cohort for enrollment in a cancer clinical trial involving aggressive cancer treatment (e.g., tumor resection and/or administration of therapeutic agent).

In various embodiments, the patient enrichment process using the risk predictions for a plurality of subjects generates an enriched cohort of patients that are more likely to develop cancer in comparison to a randomly generated patient cohort. In various embodiments, the patient enrichment process generates an enriched cohort of patients that experiences at least a 1.5-fold increase in cumulative cancer incidence in comparison to a randomly generated patient cohort. In various embodiments, the patient enrichment process generates an enriched cohort of patients that experiences at least a 1.6-fold increase, at least a 1.7-fold increase, at least a 1.8-fold increase, at least a 1.9-fold increase, at least a 2-fold increase, at least a 3-fold increase, at least a 4-fold increase, at least a 5-fold increase, at least a 6-fold increase, at least a 7-fold increase, at least a 8-fold increase, at least a 9-fold increase, at least a 10-fold increase, at least a 11-fold increase, at least a 12-fold increase, at least a 13-fold increase, at least a 14-fold increase, at least a 15-fold increase, at least a 16-fold increase, at least a 17-fold increase, at least a 18-fold increase, at least a 19-fold increase, at least a 20-fold increase, at least a 21-fold increase, at least a 22-fold increase, at least a 23-fold increase, at least a 24-fold increase, at least a 25-fold increase, at least a 26-fold increase, at least a 27-fold increase, at least a 28-fold increase, at least a 29-fold increase, or at least a 30-fold increase in cumulative cancer incidence in comparison to a randomly generated patient cohort.

V. Training a Risk Prediction Model

Generally, a risk prediction model is structured such that it analyzes features extracted from an image, such as non-nodule specific features and/or nodule specific features, and predicts a future cancer risk for the subject based on the extracted features. In various embodiments, the risk prediction model is any one of a regression model (e.g., linear regression, logistic regression, or polynomial regression), decision tree, random forest, gradient boosted machine learning model, support vector machine, Naïve Bayes model, k-means cluster, or neural network (e.g., feed-forward networks, convolutional neural networks (CNN), deep neural networks (DNN), autoencoder neural networks, generative adversarial networks, or recurrent networks (e.g., long short-term memory networks (LSTM), bi-directional recurrent networks, deep bi-directional recurrent networks), or any combination thereof. In particular embodiments, the risk prediction model is a logistic regression model. In particular embodiments, the risk prediction model is a random forest classifier. In particular embodiments, the risk prediction model is a gradient boosting model.

The risk prediction model can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques such as manifold learning, principal component analysis, factor analysis, autoencoder regularization, and independent component analysis, or combinations thereof.

In particular embodiments, the machine learning implemented method is a logistic regression algorithm. In particular embodiments, the machine learning implemented method is a random forest algorithm. In particular embodiments, the machine learning implemented method is a gradient boosting algorithm, such as XGboost. In various embodiments, the risk prediction model is trained using supervised learning algorithms, unsupervised learning algorithms, semi-supervised learning algorithms (e.g., partial supervision), weak supervision, transfer, multi-task learning, or any combination thereof.

In various embodiments, the risk prediction model has one or more parameters, such as hyperparameters or model parameters. Hyperparameters are generally established prior to training. Examples of hyperparameters include the learning rate, depth or leaves of a decision tree, number of hidden layers in a deep neural network, number of clusters in a k-means cluster, penalty in a regression model, and a regularization parameter associated with a cost function. Model parameters are generally adjusted during training. Examples of model parameters include weights associated with nodes in layers of neural network, support vectors in a support vector machine, node values in a decision tree, and coefficients in a regression model. The model parameters of the risk prediction model are trained (e.g., adjusted) using the training data to improve the predictive capacity of the risk prediction model.

The risk training module 155 trains the risk prediction model using training data. The training data can be stored and/or retrieved from training data store 170. In various embodiments, the training data includes extracted features from training images obtained from training individuals (e.g., individuals that are known to develop or not develop cancer within a period of time). In various embodiments, the training data can be obtained from a split of a dataset. For example, the dataset can undergo a 50:50 training:testing dataset split. In some embodiments, the dataset can undergo a 60:40 training:testing dataset split. In some embodiments, the dataset can undergo a 80:20 training:testing dataset split.

In various embodiments, the training data used for training the imputation model includes reference ground truths that indicate that a training individual developed cancer within a time period (hereafter also referred to as "positive" or "+") or whether the training individual did not develop cancer within the time period (hereafter also referred to as "negative" or "−"). In various embodiments, the reference ground truths in the training data are binary values, such as "1" or "0." For example, a training individual that developed cancer within a time period can be identified in the training data with a value of "1" whereas a training individual that did not develop cancer within the time period can be identified in the training data with a value of "0." In various embodiments, the risk training module 155 trains the risk prediction model using the training data to minimize a loss function such that the risk prediction model can better predict the outcome (e.g., future presence or absence of cancer within a time period) based on the input (e.g., extracted features of the training image). In various embodiments, the loss function is constructed for any of a least absolute shrinkage and selection operator (LASSO) regression, Ridge regression, or ElasticNet regression. In various embodiments, the risk prediction model is a random forest model, and is trained to minimize one of Gini impurity or Entropy metrics for feature splitting, thereby enabling the risk prediction model to more accurately predict future cancer risk.

In various embodiments, the training data can be obtained and/or derived from a publicly available database. For example, the training data can be obtained and/or derived from the National Lung Screening Trial (NLST). In some embodiments, the training data can be obtained and collected independent of publicly available databases e.g., by capturing images from a plurality of training individuals. Such training data can be a custom dataset.

In various embodiments, a risk prediction model is trained using a specific cohort of training individuals. In various embodiments, the risk prediction model is trained using a cohort of training individuals that do not have lung nodules. In various embodiments, the risk prediction model is trained using a cohort of training individuals that have lung nodules. In various embodiments, the risk prediction model is a Lung-RADS 1 prediction model that is trained using a cohort of training individuals that are previously classified in Lung-RADS 1. In various embodiments, the risk prediction model is a Lung-RADS 2 prediction model that is trained using a cohort of training individuals that are previously classified in any one of Lung-RADS 1-2. In various embodiments, the risk prediction model is a Lung-RADS 1-3 prediction model that is trained using a cohort of training individuals that are previously classified in any one of Lung-RADS 1-3. In various embodiments, the risk prediction model is a Lung-RADS 1-4A prediction model that is trained using a cohort of training individuals that are previously classified in any one of Lung-RADS 1-4A. In various embodiments, the risk prediction model is a Lung-RADS 1-4B prediction model that is trained using a cohort of training individuals that are previously classified in any one of Lung-RADS 1-4B. In various embodiments, the risk prediction model is a Lung-RADS 1-4X prediction model that is trained using a cohort of training individuals that are previously classified in any one of Lung-RADS 1-4X.

In various embodiments, for each of any of the Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model, the risk prediction model is trained using a training cohort of training individuals, where a majority (e.g., greater than 50%) of training individuals in the training cohort were previously classified as Lung-RADS 1. In various embodiments, for each of any of the Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model, the risk prediction model is trained using a training cohort of training individuals, where a majority (e.g., greater than 50%) of training individuals in the training cohort were previously classified as Lung-RADS 2. In various embodiments, for each of any of the Lung-RADS 1 prediction model, Lung-RADS 1-2 prediction model, Lung-RADS 1-3 prediction model, Lung-RADS 1-4A prediction model, Lung-RADS 1-4B prediction model, or Lung-RADS 1-4X prediction model, the risk prediction model is trained using a training cohort of training individuals, where a majority (e.g., greater than 50%) of training individuals in the training cohort were previously classified as Lung-RADS 1 or Lung-RADS 2. As shown in Table 1, ~90% of individuals likely fall in Lung-RADS 1 or Lung-RADS 2. Therefore, such individuals can be used to train any of the risk prediction models.

In various embodiments, a risk prediction model is a "M" year prediction model trained to predict a future risk of cancer within "M" years, such as within at least 1 year, at least 2 years, at least 3 years, at least 4 years, at least 5 years, at least 6 years, at least 7 years, at least 8 years, at least 9 years, at least 10 years, at least 11 years, at least 12 years, at least 13 years, at least 14 years, at least 15 years, at least 16 years, at least 17 years, at least 18 years, at least 19 years, or at least 20 years. Thus, the training data used for training the imputation model includes reference ground truths that indicate that a training individual developed cancer within "M" years.

In various embodiments, a risk prediction model 1) is trained using a specific cohort of training individuals and 2) is trained to predict a future risk of cancer within "M" years. As described above, the cohort of training individuals may be previously classified within a range of Lung-RADS scores (e.g., Lung-RADS X-Y). Thus, a risk prediction model may be a M year, Lung-RADS X-Y prediction model that 1) is trained using a cohort of training individuals classified in Lung-RADS X-Y and 2) is trained to predict a future risk of cancer with "M" years.

In various embodiments, a risk prediction model includes both non-nodule specific features and nodule specific features. Therefore, in training the risk prediction model, the risk prediction model analyzes both non-nodule specific features and nodule specific features extracted from a training image and attempts to generate a prediction that minimizes a loss function. Generally, features of the risk prediction model have importance values that reflect how heavily each feature influences the prediction generated by the risk prediction model. For example, a higher importance value for a feature indicates that the feature more heavily influences the prediction generated by the risk prediction model in comparison to a different feature with a lower importance value.

In various embodiments, the nodule specific features of the risk prediction model more heavily influence the prediction of future risk of cancer in comparison to the non-nodule specific features. For example, the nodule specific features of the risk prediction model have higher feature importance values than the non-nodule specific features of the risk prediction model. Generally, nodule specific features have higher importance values for risk prediction models that are trained to predict risk of cancer within shorter time periods (e.g., 1 year as opposed to 3 years or 5 years). Additionally, nodule specific features have higher importance values for risk prediction models that are trained using higher risk lung cancer patients (e.g., patients that are classified as Lung-RADS 4A or Lung-RADS 4B).

In various embodiments, the feature with the highest importance value of the risk prediction model is a nodule specific feature. In various embodiments, the top 2 features with the highest importance value of the risk prediction model are nodule specific features. In various embodiments, the top 3 features with the highest importance value of the risk prediction model are nodule specific features. In various embodiments, the top 4 features with the highest importance value of the risk prediction model are nodule specific features. In various embodiments, the top 5, 6, 7, 8, 9, or 10 features with the highest importance value of the risk prediction model are nodule specific features.

In various embodiments, greater than 50% of the top 3 features with the highest feature importance values are nodule specific features. In various embodiments, 2 of the top 3 features with the highest feature importance values are nodule specific features. In various embodiments, 3 of the top 5 features with the highest feature importance values are nodule specific features. In various embodiments, 4 of the top 5 features with the highest feature importance values are nodule specific features. In various embodiments, greater than 50% of the top 5 features with the highest feature importance values are nodule specific features. In various embodiments, greater than 50% of the top 10 features with the highest feature importance values are nodule specific features. In various embodiments, 6, 7, 8, 9, or 10 of the top 10 features with the highest feature importance values are nodule specific features.

In various embodiments, such a risk prediction model (e.g., a risk prediction model where nodule specific features of the risk prediction model have higher feature importance values than the non-nodule specific features of the risk prediction model) is a 1 year risk prediction model (e.g., predicts risk of developing cancer within 1 year). In various embodiments, such a risk prediction model is a model trained on training images that include high risk lung nodules. In various embodiments, such a risk prediction model can be trained on training images derived from individuals classified in Lung-RADS 4A. In various embodiments, such a risk prediction model can be trained on training images derived from individuals classified in Lung-RADS 4B. In various embodiments, such a risk prediction model can be trained on training images derived from individuals classified in Lung-RADS 4X. In various embodiments, such a risk prediction model can be trained on training images derived from individuals classified in Lung-RADS 4A, Lung-RADS 4B, Lung-RADS 4X, or any combination thereof. For example, such a risk prediction model can be any one of a Lung-RADS 1-4A, Lung-RADS 1-4B, or Lung-RADS 1-4X prediction model.

In particular embodiments, such a risk prediction model (e.g., a risk prediction model where nodule specific features of the risk prediction model have higher feature importance values than the non-nodule specific features of the risk prediction model) is a 1 year, Lung-RADS 1-4B prediction model. For example, as shown in Table 3, the top three features in terms of feature importance for a 1 year, Lung-RADS 1-4B prediction model are nodule specific features. Additionally, 4 of the top 5 features in terms of feature importance for a 1 year, Lung-RADS 1-4B prediction model are nodule specific features.

In particular embodiments, such a risk prediction model (e.g., a risk prediction model where nodule specific features of the risk prediction model have higher feature importance values than the non-nodule specific features of the risk prediction model) is a 3 year, Lung-RADS 1-4B prediction model. For example, as shown in Table 3, 2 of the top 3 features in terms of feature importance for a 3 year, Lung-RADS 1-4B prediction model are nodule specific features. Additionally, 3 of the top 5 features in terms of feature importance for a 3 year, Lung-RADS 1-4B prediction model are nodule specific features. As another example, as shown in Table 19, the top 3 features in terms of feature importance for a 3 year, Lung-RADS 1-4B prediction model are nodule specific features. Additionally, 4 of the top 5 features in terms of feature importance for a 3 year, Lung-RADS 1-4B prediction model are nodule specific features.

In particular embodiments, such a risk prediction model (e.g., a risk prediction model where nodule specific features of the risk prediction model have higher feature importance values than the non-nodule specific features of the risk prediction model) is a 5 year, Lung-RADS 1-4B prediction model. For example, as shown in Table 3, 2 of the top 3 features in terms of feature importance for a 5 year, Lung-RADS 1-4B prediction model are nodule specific features.

In particular embodiments, such a risk prediction model (e.g., a risk prediction model where nodule specific features of the risk prediction model have higher feature importance values than the non-nodule specific features of the risk prediction model) is a 1 year, Lung-RADS 1-4A prediction model. For example, as shown in Table 6, the top 3 features in terms of feature importance for a 1 year, Lung-RADS 1-4A prediction model are nodule specific features. Additionally, 4 of the top 5 features in terms of feature importance for a 1 year, Lung-RADS 1-4A prediction model are nodule specific features.

In particular embodiments, such a risk prediction model (e.g., a risk prediction model where nodule specific features of the risk prediction model have higher feature importance values than the non-nodule specific features of the risk prediction model) is a 3 year, Lung-RADS 1-4A prediction model. For example, as shown in Table 6, the top 3 features in terms of feature importance for a 3 year, Lung-RADS 1-4A prediction model are nodule specific features. Additionally, 4 of the top 5 features in terms of feature importance for a 3 year, Lung-RADS 1-4A prediction model are nodule specific features. As another example, as shown in Table 20, the top 3 features in terms of feature importance for a 3 year, Lung-RADS 1-4A prediction model are nodule specific features. Additionally, 4 of the top 5 features in terms of feature importance for a 3 year, Lung-RADS 1-4A prediction model are nodule specific features.

In particular embodiments, such a risk prediction model (e.g., a risk prediction model where nodule specific features of the risk prediction model have higher feature importance values than the non-nodule specific features of the risk prediction model) is a 5 year, Lung-RADS 1-4A prediction model. For example, as shown in Table 6, 2 of the top 3 features in terms of feature importance for a 5 year, Lung-RADS 1-4A prediction model are nodule specific features.

In particular embodiments, such a risk prediction model (e.g., a risk prediction model where nodule specific features of the risk prediction model have higher feature importance values than the non-nodule specific features of the risk prediction model) is a 1 year, Lung-RADS 1-3 prediction model. For example, as shown in Table 9, 2 of the top 3 features in terms of feature importance for a 1 year, Lung-RADS 1-3 prediction model are nodule specific features.

In particular embodiments, such a risk prediction model (e.g., a risk prediction model where nodule specific features of the risk prediction model have higher feature importance values than the non-nodule specific features of the risk prediction model) is a 3 year, Lung-RADS 2-4B prediction model. For example, as shown in Table 22, the top 3 features in terms of feature importance for a 3 year, Lung-RADS 2-4B prediction model are nodule specific features. Additionally, the top 5 features in terms of feature importance for a 3 year, Lung-RADS 2-4B prediction model are nodule specific features.

In particular embodiments, such a risk prediction model (e.g., a risk prediction model where nodule specific features of the risk prediction model have higher feature importance values than the non-nodule specific features of the risk prediction model) is a 3 year, Lung-RADS 4A-4B prediction model. For example, as shown in Table 23, the top 3 features in terms of feature importance for a 3 year, Lung-RADS 4A-4B prediction model are nodule specific features. Additionally, the top 5 features in terms of feature importance for a 3 year, Lung-RADS 4A-4B prediction model are nodule specific features.

In various embodiments, the non-nodule specific features of the risk prediction model more heavily influence the prediction of future risk of cancer in comparison to the nodule specific features. For example, the non-nodule specific features of the risk prediction model have higher feature importance values than the nodule specific features of the risk prediction model. Generally, non-nodule specific features have higher importance values for risk prediction models that are trained to predict risk of cancer within longer time periods (e.g., 3 or 5 years as opposed to 1 year). Additionally, non-nodule specific features have higher importance values for risk prediction models that are trained using patients that are at lower risk of lung cancer (e.g., patients that are classified as Lung-RADS 2 or 3) or patients that do not yet have a nodule (e.g., Lung-RADS 1).

In various embodiments, the feature with the highest importance value of the risk prediction model is a non-nodule specific feature. In various embodiments, the top 2 features with the highest importance value of the risk prediction model are non-nodule specific features. In various embodiments, the top 3 features with the highest importance value of the risk prediction model are non-nodule specific features. In various embodiments, the top 4 features with the highest importance value of the risk prediction model are non-nodule specific features. In various embodiments, the top 5, 6, 7, 8, 9, or 10 features with the highest importance value of the risk prediction model are non-nodule specific features.

In various embodiments, greater than 50% of the top 3 features with the highest feature importance values are non-nodule specific features. In various embodiments, 2 of the top 3 features with the highest feature importance values are non-nodule specific features. In various embodiments, 3 of the top 5 features with the highest feature importance values are non-nodule specific features. In various embodiments, 4 of the top 5 features with the highest feature importance values are non-nodule specific features. In various embodiments, greater than 50% of the top 5 features with the highest feature importance values are non-nodule specific features. In various embodiments, greater than 50% of the top 10 features with the highest feature importance values are non-nodule specific features. In various embodiments, 6, 7, 8, 9, or 10 of the top 10 features with the highest feature importance values are non-nodule specific features.

In various embodiments, a risk prediction model including non-nodule specific features that more heavily influence the prediction of future risk of cancer in comparison to the nodule specific features is a M year risk prediction model (e.g., predicts risk of developing cancer within M years), where M is not equal to 1 year. In various embodiments, M is greater than or equal to 2 years. For example, M can be 1.5 years, 2 years, 2.5 years, 3 years, 3.5 years, 4 years, 4.5 years, 5 years, 5.5 years, 6 years, 6.5 years, 7 years, 7.5 years, 8 years, 8.5 years, 9 years, 9.5 years, 10 years, 10.5 years, 11 years, 11.5 years, 12 years, 12.5 years, 13 years, 13.5 years, 14 years, 14.5 years, 15 years, 15.5 years, 16 years, 16.5 years, 17 years, 17.5 years, 18 years, 18.5 years, 19 years, 19.5 years, or 20 years. As a specific example, the risk prediction model is a 3 year risk prediction model that predicts risk of developing cancer within 3 years. As another specific example, the risk prediction model is a 5 year risk prediction model that predicts risk of developing cancer within 5 years.

In various embodiments, a risk prediction model including non-nodule specific features that more heavily influence the prediction of future risk of cancer in comparison to the nodule specific features is a risk prediction model trained on training images that do not include lung nodules. In various embodiments, such a risk prediction model can be trained on training images derived from individuals classified in Lung-RADS 1. In various embodiments, such a risk prediction model can be trained on training images derived from individuals classified in Lung-RADS 2. In various embodiments, such a risk prediction model can be trained on training images derived from individuals classified in Lung-RADS 3. In various embodiments, such a risk prediction model can be trained on training images derived from individuals classified in Lung-RADS 1, Lung-RADS 2, Lung-RADS 3, or any combination thereof. In various embodiments, such a risk prediction model is a Lung-RADS 1 prediction model, a Lung-RADS 1-2 prediction model, or a Lung-RADS 1-3 prediction model.

In particular embodiments, such a risk prediction model (e.g., a risk prediction model where non-nodule specific features of the risk prediction model have higher feature importance values than the nodule specific features of the risk prediction model) is a 1 year, Lung-RADS 1-4B prediction model. For example, as shown in Table 3, 6 of the top 10 features in terms of feature importance for a 1 year, Lung-RADS 1-4B prediction model are non-nodule specific features.

In particular embodiments, such a risk prediction model (e.g., a risk prediction model where non-nodule specific features of the risk prediction model have higher feature importance values than the nodule specific features of the risk prediction model) is a 3 year, Lung-RADS 1-4B prediction model. For example, as shown in Table 3, 6 of the top 10 features in terms of feature importance for a 3 year, Lung-RADS 1-4B prediction model are non-nodule specific features.

In particular embodiments, such a risk prediction model (e.g., a risk prediction model where non-nodule specific features of the risk prediction model have higher feature importance values than the nodule specific features of the risk prediction model) is a 5 year, Lung-RADS 1-4B prediction model. For example, as shown in Table 3, 3 of the top 5 features in terms of feature importance for a 5 year, Lung-RADS 1-4B prediction model are non-nodule specific features. Additionally, 7 of the top 10 features in terms of feature importance for a 5 year, Lung-RADS 1-4B prediction model are non-nodule specific features.

In particular embodiments, such a risk prediction model (e.g., a risk prediction model where non-nodule specific features of the risk prediction model have higher feature importance values than the nodule specific features of the risk prediction model) is a 5 year, Lung-RADS 1-4A prediction model. For example, as shown in Table 6, 3 of the top 5 features in terms of feature importance for a 5 year, Lung-RADS 1-4A prediction model are non-nodule specific features. Additionally, 6 of the top 10 features in terms of feature importance for a 5 year, Lung-RADS 1-4A prediction model are non-nodule specific features.

In particular embodiments, such a risk prediction model (e.g., a risk prediction model where non-nodule specific features of the risk prediction model have higher feature importance values than the nodule specific features of the risk prediction model) is a 1 year, Lung-RADS 1-3 prediction model. For example, as shown in Table 9, 3 of the top 5 features in terms of feature importance for a 1 year, Lung-RADS 1-3 prediction model are non-nodule specific features. Additionally, 7 of the top 10 features in terms of feature importance for a 1 year, Lung-RADS 1-3 prediction model are non-nodule specific features.

In particular embodiments, such a risk prediction model (e.g., a risk prediction model where non-nodule specific features of the risk prediction model have higher feature importance values than the nodule specific features of the risk prediction model) is a 3 year, Lung-RADS 1-3 prediction model. For example, as shown in Table 9, 2 of the top 3 features in terms of feature importance for a 3 year, Lung-RADS 1-3 prediction model are non-nodule specific features. Additionally, 4 of the top 5 features in terms of feature importance for a 3 year, Lung-RADS 1-3 prediction model are non-nodule specific features. Additionally, 8 of the top 10 features in terms of feature importance for a 3 year, Lung-RADS 1-3 prediction model are non-nodule specific features. As another example, as shown in Table 21, 2 of the top 3 features in terms of feature importance for a 3 year, Lung-RADS 1-3 prediction model are non-nodule specific features. Additionally, 3 of the top 5 features in terms of feature importance for a 3 year, Lung-RADS 1-3 prediction model are non-nodule specific features. Additionally, 8 of the top 10 features in terms of feature importance for a 3 year, Lung-RADS 1-3 prediction model are non-nodule specific features.

In particular embodiments, such a risk prediction model (e.g., a risk prediction model where non-nodule specific features of the risk prediction model have higher feature importance values than the nodule specific features of the risk prediction model) is a 5 year, Lung-RADS 1-3 prediction model. For example, as shown in Table 9, 2 of the top 3 features in terms of feature importance for a 5 year, Lung-RADS 1-3 prediction model are non-nodule specific features. Additionally, 4 of the top 5 features in terms of feature importance for a 5 year, Lung-RADS 1-3 prediction model are non-nodule specific features. Additionally, 9 of the top 10 features in terms of feature importance for a 5 year, Lung-RADS 1-3 prediction model are non-nodule specific features.

In particular embodiments, such a risk prediction model (e.g., a risk prediction model where non-nodule specific features of the risk prediction model have higher feature importance values than the nodule specific features of the risk prediction model) is a 1 year, Lung-RADS 1-2 prediction model. For example, as shown in Table 12, 4 of the top 5 features in terms of feature importance for a 1 year, Lung-RADS 1-2 prediction model are non-nodule specific features. Additionally, 9 of the top 10 features in terms of feature importance for a 1 year, Lung-RADS 1-2 prediction model are non-nodule specific features.

In particular embodiments, such a risk prediction model (e.g., a risk prediction model where non-nodule specific features of the risk prediction model have higher feature importance values than the nodule specific features of the risk prediction model) is a 3 year, Lung-RADS 1-2 prediction model. For example, as shown in Table 12, the top 3 features in terms of feature importance for a 3 year, Lung-RADS 1-2 prediction model are non-nodule specific features. Additionally, the top 5 features in terms of feature importance for a 3 year, Lung-RADS 1-2 prediction model are non-nodule specific features. Additionally, 8 of the top 10 features in terms of feature importance for a 3 year, Lung-RADS 1-2 prediction model are non-nodule specific features.

In particular embodiments, such a risk prediction model (e.g., a risk prediction model where non-nodule specific features of the risk prediction model have higher feature importance values than the nodule specific features of the risk prediction model) is a 5 year, Lung-RADS 1-2 prediction model. For example, as shown in Table 12, the top 3 features in terms of feature importance for a 5 year, Lung-RADS 1-2 prediction model are non-nodule specific features. Additionally, the top 5 features in terms of feature importance for a 5 year, Lung-RADS 1-2 prediction model are non-nodule specific features. Additionally, the top 10 features in terms of feature importance for a 5 year, Lung-RADS 1-2 prediction model are non-nodule specific features.

In particular embodiments, such a risk prediction model (e.g., a risk prediction model where non-nodule specific features of the risk prediction model have higher feature importance values than the nodule specific features of the risk prediction model) is a 1 year, Lung-RADS 1 prediction model. For example, as shown in Table 15, the top 3 features in terms of feature importance for a 1 year, Lung-RADS 1 prediction model are non-nodule specific features. Additionally, the top 5 features in terms of feature importance for a 1 year, Lung-RADS 1 prediction model are non-nodule specific features. Additionally, the top 10 features in terms of feature importance for a 1 year, Lung-RADS 1 prediction model are non-nodule specific features.

In particular embodiments, such a risk prediction model (e.g., a risk prediction model where non-nodule specific features of the risk prediction model have higher feature importance values than the nodule specific features of the risk prediction model) is a 3 year, Lung-RADS 1 prediction model. For example, as shown in Table 15, the top 3 features in terms of feature importance for a 3 year, Lung-RADS 1 prediction model are non-nodule specific features. Additionally, the top 5 features in terms of feature importance for a 3 year, Lung-RADS 1 prediction model are non-nodule specific features. Additionally, the top 10 features in terms of feature importance for a 3 year, Lung-RADS 1 prediction model are non-nodule specific features.

In particular embodiments, such a risk prediction model (e.g., a risk prediction model where non-nodule specific features of the risk prediction model have higher feature importance values than the nodule specific features of the risk prediction model) is a 5 year, Lung-RADS 1 prediction model. For example, as shown in Table 15, the top 3 features in terms of feature importance for a 5 year, Lung-RADS 1 prediction model are non-nodule specific features. Additionally, the top 5 features in terms of feature importance for a 5 year, Lung-RADS 1 prediction model are non-nodule specific features. Additionally, the top 10 features in terms of feature importance for a 5 year, Lung-RADS 1 prediction model are non-nodule specific features.

In various embodiments, the trained risk prediction model includes a set of trained parameters such that when the risk prediction model is deployed, the set of trained parameters are used to modify values of non-nodule specific features and nodule specific features of an image to generate a prediction of future risk of cancer for a subject. Thus, the set of trained parameters of the trained risk prediction model are set during the training phase. For example, the set of trained parameters are set such that the non-nodule specific features more heavily influence the future risk prediction than the nodule specific features. As another example, the set of trained parameters are set such that the nodule specific features more heavily influence the future risk prediction than the non-nodule specific features.

For example, if the risk prediction model is a neural network, one or more nodes of the neural network that correspond to non-nodule specific features are assigned greater weights (e.g., parameters) than one or more nodes of the neural network that correspond to nodule specific features. As another example, if the risk prediction model is a random forest model that weighs non-nodule specific features more heavily than nodule specific features.

In various embodiments, the risk prediction models may also be trained to predict a location of that future cancer. In various embodiments, training images are divided into different regions and therefore, the training of the risk predictions models are performed according to the different regions. Example different regions can include the upper, middle, and lower third of the lungs by volume or separate lobes of the lungs. It will be understood by those of skill in the art that the lung may be divided into any number of regions having any number of configurations. Enabling risk prediction models to predict locations of future cancers can guide the selection of interventions, such as regional diagnostic evaluations and therapeutic intervention using inhaled and bronchoscopically administered drugs and devices.

In various embodiments, risk prediction models disclosed herein achieve a performance metric. Example performance metrics include an area under the curve (AUC) of a receiver operating curve, a positive predictive value, and/or a negative predictive value. In various embodiments, risk prediction models disclosed herein exhibit an AUC value of at least 0.5. In various embodiments, risk prediction models disclosed herein exhibit an AUC value of at least 0.6. In various embodiments, risk prediction models disclosed herein exhibit an AUC value of at least 0.7. In various embodiments, risk prediction models disclosed herein exhibit an AUC value of at least 0.8. In various embodiments, risk prediction models disclosed herein exhibit an AUC value of at least 0.9. In various embodiments, risk prediction models disclosed herein exhibit an AUC value of at least 0.95. In various embodiments, risk prediction models disclosed herein exhibit an AUC value of at least 0.99. In various embodiments, risk prediction models disclosed herein exhibit an AUC value of at least 0.51, at least 0.52, at least 0.53, at least 0.54, at least 0.55, at least 0.56, at least 0.57, at least 0.58, at least 0.59, at least 0.60, at least 0.61, at least 0.62, at least 0.63, at least 0.64, at least 0.65, at least 0.66, at least 0.67, at least 0.68, at least 0.69, at least 0.70, at least 0.71, at least 0.72, at least 0.73, at least 0.74, at least 0.75, at least 0.76, at least 0.77, at least 0.78, at least 0.79, at least 0.80, at least 0.81, at least 0.82, at least 0.83, at least 0.84, at least 0.85, at least 0.86, at least 0.87, at least 0.88, at least 0.89, at least 0.90, at least 0.91, at least 0.92, at least 0.93, at least 0.94, at least 0.95, at least 0.96, at least 0.97, at least 0.98, or at least 0.99.

VI. Example Method for Predicting Future Risk of Cancer

Figure 3:
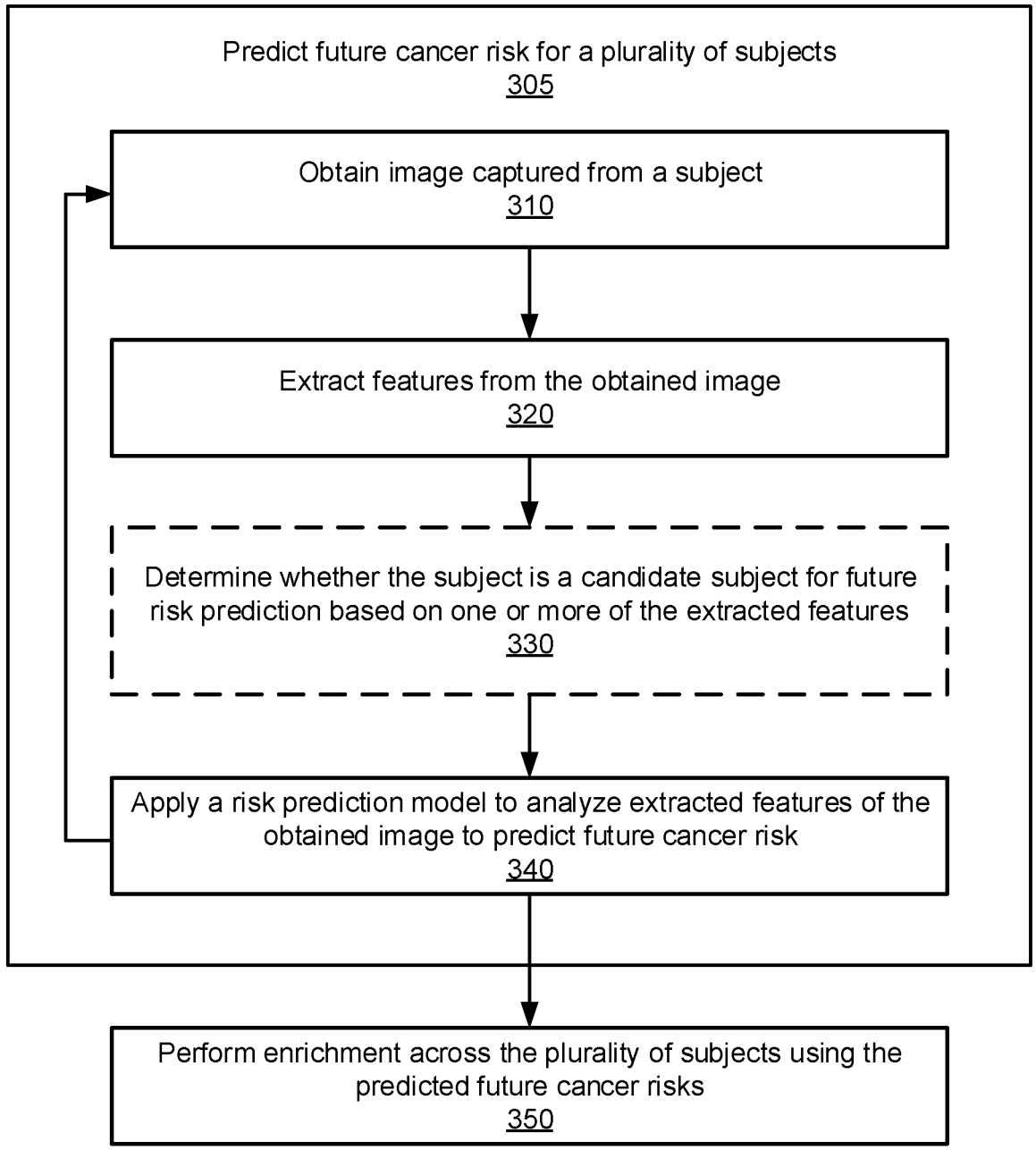
FIG. 3 is an example flow process for determining a future risk of cancer for a subject for uses such as patient enrichment, in accordance with an embodiment.

FIG. 3 is an example flow process for determining a future risk of cancer for a subject for uses such as patient enrichment, in accordance with an embodiment. Step 305 involves predicting future lung cancer risk for a plurality of subjects. Step 305 includes steps 310, 320, 330, and 340 which can be repeatedly performed for different subjects in the plurality of subjects.

At step 310, an image is captured from a subject. In various embodiments, the image is a thoracic CT scan captured from the subject.

At step 320, features are extracted from the image. In various embodiments, the features include one or both of non-nodule specific features and nodule specific features.

Step 330 is an optional step that involves determining whether the subject is a candidate subject for future risk prediction based on one or more of the extracted features. In various embodiments, step 330 involves analyzing nodule specific features to determine that the subject is a candidate subject. For example, step 330 can involve analyzing nodule specific features to determine that the subject does not have a lung nodule or does not have lung cancer and therefore, is eligible to undergo future risk of cancer analysis.

Step 340 involves applying a risk prediction model to analyze the extracted features of the obtained image to predict future cancer risk. In various embodiments, the risk prediction model analyzes both non-nodule specific features and nodule specific features. In various embodiments, the non-nodule specific features have higher feature importance values than the nodule specific features. Therefore, the non-nodule specific features more heavily influence the future cancer risk prediction in comparison to the nodule specific features.

Step 350 involves performing enrichment across the plurality of subjects using the predicted future cancer risks. Here, subjects that are predicted to develop cancer within a period of time, as indicated by their predicted future cancer risk, can be included in one or more a patient cohort for enrollment in a clinical trial. Altogether, this enables the enrollment of reduced numbers of individuals in clinical trials.

VII. Cancers

Methods described herein involve implementing risk prediction models for predicting future risk of cancer. In various embodiments, the cancer in the subject can include one or more of: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, stomach cancer, thyroid cancer, head and neck carcinoma, large bowel cancer, hematopoietic cancer, testicular cancer, colon and/or rectal cancer, uterine cancer, or prostatic cancer. In some embodiments, the cancer in the subject can be a metastatic cancer, including any one of bladder cancer, breast cancer, colon cancer, kidney cancer, lung cancer, melanoma, ovarian cancer, pancreatic cancer, prostatic cancer, rectal cancer, stomach cancer, thyroid cancer, or uterine cancer. In particular embodiments, the cancer is a lung cancer. In particular embodiments, the cancer is a type of lung cancer, including any one of small cell lung cancer, non-small cell lung cancer, non-small cell carcinoma, adenocarcinoma, squamous cell cancer, large cell carcinoma, small cell carcinoma, combined small cell carcinoma, neuroendocrine tumor, lung sarcoma, lung lymphoma, bronchial carcinoids.

In various embodiments, risk prediction models described herein predict a future risk of a presence of cancer, such as a lung cancer. In other words, risk prediction models predict for a risk of a presence or absence of cancer, such as a lung cancer. In various embodiments, risk prediction models described herein predict a future risk of a subtype of lung cancer, including any one of small cell lung cancer, non-small cell lung cancer, non-small cell carcinoma, adenocarcinoma, squamous cell cancer, large cell carcinoma, small cell carcinoma, combined small cell carcinoma, neuroendocrine tumor, lung sarcoma, lung lymphoma, bronchial carcinoids. In other words, risk prediction models classify a subject as likely to develop a particular subtype of lung cancer within a time period (e.g., 1, 3, or 5 years). In particular embodiments, risk prediction models predict a future risk of non-small cell lung cancer or small cell lung cancer.

VIII. Interventions

Embodiments described herein involve the implementing risk prediction models for predicting future risk of cancer. In various embodiments, an intervention is provided to a subject based on the future risk of cancer prediction. In various embodiments, the intervention can be any one of: application of a diagnostic, application of a prophylactic therapeutic agent, or a subsequent action. Example subsequent actions can include a subsequent testing of the subject to confirm whether the subject develops cancer. Subsequent testing can include any of a subsequent biopsy (e.g., cancer biopsy or lymph node biopsy) or subsequent image scanning (e.g., CT scanning, PET scanning, MRI scanning, ultrasound imaging, or X-ray imaging). In various embodiments, subsequent testing of the subject can during at a next scheduled visit or at a pre-determined amount of time (e.g., 1 month, 2 months, 3 months, 4 months, 5 months, 6 months, 7 months, 8 months, 9 months, 10 months, 11 months, 12 months, 18 months, or 24 months) after predicting the future risk of cancer. In various embodiments, additional subsequent actions can include subsequent actions to treat a cancer that has developed in the subject, such as tumor resection, bronchoscopic diagnosis, selection and/or administration of therapeutic(s), selection/administration of pharmaceutical composition, or any combination thereof.

In various embodiments, a therapeutic agent can be selected and/or administered to the subject based on the predicted future risk of cancer. The selected therapeutic agent is likely to delay or prevent the development of the cancer, such as lung cancer. Exemplary therapeutic agents include chemotherapies, energy therapies (e.g., external beam, microwave, radiofrequency ablation, brachytherapy, electroporation, cryoablation, photothermal ablation, laser therapy, photodynamic therapy, electrocauterization, chemoemboilization, high intensity focused ultrasound, low intensity focused ultrasound), antigen-specific monoclonal antibodies, anti-inflammatories, oncolytic viral therapies, or immunotherapies. In various embodiments, the selected therapeutic agent is an energy therapy and the amount (e.g., dose and duration) of the energy applied can be tailored to achieve a desired therapeutic effect. In various embodiments the therapeutic agent is a small molecule or biologic, e.g. a cytokine, antibody, soluble cytokine receptor, anti-sense oligonucleotide, siRNA, etc. Such biologic agents encompass muteins and derivatives of the biological agent, which derivatives can include, for example, fusion proteins, PEGylated derivatives, cholesterol conjugated derivatives, and the like as known in the art. Also included are antagonists of cytokines and cytokine receptors, e.g. traps and monoclonal antagonists. Also included are biosimilar or bioequivalent drugs to the active agents set forth herein.

Therapeutic agents for lung cancer can include chemotherapeutics such as docetaxel, cisplatin, carboplatin, gemcitabine, Nab-paclitaxel, paclitaxel, pemetrexed, gefitinib, erlotinib, brigatinib (Alunbrig®), capmatinib (Tabrecta®), selpercatinib (Retevmo®), entrectinib (Rozlytrek®), lorlatinib (Lorbrena®), larotrectinib (Vitrakvi®), dacomitinib (Vizimpro®), and vinorelbine. Therapeutic agents for lung cancer can include antibody therapies such as durvalumab (Imfinzi®), nivolumab (Opdivo®), pembrolizumab (Keytruda®), atezolizumab (Tecentriq®), canakinumab, and ramucirumab.

In various embodiments, one or more of the therapeutic agents described can be combined as a combination therapy for treating the subject.

In various embodiments, a pharmaceutical composition can be selected and/or administered to the subject based on the subject level risk of metastatic cancer, the selected therapeutic agent likely to exhibit efficacy against the cancer. A pharmaceutical composition administered to an individual includes an active agent such as the therapeutic agent described above. The active ingredient is present in a therapeutically effective amount, i.e., an amount sufficient when administered to treat a disease or medical condition mediated thereby. The compositions can also include various other agents to enhance delivery and efficacy, e.g. to enhance delivery and stability of the active ingredients. Thus, for example, the compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant.

The pharmaceutical compositions or therapeutic agents described herein can be administered in a variety of different ways. Examples include administering a composition containing a pharmaceutically acceptable carrier via oral, intranasal, intramodular, intralesional, rectal, topical, intraperitoneal, intravenous, intramuscular, subcutaneous, subdermal, transdermal, intrathecal, endobronchial, transthoracic, or intracranial method.

In various embodiments, a clinical response can be provided to the subject based on the predicted future risk of cancer generated for the subject by implementing risk prediction models. In various embodiments, a clinical response can include providing counseling to modify a behavior of the subject (e.g., counsel the patient about smoking cessation to reduce risk), initiating of an inhaled/topical, intravenous or enteral (by mouth) therapeutic that could delay/prevent malignant transformation, slow tumor growth or even prevent spread of disease (metastasis), establishing an adaptive screening schedule for future risk similar to what is done with colonoscopy for polyps (e.g., individuals predicted to be higher risk for future lung cancer should have more frequent follow up and imaging), or performing or scheduling to be performed an additional risk prediction test to confirm the predicted future risk of lung cancer (e.g., persons deemed to be higher risk for lung cancer may also then undergo additional testing to either confirm that risk or narrow the cancer type the person is at greatest risk for. In various embodiments, the additional risk prediction test could include blood based biomarkers (to look for non-specific inflammation which is a known risk for lung cancer), metabolomics/proteomics/gene expression/genetic sequencing. The person could also have additional sampling of tissue (nasal epithelium, bronchial epithelium, etc) to look at changes in gene expression in the respiratory tract.)

IX. Computer Implementation

The methods of the invention, including the methods of implementing risk prediction models for predicting future risk of cancer, are, in some embodiments, performed on one or more computers.

For example, the building and deployment of a risk prediction model can be implemented in hardware or software, or a combination of both. In one embodiment of the invention, a machine-readable storage medium is provided, the medium comprising a data storage material encoded with machine readable data which, when using a machine programmed with instructions for using said data, is capable of executing the training or deployment of risk prediction models and/or displaying any of the datasets or results (e.g., future risk of cancer predictions for subjects) described herein. The invention can be implemented in computer programs executing on programmable computers, comprising a processor, a data storage system (including volatile and non-volatile memory and/or storage elements), a graphics adapter, a pointing device, a network adapter, at least one input device, and at least one output device. A display is coupled to the graphics adapter. Program code is applied to input data to perform the functions described above and generate output information. The output information is applied to one or more output devices, in known fashion. The computer can be, for example, a personal computer, microcomputer, or workstation of conventional design.

Each program can be implemented in a high-level procedural or object-oriented programming language to communicate with a computer system. However, the programs can be implemented in assembly or machine language, if desired. In any case, the language can be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

In some embodiments, the methods of the invention, including the methods for predicting a future risk of cancer by implementing risk prediction models, are performed on one or more computers in a distributed computing system environment (e.g., in a cloud computing environment). In this description, "cloud computing" is defined as a model for enabling on-demand network access to a shared set of configurable computing resources. Cloud computing can be employed to offer on-demand access to the shared set of configurable computing resources. The shared set of configurable computing resources can be rapidly provisioned via virtualization and released with low management effort or service provider interaction, and then scaled accordingly. A cloud-computing model can be composed of various characteristics such as, for example, on-demand self-service, broad network access, resource pooling, rapid elasticity, measured service, and so forth. A cloud-computing model can also expose various service models, such as, for example, Software as a Service ("SaaS"), Platform as a Service ("PaaS"), and Infrastructure as a Service ("IaaS"). A cloud-computing model can also be deployed using different deployment models such as private cloud, community cloud, public cloud, hybrid cloud, and so forth. In this description and in the claims, a "cloud-computing environment" is an environment in which cloud computing is employed.

Figure 4:
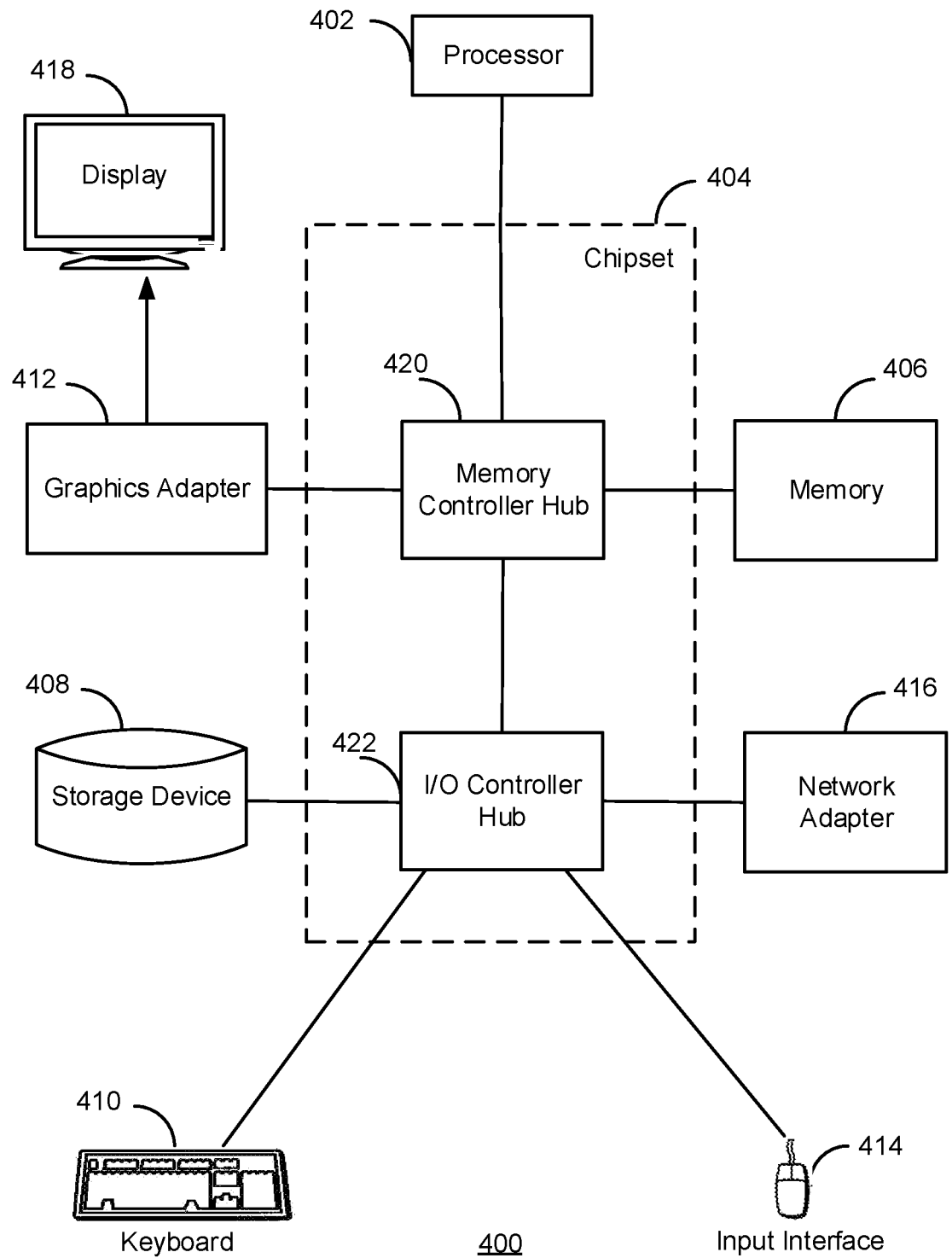
FIG. 4 illustrates an example computer for implementing the entities shown in FIGS. 1A, 1B, 2A, 2B, and 3.

FIG. 4 illustrates an example computer for implementing the entities shown in FIGS. 1A, 1, 2A, 2B, and 3. The computer 400 includes at least one processor 402 coupled to a chipset 404. The chipset 404 includes a memory controller hub 420 and an input/output (I/O) controller hub 422. A memory 406 and a graphics adapter 412 are coupled to the memory controller hub 420, and a display 418 is coupled to the graphics adapter 412. A storage device 408, an input device 414, and network adapter 416 are coupled to the I/O controller hub 422. Other embodiments of the computer 400 have different architectures.

The storage device 408 is a non-transitory computer-readable storage medium such as a hard drive, compact disk read-only memory (CD-ROM), DVD, or a solid-state memory device. The memory 406 holds instructions and data used by the processor 402. The input interface 414 is a touch-screen interface, a mouse, track ball, or other type of pointing device, a keyboard, or some combination thereof, and is used to input data into the computer 400. In some embodiments, the computer 400 may be configured to receive input (e.g., commands) from the input interface 414 via gestures from the user. The network adapter 416 couples the computer 400 to one or more computer networks.

The graphics adapter 412 displays images and other information on the display 418. In various embodiments, the display 418 is configured such that the user may (e.g., radiologist, oncologist, pulmonologist) may input user selections on the display 418 to, for example, initiate risk prediction for a patient, order any additional exams or procedures and/or set parameters for the risk prediction models. In one embodiment, the display 418 may include a touch interface. In various embodiments, the display 418 can show one or more future risk of cancer predictions for a subject. Thus, a user who accesses the display 418 can inform the subject of the future risk of cancer that is predicted for the subject. In various embodiments, the display 418 can show information such as the features that most heavily contributed to the future risk of cancer prediction for a subject. For example, a subject predicted to have a future risk of cancer can be largely due to a percentage of the subject's lung occupied by centrilobular emphysema. Thus, the identification of the feature and/or the value of the feature (e.g., percentage of the subject's lung occupied by centrilobular emphysema) can be shown on the display 418 to a user e.g., clinician user. In various embodiments, the top 1, top 2, top 3, top 4, top 5, top 6, top 7, top 8, top 9, or top 10 features that most heavily contributed to the future risk of cancer prediction for the subject can be shown on the display 418. Displaying the top contributing features can provide context to a user e.g., clinician user in understanding the features that resulted in the future risk of cancer prediction. Patient profiles, CT images, generated risk assessments and any other relevant information may be stored to the memory so that patient information/results may be accessible at any given time.

The computer 400 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 408, loaded into the memory 406, and executed by the processor 402.

The types of computers 400 used by the entities of FIG. 1A or 1B can vary depending upon the embodiment and the processing power required by the entity. For example, the cancer prediction system 130 can run in a single computer 400 or multiple computers 400 communicating with each other through a network such as in a server farm. The computers 400 can lack some of the components described above, such as graphics adapters 412, and displays 418.

X. Systems

Further disclosed herein are systems for implementing risk prediction models for predicting future risk of cancer. In various embodiments, such a system can include at least the cancer prediction system 130 described above in FIG. 1A. In various embodiments, the cancer prediction system 130 is embodied as a computer system, such as a computer system with example computer 400 described in FIG. 4.

In various embodiments, the system includes an imaging device, such as imaging device 120 described above in FIG. 1A. In various embodiments, the system includes both the cancer prediction system 130 (e.g., a computer system) and an imaging device. In such embodiments, the cancer prediction system 130 can be communicatively coupled with the imaging device 120 to receive images (e.g., CT scans) captured from a subject. The computer system implements, in silico, risk prediction models to analyze the images and to determine a future risk of lung cancer for the subject.

XI. Additional Embodiments

There has been extensive investigation to determine the earliest molecular changes that mark the transition from normal tissue repair to uncontrolled cell growth and cancer. Much of this work has focused on identifying who is most resilient or susceptible to lung injury from smoking. These patterns of injury include distal small airway disease leading to expiratory airflow obstruction, emphysematous destruction of the lung parenchyma, aberrant deposition of collagen and scar tissue (interstitial change and fibrosis) and pulmonary vascular remodeling. It is increasingly clear that the development of some admixture of these patterns of lung injury, all unique manifestations of susceptibility, increases the risk of developing lung cancer.

Observational studies have repeatedly demonstrated that smokers who develop expiratory airflow obstruction (a defining feature of COPD—Chronic Obstructive Pulmonary Disease) are at increased risk for future lung cancer. That risk is further increased in those people with COPD who have emphysematous destruction of their distal airspaces. Additional investigation has linked interstitial lung disease and pulmonary fibrosis (another form of smoking related lung injury) to a heightened risk of lung cancer, again supporting the general contention that conditions characterized by chronic injury and repair may lead to malignancy. Lastly, there are extra-pulmonary manifestations of susceptibility to chronic tobacco smoke exposure such as muscle wasting that may also identify those at increased risk of disease, possibly because of a direct link between the musculature and cancer but also because the loss of fat free mass and skeletal musculature may be a reflection of inflammatory overspill from already injured lungs. All of these pulmonary and extrapulmonary manifestations of injury from chronic tobacco smoke exposure are detectable on computed tomographic (CT) imaging.

The present disclosure may be understood with reference to the following description and the appended drawings. The present disclosure relates to a system and method integrating expertise in medical image analysis and applied advanced machine learning techniques to metrics extracted from medical images obtained in the National Lung Screening Trial (NLST). Features extracted from these medical images are used to generate a risk model to predict future lung cancer. In particular, the risk model identifies a pattern/admixture of features that could be used to identify smokers with an increased risk of future lung cancer.

The National Lung Screening Trial (NLST) was a randomized controlled trial to determine if annual CT scanning could reduce death due to lung cancer. The primary hypothesis that drove this investigation was that CT imaging provides higher resolution in-vivo data that would detect cancer at an earlier stage (or smaller size nodule) which is more amenable to treatment and cure. The investigation recruited approximately 53,000 smokers, randomizing half to annual CT scanning and the other half to annual chest X-ray (CXR). Those smokers who underwent annual CT scanning experienced an approximate 20% reduction in mortality due to lung cancer. These exciting results led to a change in health care with lung cancer screening CTs being a reimbursed part of preventive medicine.

The NLST CT scans and clinical data are now freely available to the biomedical community and the baseline (T0), year 1 (T1) and year 2 (T2) CT scans from 15,000 individuals were obtained. According to an exemplary embodiment, image analytic algorithms were applied to all of these scans to extract measures of emphysema, interstitial change, preserved lung tissue and pectoralis muscle size (area) where the latter muscle measure is used as a proxy for body composition or fat free mass. In one embodiment, the 15,000 T0 CT scans were divided in half to build a dedicated training set of data (n=7,500) and testing set of data (n=7,500). Using the objective features extracted from the CT images as well as the subjective reports of visually ascertained nodules and their characteristics (size, shape, etc.), a robust model to predict future lung cancer was created. The model strategy was based on a Random Forest approach to develop and optimize decision trees in the training data to predict a desired outcome. This approach was used rather than selecting a fixed threshold for a certain burden of disease (i.e. >10% emphysema or >10% interstitial change) because there are almost certainly several combinations of emphysema, interstitial change and sarcopenia that identify a heightened risk of lung cancer. For example, a smoker having 25% of their lung with emphysema may have the same heightened risk for future lung cancer as the smoker with 2% emphysema, 12% interstitial change and decreased pectoralis muscle area.

The random forest-based models were independently trained to predict 1, 3 and 5-year risk of future lung cancer in smokers enrolled in the NLST. These models were then modified to enable prediction of incident (new) cancer rather than just identify those with prevalent (already present) cancer on the T0 CT scan. This final step leveraged visual data describing features of any lung nodules in the CT image. Although the exemplary embodiments show and describe random forest-based models, it will be understood by those of skill in the art that other modeling approaches such as, for example, logistic regression and XGBoost may also be utilized. It will also be understood by those of skill in the art that although the risk prediction models are specifically shown and described as providing 1, 3 and 5 year risk predictions, prediction terms may be varied, as desired.

The life course of lung cancer most commonly begins with the development of a lung nodule. This nodule may be cancerous or may be a benign overgrowth of tissue that subsequently undergoes malignant transformation. The Radiologic community recognizes this process, and in an attempt to standardize medical management developed a scoring system to stage nodules discovered on CT scan by their likelihood of being cancer. This staging system is called Lung CT screening, Reporting and Data System (LungRADS) and is based upon the size of the nodule, the rate of growth of the nodule and the appearance of the nodule. Generally, the larger the nodule, the more rapid its growth or the more irregular it is in appearance, the more likely it is to be cancer.

In one embodiment, the LungRADS scoring system was used to remove people from the risk model that were most likely to have prevalent cancer at the time of the T0 scan. To do this, people with the highest LungRADS score (4A, 4B and 4X) were excluded from this specific analysis (but were included in other models) while keeping people with smaller, lower risk nodules (2 and 3) that may become cancer at a future date. The models for 1, 3 and 5-year risk prediction were retrained after excluding all people with LungRADS 4 nodules and then applied to the testing sub cohort (n=7,500) of the NLST.

A combination of radiologic features could still identify people with a 10+% absolute 3-year risk of developing lung cancer. Further, approximately ⅓ of those people did not have a nodule on the baseline T0 scan suggesting that these models are not just predicting which nodules may become cancerous but rather which people may develop a nodule and then be diagnosed with lung cancer. A series of risk prediction models were generated using this approach. These models varied by the time to cancer (1, 3 and 5-year risk) as well as the nature of the nodules that were excluded. This submission therefore includes all models across the LungRADS stages, including LungRADS 4A, 4B and 4X.

Additional radiologic features such as vascular and airway calcification, pulmonary vascular morphology and bone mineral density may also represent unique metrics of disease susceptibility that can be used to predict future lung cancer. Nodule specific features may also be integrated into these models. Nodule specific features may include, for example, nodule location, proximity to emphysema and interstitial change, rate of change of nodule characteristics (both absolute and relative to normative standards).

In a further embodiment, these image-based models may be integrated into more comprehensive biomarker panels for risk assessment and nodule discrimination. Those panels include but are not limited to proteomics, genetics, gene expression, cell free circulating tumor DNA, etc., where it is expected that optimal model performance may result for combinations and highly sensitive and specific markers.

These risk prediction models are predicated on a mixture of objective and subjective features extracted from the CT image. Extensive prior investigation suggests that objective and not subjective features on CT vary by CT scanner brand, generation and image reconstruction software. Additional geographic variability in the burden of disease between subjects may reflect actual differences to noxious exposure (i.e. some people may be more or less susceptible to injury from exposure and more or less likely to develop emphysema or interstitial changes in the lung tissue). For these reasons, absolute thresholds to determine the presence and severity of CT metrics of disease were not used. Instead, the data in the test sub cohort were each normalized by subtracting the mean and dividing by the standard deviation for each covariable. As additional cohorts are aggregated for model refinement, data normalization will be performed using all existing data (cross cohort) or select subsets of the data including but not limited to those thought to best reflect the patient specific biology, exposure history, ethnicity or type of medical image being processed. Once normalized, the data were used in the random forest-based approach to modeling.

In one embodiment, objective features include, for example, lung parenchyma features (e.g., densitometric measures of the lung parenchyma and measures of interstitial changes in the lung parenchyma) and body composition measures of the musculature/chest wall. Densitometric measures of the lung parenchyma may include, for example, the percentage of the lung occupied by (i) low attenuation area (LAA), which is defined as the area/volume having an attenuation less than −950 Hounsfield Units (HU) and (ii) high attenuation area (HAA), which is defined as the area/volume of lung having attenuation between −600 HU and −250 HU, and the ratio between LAA in the upper lung zone to that in the lower lung zone. Measures of interstitial changes in the lung parenchyma include local histogram measures of the lung parenchyma, the percentage of lung occupied by, for example, normal tissue, centrilobular emphysema, centrilobular nodule, ground glass, honeycombing, linear scar, nodular, reticular, subpleural line, other emphysema and/or cyst. Body composition measures of the musculature/chest wall may include, for example, pectoralis major cross-sectional area, pectoralis minor cross-sectional area, pectoralis major lean cross-sectional area, pectoralis minor lean cross-sectional area, aggregate cross-sectional area of the left or right pectoralis major or minor muscles, and subcutaneous fat cross-sectional area.

The risk prediction models trained using the data from the NLST provide a multi-modal risk assessment and enrichment approach. For example, consider two patients who developed cancer within 3 years of enrollment in NLST. Both had Lung-RADS 3 nodules at baseline, both were predicted to develop cancer within 3 years by the algorithm and both developed stage IA adenocarcinoma within 3 years. In fact, the predicted probabilities of developing cancer for both patients are within 2% of each other (84.8% for Patient 1 and 86.4% for Patient 2). Patient 1 was a 65-year-old white female former smoker with a 76 pack year smoking history, a BMI of 23.5, relatively small pectoralis mass, and significant, upper lobe predominant emphysema (31% emphysema by volume based on local histogram analysis). A 76 pack year smoking history is equivalent to smoking a pack (20) of cigarettes everyday for 76 years or two packs a day for 38 years. By contrast, Patient 2 was a 59 year old white male former smoker with a 43 pack year smoking history, a BMI of 29.8, relatively preserved pectoralis mass, and minimal emphysema (2.6% emphysema by volume based on local histogram analysis), but significantly more interstitial features (7.1% compared to 4%). In this second case it is this last feature and the strong relationship between interstitial features and cancer that likely leads to the algorithm predicting the development of cancer within 3 years. The clinical and radiologic differences between these two cases highlight the ability of the risk prediction models to identify patients with distinct and differing phenotypes who are likely to develop cancer.

According to a further embodiment, the models used to predict per person risk of future cancer may also be used to predict the location of that future cancer. In one embodiment, the data is divided into thirds to represent the upper, middle, and lower third of the lungs by volume as well as by lobe. Model training and testing may be performed and the regional (volume by ⅓rds as well as by lobe) risk of future lung cancer may be calculated. These additional data enable focused regional diagnostic evaluations and therapeutic intervention using inhaled and bronchoscopically administered drugs and devices. It will be understood by those of skill in the art that the lung may be divided into any number of regions having any number of configurations.

A system according to an exemplary embodiment of the present disclosure predicts a risk of future lung cancer based on a CT image of the lungs of a patient. The system can comprise a processor along with a user interface, a display, and a memory. The processor includes risk prediction models, as described above, which may provide a patient-specific assessment regarding a likelihood for developing cancer in future. The risk prediction models may implemented by the processor as, for example, lines of code that are executed by the processor, as firmware executed by the processor, as a function of the processor being an application specific integrated circuit (ASIC), etc. It will also be understood by those of skill in the art that although the system is shown and described as comprising a computing system comprising a single processor, user interface, display and memory, the system may be comprised of a network of computing systems, each of which includes one or more of the components described above. In one example, the risk prediction models may be executed via a central processor of a network, which is accessible via a number of different user stations. Alternatively, the risk prediction models may be executed via one or more processors.

The risk prediction models created to identify people at greatest risk for future cancer will enable clinical trials focused on cancer prevention and treatment of high risk individuals, as well as to enable clinical care by identifying which people should have the most aggressive follow up and screening to detect cancer at its earliest stages. The patient-specific risk assessment may be output and displayed to the user on the display of one or more computing stations. The patient-specific risk assessment may be provided in any of a variety of configurations. The risk assessment may include a predicted level of risk and/or a timeframe for the risk (e.g., 1, 3 and 5-year risk). In one embodiment, to enable visualization of the modeling data, the CT scans will be color coded by person and by region. Those regions with the highest risk will be colored red. Moderate risk regions will be yellow and low risk regions will be green. The result of this is that a person of low risk for future lung cancer may have their whole lung image shaded green while someone at high risk for future lung cancer may have a CT image with regions of red (corresponding to high risk), yellow (moderate risk) and green (low risk). For example, these color-coded maps may be presented on a display in the Radiology reading room for the chest radiologist (to assist in clinical interpretation) as well as on a display of the image based workstation used by the pulmonologist, oncologist and proceduralist to target therapy. According to one embodiment, these maps will be generated using three colors as well as continuous gradients of colors from red to green based upon the use case and mode of visualization. It will be understood by those of skill in the art, however, that the maps may be generated using any of a variety of colors and configurations so long as the generated map indicates a predicted risk of future lung cancer to the user.

The user may (e.g., radiologist, oncologist, pulmonologist) may input user selections on the user interface to, for example, initiate risk prediction for a patient, order any additional exams or procedures and/or set parameters for the risk prediction models. The user interface may include input devices such as, for example, a keyboard and/or mouse. In one embodiment, the user interface may include a touch interface enabled on the display. Patient profiles, CT images, generated risk assessments and any other relevant may be stored to the memory so that patient information/results may be accessible via a user at any given time.

Image based risk prediction may include predictions for 1, 3 and 5-year risk of lung cancer. This series of models will be used to develop preventive therapies for lung cancer by enabling clinical trials and ultimately clinical care. Clinical trials will be more efficient and feasible because the event rate (future lung cancer) will be above background thereby allowing smaller cohort size and potentially reducing the numbers of patients that need to be treated to reduce one case of lung cancer. Following identification of efficacious therapies for the prevention of lung cancer, this model may be used outside of clinical trials as a biomarker in clinical care to identify those people who may best benefit from treatment. Since all treatments involve some degree of risk, knowing who is most likely to develop lung cancer will influence the risk/benefit decision analysis and reimbursement around the implementation of therapy in the individual.

According to a further embodiment, the risk prediction models may provide a foundation for identifying different risk for cellular types of lung cancer including adenocarcinoma and squamous cell carcinoma. These differences are based on the cell type from which cancer arose and may likely influence decisions related to methods of treatment and patient outcomes.

The risk prediction models described herein provide per patient level probabilities of developing lung cancer. These models may be modified using regional metrics of lung susceptibility to predict the future location of the lung cancer in that individual. As bronchoscopic procedures may increasingly be utilized to diagnose, treat and prevent lung cancer, knowledge of the lobe and region of the lobe where lung cancer will develop will facilitate a diagnostic biopsy of a suspicious lesion or nodule and/or the local administration of therapy to prevent malignant transformation.

The risk prediction models described herein may also be used for the selection of therapies and medical decision making. There are competing risks of disease development and death in all people. For example, smokers may develop lung cancer, heart disease or cerebrovascular disease, all of which may be aggressive and life threatening. The risk prediction models detailed in this document may be integrated with other existing clinically utilized risk models such as the Framingham Heart Study Risk Score (to predict future heart disease) to provide a more holistic assessment of how to maintain patient health and inform them about their most pressing health care needs.

A processor of the system processes a CT image of a patient to extract features related to parenchymal damage and body composition. Note that additional modeling may expand the list of those features to include other data (including but not limited to vascular and airway calcification, pulmonary vascular morphology, bone mineral density as well as nodule specific features such as rate of growth and proximity to both emphysema and interstitial change). Data is normalized at the per subject level using distributions of the CT features collected in the training set. This training set will include multiple cohorts representing differing geographic regions, exposures and tumor biology. Utilization of Random Forest generated risk prediction model to predict risk of future lung cancer (per person and per lung region). The risk assessment, which in one embodiment may include a color coding of lung based upon regional risk of future cancer (red, yellow and green to represent high, medium and low risk of future cancer), may be displayed to the user on the display.

Disclosed herein are additional embodiments including a method, comprising: extracting features from a CT image of a lung of a patient; normalizing data including extracted features from the CT image of the lung of the patient; and generating, using a risk prediction model, a risk assessment including a prediction of a future risk of lung cancer. In various embodiments, the risk assessment includes a color-coded image of a lung of the patient, based upon regional risk of future cancer. In various embodiments, the risk prediction model identifies one of a pattern and admixture of lung features indicative of an increased risk in lung cancer. In various embodiments, the extracted features include one of measures of emphysema, interstitial change, preserved lung issue and pectoralis muscle size.

Additionally disclosed herein is a system, comprising: a non-transitory computer readable storage medium storing an executable program; and a processor executing the executable program to cause the processor to: extract features from a CT image of a lung of a patient; normalize data including extracted features from the CT image of the lung of the patient; and generate, using a risk prediction model, a risk assessment including a prediction of a future risk of lung cancer.

EXAMPLES

Below are examples of specific embodiments for carrying out the present invention. The examples are offered for illustrative purposes only and are not intended to limit the scope of the present invention in any way. Efforts have been made to ensure accuracy with respect to numbers used (e.g., amounts, temperatures, etc.), but some experimental error and deviation should be allowed for.

Example 1: Building Risk Prediction Models and Summary of Analysis

Computed tomography (CT) images from the National Lung Cancer Screening Trial (NLST) cohort were analyzed to predict likelihood of cancer in patients across different future horizon timepoints (e.g., within 1 year, within 3 years, or within 5 years). The predicted future risk of cancer was used to identify a population of patients enriched for the development of lung cancer.

The National Lung Screening Trial (NLST) was a randomized controlled trial to determine if annual CT scanning could reduce death due to lung cancer. The primary hypothesis that drove this investigation was that CT imaging provides higher resolution in-vivo data that would detect cancer at an earlier stage (or smaller size nodule) which is more amenable to treatment and cure. The investigation recruited approximately 53,000 smokers, randomizing half to annual CT scanning and the other half to annual chest X-ray (CXR). Those smokers who underwent annual CT scanning experienced an approximate 20% reduction in mortality due to lung cancer. These exciting results led to a change in health care with lung cancer screening CTs being a reimbursed part of preventive medicine.

The NLST CT images and clinical data are now freely available to the biomedical community and CT scans were obtained. The overall demographics and details of the full patient are shown in Table 2. Image analytic algorithms were applied to CT images to extract features such as emphysema, interstitial change, preserved lung tissue and pectoralis muscle size (area) where the latter muscle measure is used as a proxy for body composition or fat free mass. The CT scans were divided in half to build a dedicated training set of data and testing set of data. Using the objective features (e.g., non-nodule specific features) extracted from the CT images as well as the subjective features of visually ascertained nodules and their characteristics (e.g., nodule specific features such as nodule size, shape, etc.), a robust model to predict future lung cancer was created.

Features (e.g., variables) were extracted from the CT images. The features included were chosen based on prior experience and based on likely biologic relevance.

For the risk prediction models described in Examples 2-11 below, the following non-nodule specific features were used:
1) Densitometric measures of the lung parenchyma
   a. The percentage of lung occupied by:
      i. Low attenuation area (LAA), which was defined as the area/volume having an attenuation less than −950 Hounsfield units (HU)
      ii. High attenuation area (HAA), which was defined as the area/volume of lung having attenuation between −600 HU and −250 HU.
   b. The ratio between LAA in the upper lung zone to that in the lower lung zone (Ratio LAA)
2) Body composition measures of the musculature/chest wall
   a. Pectoralis major cross-sectional area
   b. Pectoralis minor cross-sectional area
   c. Pectoralis major lean cross-sectional area
   d. Pectoralis minor lean cross-sectional area
   e. Subcutaneous fat cross-sectional area (axial or coronal)
3) Local histogram measures of the lung parenchyma
   a. The percentage of lung occupied by:
      i. Normal tissue
      ii. Centrilobular emphysema
      iii. Centrilobular nodule
      iv. Ground glass
      v. Honeycombing
      vi. Linear scar
      vii. Nodular
      viii. Reticular
      ix. Subpleural line x. Other emphysema xi. Cyst For the risk prediction models described in Examples 2-6 below, the following nodule-specific features include:
1) Attenuation
2) Margin description
3) Diameter
4) Lung CT Screening, Reporting and Data System (Lung-RADS) Score For the risk prediction models described in Examples 7-11 below, the following radiomic features (e.g., nodule-specific features) were extracted from the original CT image, a wavelet transformed CT image, and a Gaussian transformed CT image.
1) First order statistics
2) 3D shape based features
3) 2D shape based features
4) Gray level cooccurrence matrix
5) Gray level run length matrix
6) Gray level size zone matrix
7) Neighboring gray tone difference matrix
8) Gray level dependence matrix.

The features used specifically did not include clinical characteristics, meaning that the clinical characteristics of the overall cohort are the NLST characteristics. The clinical characteristics by lung cancer prediction category are shown below.

Risk prediction models are predicated on a mixture of objective (e.g., non-nodule specific) and subjective (e.g., nodule specific) features extracted from the CT image. Objective and not subjective features on CT vary by CT scanner brand, generation and image reconstruction software. Additional geographic variability in the burden of disease between subjects may reflect actual differences to noxious exposure (i.e. some people may be more or less susceptible to injury from exposure and more or less likely to develop emphysema or interstitial changes in the lung tissue). For these reasons, absolute thresholds to determine the presence and severity of CT metrics of disease were not used. Instead, the data in the test sub cohort were each normalized by subtracting the mean and dividing by the standard deviation for each covariable. As additional cohorts are aggregated for model refinement, data normalization will be performed using all existing data (cross cohort) or select subsets of the data including but not limited to those thought to best reflect the patient specific biology, exposure history, ethnicity or type of medical image being processed. Once normalized, the data were used in the random forest-based approach to modeling.

Pre-processing of the data was first conducted. This included normalizing values of continuous features (e.g., by centering (subtraction of the mean) and scaling (division by the standard deviation). The normalization of the test set was performed using information from the training set only. That is, the training set mean and standard deviation were used to normalize both the training set and the test set. Additionally, pre-processing included down sampling of the majority class (no cancer) was performed in order to account for imbalanced data, i.e. to account for the fact that cancer diagnosis is relatively uncommon. Alternative approaches such as SMOTE and ROSE were considered but had similar performance as down sampling with higher computational requirements.

Multiple modeling approaches were evaluated to build the risk prediction model including logistic regression, XGBoost and Random Forest. The random forest-based models were independently trained to predict 1, 3 and 5-year risk of future lung cancer in smokers enrolled in the NLST. The model strategy was based on a Random Forest approach to develop and optimize decision trees in the training data to predict a desired outcome. This approach was used rather than selecting a fixed threshold for a certain burden of disease (i.e. >10% emphysema or >10% interstitial change) because there are almost certainly several combinations of emphysema, interstitial change and sarcopenia that identify a heightened risk of lung cancer. For example, a smoker having 25% of their lung with emphysema may have the same heightened risk for future lung cancer as the smoker with 2% emphysema, 12% interstitial change and decreased pectoralis muscle area. These models were then modified to enable prediction of incident (new) cancer rather than just identify those with prevalent (already present) cancer on the CT scan. This final step leveraged visual data describing features of any lung nodules in the CT image. Although the exemplary embodiments show and describe random forest-based models and gradient boosted models, it will be understood by those of skill in the art that other modeling approaches such as, for example, logistic regression may also be utilized. It will also be understood by those of skill in the art that although the risk prediction models are specifically shown and described as providing 1, 3 and 5 year risk predictions, prediction terms may be varied, as desired.

To build the risk prediction model, the cohort was split 50/50 into training and testing groups. Models were trained on the testing group with tuning performed using 10 fold cross validation repeated three times. Dichotomization of predicted probabilities was performed by maximizing F-score in the cross-sampled training cohort. Outcomes modeled included the diagnosis of cancer at 1, 3 and 5 years. Performance measures and visualization include presentation of ROC curves and enrichment for all time points (as described in the Examples below). The cumulative incidence function and the demographics of the enriched and non-enriched cohort based on 3 year cancer prediction are also predicted/shown in the Examples below.

Models were constructed to predict future risk of cancer for either the entire cohort of patients or a subgroup of patients. Subgroups of patients were categorized based on nodules which were at baseline rated/categorized as Lung-RADS <4B, <4A, <3 and <2. Lung-RADS<4B includes patients categorized as Lung-RADS 1-4A. Lung-RADS <4A includes patients categorized as Lung_RADS 1-3. Lung-RADS <3 includes patients categorized as Lung_RADS 1-2. Lung-Rads <2 includes patients categorized as Lung_RADS 1. Table 1 summarizes the characteristics for different Lung-RADS classifications. Demographic information and patient characteristics of the full cohort (including Lung-RADS classification) is shown in Table 2.

Separate risk prediction models were created for each subgroup of patients. That is, the performance specified is not the performance of the model of the entire cohort simply applied to the stated subgroup, but rather it is the performance of a subgroup specific model that was trained on patients of that subgroup.

As shown in the Examples below, all results represent the performance/findings based on models developed/trained in the training cohort and then applied to the testing cohort. In the enrichment tables, the risk prediction model for each time horizon (1 year, 3 year, and 5 year) was trained separately as the most important features for 1 year cancer risk are not necessarily the same as those for 3 and 5 year cancer risk. This means that the cumulative incidence at 3 years, for example, is not just the cumulative incidence from the row above (1 year) plus the interval number of cases.

When interpreting the cumulative incidence function plots, the raw probabilities on the y axis are affected significantly by changes in the risk set due to censoring and death. These plots are included primarily to demonstrate the change in their shape by subgroup. Of particular note is the fact that with the exclusion of larger/more concerning nodules, there is a less abrupt rise in cancer diagnosis in the first year.

When reviewing the receiver operating characteristic (ROC) curves and the area under the curve (AUC) values, note that these are primarily included for reference given their familiarity and use in the literature. Because the models were tuned (e.g., referred to as "tuned risk prediction model") to the area under the precision recall curve, the area under the ROC does not improve significantly with the tuning process.

When considering potential eligibility for enrollment, note that based on Lung-RADS criteria, those individuals with 4A and 4B nodules will warrant early evaluation. However, a significant percentage of both, and especially 4A, will not be prevalent cancers and therefore may be potentially able to be enrolled in a potential study of future incident cancer.

The relative enrollment ratios and percentages are the CT screen to enroll ratio of that Lung-RADS subgroup. The absolute enrollment percentage is based on the size of the overall cohort.

Example 2: Predicting Future Risk for Lung-RADS 1-4B

Three separate models were constructed using the full patient cohort using the methods described in Example 1. Specifically, the first model is a 1 year, Lung-RADS 1-4B risk prediction model, the second model is a 3 year, Lung-RADS 1-4B risk prediction model, and the third model is a 5 year, Lung-RADS 1-4B risk prediction model. For each risk prediction model, a training set (e.g., 50% of the cohort) was used to train the risk prediction model and a testing set (e.g., other 50% of the cohort) was used to test the risk prediction model.

The top 10 important features for each of the 1 year, 3 year, and 5 year risk prediction models is shown in Table 3. Notably, the majority of important features of the 1 year risk prediction model include nodule-specific features whereas the majority of important features of the 3 year and 5 year risk prediction model are objective features (e.g., non-nodule specific features such as features of the body and/or lung parenchyma).

Notably, for the 1 year, Lung-RADS 1-4B prediction model, the top three features in terms of feature importance are nodule specific features. Additionally, 4 of the top 5 features in terms of feature importance for the 1 year, Lung-RADS 1-4B prediction model are nodule specific features. Additionally, 6 of the top 10 features in terms of feature importance for the 1 year, Lung-RADS 1-4B prediction model are non-nodule specific features. For the 3 year, Lung-RADS 1-4B prediction model, 2 of the top 3 features in terms of feature importance are nodule specific features. Additionally, 3 of the top 5 features in terms of feature importance for a 3 year, Lung-RADS 1-4B prediction model are nodule specific features. Additionally, 6 of the top 10 features in terms of feature importance for a 3 year, Lung-RADS 1-4B prediction model are non-nodule specific features. For the 5 year, Lung-RADS 1-4B prediction model, 2 of the top 3 features in terms of feature importance are nodule specific features. Additionally, 3 of the top 5 features in terms of feature importance for a 5 year, Lung-RADS 1-4B prediction model are non-nodule specific features. Additionally, 7 of the top 10 features in terms of feature importance for a 5 year, Lung-RADS 1-4B prediction model are non-nodule specific features.

Figure 5A:
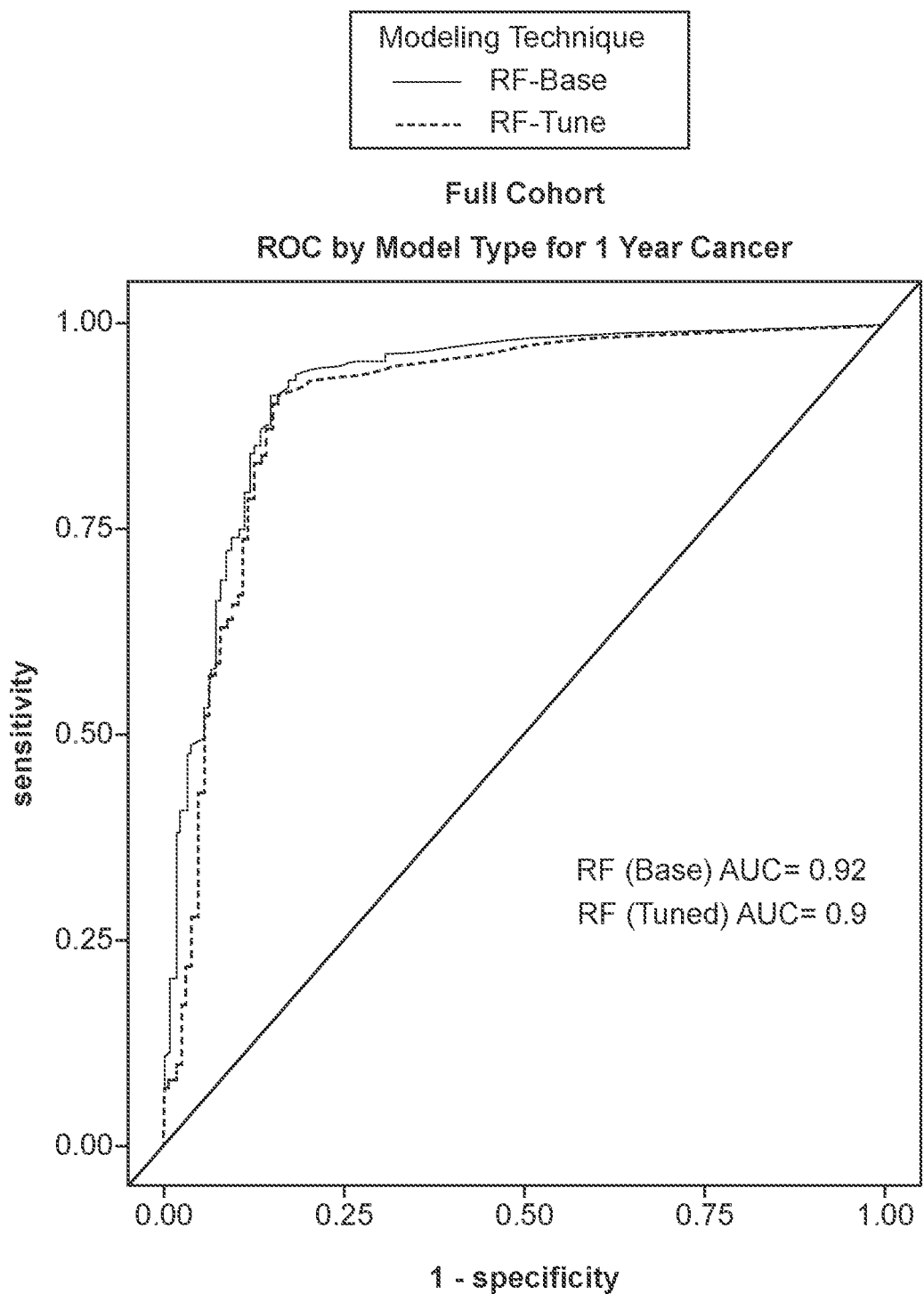
FIG. 5A depicts performance of a risk prediction model for predicting likelihood of cancer within 1 year across Lung-RADS 1-4B patients.
Figure 5B:
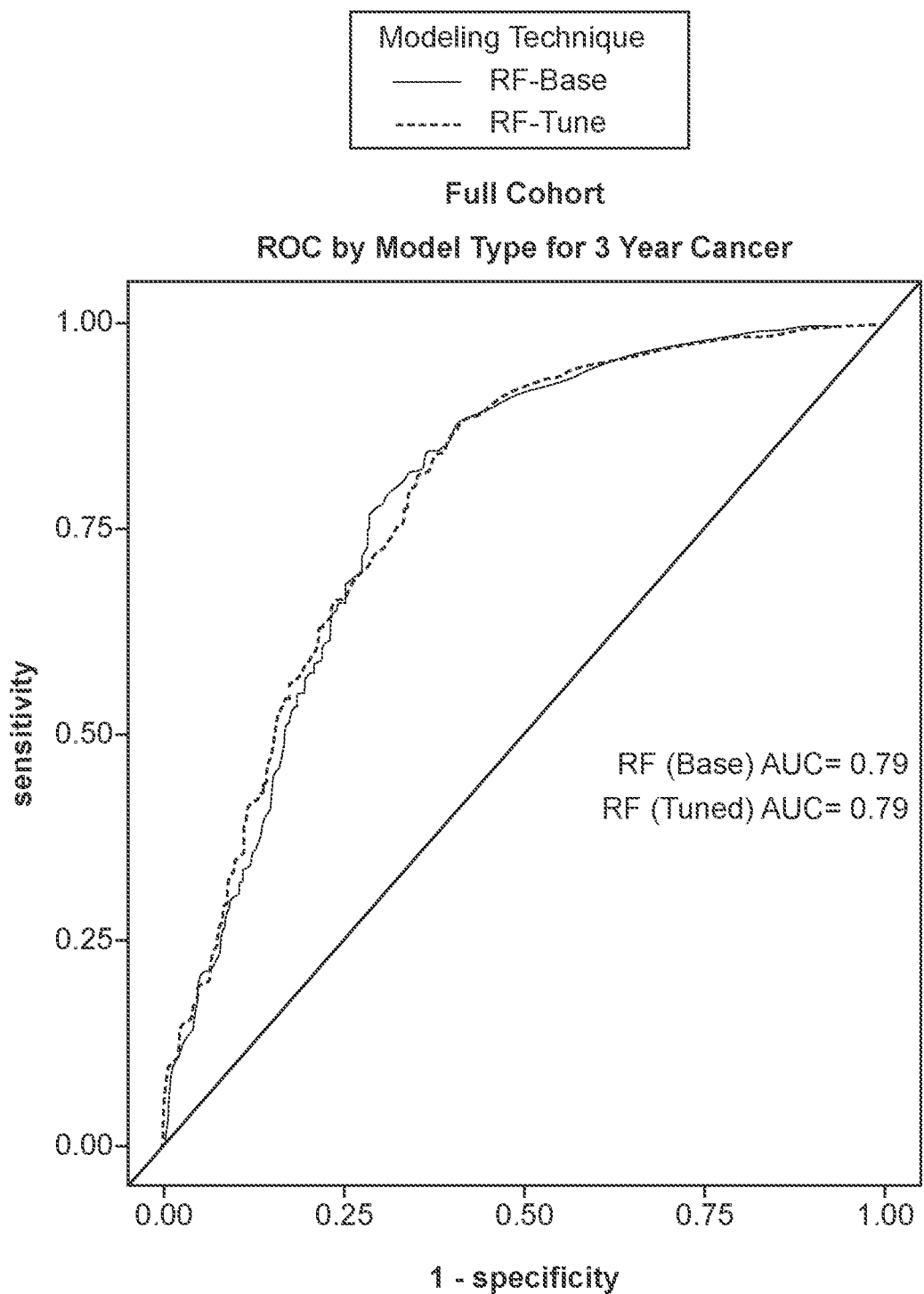
FIG. 5B depicts performance of a risk prediction model for predicting likelihood of cancer within 3 years across Lung-RADS 1-4B patients.

FIG. 5A depicts performance of a risk prediction model for predicting likelihood of cancer within 1 year across the Lung-RADS 1-4B of patients. The base random forest risk prediction model exhibited an AUC value of 0.92 whereas the tuned random forest risk prediction model exhibited an AUC value of 0.90. FIG. 5B depicts performance of a risk prediction model for predicting likelihood of cancer within 3 years across the Lung-RADS 1-4B of patients. The base random forest risk prediction model exhibited AUC value of 0.79 whereas the tuned random forest risk prediction model exhibited an AUC value of 0.79. Additionally, Table 4 documents the characteristics of the Lung-RADS 1-4B of patients according to the cancer prediction determined by the 3 year risk prediction model.

Figure 5C:
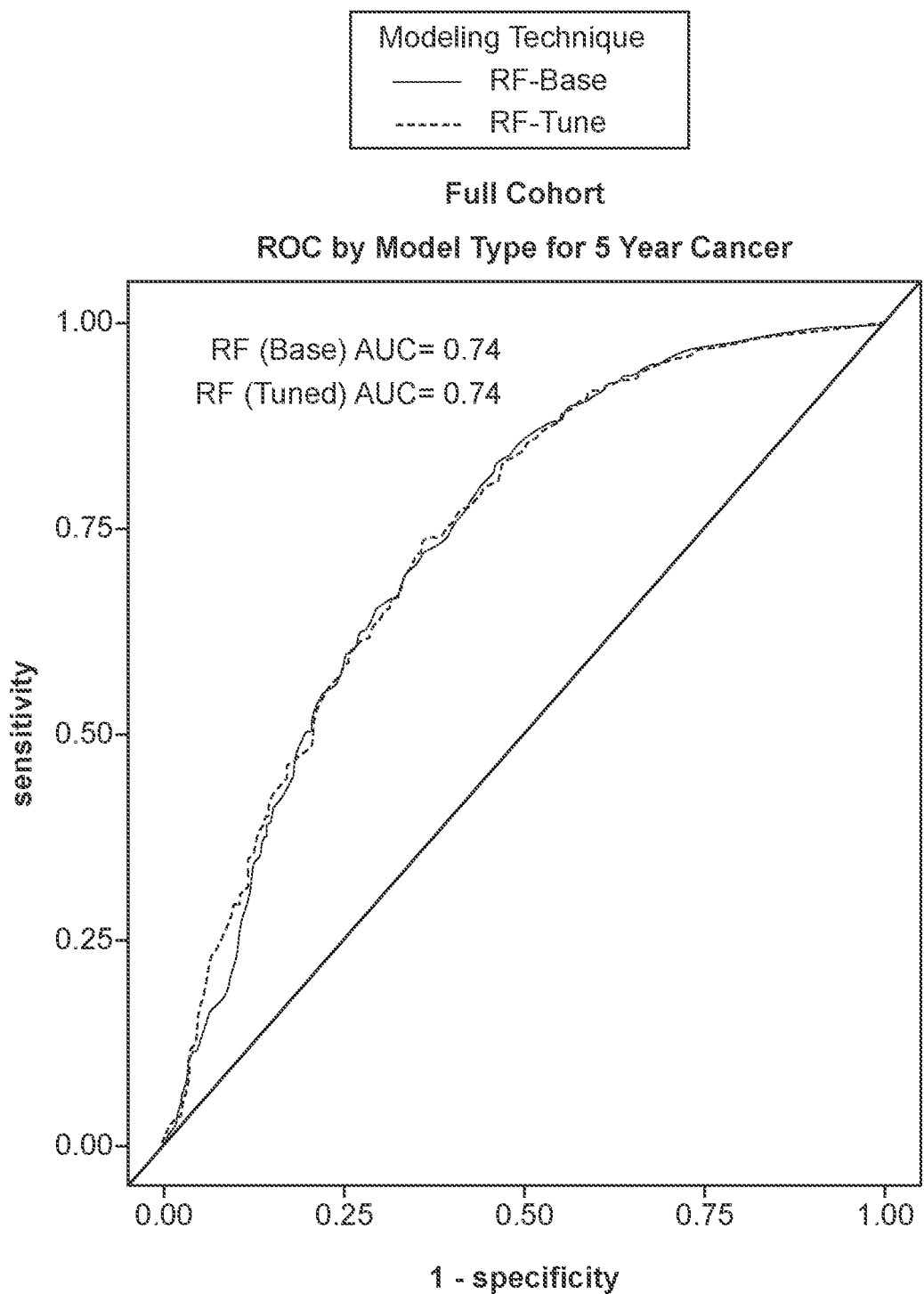
FIG. 5C depicts performance of a risk prediction model for predicting likelihood of cancer within 5 years across the Lung-RADS 1-4B patients.

FIG. 5C depicts performance of a risk prediction model for predicting likelihood of cancer within 5 years across the Lung-RADS 1-4B of patients. The base random forest risk prediction model exhibited AUC value of 0.74 whereas the tuned random forest risk prediction model exhibited an AUC value of 0.74. Altogether, the results of FIGS. 5A-5C indicate that different risk prediction models can be constructed and deployed to predict likelihood of cancer in Lung-RADS 1-4Bs of patients across different future horizon timepoints.

Figure 5D:
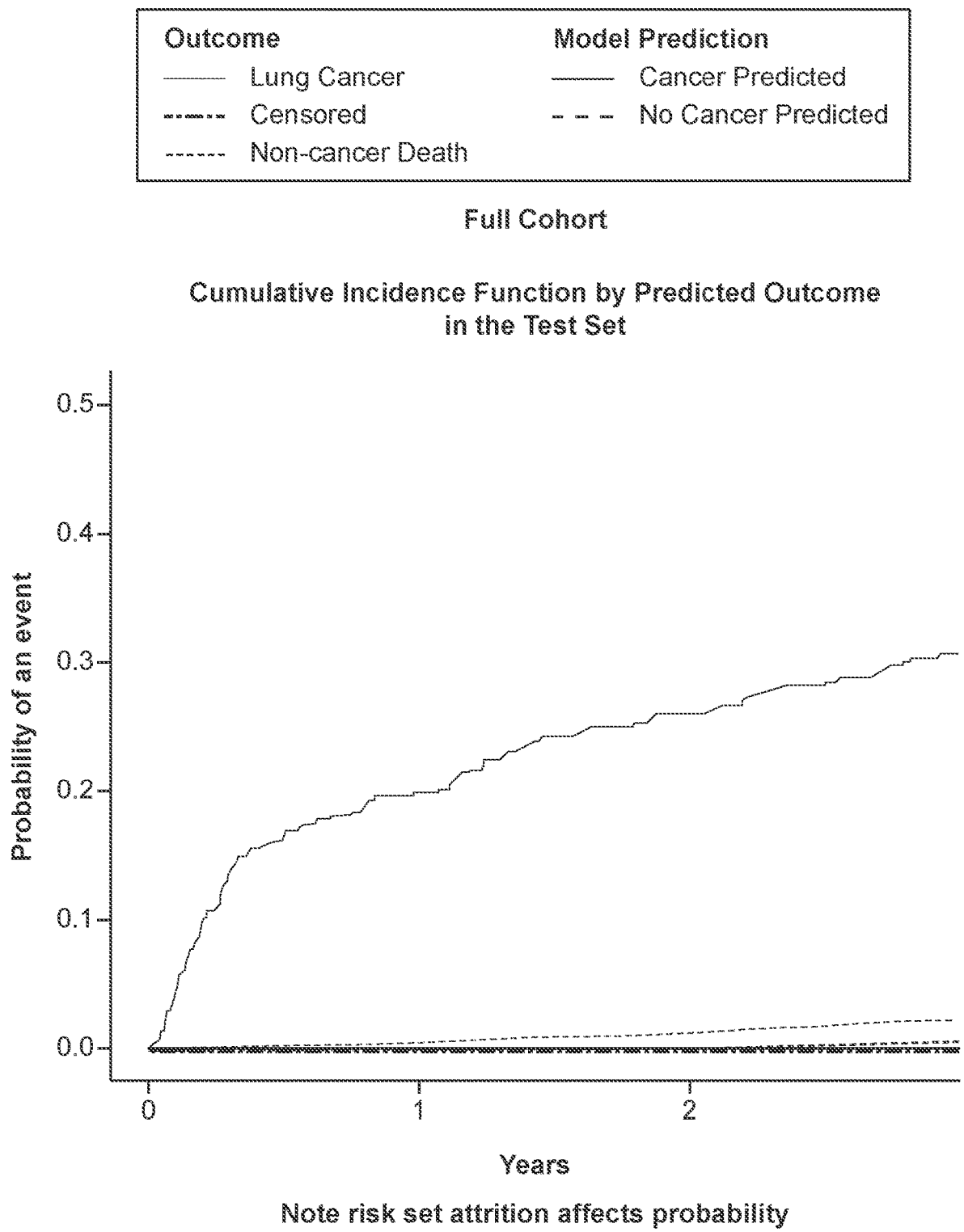
FIG. 5D depicts the 3 year cumulative incidence function across the Lung-RADS 1-4B patients.

FIG. 5D depicts the 3 year cumulative incidence function across the Lung-RADS 1-4B of patients. Here, the risk prediction model predicted cancer for 450 patients and no cancer for the other 6643 patients. Given that that this includes the Lung-RADS 1-4B of patients (which includes the most at risk lung cancer nodules e.g., Lung-RADS 4A/4B), the cumulative incidence function for the 450 predicted cancer patients reflects the higher rate of incidence in the early months (e.g., between 0 and 6 months) in comparison to a lower rate of incidence in subsequent years.

Table 5 depicts the enrichment results of the full patient cohort using the future cancer predictions from the 1 year, 3 year, or 5 year risk prediction models. Specifically, Table 5 shows the enrichment results of the risk prediction models in comparison to background rate of cancers in the original cohort (referred to in Table 5 as "Null Model"). The application of the risk prediction models significantly improves the cumulative incidence (last column of Table 5).

Specifically, for the 1 year model, the background rate ("Null Model") has a cumulative incidence of 1.79 (e.g., 1.79% of patients in the cohort are diagnosed with cancer within 1 year). Applying the 1 year risk prediction model ("Random Forest") enables patient enrichment, which achieves a cumulative incidence of 19.72 (e.g., 19.72% of patients included in the cohort due to the prediction of the 1 year risk prediction model are diagnosed with cancer within 1 year). Thus, the application of the 1 year risk prediction model achieves a 11-fold increase in cumulative incidence.

For the 3 year model, the background rate ("Null Model") has a cumulative incidence of 4.2 (e.g., 4.2% of patients in the cohort are diagnosed with cancer within 3 years). Applying the 3 year risk prediction model ("Random Forest") enables patient enrichment, which achieves a cumulative incidence of 26.44 (e.g., 26.44% of patients included in the cohort due to the prediction of the 3 year risk prediction model are diagnosed with cancer within 3 years). Thus, the application of the 3 year risk prediction model achieves a 6.3-fold increase in cumulative incidence.

For the 5 year model, the background rate ("Null Model") has a cumulative incidence of 5.58 (e.g., 5.58% of patients in the cohort are diagnosed with cancer within 5 years). Applying the 5 year risk prediction model ("Random Forest") enables patient enrichment, which achieves a cumulative incidence of 28.43 (e.g., 28.43% of patients included in the cohort due to the prediction of the 5 year risk prediction model are diagnosed with cancer within 5 years). Thus, the application of the 5 year risk prediction model achieves a 5.1-fold increase in cumulative incidence.

Altogether, Table 5 indicates that the various risk prediction models can be implemented for enriching Lung-RADS 1-4B patients, thereby reducing the number of patients that need to be enrolled in clinical trials.

Example 3: Predicting Future Risk for Lung-RADS 1-4A Patients

Three separate models were constructed using the Lung-RADS 1-4A patients using the methods described in Example 1. Specifically, the first model is a 1 year, Lung-RADS 1-4A risk prediction model, the second model is a 3 year, Lung-RADS 1-4A risk prediction model, and the third model is a 5 year, Lung-RADS 1-4A risk prediction model. For each risk prediction model, a training set (e.g., 50% of the cohort) was used to train the risk prediction model and a testing set (e.g., other 50% of the cohort) was used to test the risk prediction model.

The top 10 important features for each of the 1 year, 3 year, and 5 year risk prediction models is shown in Table 6. Notably, 5 of the top 10 features of the 1 year risk prediction model include nodule-specific features whereas the majority of important features of the 3 year and 5 year risk prediction model are objective features (e.g., non-nodule specific features such as features of the body and/or lung parenchyma).

Specifically, for the 1 year, Lung-RADS 1-4A prediction model, the top 3 features in terms of feature importance are nodule specific features. Additionally, 4 of the top 5 features in terms of feature importance for the 1 year, Lung-RADS 1-4A prediction model are nodule specific features. Additionally, 5 of the top 10 features in terms of feature importance for the 1 year, Lung-RADS 1-4A prediction model are nodule specific features.

For the 3 year, Lung-RADS 1-4A prediction model, 2 of the top 3 features in terms of feature importance are nodule specific features. Additionally, 4 of the top 5 features in terms of feature importance for the 3 year, Lung-RADS 1-4A prediction model are nodule specific features. Additionally, 5 of the top 10 features in terms of feature importance for the 3 year, Lung-RADS 1-4A prediction model are nodule specific features.

For the 5 year, Lung-RADS 1-4A prediction model, 2 of the top 3 features in terms of feature importance are nodule specific features. Additionally, 3 of the top 5 features in terms of feature importance for the 5 year, Lung-RADS 1-4A prediction model are non-nodule specific features. Additionally, 8 of the top 10 features in terms of feature importance for the 5 year, Lung-RADS 1-4A prediction model are non-nodule specific features.

Figure 6A:
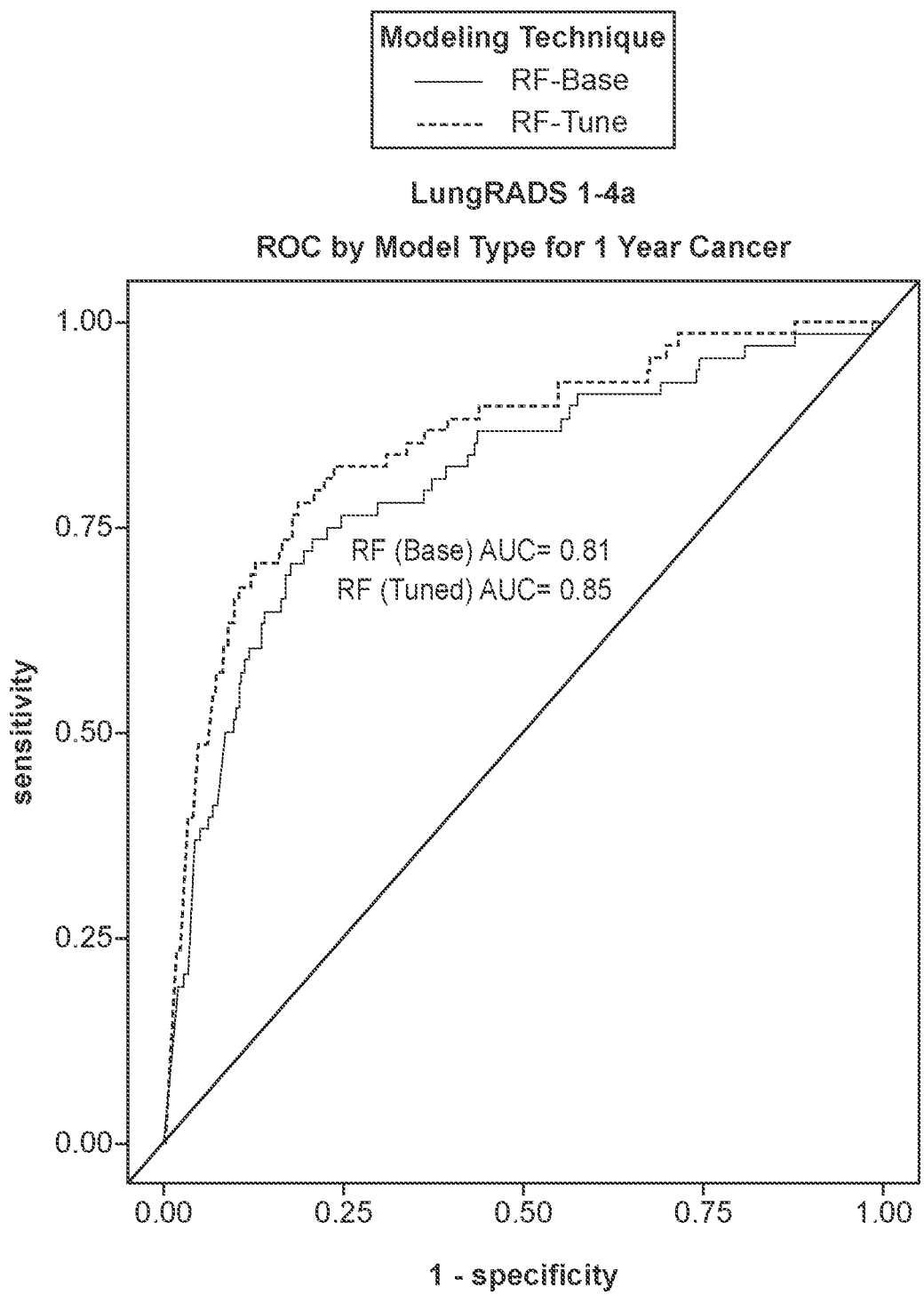
FIG. 6A depicts performance of a risk prediction model for predicting likelihood of cancer within 1 year across Lung-RADS 1-4A patients.
Figure 6B:
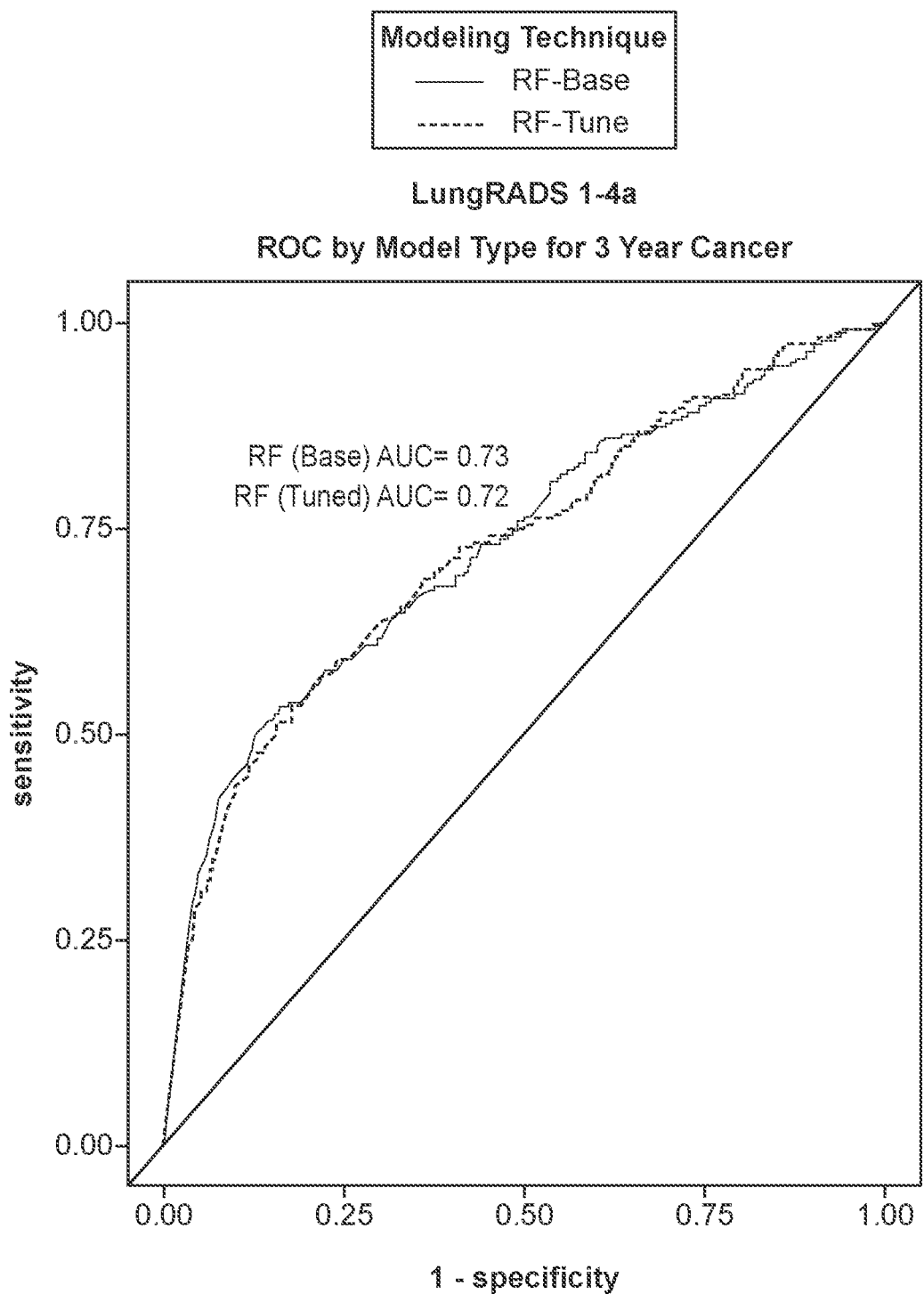
FIG. 6B depicts performance of a risk prediction model for predicting likelihood of cancer within 3 years across Lung-RADS 1-4A patients.

FIG. 6A depicts performance of a risk prediction model for predicting likelihood of cancer within 1 year across Lung-RADS 1-4A patients. The base random forest risk prediction model exhibited an AUC value of 0.81 whereas the tuned random forest risk prediction model exhibited an AUC value of 0.85. FIG. 6B depicts performance of a risk prediction model for predicting likelihood of cancer within 3 years across Lung-RADS 1-4A patients. The base random forest risk prediction model exhibited AUC value of 0.73 whereas the tuned random forest risk prediction model exhibited an AUC value of 0.72. Additionally, Table 7 documents the characteristics of the Lung-RADS 1-4A cohort of patients according to the cancer prediction determined by the 3 year risk prediction model.

Figure 6C:
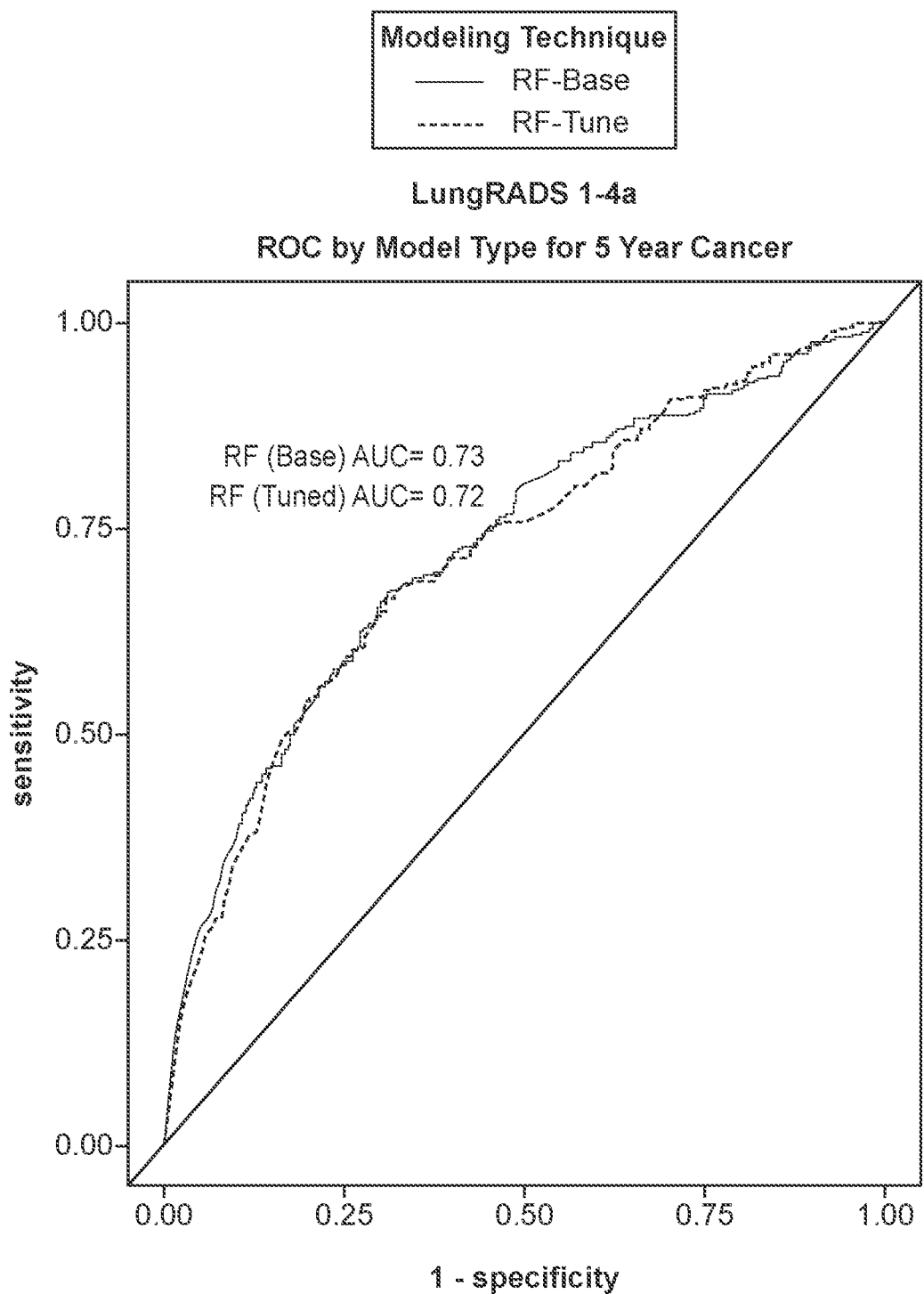
FIG. 6C depicts performance of a risk prediction model for predicting likelihood of cancer within 5 years across Lung-RADS 1-4A patients.

FIG. 6C depicts performance of a risk prediction model for predicting likelihood of cancer within 5 years across Lung-RADS 1-4A patients. The base random forest risk prediction model exhibited AUC value of 0.73 whereas the tuned random forest risk prediction model exhibited an AUC value of 0.72. Altogether, the results of FIGS. 6A-6C indicate that different risk prediction models can be constructed and deployed to predict likelihood of cancer in Lung-RADS 1-4A patient cohorts across different future horizon timepoints. In other words, even though the highest at-risk patients (e.g., Lung-RADS 4B) have been removed, the risk prediction model is still able to accurately predict likelihood of future risk of cancer in the lower risk patients (e.g., Lung-RADS 1-4A).

Figure 6D:
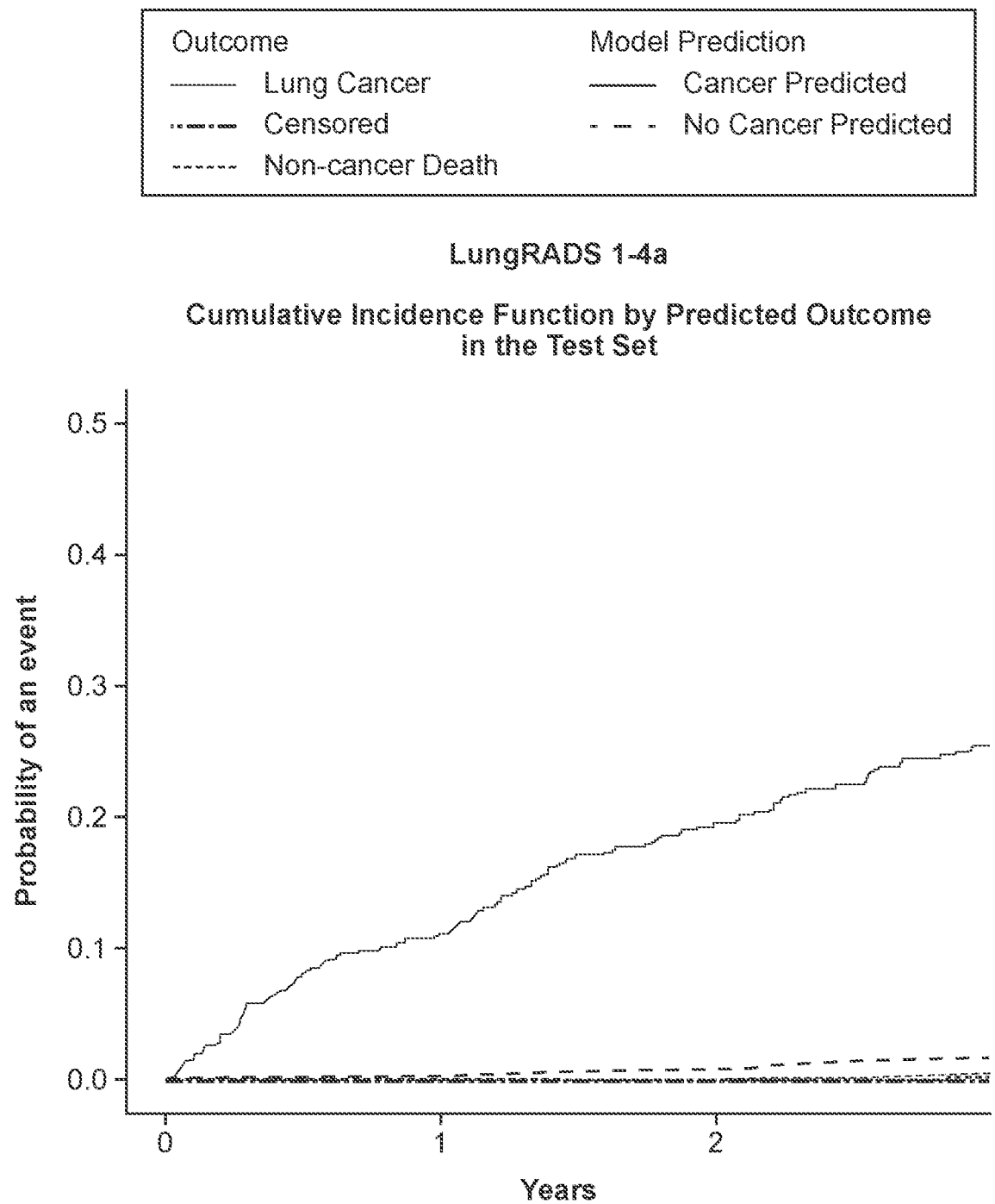
FIG. 6D depicts the 3 year cumulative incidence function across Lung-RADS 1-4A patients.

FIG. 6D depicts the 3 year cumulative incidence function across Lung-RADS 1-4A patients. Here, the risk prediction model predicted cancer for 392 patients and no cancer for the other 6531 patients. Given that the cohort of patients excludes Lung-RADS 4B patients, in comparison to Example 2 (shown in FIG. 5D), the cumulative incidence function for the 392 predicted cancer patients shown in FIG. 6D reflects a lower rate of incidence (e.g., fewer prevalent cancers or fewer cancers that were present at the time of the T0 CT scan) in the early months (e.g., between 0 and 6 months).

Table 8 depicts the enrichment results of the Lung-RADS 1-4A patient cohort using the future cancer predictions from the 1 year, 3 year, or 5 year risk prediction models. Specifically, Table 8 shows the enrichment results of the risk prediction models in comparison to background rate of cancers in the original cohort (referred to in Table 8 as "Null Model"). The application of the risk prediction models significantly improves the cumulative incidence (last column of Table 8).

Specifically, for the 1 year model, the background rate ("Null Model") has a cumulative incidence of 0.98 (e.g., 0.98% of patients in the cohort are diagnosed with cancer within 1 year). Applying the 1 year risk prediction model ("Random Forest") enables patient enrichment, which achieves a cumulative incidence of 7.48 (e.g., 7.48% of patients included in the cohort due to the prediction of the 1 year risk prediction model are diagnosed with cancer within 1 year). Thus, the application of the 1 year risk prediction model achieves a 7.6-fold increase in cumulative incidence.

For the 3 year model, the background rate ("Null Model") has a cumulative incidence of 3.28 (e.g., 3.28% of patients in the cohort are diagnosed with cancer within 3 years). Applying the 3 year risk prediction model ("Random Forest") enables patient enrichment, which achieves a cumulative incidence of 16.84 (e.g., 26.44% of patients included in the cohort due to the prediction of the 3 year risk prediction model are diagnosed with cancer within 3 years). Thus, the application of the 3 year risk prediction model achieves a 5.1-fold increase in cumulative incidence.

For the 5 year model, the background rate ("Null Model") has a cumulative incidence of 4.65 (e.g., 4.65% of patients in the cohort are diagnosed with cancer within 5 years). Applying the 5 year risk prediction model ("Random Forest") enables patient enrichment, which achieves a cumulative incidence of 17.97 (e.g., 17.97% of patients included in the cohort due to the prediction of the 5 year risk prediction model are diagnosed with cancer within 5 years). Thus, the application of the 5 year risk prediction model achieves a 3.9-fold increase in cumulative incidence.

Altogether, Table 8 indicates that the various future risk prediction models can be implemented for enriching patients in the Lung-RADS 1-4A cohort, thereby reducing the number of patients that need to be enrolled in clinical trials.

Example 4: Predicting Future Risk for Lung-RADS 1-3 Patients

Three separate models were constructed using the Lung-RADS 1-3 patients using the methods described in Example 1. Specifically, the first model is a 1 year, Lung-RADS 1-3 risk prediction model, the second model is a 3 year, Lung-RADS 1-3 risk prediction model, and the third model is a 5 year, Lung-RADS 1-3 risk prediction model. For each risk prediction model, a training set (e.g., 50% of the cohort) was used to train the risk prediction model and a testing set (e.g., other 50% of the cohort) was used to test the risk prediction model.

The top 10 important features for each of the 1 year, 3 year, and 5 year risk prediction models is shown in Table 9. Notably, the majority of important features of the 1 year risk prediction model include nodule-specific features whereas the majority of important features of the 3 year and 5 year risk prediction model are objective features (e.g., non-nodule specific features such as features of the body and/or lung parenchyma).

Notably, for the 1 year, Lung-RADS 1-3 prediction model, 2 of the top 3 features in terms of feature importance are nodule specific features. Additionally, 3 of the top 5 features in terms of feature importance for the 1 year, Lung-RADS 1-3 prediction model are non-nodule specific features. Additionally, 7 of the top 10 features in terms of feature importance for the 1 year, Lung-RADS 1-3 prediction model are non-nodule specific features.

For the 3 year, Lung-RADS 1-3 prediction model, 2 of the top 3 features in terms of feature importance are non-nodule specific features. Additionally, 4 of the top 5 features in terms of feature importance for the 3 year, Lung-RADS 1-3 prediction model are non-nodule specific features. Additionally, 8 of the top 10 features in terms of feature importance for the 3 year, Lung-RADS 1-3 prediction model are non-nodule specific features.

For the 5 year, Lung-RADS 1-3 prediction model, 2 of the top 3 features in terms of feature importance are non-nodule specific features. Additionally, 4 of the top 5 features in terms of feature importance for the 5 year, Lung-RADS 1-3 prediction model are non-nodule specific features. Additionally, 9 of the top 10 features in terms of feature importance for the 5 year, Lung-RADS 1-3 prediction model are non-nodule specific features.

Figure 7A:
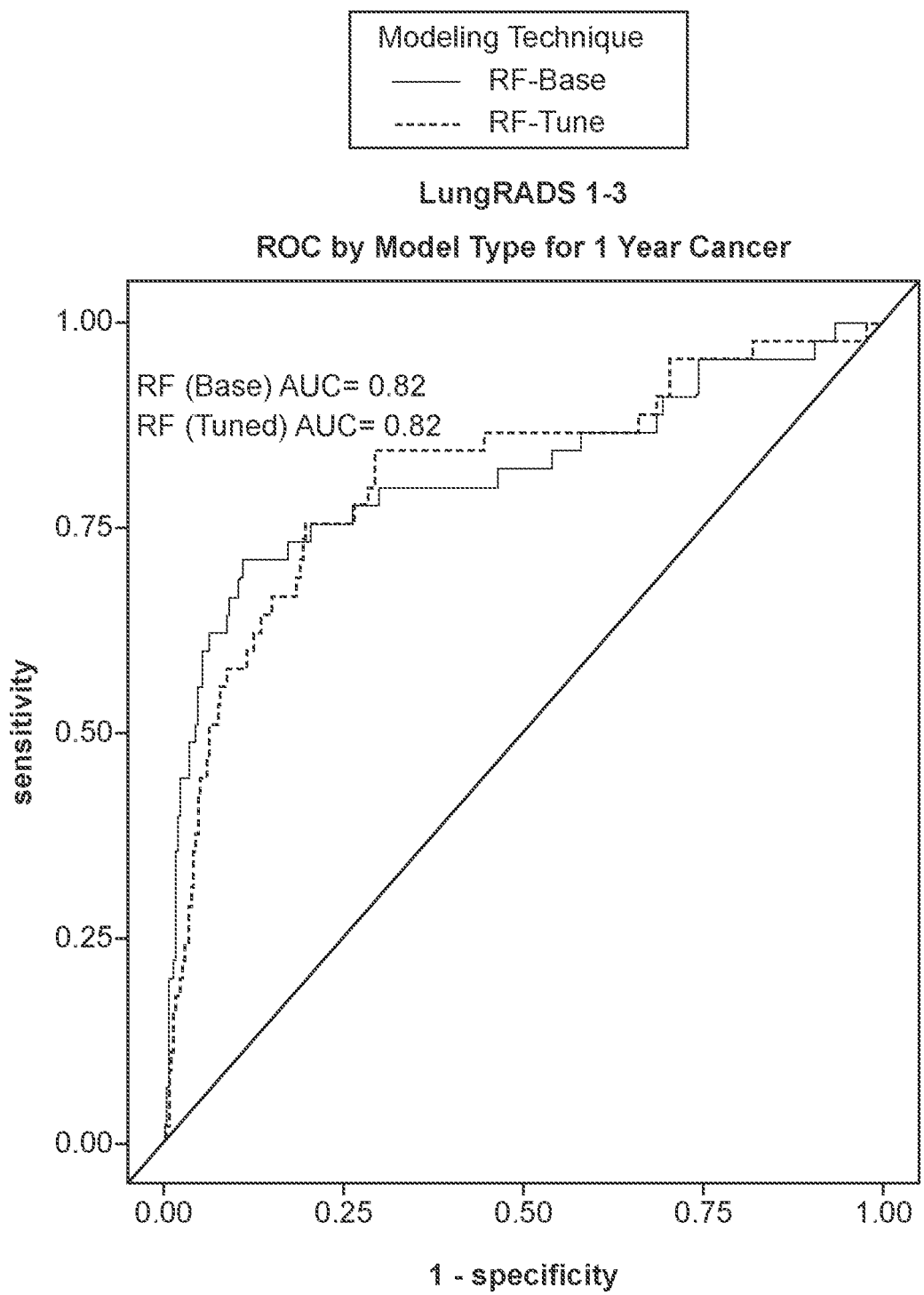
FIG. 7A depicts performance of a risk prediction model for predicting likelihood of cancer within 1 year across Lung-RADS 1-3 patients.
Figure 7B:
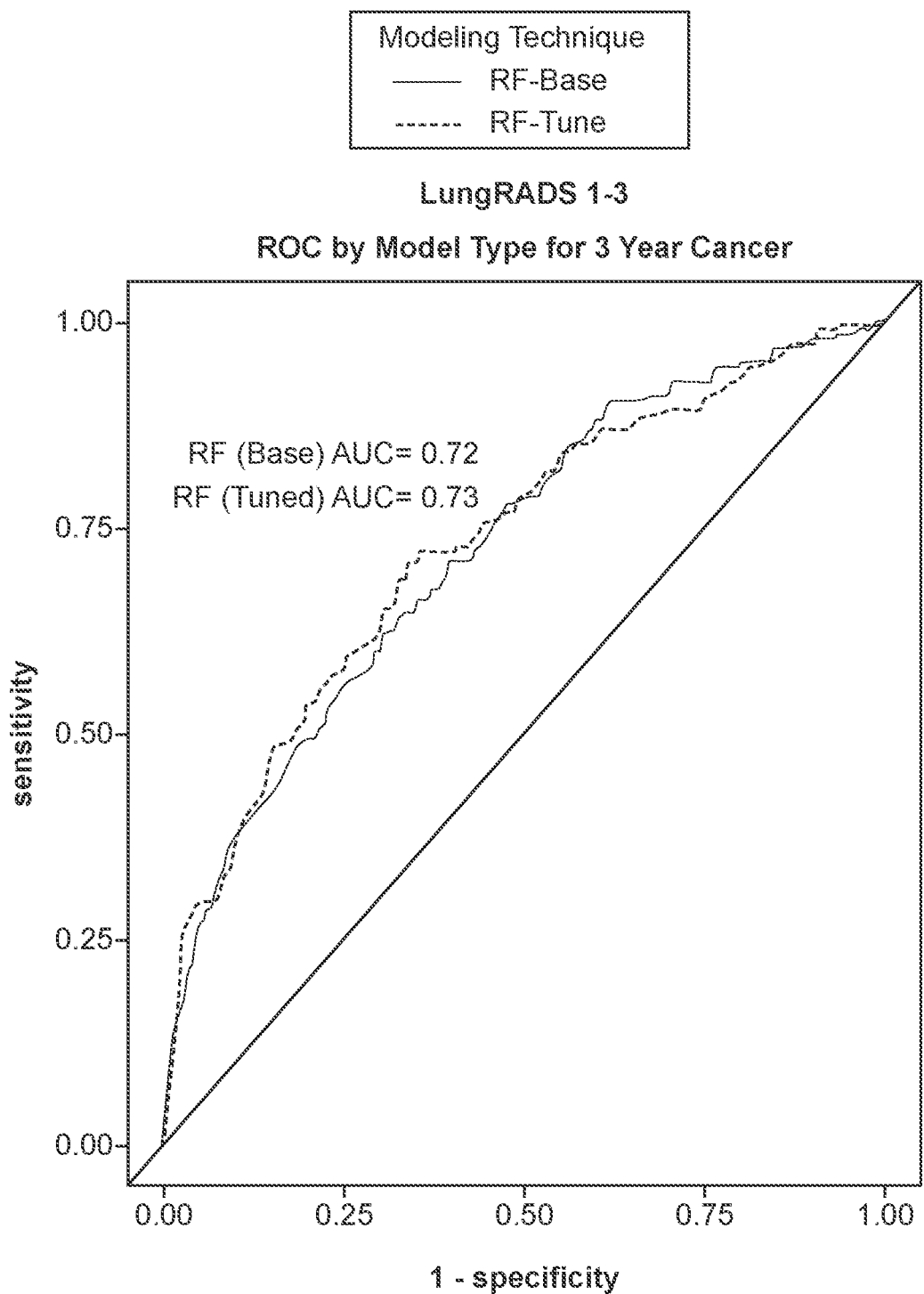
FIG. 7B depicts performance of a risk prediction model for predicting likelihood of cancer within 3 years across Lung-RADS 1-3 patients.

FIG. 7A depicts performance of a risk prediction model for predicting likelihood of cancer within 1 year across Lung-RADS 1-3 patients. The base random forest risk prediction model exhibited an AUC value of 0.82 whereas the tuned random forest risk prediction model exhibited an AUC value of 0.82. FIG. 7B depicts performance of a risk prediction model for predicting likelihood of cancer within 3 years across Lung-RADS 1-3 patients. The base random forest risk prediction model exhibited AUC value of 0.72 whereas the tuned random forest risk prediction model exhibited an AUC value of 0.73. Additionally, Table 10 documents the characteristics of the Lung-RADS 1-3 patient cohort according to the cancer prediction determined by the 3 year risk prediction model.

Figure 7C:
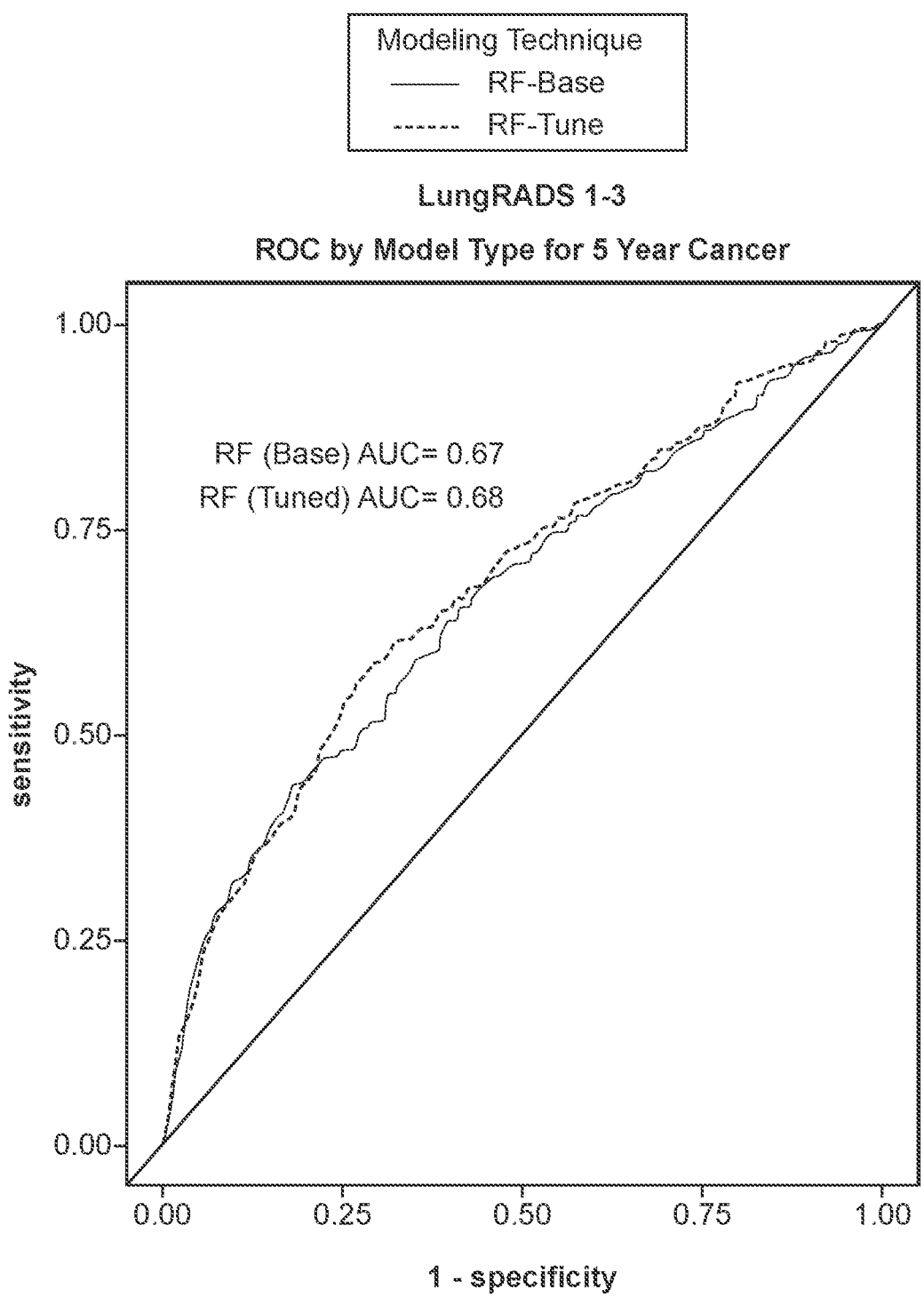
FIG. 7C depicts performance of a risk prediction model for predicting likelihood of cancer within 5 years across Lung-RADS 1-3 patients.

FIG. 7C depicts performance of a risk prediction model for predicting likelihood of cancer within 5 years across Lung-RADS 1-3 patients. The base random forest risk prediction model exhibited AUC value of 0.67 whereas the tuned random forest risk prediction model exhibited an AUC value of 0.68. Altogether, the results of FIGS. 7A-7C indicate that different risk prediction models can be constructed and deployed to predict likelihood of cancer in Lung-RADS 1-3 patient cohorts across different future horizon timepoints. In other words, even though the highest at-risk patients (e.g., Lung-RADS 4A/4B) have been removed, the risk prediction model is still able to accurately predict likelihood of future risk of cancer in the lower risk patients (e.g., Lung-RADS 1-3).

Figure 7D:
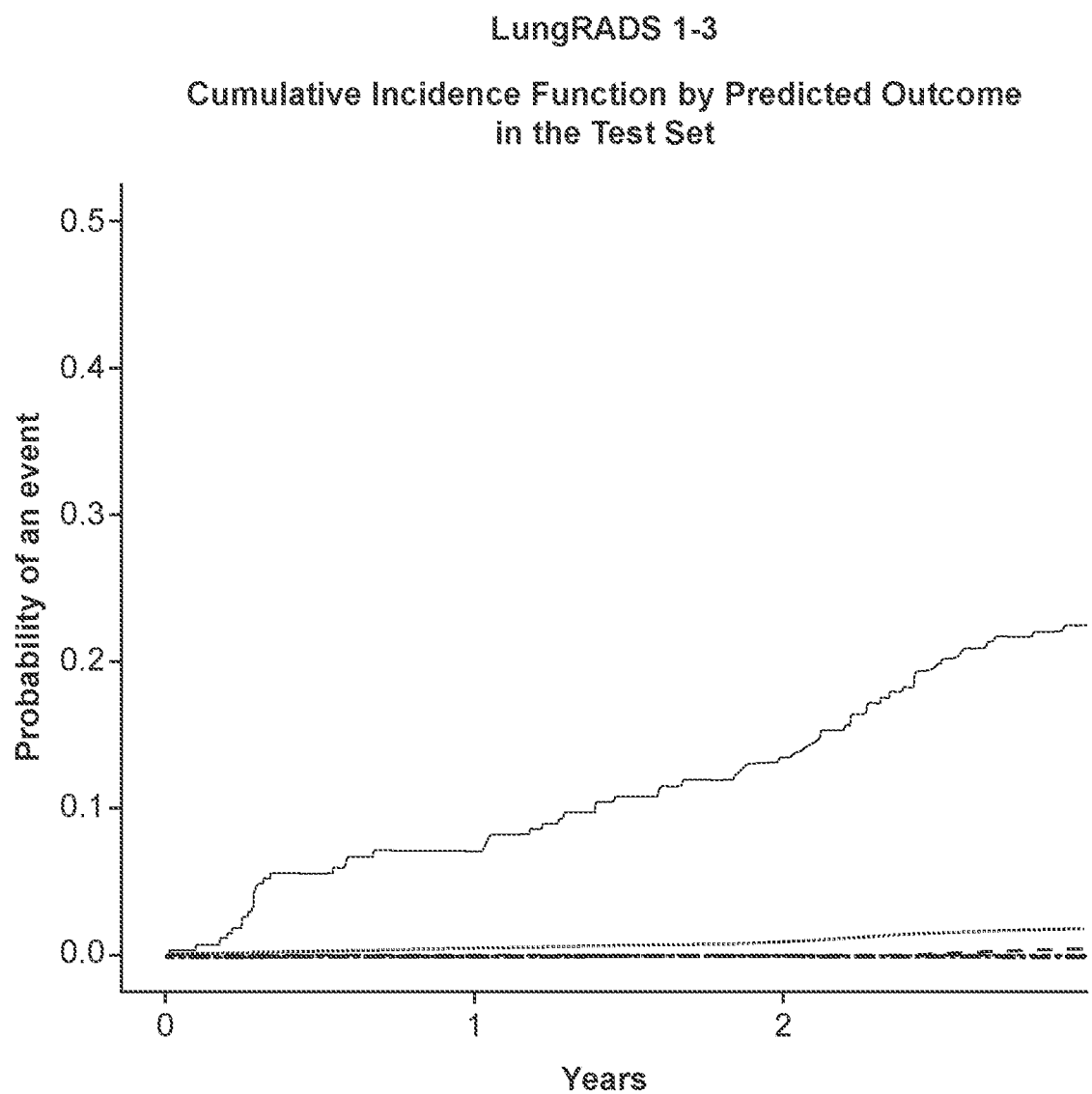
FIG. 7D depicts the 3 year cumulative incidence function across Lung-RADS 1-3 patients.

FIG. 7D depicts the 3 year cumulative incidence function across Lung-RADS 1-3 patients. Here, the risk prediction model predicted cancer for 324 patients and no cancer for the other 6085 patients. Given that the cohort of patients excludes both Lung-RADS 4A and 4B patients, the removal of the 4A and 4B patients manifests as a lower incidence of cancer in the 324 predicted cancer patients in the early months (e.g., between 0 and 6 months) in comparison to predicted cancer patients in Example 2 shown in FIG. 5D. Specifically, the cumulative incidence at the 1 year mark for the Lung-RADS 1-3 patient cohort is less than 0.1 (shown in FIG. 7D) whereas the cumulative incidence at the 1 year mark for the full patient cohort (e.g., Lung-RADS 1-4B) is ~0.2.

Table 11 depicts the enrichment results of the Lung-RADS 1-3 patient cohort using the future cancer predictions from the 1 year, 3 year, or 5 year risk prediction models. Specifically, Table 11 shows the enrichment results of the risk prediction models in comparison to background rate of cancers in the original cohort (referred to in Table 11 as "Null Model"). The application of the risk prediction models significantly improves the cumulative incidence (last column of Table 11).

Specifically, for the 1 year model, the background rate ("Null Model") has a cumulative incidence of 0.70 (e.g., 0.70% of patients in the cohort are diagnosed with cancer within 1 year). Applying the 1 year risk prediction model ("Random Forest") enables patient enrichment, which achieves a cumulative incidence of 6.03 (e.g., 6.03% of patients included in the cohort due to the prediction of the 1 year risk prediction model are diagnosed with cancer within 1 year). Thus, the application of the 1 year risk prediction model achieves a 8.6-fold increase in cumulative incidence.

For the 3 year model, the background rate ("Null Model") has a cumulative incidence of 2.73 (e.g., 2.73% of patients in the cohort are diagnosed with cancer within 3 years). Applying the 3 year risk prediction model ("Random Forest") enables patient enrichment, which achieves a cumulative incidence of 15.43 (e.g., 15.43% of patients included in the cohort due to the prediction of the 3 year risk prediction model are diagnosed with cancer within 3 years). Thus, the application of the 3 year risk prediction model achieves a 5.7-fold increase in cumulative incidence.

For the 5 year model, the background rate ("Null Model") has a cumulative incidence of 4.06 (e.g., 4.06% of patients in the cohort are diagnosed with cancer within 5 years). Applying the 5 year risk prediction model ("Random Forest") enables patient enrichment, which achieves a cumulative incidence of 14.88 (e.g., 14.88% of patients included in the cohort due to the prediction of the 5 year risk prediction model are diagnosed with cancer within 5 years). Thus, the application of the 5 year risk prediction model achieves a 3.7-fold increase in cumulative incidence.

Altogether, Table 11 indicates that the various risk prediction models can be implemented for enriching patients in the Lung-RADS 1-3 cohort, thereby reducing the number of patients that need to be enrolled in clinical trials.

Example 5: Predicting Future Risk for Lung-RADS 1-2 Patients

Three separate models were constructed using the Lung-RADS 1-2 patients using the methods described in Example 1. Specifically, the first model is a 1 year, Lung-RADS 1-2 risk prediction model, the second model is a 3 year risk, Lung-RADS 1-2 prediction model, and the third model is a 5 year risk, Lung-RADS 1-2 prediction model. For each risk prediction model, a training set (e.g., 50% of the cohort) was used to train the risk prediction model and a testing set (e.g., other 50% of the cohort) was used to test the risk prediction model.

The top 10 important features for each of the 1 year, 3 year, and 5 year risk prediction models is shown in Table 12. Notably, the majority of important features of the 1 year risk prediction model include nodule-specific features whereas the majority of important features of the 3 year and 5 year risk prediction model are objective features (e.g., non-nodule specific features such as features of the body and/or lung parenchyma).

Notably, for the 1 year, Lung-RADS 1-2 prediction model, 2 of the top 3 features in terms of feature importance are nodule specific features. Additionally, 3 of the top 5 features in terms of feature importance for the 1 year, Lung-RADS 1-2 prediction model are non-nodule specific features. Additionally, 8 of the top 10 features in terms of feature importance for the 1 year, Lung-RADS 1-2 prediction model are non-nodule specific features.

For the 3 year, Lung-RADS 1-2 prediction model, the top 3 features in terms of feature importance are non-nodule specific features. Additionally, the top 5 features in terms of feature importance for the 3 year, Lung-RADS 1-2 prediction model are non-nodule specific features. Additionally, 8 of the top 10 features in terms of feature importance for the 3 year, Lung-RADS 1-2 prediction model are non-nodule specific features.

For the 5 year, Lung-RADS 1-2 prediction model, the top 3 features in terms of feature importance are non-nodule specific features. Additionally, the top 5 features in terms of feature importance for the 5 year, Lung-RADS 1-2 prediction model are non-nodule specific features. Additionally, the top 10 features in terms of feature importance for the 5 year, Lung-RADS 1-2 prediction model are non-nodule specific features.

Figure 8A:
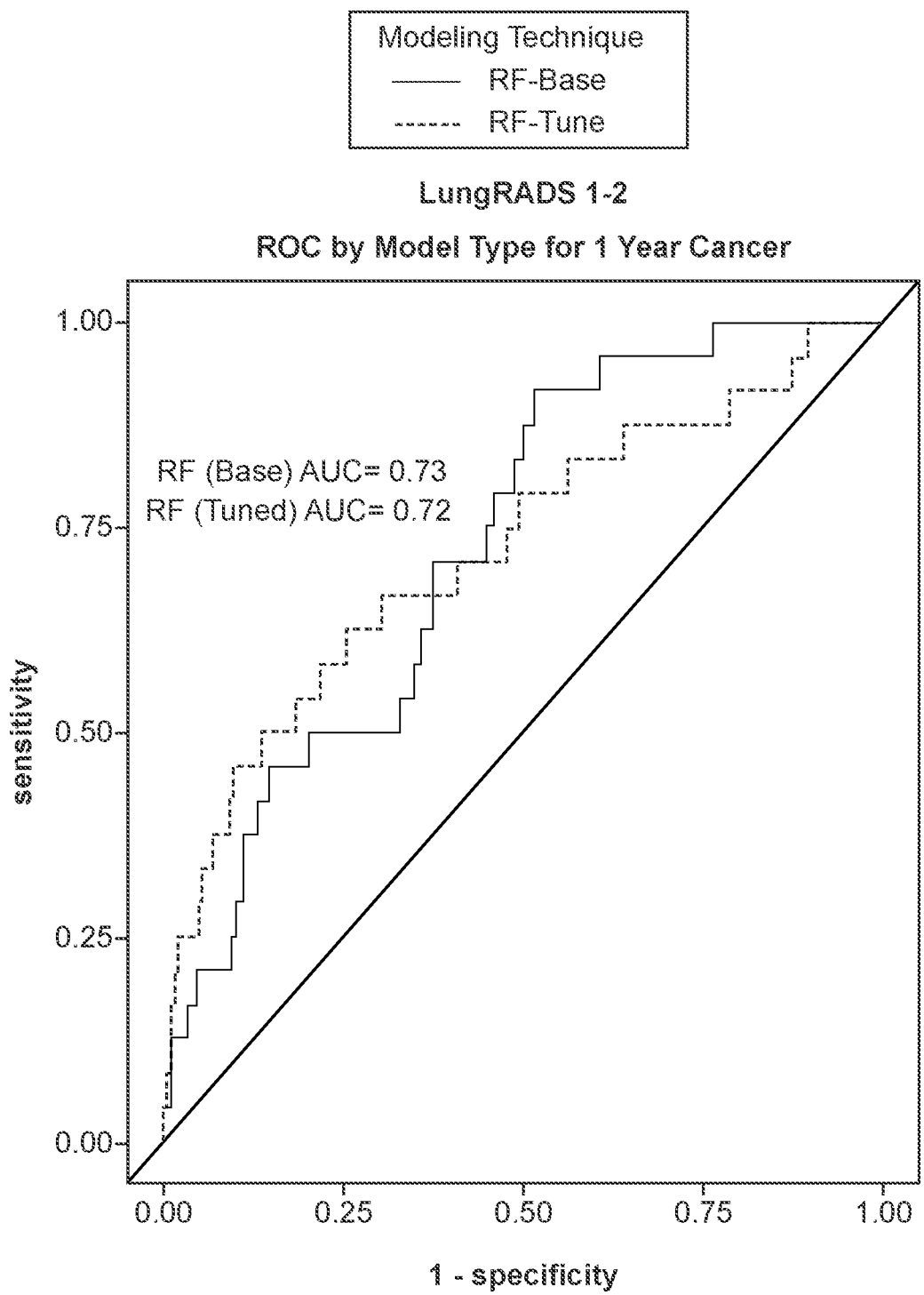
FIG. 8A depicts performance of a risk prediction model for predicting likelihood of cancer within 1 year across Lung-RADS 1-2 patients.
Figure 8B:
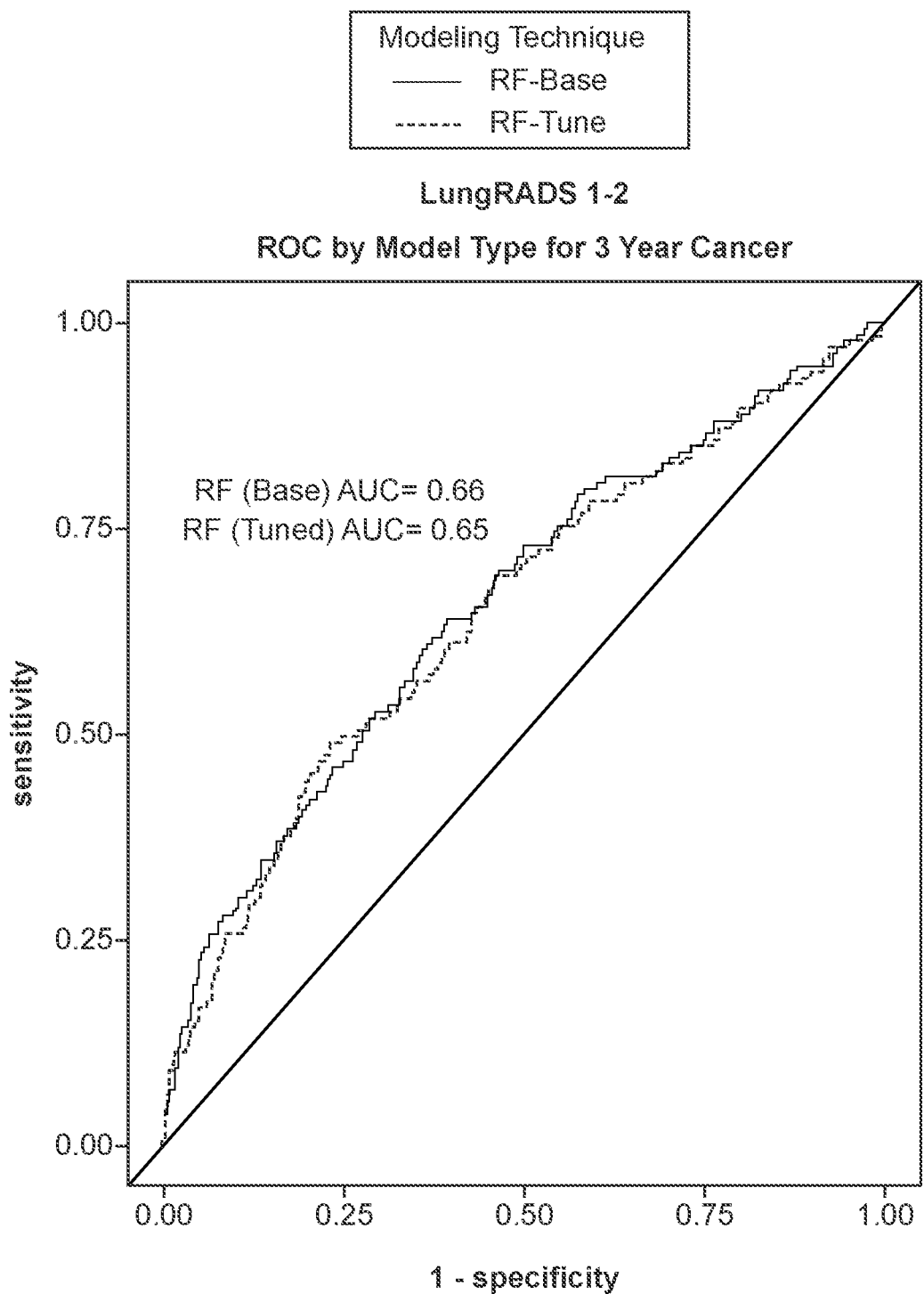
FIG. 8B depicts performance of a risk prediction model for predicting likelihood of cancer within 3 years across Lung-RADS 1-2 patients.

FIG. 8A depicts performance of a risk prediction model for predicting likelihood of cancer within 1 year across Lung-RADS 1-2 patients. The base random forest risk prediction model exhibited an AUC value of 0.73 whereas the tuned random forest risk prediction model exhibited an AUC value of 0.72. FIG. 8B depicts performance of a risk prediction model for predicting likelihood of cancer within 3 years across Lung-RADS 1-2 patients. The base random forest risk prediction model exhibited AUC value of 0.66 whereas the tuned random forest risk prediction model exhibited an AUC value of 0.65. Additionally, Table 13 documents the characteristics of the Lung-RADS 1-2 patient cohort according to the cancer prediction determined by the 3 year risk prediction model.

Figure 8C:
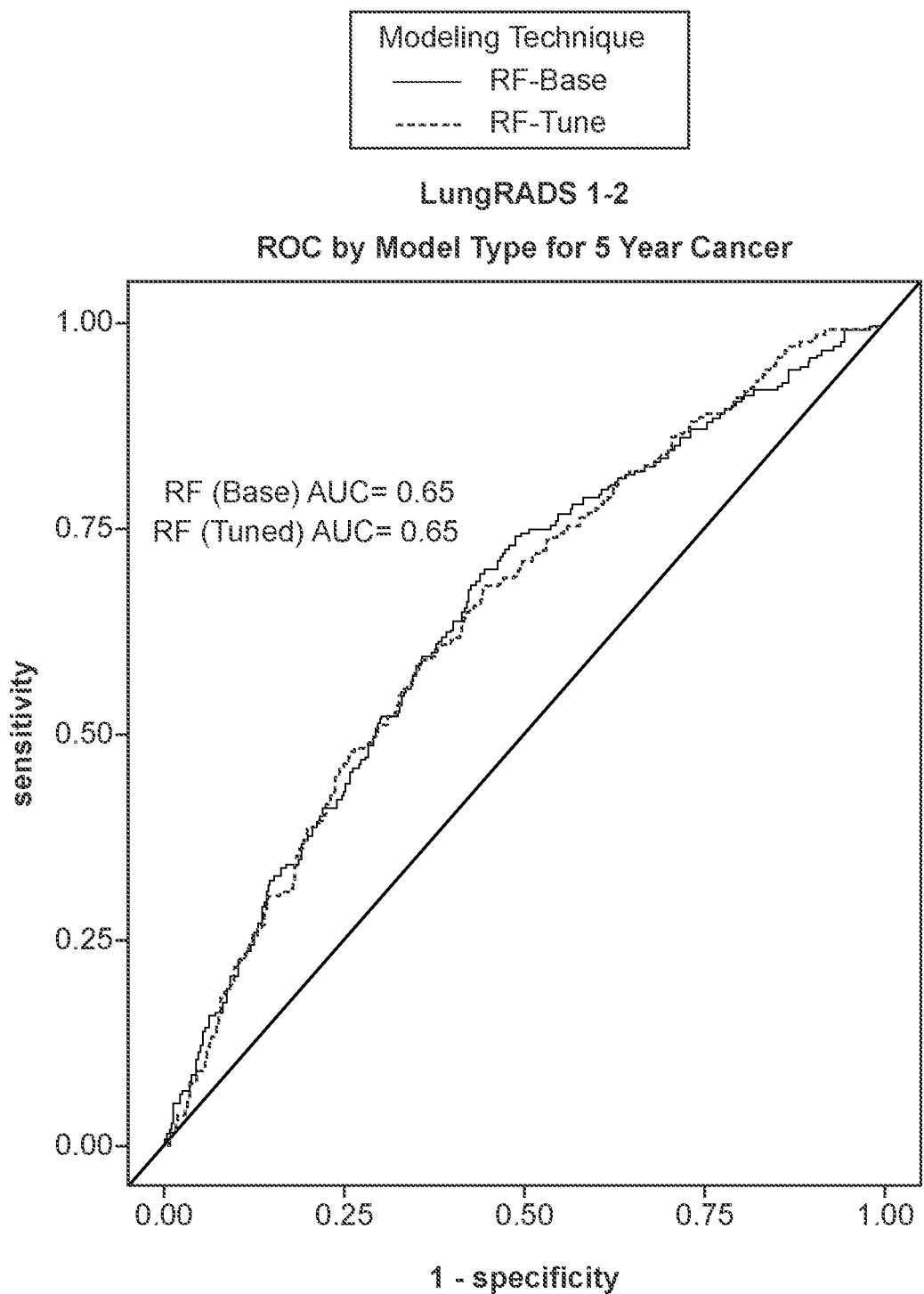
FIG. 8C depicts performance of a risk prediction model for predicting likelihood of cancer within 5 years across Lung-RADS 1-2 patients.

FIG. 8C depicts performance of a risk prediction model for predicting likelihood of cancer within 5 years across Lung-RADS 1-2 patients. The base random forest risk prediction model exhibited AUC value of 0.65 whereas the tuned random forest risk prediction model exhibited an AUC value of 0.65. Altogether, the results of FIGS. 8A-8C indicate that different risk prediction models can be constructed and deployed to predict likelihood of cancer in Lung-RADS 1-2 patient cohorts across different future horizon timepoints. In other words, even though the higher at-risk patients (e.g., Lung-RADS 3/4A/4B) have been removed, the risk prediction model is still able to accurately predict likelihood of future risk of cancer in the low risk patients (e.g., Lung-RADS 1-2). Notably, as shown in Table 1, the prevalence of Lung-RADS 1-2 individuals is ~90% of the population. Thus, risk prediction models that are able to predict likelihood of cancer for Lung-RADS 1-2 patient cohorts is highly valuable as it can be applied to a large majority of the patient population.

Figure 8D:
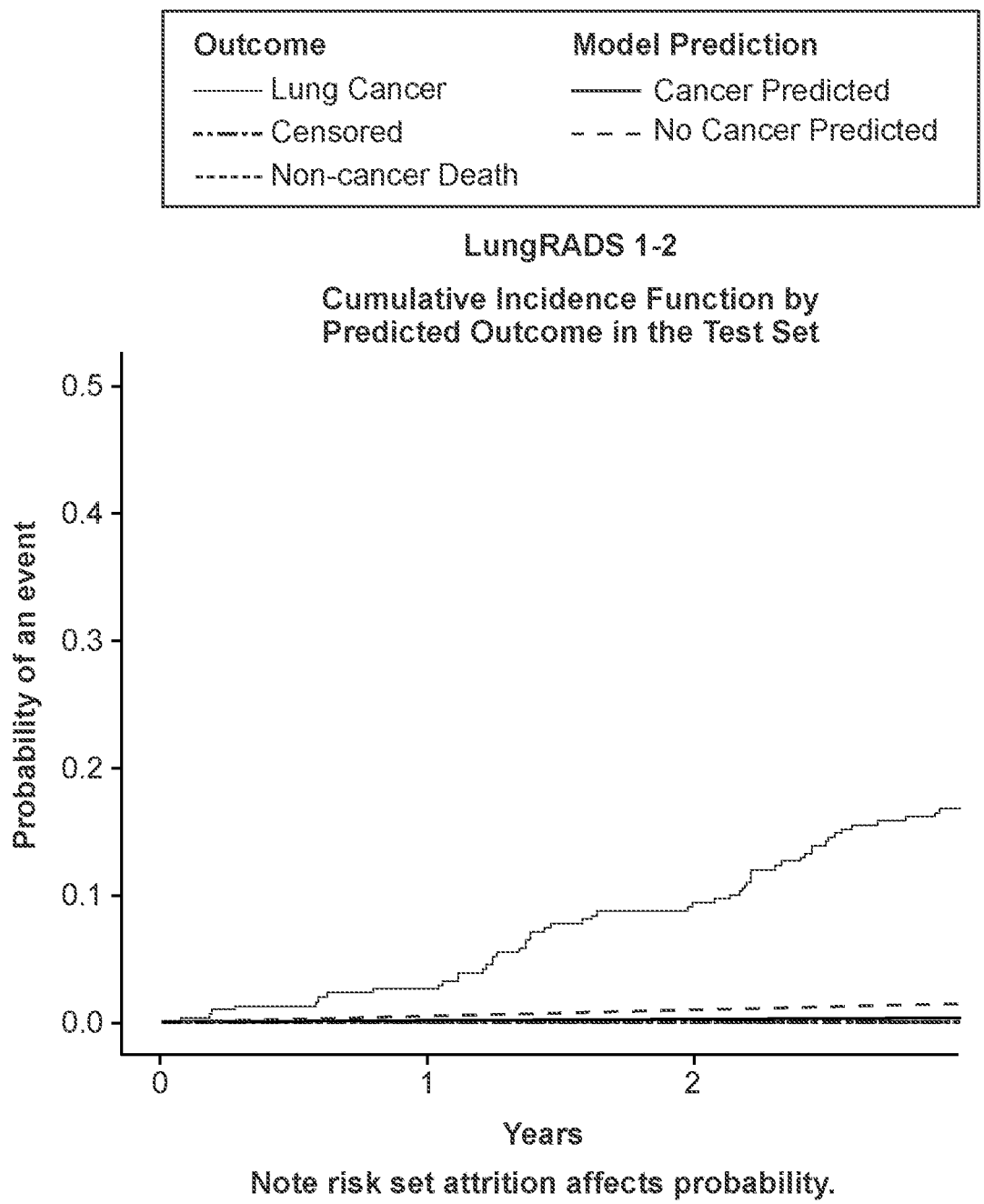
FIG. 8D depicts the 3 year cumulative incidence function across Lung-RADS 1-2 patients.

FIG. 8D depicts the 3 year cumulative incidence function across Lung-RADS 1-2 patients. Here, the risk prediction model predicted cancer for 294 patients and no cancer for the other 5314 patients. Given that the cohort of patients excludes Lung-RADS 3, 4A, and 4B patients, the removal of the Lung-RADS 3, 4A, and 4B patients manifests as a lower incidence of cancer in the 294 predicted cancer patients in the early months (e.g., between 0 and 6 months) in comparison to Example 2 shown in FIG. 5D. Specifically, the cumulative incidence at the 1 year mark for the Lung-RADS 1-2 patient cohort is ~0.025 (shown in FIG. 8D) whereas the cumulative incidence at the 1 year mark for the full patient cohort (e.g., Lung-RADS 1-4B) is ~0.2.

Table 14 depicts the enrichment results of the Lung-RADS 1-2 patient cohort using the future cancer predictions from the 1 year, 3 year, or 5 year risk prediction models. Specifically, Table 14 shows the enrichment results of the risk prediction models in comparison to background rate of cancers in the original cohort (referred to in Table 14 as "Null Model"). The application of the risk prediction models significantly improves the cumulative incidence (last column of Table 14).

Specifically, for the 1 year model, the background rate ("Null Model") has a cumulative incidence of 0.43 (e.g., 0.43% of patients in the cohort are diagnosed with cancer within 1 year). Applying the 1 year risk prediction model ("Random Forest") enables patient enrichment, which achieves a cumulative incidence of 2.37 (e.g., 2.37% of patients included in the cohort due to the prediction of the 1 year risk prediction model are diagnosed with cancer within 1 year). Thus, the application of the 1 year risk prediction model achieves a 5.5-fold increase in cumulative incidence.

For the 3 year model, the background rate ("Null Model") has a cumulative incidence of 2.37 (e.g., 2.37% of patients in the cohort are diagnosed with cancer within 3 years). Applying the 3 year risk prediction model ("Random Forest") enables patient enrichment, which achieves a cumulative incidence of 7.14 (e.g., 7.14% of patients included in the cohort due to the prediction of the 3 year risk prediction model are diagnosed with cancer within 3 years). Thus, the application of the 3 year risk prediction model achieves a 3-fold increase in cumulative incidence.

For the 5 year model, the background rate ("Null Model") has a cumulative incidence of 3.67 (e.g., 3.67% of patients in the cohort are diagnosed with cancer within 5 years). Applying the 5 year risk prediction model ("Random Forest") enables patient enrichment, which achieves a cumulative incidence of 7.06 (e.g., 7.06% of patients included in the cohort due to the prediction of the 5 year risk prediction model are diagnosed with cancer within 5 years). Thus, the application of the 5 year risk prediction model achieves a 1.9-fold increase in cumulative incidence.

Altogether, Table 14 indicates that the various risk prediction models can be implemented for enriching patients in the Lung-RADS 1-2 cohort, thereby reducing the number of patients that need to be enrolled in clinical trials.

Example 6: Predicting Future Risk for Lung-RADS 1 Patients

Three separate models were constructed using the Lung-RADS 1 patients using the methods described in Example 1. Specifically, the first model is a 1 year, Lung-RADS 1 risk prediction model, the second model is a 3 year, Lung-RADS 1 risk prediction model, and the third model is a 5 year risk, Lung-RADS 1 prediction model. For each risk prediction model, a training set (e.g., 50% of the cohort) was used to train the risk prediction model and a testing set (e.g., other 50% of the cohort) was used to test the risk prediction model.

The top 10 important features for each of the 1 year, 3 year, and 5 year risk prediction models is shown in Table 15. Notably, the majority of important features of the 1 year risk prediction model include nodule-specific features whereas the majority of important features of the 3 year and 5 year risk prediction model are objective features (e.g., non-nodule specific features such as features of the body and/or lung parenchyma).

Notably, for the 1 year, Lung-RADS 1 prediction model, the top 3 features in terms of feature importance are non-nodule specific features. Additionally, the top 5 features in terms of feature importance for the 1 year, Lung-RADS 1 prediction model are non-nodule specific features.

For the 3 year, Lung-RADS 1 prediction model, the top 3 features in terms of feature importance are non-nodule specific features. Additionally, the top 5 features in terms of feature importance for the 3 year, Lung-RADS 1 prediction model are non-nodule specific features. Additionally, the top 10 features in terms of feature importance for the 3 year, Lung-RADS 1 prediction model are non-nodule specific features.

For the 5 year, Lung-RADS 1 prediction model, the top 3 features in terms of feature importance are non-nodule specific features. Additionally, the top 5 features in terms of feature importance for the 5 year, Lung-RADS 1 prediction model are non-nodule specific features. Additionally, the top 10 features in terms of feature importance for the 5 year, Lung-RADS 1 prediction model are non-nodule specific features.

Figure 9A:
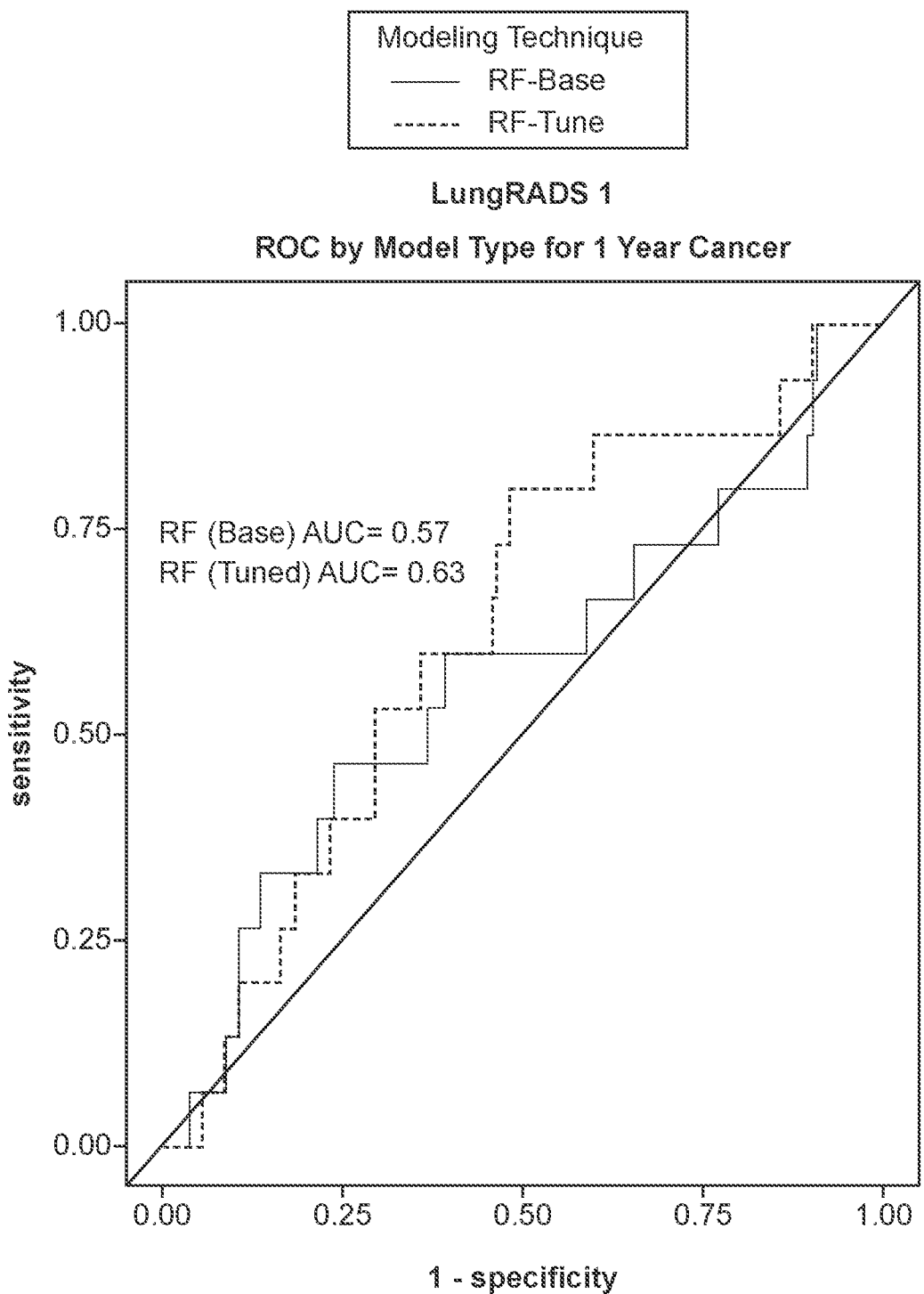
FIG. 9A depicts performance of a risk prediction model for predicting likelihood of cancer within 1 year across Lung-RADS 1 patients.
Figure 9B:
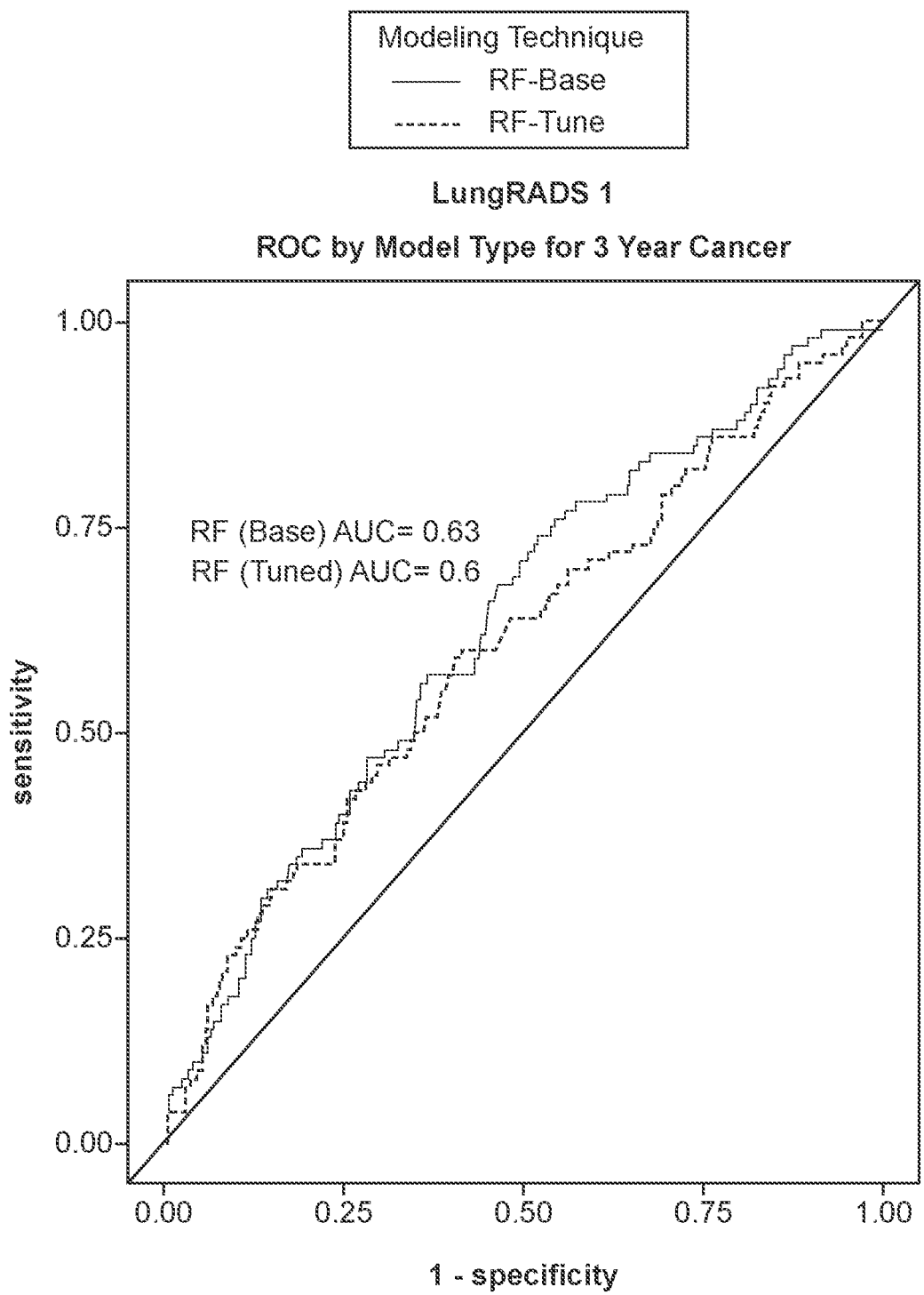
FIG. 9B depicts performance of a risk prediction model for predicting likelihood of cancer within 3 years across Lung-RADS 1 patients.

FIG. 9A depicts performance of a risk prediction model for predicting likelihood of cancer within 1 year across Lung-RADS 1 patients. The base random forest risk prediction model exhibited an AUC value of 0.57 whereas the tuned random forest risk prediction model exhibited an AUC value of 0.63. FIG. 9B depicts performance of a risk prediction model for predicting likelihood of cancer within 3 years across Lung-RADS 1 patients. The base random forest risk prediction model exhibited AUC value of 0.63 whereas the tuned random forest risk prediction model exhibited an AUC value of 0.60. Additionally, Table 16 documents the characteristics of the Lung-RADS 1 patient cohort according to the cancer prediction determined by the 3 year risk prediction model.

Figure 9C:
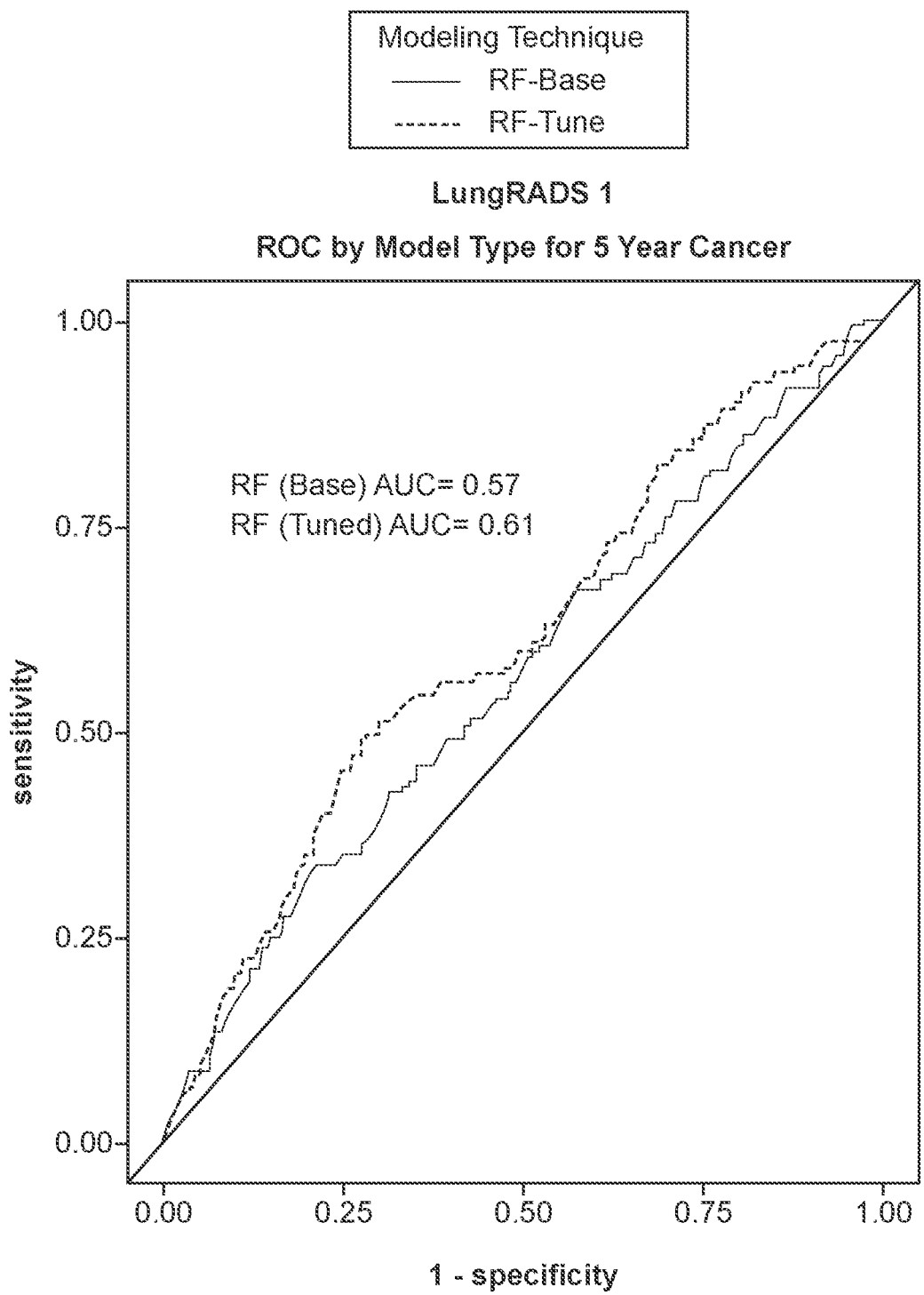
FIG. 9C depicts performance of a risk prediction model for predicting likelihood of cancer within 5 years across Lung-RADS 1 patients.

FIG. 9C depicts performance of a risk prediction model for predicting likelihood of cancer within 5 years across Lung-RADS 1 patients. The base random forest risk prediction model exhibited AUC value of 0.57 whereas the tuned random forest risk prediction model exhibited an AUC value of 0.61. Altogether, the results of FIGS. 9A-9C indicate that different risk prediction models can be constructed and deployed to predict likelihood of cancer in Lung-RADS 1 patient cohorts across different future horizon timepoints.

Figure 9D:
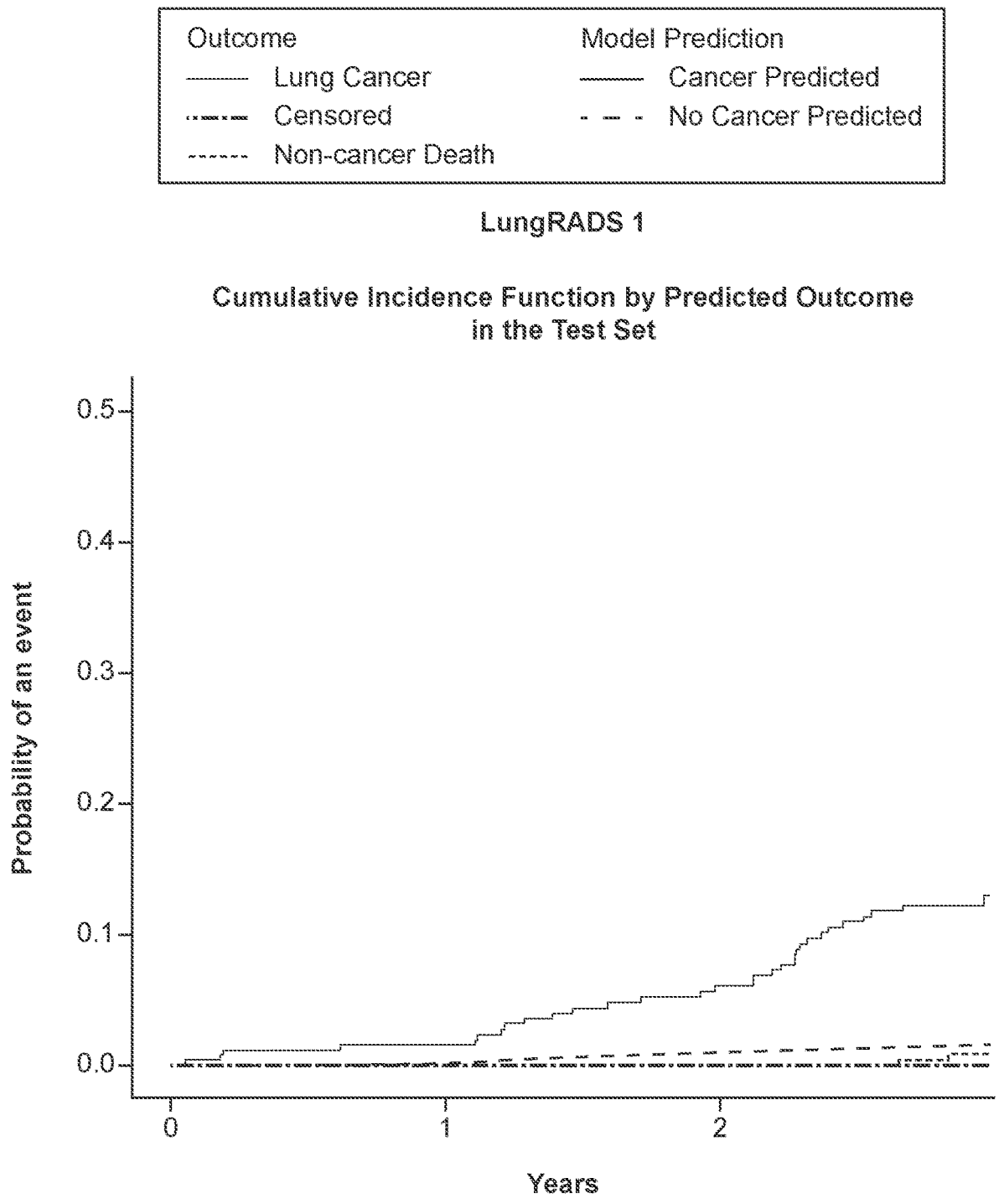
FIG. 9D depicts the 3 year cumulative incidence function across Lung-RADS 1 patients.

FIG. 9D depicts the 3 year cumulative incidence function across Lung-RADS 1 patients. Here, the risk prediction model predicted cancer for 261 patients and no cancer for the other 4077 patients. Here, the cohort of patients only includes Lung-RADS 1 patients, which are patients are at lowest risk of developing cancer in the immediate future. As shown in FIG. 9D, the cumulative incidence at the 1 year mark for the 261 predicted cancer patients of the Lung-RADS 1 patient cohort is less than 0.02 whereas the cumulative incidence at the 1 year mark for the full patient cohort (e.g., Lung-RADS 1-4B) is ~0.2.

Table 17 depicts the enrichment results of the Lung-RADS 1 patient cohort using the future cancer predictions from the 1 year, 3 year, or 5 year risk prediction models. Specifically, Table 17 shows the enrichment results of the risk prediction models in comparison to background rate of cancers in the original cohort (referred to in Table 17 as "Null Model"). The application of the risk prediction models significantly improves the cumulative incidence (last column of Table 17).

Specifically, for the 3 year model, the background rate ("Null Model") has a cumulative incidence of 2.31 (e.g., 2.31% of patients in the cohort are diagnosed with cancer within 3 years). Applying the 3 year risk prediction model ("Random Forest") enables patient enrichment, which achieves a cumulative incidence of 5.36 (e.g., 5.36% of patients included in the cohort due to the prediction of the 3 year risk prediction model are diagnosed with cancer within 3 years). Thus, the application of the 3 year risk prediction model achieves a 2.3-fold increase in cumulative incidence.

For the 5 year model, the background rate ("Null Model") has a cumulative incidence of 3.67 (e.g., 3.67% of patients in the cohort are diagnosed with cancer within 5 years). Applying the 5 year risk prediction model ("Random Forest") enables patient enrichment, which achieves a cumulative incidence of 6.80 (e.g., 6.80% of patients included in the cohort due to the prediction of the 5 year risk prediction model are diagnosed with cancer within 5 years). Thus, the application of the 5 year risk prediction model achieves a 1.9-fold increase in cumulative incidence.

Altogether, Table 17 indicates that the various risk prediction models can be implemented for enriching patients in the Lung-RADS 1 cohort, thereby reducing the number of patients that need to be enrolled in clinical trials.

Example 7: Predicting Future Risk of Cancer for Lung-RADS 1-4B Subjects Using Radiomic Features Two separate models were constructed using the Lung-RADS 1-4B subjects using the methods described in Example 1. Specifically, the first model is a 1 year, Lung-RADS 1-4B risk prediction model and the second model is a 3 year, Lung-RADS 1-4B risk prediction model. For each risk prediction model, a training set (e.g., 50% of the cohort) was used to train the risk prediction model and a testing set (e.g., other 50% of the cohort) was used to test the risk prediction model. The performance of 1 year Lung-RADS 1-4B and 3 year Lung-RADS 1-4B risk prediction models are shown in Table 18.

The top 10 important features (e.g., nodule specific features including radiomic features and non-nodule specific features) for each of the 1 year and 3 year risk prediction models are shown in Table 19. Notably, for the 1 year, Lung-RADS 1-4B prediction model, 2 of the top 3 features in terms of feature importance are nodule specific features. Additionally, 3 of the top 5 features in terms of feature importance for the 1 year, Lung-RADS 1-4B prediction model are nodule specific features.

For the 3 year, Lung-RADS 1-4B prediction model, the top 3 features in terms of feature importance are nodule specific features. Additionally, the top 5 features in terms of feature importance for the 3 year, Lung-RADS 1-4B prediction model are nodule specific features.

Figure 10A:
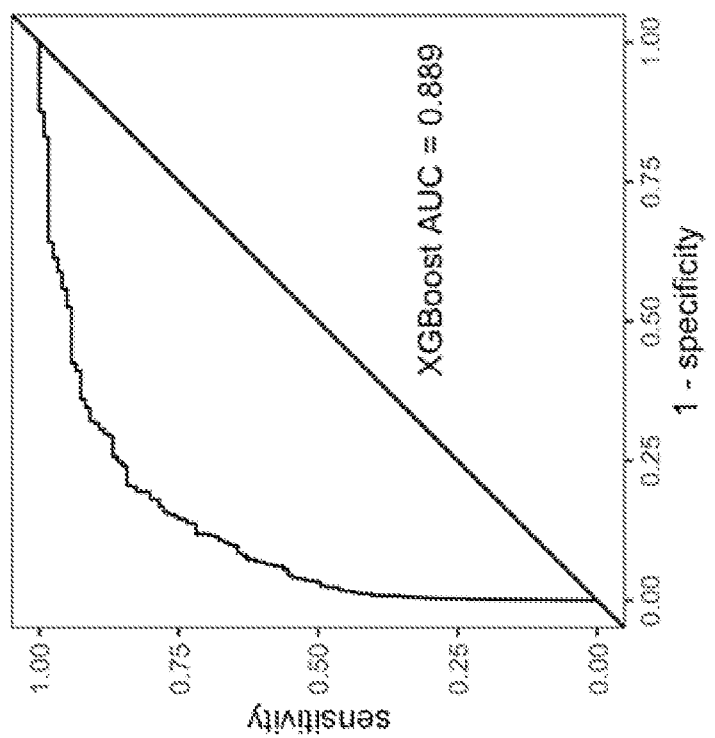
FIG. 10A depicts performance of a risk prediction model incorporating radiomic features for predicting likelihood of cancer within 1 year across Lung-RADS 1-4B patients
Figure 10B:
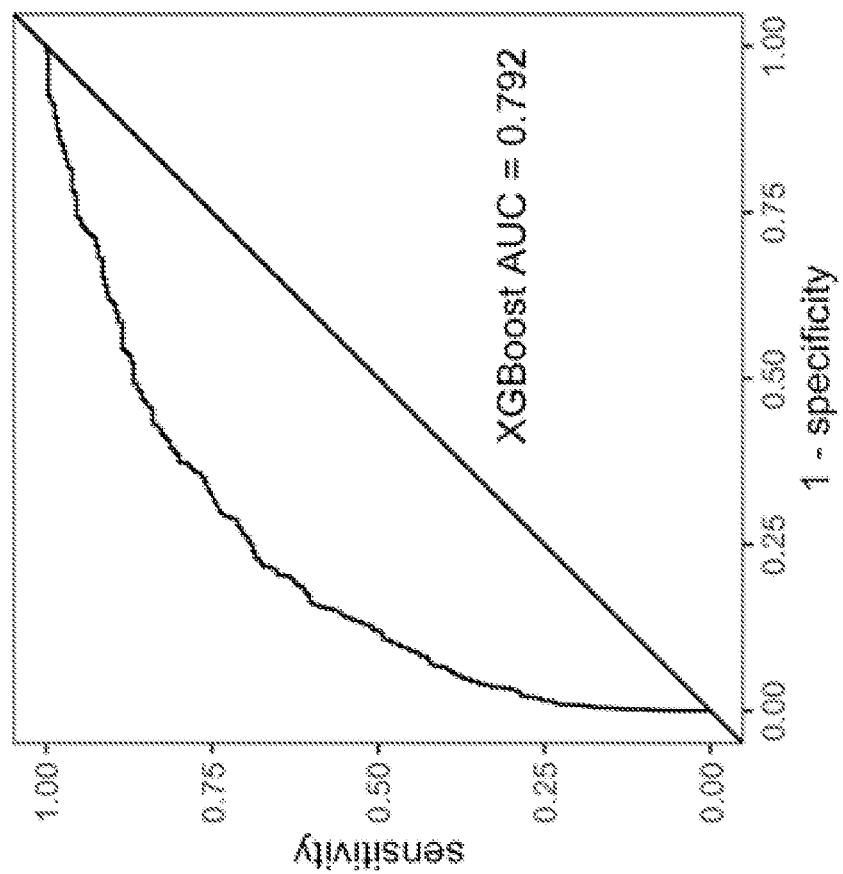
FIG. 10B depicts performance of a risk prediction model incorporating radiomic features for predicting likelihood of cancer within 3 years across Lung-RADS 1-4B patients.

FIG. 10A depicts performance of a risk prediction model incorporating radiomic features for predicting likelihood of cancer within 1 year across Lung-RADS 1-4B patients. The XGboost risk prediction model exhibited an AUC value of 0.889. FIG. 10B depicts performance of a risk prediction model incorporating radiomic features for predicting likelihood of cancer within 3 years across Lung-RADS 1-4B patients. The XGboost risk prediction model exhibited an AUC value of 0.792.

Example 8: Predicting Future Risk of Cancer for Lung-RADS 1-4A Subjects Using Radiomic Features Two separate models were constructed using the Lung-RADS 1-4A subjects using the methods described in Example 1. Specifically, the first model is a 1 year, Lung-RADS 1-4A risk prediction model and the second model is a 3 year, Lung-RADS 1-4A risk prediction model. For each risk prediction model, a training set (e.g., 50% of the cohort) was used to train the risk prediction model and a testing set (e.g., other 50% of the cohort) was used to test the risk prediction model. The performance of 1 year Lung-RADS 1-4A and 3 year Lung-RADS 1-4A risk prediction models are shown in Table 18.

The top 10 important features (e.g., nodule specific features including radiomic features and non-nodule specific features) for each of the 1 year and 3 year risk prediction models are shown in Table 20. Notably, for the 1 year, Lung-RADS 1-4A prediction model, the top 3 features in terms of feature importance are non-nodule specific features. Additionally, 3 of the top 5 features in terms of feature importance for the 1 year, Lung-RADS 1-4A prediction model are non-nodule specific features.

For the 3 year, Lung-RADS 1-4A prediction model, the top 3 features in terms of feature importance are nodule specific features. Additionally, 4 of the top 5 features in terms of feature importance for the 3 year, Lung-RADS 1-4A prediction model are nodule specific features.

Figure 11A:
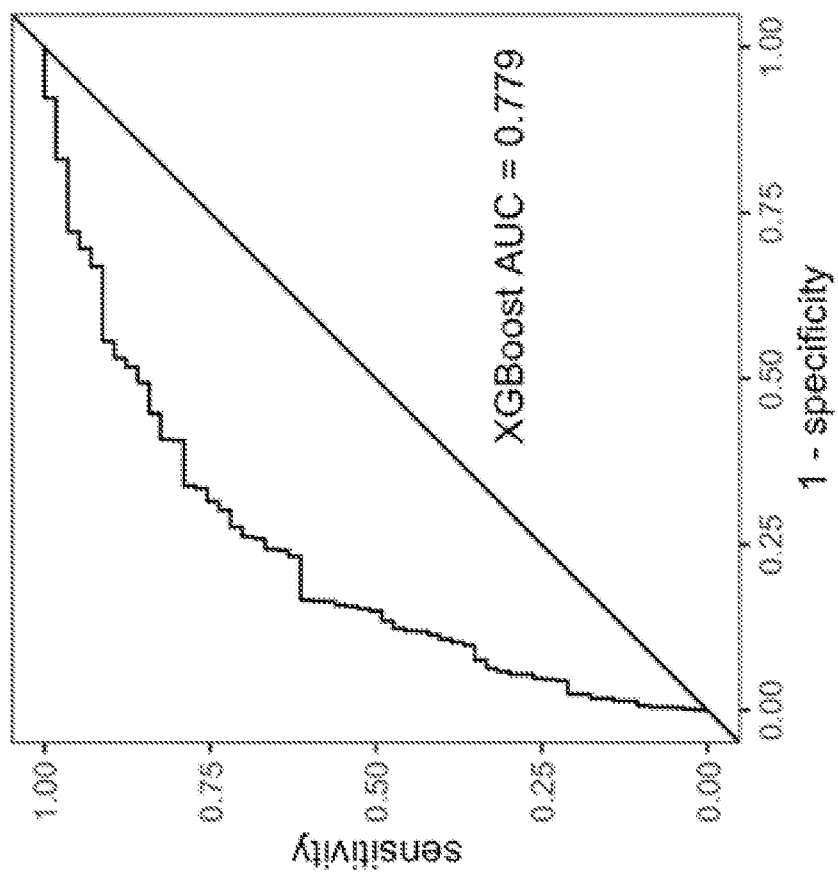
FIG. 11A depicts performance of a risk prediction model incorporating radiomic features for predicting likelihood of cancer within 1 year across Lung-RADS 1-4A patients
Figure 11B:
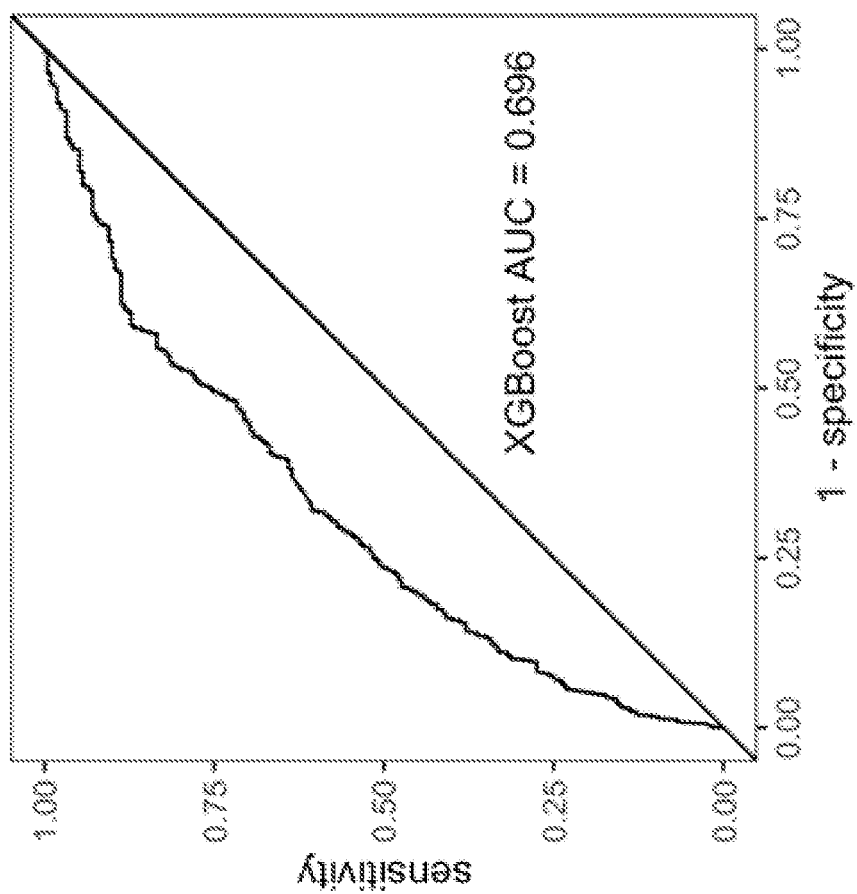
FIG. 11B depicts performance of a risk prediction model incorporating radiomic features for predicting likelihood of cancer within 3 years across Lung-RADS 1-4A patients.

FIG. 11A depicts performance of a risk prediction model incorporating radiomic features for predicting likelihood of cancer within 1 year across Lung-RADS 1-4A patients. The XGboost risk prediction model exhibited an AUC value of 0.779. FIG. 11B depicts performance of a risk prediction model incorporating radiomic features for predicting likelihood of cancer within 3 years across Lung-RADS 1-4A patients. The XGboost risk prediction model exhibited an AUC value of 0.696.

Example 9: Predicting Future Risk of Cancer for Lung-RADS 1-3 Subjects Using Radiomic Features Two separate models were constructed using the Lung-RADS 1-3 subjects using the methods described in Example 1. Specifically, the first model is a 1 year, Lung-RADS 1-3 risk prediction model and the second model is a 3 year, Lung-RADS 1-3 risk prediction model. For each risk prediction model, a training set (e.g., 50% of the cohort) was used to train the risk prediction model and a testing set (e.g., other 50% of the cohort) was used to test the risk prediction model. The performance of 1 year Lung-RADS 1-3 and 3 year Lung-RADS 1-3 risk prediction models are shown in Table 18.

The top 10 important features (e.g., nodule specific features including radiomic features and non-nodule specific features) for each of the 1 year and 3 year risk prediction models are shown in Table 21. Notably, for the 1 year, Lung-RADS 1-3 prediction model, the top 3 features in terms of feature importance are non-nodule specific features. Additionally, 3 of the top 5 features in terms of feature importance for the 1 year, Lung-RADS 1-3 prediction model are non-nodule specific features.

For the 3 year, Lung-RADS 1-3 prediction model, 2 of the top 3 features in terms of feature importance are non-nodule specific features. Additionally, 3 of the top 5 features in terms of feature importance for the 3 year, Lung-RADS 1-3 prediction model are non-nodule specific features.

Figure 12A:
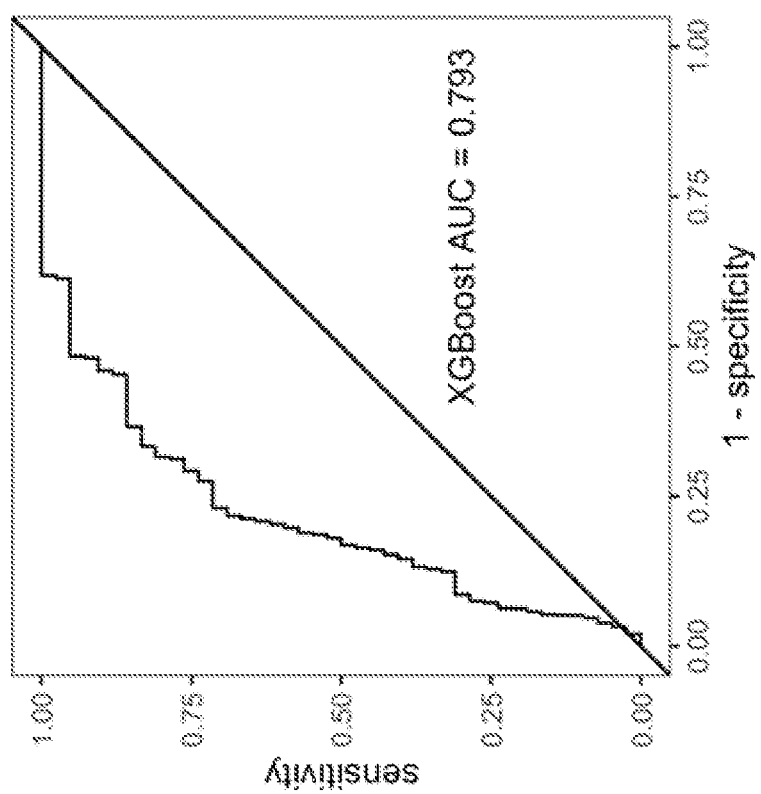
FIG. 12A depicts performance of a risk prediction model incorporating radiomic features for predicting likelihood of cancer within 1 year across Lung-RADS 1-3 patients
Figure 12B:
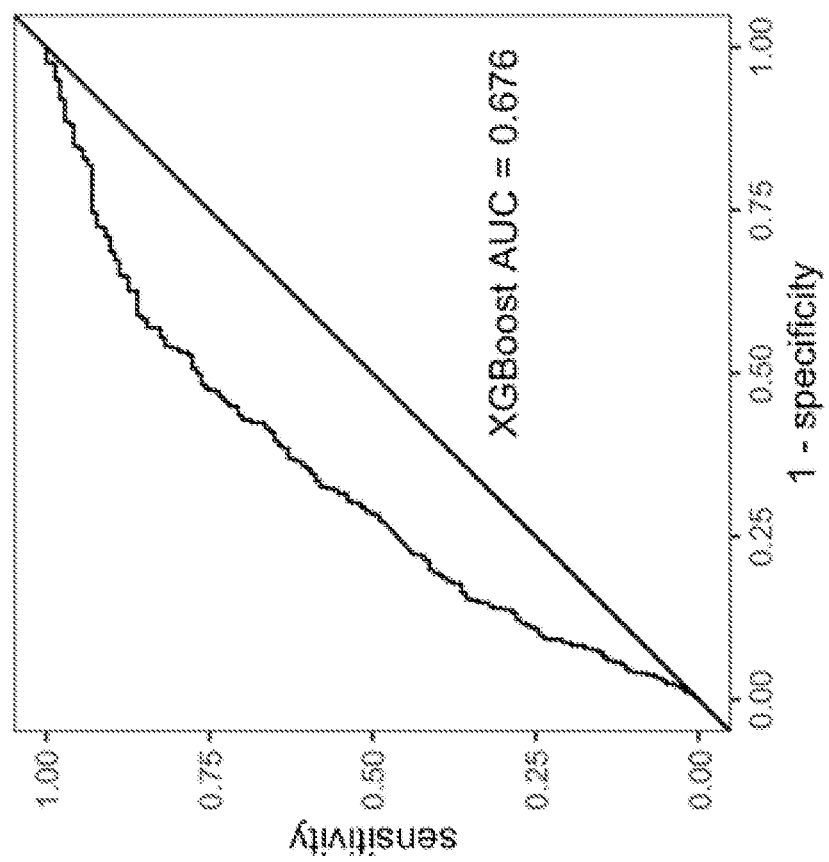
FIG. 12B depicts performance of a risk prediction model incorporating radiomic features for predicting likelihood of cancer within 3 years across Lung-RADS 1-3 patients.

FIG. 12A depicts performance of a risk prediction model incorporating radiomic features for predicting likelihood of cancer within 1 year across Lung-RADS 1-3 patients. The XGboost risk prediction model exhibited an AUC value of 0.793. FIG. 12B depicts performance of a risk prediction model incorporating radiomic features for predicting likelihood of cancer within 3 years across Lung-RADS 1-3 patients. The XGboost risk prediction model exhibited an AUC value of 0.676.

Example 10: Predicting Future Risk of Cancer for Lung-RADS 2-4B Subjects Using Radiomic Features Two separate models were constructed using the Lung-RADS 2-4B subjects using the methods described in Example 1. Specifically, the first model is a 1 year, Lung-RADS 2-4B risk prediction model and the second model is a 3 year, Lung-RADS 2-4B risk prediction model. For each risk prediction model, a training set (e.g., 50% of the cohort) was used to train the risk prediction model and a testing set (e.g., other 50% of the cohort) was used to test the risk prediction model. The performance of 1 year Lung-RADS 2-4B and 3 year Lung-RADS 2-4B risk prediction models are shown in Table 18.

The top 10 important features (e.g., nodule specific features including radiomic features and non-nodule specific features) for each of the 1 year and 3 year risk prediction models are shown in Table 22. Notably, for the 1 year, Lung-RADS 2-4B prediction model, the top 3 features in terms of feature importance are nodule specific features. Additionally, the top 5 features in terms of feature importance for the 1 year, Lung-RADS 2-4B prediction model are nodule specific features.

For the 3 year, Lung-RADS 2-4B risk prediction model, the top 3 features in terms of feature importance are nodule specific features. Additionally, the top 5 features in terms of feature importance for the 3 year, Lung-RADS 2-4B risk prediction model are nodule specific features.

Figure 13A:
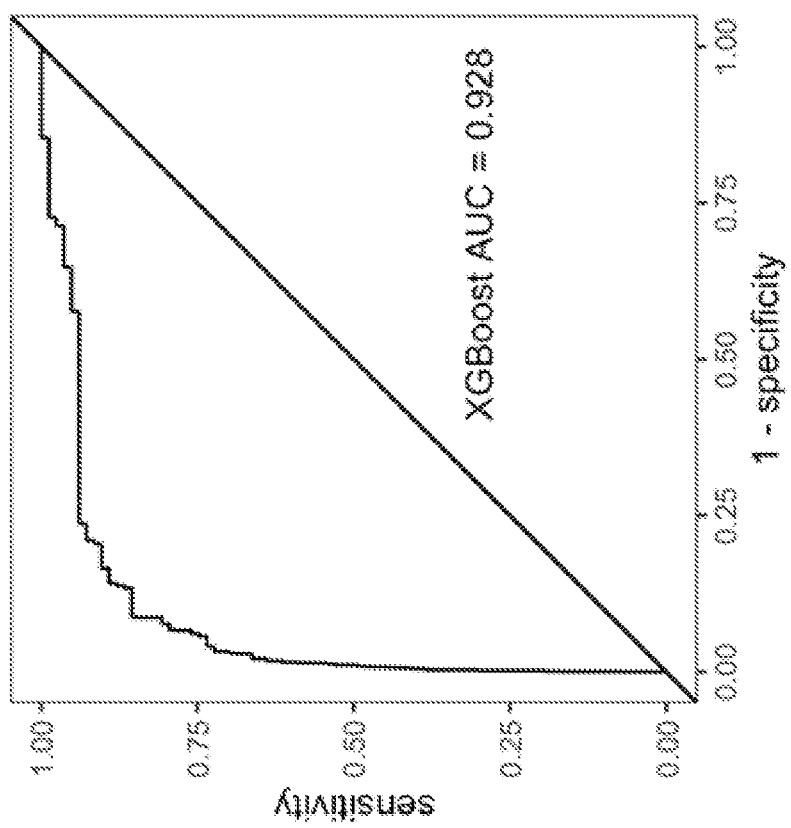
FIG. 13A depicts performance of a risk prediction model incorporating radiomic features for predicting likelihood of cancer within 1 year across Lung-RADS 2-4B patients
Figure 13B:
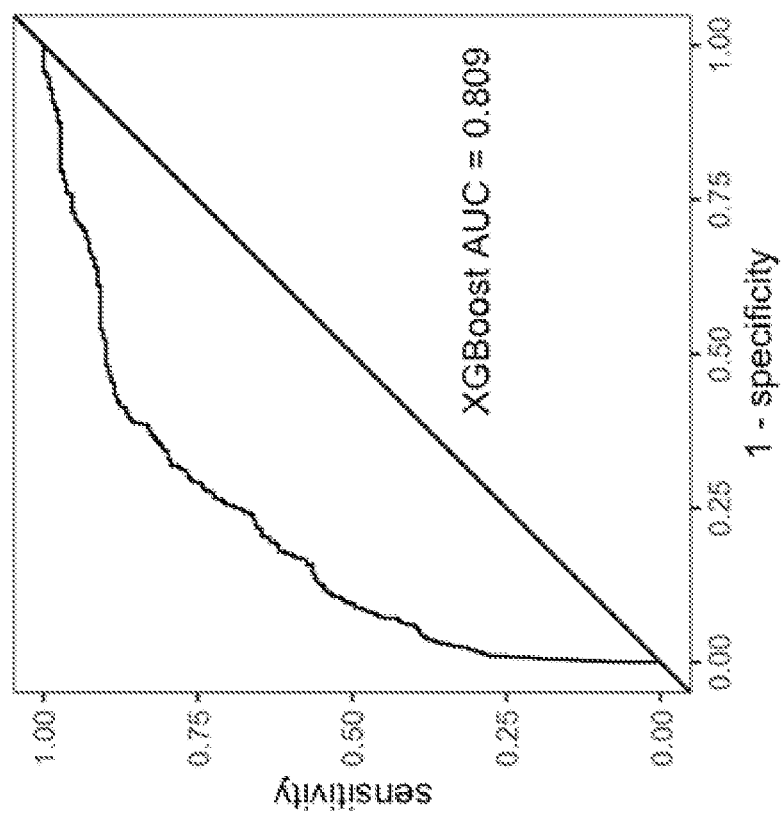
FIG. 13B depicts performance of a risk prediction model incorporating radiomic features for predicting likelihood of cancer within 3 years across Lung-RADS 2-4B patients.

FIG. 13A depicts performance of a risk prediction model incorporating radiomic features for predicting likelihood of cancer within 1 year across Lung-RADS 2-4B patients. The XGboost risk prediction model exhibited an AUC value of 0.928. FIG. 13B depicts performance of a risk prediction model incorporating radiomic features for predicting likelihood of cancer within 3 years across Lung-RADS 2-4B patients. The XGboost risk prediction model exhibited an AUC value of 0.809.

Example 11: Predicting Future Risk of Cancer for Lung-RADS 4A-4B Subjects Using Radiomic Features Two separate models were constructed using the Lung-RADS 4A-4B subjects using the methods described in Example 1. Specifically, the first model is a 1 year, Lung-RADS 4A-4B risk prediction model and the second model is a 3 year, Lung-RADS 4A-4B risk prediction model. For each risk prediction model, a training set (e.g., 50% of the cohort) was used to train the risk prediction model and a testing set (e.g., other 50% of the cohort) was used to test the risk prediction model. The performance of 1 year Lung-RADS 4A-4B and 3 year Lung-RADS 4A-4B risk prediction models are shown in Table 18.

The top 10 important features (e.g., nodule specific features including radiomic features and non-nodule specific features) for each of the 1 year and 3 year risk prediction models are shown in Table 23. Notably, for the 1 year, Lung-RADS 4A-4B prediction model, the top 3 features in terms of feature importance are nodule specific features. Additionally, the top 5 features in terms of feature importance for the 1 year, Lung-RADS 4A-4B prediction model are nodule specific features.

For the 3 year, Lung-RADS 4A-4B risk prediction model, the top 3 features in terms of feature importance are nodule specific features. Additionally, the top 5 features in terms of feature importance for the 3 year, Lung-RADS 4A-4B risk prediction model are nodule specific features.

Figure 14A:
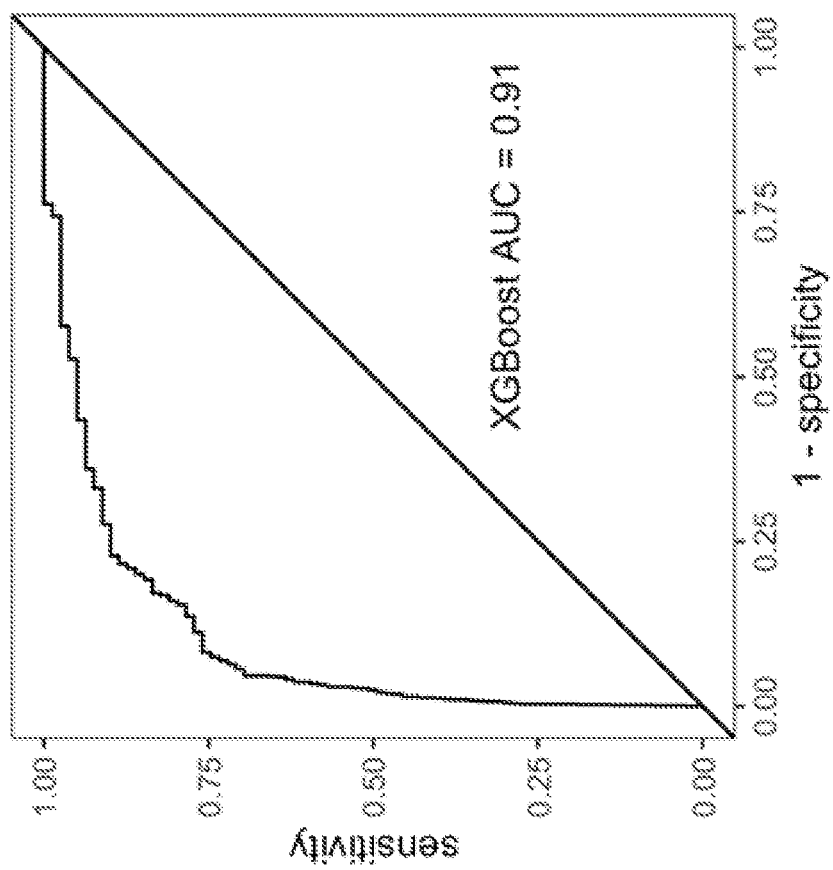
FIG. 14A depicts performance of a risk prediction model incorporating radiomic features for predicting likelihood of cancer within 1 year across Lung-RADS 4A-4B patients
Figure 14B:
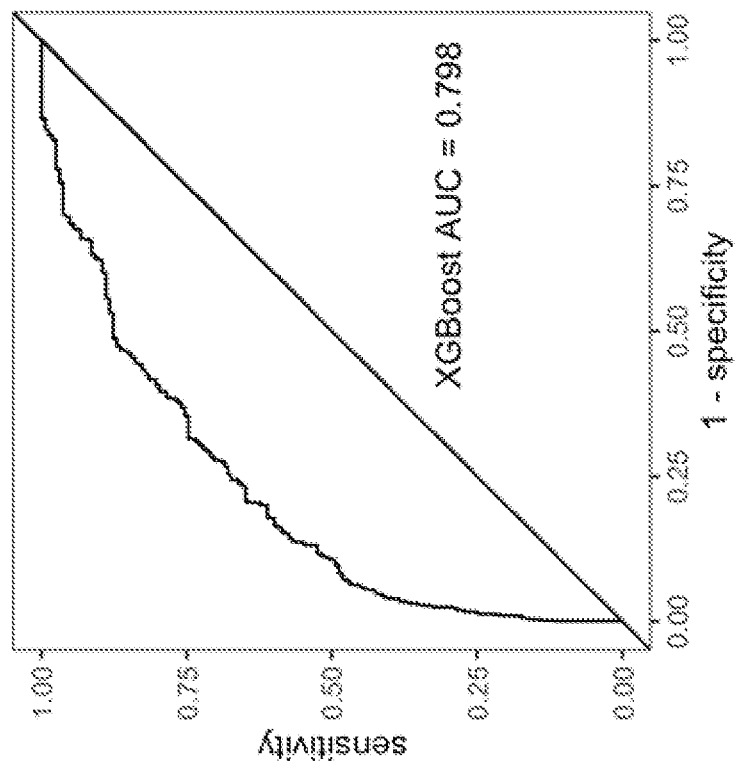
FIG. 14B depicts performance of a risk prediction model incorporating radiomic features for predicting likelihood of cancer within 3 years across Lung-RADS 4A-4B patients.

FIG. 14A depicts performance of a risk prediction model incorporating radiomic features for predicting likelihood of cancer within 1 year across Lung-RADS 4A-4B patients. The XGboost risk prediction model exhibited an AUC value of 0.91. FIG. 14B depicts performance of a risk prediction model incorporating radiomic features for predicting likelihood of cancer within 3 years across Lung-RADS 4A-4B patients. The XGboost risk prediction model exhibited an AUC value of 0.798.

Example 12: Additional Examples of Predicting Future Risk of Cancer for Lung-RADS 1-4B Subjects Additional models are constructed using Lung-RADS 1-4B subjects using the methods described in Example 1. For example, such models can incorporate the non-nodule features described in Example 1 as well as nodule specific features (such as radiomic features) described in Example 1.

The additional models are either random forest models or gradient boosted models. Specifically, a first model is a 6 month, Lung-RADS 1-4B risk prediction model, a second model is a 1.5 year, Lung-RADS 1-4B risk prediction model, a third model is a 2.5 year, Lung-RADS 1-4B risk prediction model, a fourth model is a 4 year, Lung-RADS 1-4B risk prediction model, a fifth model is a 4.5 year, Lung-RADS 1-4B risk prediction model, a sixth model is a 5.5 year, Lung-RADS 1-4B risk prediction model, a seventh model is a 6 year, Lung-RADS 1-4B risk prediction model, an eight model is a 7 year, Lung-RADS 1-4B risk prediction model, a ninth model is a 8 year, Lung-RADS 1-4B risk prediction model, a tenth model is a 9 year, Lung-RADS 1-4B risk prediction model, an eleventh model is a 10 year, Lung-RADS 1-4B risk prediction model, a twelfth model is a 11 year, Lung-RADS 1-4B risk prediction model, a thirteenth model is a 11 year, Lung-RADS 1-4B risk prediction model, a fourteenth model is a 12 year, Lung-RADS 1-4B risk prediction model, a fifteenth model is a 13 year, Lung-RADS 1-4B risk prediction model, a sixteenth model is a 14 year, Lung-RADS 1-4B risk prediction model, a seventeenth model is a 15 year, Lung-RADS 1-4B risk prediction model, an eighteenth model is a 16 year, Lung-RADS 1-4B risk prediction model, a nineteenth model is a 17 year, Lung-RADS 1-4B risk prediction model, a twentieth model is a 18 year, Lung-RADS 1-4B risk prediction model, a twenty-first model is a 19 year, Lung-RADS 1-4B risk prediction model, and a twenty-second model is a 20 year, Lung-RADS 1-4B risk prediction model.

The additional models exhibit an AUC value of at least 0.55. At least one of the additional models exhibits an AUC value of at least 0.60. At least one of the additional models exhibits an AUC value of at least 0.65. At least one of the additional models exhibits an AUC value of at least 0.70. At least one of the additional models exhibits an AUC value of at least 0.75. At least one of the additional models exhibits an AUC value of at least 0.80.

Example 13: Additional Examples of Predicting Future Risk of Cancer for Lung-RADS 1-4A Subjects Additional models are constructed using Lung-RADS 1-4A subjects using the methods described in Example 1. For example, such models can incorporate the non-nodule features described in Example 1 as well as nodule specific features (such as radiomic features) described in Example 1.

The additional models are either random forest models or gradient boosted models. Specifically, a first model is a 6 month, Lung-RADS 1-4A risk prediction model, a second model is a 1.5 year, Lung-RADS 1-4A risk prediction model, a third model is a 2.5 year, Lung-RADS 1-4A risk prediction model, a fourth model is a 4 year, Lung-RADS 1-4A risk prediction model, a fifth model is a 4.5 year, Lung-RADS 1-4A risk prediction model, a sixth model is a 5.5 year, Lung-RADS 1-4A risk prediction model, a seventh model is a 6 year, Lung-RADS 1-4A risk prediction model, an eight model is a 7 year, Lung-RADS 1-4A risk prediction model, a ninth model is a 8 year, Lung-RADS 1-4A risk prediction model, a tenth model is a 9 year, Lung-RADS 1-4A risk prediction model, an eleventh model is a 10 year, Lung-RADS 1-4A risk prediction model, a twelfth model is a 11 year, Lung-RADS 1-4A risk prediction model, a thirteenth model is a 11 year, Lung-RADS 1-4A risk prediction model, a fourteenth model is a 12 year, Lung-RADS 1-4A risk prediction model, a fifteenth model is a 13 year, Lung-RADS 1-4A risk prediction model, a sixteenth model is a 14 year, Lung-RADS 1-4A risk prediction model, a seventeenth model is a 15 year, Lung-RADS 1-4A risk prediction model, an eighteenth model is a 16 year, Lung-RADS 1-4A risk prediction model, a nineteenth model is a 17 year, Lung-RADS 1-4A risk prediction model, a twentieth model is a 18 year, Lung-RADS 1-4A risk prediction model, a twenty-first model is a 19 year, Lung-RADS 1-4A risk prediction model, and a twenty-second model is a 20 year, Lung-RADS 1-4A risk prediction model.

The additional models exhibit an AUC value of at least 0.55. At least one of the additional models exhibits an AUC value of at least 0.60. At least one of the additional models exhibits an AUC value of at least 0.65. At least one of the additional models exhibits an AUC value of at least 0.70. At least one of the additional models exhibits an AUC value of at least 0.75. At least one of the additional models exhibits an AUC value of at least 0.80.

Example 14: Additional Examples of Predicting Future Risk of Cancer for Lung-RADS 1-3 Subjects Additional models are constructed using Lung-RADS 1-3 subjects using the methods described in Example 1. For example, such models can incorporate the non-nodule features described in Example 1 as well as nodule specific features (such as radiomic features) described in Example 1.

The additional models are either random forest models or gradient boosted models. Specifically, a first model is a 6 month, Lung-RADS 1-3 risk prediction model, a second model is a 1.5 year, Lung-RADS 1-3 risk prediction model, a third model is a 2.5 year, Lung-RADS 1-3 risk prediction model, a fourth model is a 4 year, Lung-RADS 1-3 risk prediction model, a fifth model is a 4.5 year, Lung-RADS 1-3 risk prediction model, a sixth model is a 5.5 year, Lung-RADS 1-3 risk prediction model, a seventh model is a 6 year, Lung-RADS 1-3 risk prediction model, an eight model is a 7 year, Lung-RADS 1-3 risk prediction model, a ninth model is a 8 year, Lung-RADS 1-3 risk prediction model, a tenth model is a 9 year, Lung-RADS 1-3 risk prediction model, an eleventh model is a 10 year, Lung-RADS 1-3 risk prediction model, a twelfth model is a 11 year, Lung-RADS 1-3 risk prediction model, a thirteenth model is a 11 year, Lung-RADS 1-3 risk prediction model, a fourteenth model is a 12 year, Lung-RADS 1-3 risk prediction model, a fifteenth model is a 13 year, Lung-RADS 1-3 risk prediction model, a sixteenth model is a 14 year, Lung-RADS 1-3 risk prediction model, a seventeenth model is a 15 year, Lung-RADS 1-3 risk prediction model, an eighteenth model is a 16 year, Lung-RADS 1-3 risk prediction model, a nineteenth model is a 17 year, Lung-RADS 1-3 risk prediction model, a twentieth model is a 18 year, Lung-RADS 1-3 risk prediction model, a twenty-first model is a 19 year, Lung-RADS 1-3 risk prediction model, and a twenty-second model is a 20 year, Lung-RADS 1-3 risk prediction model.

The additional models exhibit an AUC value of at least 0.55. At least one of the additional models exhibits an AUC value of at least 0.60. At least one of the additional models exhibits an AUC value of at least 0.65. At least one of the additional models exhibits an AUC value of at least 0.70. At least one of the additional models exhibits an AUC value of at least 0.75. At least one of the additional models exhibits an AUC value of at least 0.80.

Example 15: Additional Examples of Predicting Future Risk of Cancer for Lung-RADS 1-2 Subjects Additional models are constructed using Lung-RADS 1-2 subjects using the methods described in Example 1. For example, such models can incorporate the non-nodule features described in Example 1 as well as nodule specific features (such as radiomic features) described in Example 1.

The additional models are either random forest models or gradient boosted models. Specifically, a first model is a 6 month, Lung-RADS 1-2 risk prediction model, a second model is a 1.5 year, Lung-RADS 1-2 risk prediction model, a third model is a 2.5 year, Lung-RADS 1-2 risk prediction model, a fourth model is a 4 year, Lung-RADS 1-2 risk prediction model, a fifth model is a 4.5 year, Lung-RADS 1-2 risk prediction model, a sixth model is a 5.5 year, Lung-RADS 1-2 risk prediction model, a seventh model is a 6 year, Lung-RADS 1-2 risk prediction model, an eight model is a 7 year, Lung-RADS 1-2 risk prediction model, a ninth model is a 8 year, Lung-RADS 1-2 risk prediction model, a tenth model is a 9 year, Lung-RADS 1-2 risk prediction model, an eleventh model is a 10 year, Lung-RADS 1-2 risk prediction model, a twelfth model is a 11 year, Lung-RADS 1-2 risk prediction model, a thirteenth model is a 11 year, Lung-RADS 1-2 risk prediction model, a fourteenth model is a 12 year, Lung-RADS 1-2 risk prediction model, a fifteenth model is a 13 year, Lung-RADS 1-2 risk prediction model, a sixteenth model is a 14 year, Lung-RADS 1-2 risk prediction model, a seventeenth model is a 15 year, Lung-RADS 1-2 risk prediction model, an eighteenth model is a 16 year, Lung-RADS 1-2 risk prediction model, a nineteenth model is a 17 year, Lung-RADS 1-2 risk prediction model, a twentieth model is a 18 year, Lung-RADS 1-2 risk prediction model, a twenty-first model is a 19 year, Lung-RADS 1-2 risk prediction model, and a twenty-second model is a 20 year, Lung-RADS 1-2 risk prediction model.

The additional models exhibit an AUC value of at least 0.55. At least one of the additional models exhibits an AUC value of at least 0.60. At least one of the additional models exhibits an AUC value of at least 0.65. At least one of the additional models exhibits an AUC value of at least 0.70. At least one of the additional models exhibits an AUC value of at least 0.75. At least one of the additional models exhibits an AUC value of at least 0.80.

Example 15: Additional Examples of Predicting Future Risk of Cancer for Lung-RADS 1 Subjects Additional models are constructed using Lung-RADS 1 subjects using the methods described in Example 1. For example, such models can incorporate the non-nodule features described in Example 1 as well as nodule specific features (such as radiomic features) described in Example 1.

The additional models are either random forest models or gradient boosted models. Specifically, a first model is a 6 month, Lung-RADS 1 risk prediction model, a second model is a 1.5 year, Lung-RADS 1 risk prediction model, a third model is a 2.5 year, Lung-RADS 1 risk prediction model, a fourth model is a 4 year, Lung-RADS 1 risk prediction model, a fifth model is a 4.5 year, Lung-RADS 1 risk prediction model, a sixth model is a 5.5 year, Lung-RADS 1 risk prediction model, a seventh model is a 6 year, Lung-RADS 1 risk prediction model, an eight model is a 7 year, Lung-RADS 1 risk prediction model, a ninth model is a 8 year, Lung-RADS 1 risk prediction model, a tenth model is a 9 year, Lung-RADS 1 risk prediction model, an eleventh model is a 10 year, Lung-RADS 1 risk prediction model, a twelfth model is a 11 year, Lung-RADS 1 risk prediction model, a thirteenth model is a 11 year, Lung-RADS 1 risk prediction model, a fourteenth model is a 12 year, Lung-RADS 1 risk prediction model, a fifteenth model is a 13 year, Lung-RADS 1 risk prediction model, a sixteenth model is a 14 year, Lung-RADS 1 risk prediction model, a seventeenth model is a 15 year, Lung-RADS 1 risk prediction model, an eighteenth model is a 16 year, Lung-RADS 1 risk prediction model, a nineteenth model is a 17 year, Lung-RADS 1 risk prediction model, a twentieth model is a 18 year, Lung-RADS 1 risk prediction model, a twenty-first model is a 19 year, Lung-RADS 1 risk prediction model, and a twenty-second model is a 20 year, Lung-RADS 1 risk prediction model.

The additional models exhibit an AUC value of at least 0.55. At least one of the additional models exhibits an AUC value of at least 0.60. At least one of the additional models exhibits an AUC value of at least 0.65. At least one of the additional models exhibits an AUC value of at least 0.70. At least one of the additional models exhibits an AUC value of at least 0.75. At least one of the additional models exhibits an AUC value of at least 0.80.

Example 16: Example Future Risk Predictions for Two Patients

The risk prediction models trained using the data from the NLST provide a multi-modal risk assessment and enrichment approach. For example, consider two patients who developed cancer within 3 years of enrollment in NLST. Both had Lung-RADS 3 nodules at baseline, both were predicted to develop cancer within 3 years by the algorithm and both developed stage IA adenocarcinoma within 3 years. In fact, the predicted probabilities of developing cancer for both patients are within 2% of each other (84.8% for Patient 1 and 86.4% for Patient 2). Patient 1 was a 65-year-old white female former smoker with a 76 pack year smoking history, a BMI of 23.5, relatively small pectoralis mass, and significant, upper lobe predominant emphysema (31% emphysema by volume based on local histogram analysis). A 76 pack year smoking history is equivalent to smoking a pack (20) of cigarettes every day for 76 years or two packs a day for 38 years. By contrast, Patient 2 was a 59 year old white male former smoker with a 43 pack year smoking history, a BMI of 29.8, relatively preserved pectoralis mass, and minimal emphysema (2.6% emphysema by volume based on local histogram analysis), but significantly more interstitial features (7.1% compared to 4%). In this second case, it is this last feature and the strong relationship between interstitial features and cancer that likely leads to the algorithm predicting the development of cancer within 3 years. The clinical and radiologic differences between these two cases highlight the ability of the risk prediction models to identify patients with distinct and differing phenotypes who are likely to develop cancer.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, the above specification is not restrictive. It will be appreciated that various changes can be made without departing from the spirit and scope of the present disclosure(s). Many variations will become apparent to those skilled in the art upon review of this specification.

TABLES

TABLE 1

Summary of Lung-RADS classification

| Category Descriptor | Lung-RADS score | Findings | Management | Risk of Malignancy | Estimated Population Prevalence |
|---|---|---|---|---|---|
| Incomplete | 0 | Prior Chest CT examination(s) being located for comparison. Part or all of lungs cannot be evaluated | Additional Lung cancer screening CT images and/or comparison to prior chest CT examinations is needed | N/A | 1% |
| Negative (No nodules and definitely benign nodules) | 1 | No lung nodules or nodules with specific calculations: complete, central, popcorn, concentric rings, and fat containing nodules | Continue annual screening with LDCT in 12 months | <1% | 90% |
| Benign appearance or behavior (Nodules with very low likelihood of becoming a clinically active cancer due to size or lack of growth) | 2 | Solid nodules: < 6 mm, new < 4 mm Part solid nodules: < 6 mm total diameter on baseline screening Non solid nodules (GGN): < 30 mm OR ≥ 30 mm and unchanged or slowly growing Category 3 or 4 nodules unchanged for ≥ 3 months | | | |
| Probably benign (probably benign findings-short term follow up suggested; includes nodules with a low likelihood of becoming a clinically active cancer) | 3 | Solid nodules: ≥6 to <8 mm at baseline OR new 4 mm to <6 mm Part solid nodules: ≥6 mm total diameter with solid component <6 mm OR new <6 mm total diameter Non solid nodules (GGN) ≥30 mm on baseline CT or new | 6 month LDCT | 1-2% | 5% |
| Probably suspicious (findings for which additional diagnostic testing is | 4A | Solid nodule(s): ≥8 to <15 mm at baseline OR growing <8 mm OR | 3 month LDCT: PET/CT may be used when there is a ≥8 mm solid | 5-15% | 2% |

TABLE 1-continued

Summary of Lung-RADS classification

| Category Descriptor | Lung-RADS score | Findings | Management | Risk of Malignancy | Estimated Population Prevalence |
|---|---|---|---|---|---|
| recommended) | | new 6 to <8 mm Part solid nodules: ≥6 mm with solid component ≥6 mm to <8 mm OR with a new or growing <4 mm solid component Endobronchial nodule | component | | |
| Suspicious (Findings for which additional diagnostic testing and/or tissue sampling is recommended) | 4B | Solid nodule: ≥15 mm OR new or growing and ≥8 mm Part solid nodule(s) with: a solid component ≥8 mm OR a new or growing ≥4 mm solid component | Chest CT with or without contrast, PET/CT and/or tissue sampling depending on the probability of malignancy and comorbidities. PET/CT may be used when there is a ≥8 mm solid component. For new large nodules that develop on an annual repeat screening CT, a 1 month LDCT may be recommended to address potentially infectious or inflammatory conditions | >15% | 2% |
| | 4X | Category 3 or 4 nodules with aditional features or imaging findings that increases the suspicion of malignancy | | | |

TABLE 2

Overall demographics of full patient cohort

| Demographic Characteristics | | |
|---|---|---|
| n | | 7093 |
| Age (Years) (mean (SD)) | | 61.7 (5.0) |
| Gender (%) | Female | 2853 (40.2) |
| | Male | 4240 (59.8) |
| Race (%) | American Indian or Alaskan Native | 14 (0.2) |
| | Asian | 149 (2.1) |
| | Black | 259 (3.7) |
| | Missing/Unknown | 13 (0.2) |
| | More than One Race | 88 (1.2) |
| | Native Hawaiian or Other Pacific Islander | 16 (0.2) |
| | White | 6534 (92.4) |
| Current Smoking Status (%) | Current Smoker | 3670 (51.7) |
| | Former Smoker | 3423 (48.3) |
| Pack Years (mean (SD)) | | 56.8 (24.1) |
| Diagnosis with Lung Cancer over 3 Years of Follow-up (%) | Lung Cancer | 298 (4.2) |
| | No Lung Cancer | 6795 (95.8) |
| Lung cancer stage (%) | Stage IA | 140 (47.0) |
| | Stage IB | 30 (10.1) |
| | Stage IIA | 17 (5.7) |
| | Stage IIB | 11 (3.7) |
| | Stage IIIA | 33 (11.1) |
| | Stage IIIB | 6 (2.0) |
| | Stage IV | 50 (16.8) |
| | Unknown/Other | 11 (3.7) |
| Lung cancer type (%) | Adenocarcinoma | 160 (53.7) |
| | Squamous cell carcinoma | 59 (19.8) |
| | Non-small cell carcinoma, NOS | 29 (9.7) |
| | Small cell carcinoma | 25 (8.4) |
| | Neuroendocrine tumor | 21 (7.0) |
| | Other | 3 (1.0) |
| | Unknown | 1 (0.3) |
| Lung-RADS Score (%) | 1 | 4318 (60.9) |
| | 2 | 1246 (17.6) |
| | 3 | 830 (11.7) |
| | 4A | 539 (7.6) |
| | 4B | 160 (2.3) |

TABLE 3

Top 10 features for 1 year, 3 year, and 5 year future risk models for full cohort. For features categories, a "1" indicates a nodule specific feature whereas a "2" indicates a non-nodule specific feature.

| Feature ranked based on importance | 1 year features | 1 year feature category | 3 year | 3 year feature category | 5 year | 5 year feature category |
|---|---|---|---|---|---|---|
| 1 | Perpendicular diameter of largest lung nodule | 1 | Perpendicular diameter of largest lung nodule | 1 | Perpendicular diameter of largest lung nodule | 1 |
| 2 | Longest diameter of largest lung nodule | 1 | Longest diameter of largest lung nodule | 1 | Longest diameter of largest lung nodule | 1 |
| 3 | Margin type of largest lung nodule | 1 | Ratio of low attenuation area in the upper third of the lung to that in the lower third | 2 | Ratio of low attenuation area in the upper third of the lung to that in the lower third | 2 |
| 4 | Lung-RADS | 1 | Percentage of lung occupied by normal parenchyma | 2 | Percentage of lung occupied by normal parenchyma | 2 |
| 5 | Percentage of lung occupied by reticular features | 2 | Lung-RADS | 1 | Coronal cross sectional area of subcutaneous fat | 2 |
| 6 | Coronal cross sectional area of pectoralis minor muscle | 2 | Percentage of lung occupied by centrilobular emphysema | 2 | Percentage of lung occupied by centrilobular emphysema | 2 |
| 7 | Percentage of lung occupied by linear scar | 2 | Coronal cross sectional area of subcutaneous fat | 2 | Axial cross sectional area of subcutaneous fat | 2 |
| 8 | Axial cross sectional area of subcutaneous fat | 2 | Axial cross sectional area of subcutaneous fat | 2 | Margin type of largest lung nodule | 1 |
| 9 | Ratio of low attenuation area in the upper third of the lung to that in the lower third | 2 | Percentage of lung occupied by subpleural line | 2 | Percentage of lung occupied by reticular features | 2 |
| 10 | Axial cross sectional area of pectoralis major muscle | 2 | Margin type of largest lung nodule | 1 | Percentage of lung occupied by honeycombing | 2 |

TABLE 4

Characteristics of the Full Cohort by Cancer Prediction

| Subgroup | | Cancer Predicted | No Cancer Predicted | p |
|---|---|---|---|---|
| Demographic Characteristics | | | | |
| n | | 450 | 6643 | |
| Age (Years) (mean (SD)) | | 62.9 (5.5) | 61.6 (5.0) | <0.001 |
| Gender (%) | Female | 160 (35.6) | 2766 (41.6) | 0.013 |
| | Male | 290 (64.4) | 3877 (58.4) | |
| Race (%) | American Indian or Alaskan Native | 1 (0.2) | 23 (0.3) | 0.272 |
| | Asian | 4 (0.9) | 141 (2.1) | |
| | Black | 10 (2.2) | 223 (3.4) | |
| | Missing/Unknown | 1 (0.2) | 11 (0.2) | |
| | More than One Race | 4 (0.9) | 89 (1.3) | |
| | Native Hawaiian or Other Pacific Islander | 2 (0.4) | 12 (0.2) | |
| | White | 428 (95.1) | 6128 (92.5) | |
| Current Smoking | Current Smoker | 235 (52.2) | 3472 (52.3) | 1 |
| Status (%) | Former Smoker | 215 (47.8) | 3171 (47.7) | |
| Pack Years (mean (SD)) | | 59.6 (26.0) | 55.8 (23.8) | 0.001 |
| Lung Cancer Outcomes | | | | |
| Diagnosis with Lung Cancer over 3 Years of Follow-up (%) | Lung Cancer | 119 (26.4) | 179 (2.7) | <0.001 |
| | No Lung Cancer | 331 (73.6) | 6464 (97.3) | |
| Lung cancer stage (%) | Stage IA | 47 (39.5) | 84 (46.9) | 0.336 |
| | Stage IB | 16 (13.4) | 16 (8.9) | |
| | Stage IIA | 7 (5.9) | 16 (8.9) | |
| | Stage IIB | 4 (3.4) | 3 (1.7) | |
| | Stage IIIA | 19 (16.0) | 15 (8.4) | |
| | Stage IIIB | 4 (3.4) | 7 (3.9) | |
| | Stage IV | 19 (16.0) | 32 (17.9) | |
| | Unknown/Other | 3 (2.5) | 6 (3.4) | |
| Lung cancer type (%) | Adenocarcinoma | 78 (65.5) | 84 (46.9) | 0.035 |
| | Squamous cell carcinoma | 14 (11.8) | 38 (21.2) | |
| | Non-small cell carcinoma, NOS | 13 (10.9) | 17 (9.5) | |
| | Small cell carcinoma | 7 (5.9) | 24 (13.4) | |

TABLE 4-continued

Characteristics of the Full Cohort by Cancer Prediction

| Subgroup | Cancer Predicted | No Cancer Predicted | p |
|---|---|---|---|
| Neuroendocrine tumor | 5 (4.2) | 11 (6.1) | |
| Other | 2 (1.7) | 4 (2.2) | |
| Unknown | 0 (0.0) | 1 (0.6) | |
| Nodule Characteristics | | | |
| Lung-RADS Score (%) 1 | 16 (3.6) | 4369 (65.8) | <0.001 |
| 2 | 108 (24.0) | 1159 (17.4) | |
| 3 | 52 (11.6) | 736 (11.1) | |
| 4A | 122 (27.1) | 364 (5.5) | |
| 4B | 152 (33.8) | 15 (0.2) | |
| Densitometric Measures | | | |
| Low Attenuation Area (Percent of Lung) (mean (SD)) | 6.5 (7.6) | 6.2 (9.2) | 0.505 |
| High Attenuation Area (Percent of Lung) (mean (SD)) | 4.6 (1.8) | 4.6 (1.8) | 0.489 |
| Body Composition | | | |
| Pectoralis Minor Cross Axial Sectional Area (mean (SD)) | 1087.8 (322.2) | 1105.3 (354.3) | 0.308 |
| Pectoralis Major Cross Axial Sectional Area (mean (SD)) | 3047.3 (1049.2) | 3093.0 (1174.5) | 0.422 |
| Subcutaneous Fat Axial Cross Sectional Area (mean (SD)) | 5198.9 (2801.1) | 5674.8 (2889.1) | 0.001 |
| Local Histogram | | | |
| Normal Parenchyma (Percent of Lung) (mean (SD)) | 89.3 (7.8) | 89.4 (9.7) | 0.914 |
| Centrilobular Emphysema (Percent of Lung) (mean (SD)) | 4.2 (7.0) | 4.2 (8.8) | 0.921 |
| Centrilobular Nodule (Percent of Lung) (mean (SD)) | 0.0 (0.0) | 0.0 (0.0) | 0.379 |
| Ground Glass (Percent of Lung) (mean (SD)) | 0.0 (0.0) | 0.0 (0.0) | 0.716 |
| Honeycombing (Percent of Lung) (mean (SD)) | 0.1 (0.1) | 0.1 (0.1) | 0.017 |
| Linear Scar (Percent of Lung) (mean (SD)) | 0.1 (0.1) | 0.1 (0.1) | 0.528 |
| Nodular (Percent of Lung) (mean (SD)) | 0.1 (0.1) | 0.1 (0.2) | 0.287 |
| Reticular (Percent of Lung) (mean (SD)) | 5.3 (2.8) | 5.1 (2.9) | 0.166 |
| Subpleural Line (Percent of Lung) (mean (SD)) | 0.2 (0.1) | 0.2 (0.2) | 0.048 |
| Other Emphysema (Percent of Lung) (mean (SD)) | 0.0 (0.1) | 0.0 (0.1) | 0.803 |
| Cyst (Percent of Lung) (mean (SD)) | 0.0 (0.0) | 0.0 (0.0) | 0.471 |

TABLE 5

Enrichment results of 1 year, 3 year, and 5 year future risk models for full cohort

| Method | Area Under the Precision Recall Curve | Relative Enrollment Ratio | Relative Enrollment Percentage | Absolute Enrollment Percentage | Cumulative Incidence |
|---|---|---|---|---|---|
| 1 Year | | | | | |
| Null Model | NA | 1 to 1 | 100 | 100 | 1.79 |
| Random Forest | 0.22 | 17 to 1 | 6.01 | 6.01 | 19.72 |
| 3 Year | | | | | |
| Null Model | NA | 1 to 1 | 100 | 100 | 4.20 |
| Random Forest | 0.36 | 16 to 1 | 6.34 | 6.34 | 26.44 |
| 5 Year | | | | | |
| Null Model | NA | 1 to 1 | 100 | 100 | 5.58 |
| Random Forest | 0.40 | 17 to 1 | 5.85 | 5.85 | 28.43 |

[1] The random forest model is tuned random forest model

[2] The relative enrollment ratio and the relative enrollment percentage are based on the ratio of the number of individuals predicted positive by the model to the number of individuals in the tested subgroup, in this case, the entire cohort

[3] The absolute enrollment percentage is the percent of the total cohort who are predicted positive, i.e. suggested to be enrolled, by the model.

[4] Note that each model is trained independently and so those predicted positive by the 5 year model do not necessarily include all of those predicted positive by the 3 year model.

TABLE 6

Top 10 features for 1 year, 3 year, and 5 year future risk models for Lung-RADS 1-4A. For features categories, a "1" indicates a nodule specific feature whereas a "2" indicates a non-nodule specific feature.

| Feature ranked based on importance | 1 year features | 1 year feature category | 3 year | 3 year feature category | 5 year | 5 year feature category |
|---|---|---|---|---|---|---|
| 1 | Perpendicular diameter of largest lung nodule | 1 | Perpendicular diameter of largest lung nodule | 1 | Perpendicular diameter of largest lung nodule | 1 |
| 2 | Longest diameter of largest lung nodule | 1 | Longest diameter of largest lung nodule | 1 | Longest diameter of largest lung nodule | 1 |
| 3 | Margin type of largest lung nodule | 1 | Margin type of largest lung nodule | 1 | Axial cross sectional area of subcutaneous fat | 2 |
| 4 | Lung-RADS | 1 | Lung-RADS | 1 | Coronal cross sectional area of subcutaneous fat | 2 |
| 5 | Axial cross sectional area of subcutaneous fat | 2 | Axial cross sectional area of subcutaneous fat | 2 | Axial cross sectional area of pectoralis minor muscle | 2 |
| 6 | Coronal cross sectional area of subcutaneous fat | 2 | Coronal cross sectional area of subcutaneous fat | 2 | Ratio of low attenuation area in the upper third of the lung to that in the lower third | 2 |
| 7 | Percentage of lung occupied by reticular features | 2 | Percentage of lung occupied by reticular features | 2 | Percentage of lung occupied by subpleural line | 2 |
| 8 | Attenuation/density type of largest lung nodule | 1 | Attenuation/density type of largest lung nodule | 1 | Percentage of lung occupied by linear scar | 2 |
| 9 | Percentage of lung occupied by normal parenchyma | 2 | Percentage of lung occupied by normal parenchyma | 2 | Percentage of lung occupied by centrilobular emphysema | 2 |
| 10 | Percentage of lung occupied by linear scar | 2 | Percentage of lung occupied by linear scar | 2 | Percentage of lung occupied by honeycombing | 2 |

TABLE 7

Characteristics of the Lung-RADS 1-4A Cohort by Cancer Prediction

| | Subgroup | Cancer Predicted | No Predicted Cancer | p |
|---|---|---|---|---|
| Demographic Characteristics | | | | |
| n | | 392 | 6531 | 0 |
| Age (Years) (mean (SD)) | | 62.5 (5.2) | 61.5 (5.1) | <0.001 |
| Gender (%) | Female | 119 (30.4) | 2777 (42.5) | <0.001 |
| | Male | 273 (69.6) | 3754 (57.5) | |
| Race (%) | American Indian or Alaskan Native | 2 (0.5) | 15 (0.2) | 0.118 |
| | Asian | 9 (2.3) | 124 (1.9) | |
| | Black | 4 (1.0) | 247 (3.8) | |
| | Missing/Unknown | 0 (0.0) | 8 (0.1) | |
| | More than One Race | 6 (1.5) | 81 (1.2) | |
| | Native Hawaiian or Other Pacific Islander | 1 (0.3) | 17 (0.3) | |
| | White | 370 (94.4) | 6023 (92.4) | |
| Current Smoking Status (%) | Current Smoker | 215 (54.8) | 3403 (52.1) | 0.316 |
| | Former Smoker | 177 (45.2) | 3128 (47.9) | |
| Pack Years (mean (SD)) | | 58.2 (23.2) | 55.4 (23.6) | 0.022 |
| Lung Cancer Outcomes | | | | |
| Diagnosis with Lung Cancer over 3 Years of Follow-up (%) | Lung Cancer | 66 (16.8) | 161 (2.5) | <0.001 |
| | No Lung Cancer | 326 (83.2) | 6370 (97.5) | |
| Lung cancer stage (%) | Stage IA | 44 (66.7) | 69 (42.9) | 0.013 |
| | Stage IB | 2 (3.0) | 15 (9.3) | |
| | Stage IIA | 5 (7.6) | 14 (8.7) | |
| | Stage IIB | 2 (3.0) | 1 (0.6) | |
| | Stage IIIA | 2 (3.0) | 19 (11.8) | |
| | Stage IIIB | 0 (0.0) | 7 (4.3) | |
| | Stage IV | 8 (12.1) | 29 (18.0) | |
| | Unknown/Other | 3 (4.5) | 7 (4.3) | |
| Lung cancer type (%) | Adenocarcinoma | 43 (65.2) | 79 (49.1) | 0.397 |
| | Squamous cell carcinoma | 12 (18.2) | 34 (21.1) | |
| | Non-small cell carcinoma, NOS | 4 (6.1) | 14 (8.7) | |
| | Small cell carcinoma | 3 (4.5) | 19 (11.8) | |
| | Neuroendocrine tumor | 3 (4.5) | 10 (6.2) | |
| | Other | 1 (1.5) | 4 (2.5) | |
| | Uknown | 0 (0.0) | 1 (0.6) | |
| Nodule Characteristics | | | | |

TABLE 7-continued

Characteristics of the Lung-RADS 1-4A Cohort by Cancer Prediction

| | Subgroup | Cancer Predicted | No Predicted Cancer | p |
|---|---|---|---|---|
| Lung-RADS Score (%) | 1 | 71 (18.1) | 4276 (65.5) | <0.001 |
| | 2 | 72 (18.4) | 1176 (18.0) | |
| | 3 | 69 (17.6) | 754 (11.5) | |
| | 4A | 180 (45.9) | 325 (5.0) | |
| Densitometric Measures | | | | |
| Low Attenuation Area (Percent of Lung) (mean (SD)) | | 9.8 (11.0) | 5.9 (8.7) | <0.001 |
| High Attenuation Area (Percent of Lung) (mean (SD)) | | 4.1 (1.5) | 4.7 (2.0) | <0.001 |
| Body Composition | | | | |
| Pectoralis Minor Cross Axial Sectional Area (mean (SD)) | | 1090.1 (305.3) | 1110.9 (352.6) | 0.252 |
| Pectoralis Major Cross Axial Sectional Area (mean (SD)) | | 2956.2 (854.1) | 3095.2 (1179.1) | 0.022 |
| Subcutaneous Fat Axial Cross Sectional Area (mean (SD)) | | 4478.6 (2122.2) | 5799.8 (2969.3) | <0.001 |
| Local Histogram | | | | |
| Normal Parenchyma (Percent of Lung) (mean (SD)) | | 87.1 (11.9) | 89.6 (9.0) | <0.001 |
| Centrilobular Emphysema (Percent of Lung) (mean (SD)) | | 7.1 (11.5) | 4.0 (8.2) | <0.001 |
| Centrilobular Nodule (Percent of Lung) (mean (SD)) | | 0.0 (0.0) | 0.0 (0.0) | 0.002 |
| Ground Glass (Percent of Lung) (mean (SD)) | | 0.0 (0.0) | 0.0 (0.0) | 0.096 |
| Honeycombing (Percent of Lung) (mean (SD)) | | 0.1 (0.2) | 0.1 (0.1) | 0.138 |
| Linear Scar (Percent of Lung) (mean (SD)) | | 0.1 (0.1) | 0.1 (0.1) | 0.003 |
| Nodular (Percent of Lung) (mean (SD)) | | 0.1 (0.3) | 0.1 (0.3) | 0.094 |
| Reticular (Percent of Lung) (mean (SD)) | | 4.6 (2.5) | 5.2 (2.9) | <0.001 |
| Subpleural Line (Percent of Lung) (mean (SD)) | | 0.1 (0.1) | 0.2 (0.2) | <0.001 |
| Other Emphysema (Percent of Lung) (mean (SD)) | | 0.1 (0.2) | 0.0 (0.1) | <0.001 |
| Cyst (Percent of Lung) (mean (SD)) | | 0.0 (0.0) | 0.0 (0.0) | 0.588 |

TABLE 8

Enrichment results of 1 year, 3 year, and 5 year future risk models for Lung-RADS 1-4A

| Method | Area Under the Precision Recall Curve | Relative Enrollment Ratio | Relative Enrollment Percentage | Absolute Enrollment Percentage | Cumulative Incidence |
|---|---|---|---|---|---|
| 1 Year | | | | | |
| Null Model | NA | 1 to 1 | 100 | 100 | 0.98 |
| Random Forest | 0.32 | 16 to 1 | 6.37 | 6.22 | 7.48 |
| 3 Year | | | | | |
| Null Model | NA | 1 to 1 | 100 | 100 | 3.28 |
| Random Forest | 0.41 | 18 to 1 | 5.66 | 5.53 | 16.84 |
| 5 Year | | | | | |
| Null Model | NA | 1 to 1 | 100 | 100 | 4.65 |
| Random Forest | 0.44 | 16 to 1 | 6.27 | 6.12 | 17.97 |

[1] The random forest model is tuned random forest model

[2] The relative enrollment ratio and the relative enrollment percentage are based on the ratio of the number of individuals predicted positive by the model to the number of individuals in the tested subgroup, in this case those with Lung-RADS <4B

[3] The absolute enrollment percentage is the percent of the total cohort who are predicted positive, i.e. suggested to be enrolled, by the model.

[4] Note that each model is trained independently and so those predicted positive by the 5 year model do not necessarily include all of those predicted positive by the 3 year model.

TABLE 9

Top 10 features for 1 year, 3 year, and 5 year future risk models for Lung-RADS 1-3. For features categories, a "1" indicates a nodule specific feature whereas a "2" indicates a non-nodule specific feature.

| Feature ranked based on importance | 1 year features | 1 year feature category | 3 year | 3 year feature category | 5 year | 5 year feature category |
|---|---|---|---|---|---|---|
| 1 | Perpendicular diameter of largest lung nodule | 1 | Perpendicular diameter of largest lung nodule | 1 | Coronal cross sectional area of subcutaneous fat | 2 |
| 2 | Margin type of largest lung nodule | 1 | Coronal cross sectional area of subcutaneous fat | 2 | Axial cross sectional area of subcutaneous fat | 2 |
| 3 | Axial cross sectional area of subcutaneous fat | 2 | Ratio of low attenuation area in the upper third of the lung to that in the lower third | 2 | Perpendicular diameter of largest lung nodule | 1 |
| 4 | Percentage of lung occupied by linear scar | 2 | Axial cross sectional area of pectoralis minor muscle | 2 | Percentage of lung occupied by centrilobular emphysema | 2 |
| 5 | Ratio of low attenuation area in the upper third of the lung to that in the lower third | 2 | Axial cross sectional area of subcutaneous fat | 2 | Ratio of low attenuation area in the upper third of the lung to that in the lower third | 2 |
| 6 | Percentage of lung occupied by reticular features | 2 | Percentage of lung occupied by subpleural line | 2 | Percentage of lung occupied by honeycombing | 2 |
| 7 | Percentage of lung occupied by normal parenchyma | 2 | Longest diameter of largest lung nodule | 1 | Axial cross sectional area of pectoralis major muscle | 2 |
| 8 | Coronal cross sectional area of lean pectoralis major muscle | 2 | Percentage of lung occupied by linear scar | 2 | Axial cross sectional area of lean pectoralis major muscle | 2 |
| 9 | Percentage of lung occupied by subpleural line | 2 | Percentage of lung occupied by honeycombing | 2 | Percentage of lung occupied by normal parenchyma | 2 |
| 10 | Attenuation/density type of largest lung nodule | 1 | Percentage of lung occupied by normal parenchyma | 2 | Axial cross sectional area of pectoralis minor muscle | 2 |

TABLE 10

Characteristics of the Lung-RADS 1-3 Cohort by Cancer Prediction

|  | Subgroup | Cancer Predicted | No Predicted Cancer | p |
|---|---|---|---|---|
|  | Demographic Characteristics | | | |
| n |  | 324 | 6085 |  |
| Age (Years) (mean (SD)) |  | 62.8 (5.1) | 61.5 (5.0) | <0.001 |
| Gender (%) | Female | 138 (42.6) | 2474 (40.7) | 0.527 |
|  | Male | 186 (57.4) | 3611 (59.3) |  |
| Race (%) | American Indian or Alaskan Native | 1 (0.3) | 16 (0.3) | 0.528 |
|  | Asian | 5 (1.5) | 141 (2.3) |  |
|  | Black | 7 (2.2) | 232 (3.8) |  |
|  | Missing/Unknown | 0 (0.0) | 10 (0.2) |  |
|  | More than One Race | 3 (0.9) | 77 (1.3) |  |
|  | Native Hawaiian or Other Pacific Islander | 0 (0.0) | 16 (0.3) |  |
|  | White | 308 (95.1) | 5578 (91.9) |  |
| Current Smoking Status (%) | Current Smoker | 177 (54.6) | 3162 (52.0) | 0.379 |
|  | Former Smoker | 147 (45.4) | 2923 (48.0) |  |
| Pack Years (mean (SD)) |  | 59.0 (24.2) | 55.9 (23.6) | 0.024 |
|  | Lung Cancer Outcomes | | | |
| Diagnosis with Lung Cancer over 3 Years of Follow-up (%) | Lung Cancer | 50 (15.4) | 125 (2.1) | <0.001 |
|  | No Lung Cancer | 274 (84.6) | 5960 (97.9) |  |
| Lung cancer stage (%) | Stage IA | 30 (60.0) | 59 (47.2) | 0.348 |
|  | Stage IB | 3 (6.0) | 6 (4.8) |  |
|  | Stage IIA | 3 (6.0) | 10 (8.0) |  |
|  | Stage IIB | 2 (4.0) | 1 (0.8) |  |
|  | Stage IIIA | 3 (6.0) | 11 (8.8) |  |
|  | Stage IIIB | 0 (0.0) | 8 (6.4) |  |
|  | Stage IV | 7 (14.0) | 25 (20.0) |  |
|  | Unknown/Other | 2 (4.0) | 5 (4.0) |  |
| Lung cancer type (%) | Adenocarcinoma | 33 (66.0) | 53 (42.4) | 0.093 |
|  | Squamous cell carcinoma | 8 (16.0) | 32 (25.6) |  |
|  | Non-small cell | 3 (6.0) | 18 (14.4) |  |

TABLE 10-continued

Characteristics of the Lung-RADS 1-3 Cohort by Cancer Prediction

| Subgroup | Cancer Predicted | No Predicted Cancer | p |
|---|---|---|---|
| carcinoma, NOS | | | |
| Small cell carcinoma | 2 (4.0) | 13 (10.4) | |
| Neuroendocrine tumor | 3 (6.0) | 6 (4.8) | |
| Other | 1 (2.0) | 3 (2.4) | |
| *Nodule Characteristics* | | | |
| Lung-RADS Score (%)  1 | 97 (29.9) | 4182 (68.7) | <0.001 |
| 2 | 148 (45.7) | 1189 (19.5) | |
| 3 | 79 (24.4) | 714 (11.7) | |
| *Densitometric Measures* | | | |
| Low Attenuation Area (Percent of Lung) (mean (SD)) | 7.2 (8.1) | 6.2 (9.1) | 0.06 |
| High Attenuation Area (Percent of Lung) (mean (SD)) | 4.3 (1.2) | 4.6 (1.9) | 0.002 |
| *Body Composition* | | | |
| Pectoralis Minor Cross Axial Sectional Area (mean (SD)) | 1047.1 (300.0) | 1113.3 (349.1) | 0.001 |
| Pectoralis Major Cross Axial Sectional Area (mean (SD)) | 2908.6 (1101.6) | 3126.1 (1196.2) | 0.001 |
| Subcutaneous Fat Axial Cross Sectional Area (mean (SD)) | 5363.8 (2926.3) | 5687.1 (2876.3) | 0.049 |
| *Local Histogram* | | | |
| Normal Parenchyma (Percent of Lung) (mean (SD)) | 88.7 (8.9) | 89.5 (9.3) | 0.119 |
| Centrilobular Emphysema (Percent of Lung) (mean (SD)) | 5.3 (8.7) | 4.1 (8.4) | 0.015 |
| Centrilobular Nodule (Percent of Lung) (mean (SD)) | 0.0 (0.0) | 0.0 (0.0) | 0.938 |
| Ground Glass (Percent of Lung) (mean (SD)) | 0.0 (0.0) | 0.0 (0.0) | 0.003 |
| Honeycombing (Percent of Lung) (mean (SD)) | 0.1 (0.1) | 0.1 (0.1) | 0.09 |
| Linear Scar (Percent of Lung) (mean (SD)) | 0.1 (0.1) | 0.1 (0.1) | 0.593 |
| Nodular (Percent of Lung) (mean (SD)) | 0.0 (0.1) | 0.1 (0.3) | 0.087 |
| Reticular (Percent of Lung) (mean (SD)) | 5.1 (2.6) | 5.1 (3.0) | 0.992 |
| Subpleural Line (Percent of Lung) (mean (SD)) | 0.2 (0.1) | 0.2 (0.2) | 0.897 |
| Other Emphysema (Percent of Lung) (mean (SD)) | 0.0 (0.1) | 0.0 (0.1) | 0.074 |
| Cyst (Percent of Lung) (mean (SD)) | 0.0 (0.0) | 0.0 (0.0) | 0.574 |

TABLE 11

Enrichment results of 1 year, 3 year, and 5 year future risk models for Lung-RADS 1-3

| Method | Area Under the Precision Recall Curve | Relative Enrollment Ratio | Relative Enrollment Percentage | Absolute Enrollment Percentage | Cumulative Incidence |
|---|---|---|---|---|---|
| *1 Year* | | | | | |
| Null Model | NA | 1 to 1 | 100 | 100 | 0.70 |
| Random Forest | 0.35 | 20 to 1 | 4.91 | 4.44 | 6.03 |
| *3 Year* | | | | | |
| Null Model | NA | 1 to 1 | 100 | 100 | 2.73 |
| Random Forest | 0.43 | 20 to 1 | 5.06 | 4.57 | 15.43 |
| *5 Year* | | | | | |
| Null Model | NA | 1 to 1 | 100 | 100 | 4.06 |
| Random Forest | 0.44 | 18 to 1 | 5.66 | 5.12 | 14.88 |

[1] The random forest model is tuned random forest model
[2] The relative enrollment ratio and the relative enrollment percentage are based on the ratio of the number of individuals predicted positive by the model to the number of individuals in the tested subgroup, in this case those with Lung-RADS <4
[3] The absolute enrollment percentage is the percent of the total cohort who are predicted positive, i.e. suggested to be enrolled, by the model.
[4] Note that each model is trained independently and so those predicted positive by the 5 year model do not necessarily include all of those predicted positive by the 3 year model.

TABLE 12

Top 10 features for 1 year, 3 year, and 5 year future risk models for Lung-RADS 1-2. For features categories, a "1" indicates a nodule specific feature whereas a "2" indicates a non-nodule specific feature.

| Feature ranked based on importance | 1 year features | 1 year feature category | 3 year | 3 year feature category | 5 year | 5 year feature category |
|---|---|---|---|---|---|---|
| 1 | Longest diameter of largest lung nodule | 1 | Coronal cross sectional area of subcutaneous fat | 2 | Axial cross sectional area of subcutaneous fat | 2 |
| 2 | Percentage of lung occupied by linear scar | 2 | Axial cross sectional area of subcutaneous fat | 2 | Ratio of low attenuation area in the upper third of the lung to that in the lower third | 2 |
| 3 | Perpendicular diameter of largest lung nodule | 1 | Percentage of lung occupied by honeycombing | 2 | Coronal cross sectional area of subcutaneous fat | 2 |
| 4 | Percentage of lung occupied by subpleural line | 2 | Ratio of low attenuation area in the upper third of the lung to that in the lower third | 2 | Axial cross sectional area of pectoralis minor muscle | 2 |
| 5 | Coronal cross sectional area of subcutaneous fat | 2 | Percentage of lung occupied by low attenuation area | 2 | Axial cross sectional area of pectoralis major muscle | 2 |
| 6 | Coronal cross sectional area of lean pectoralis minor muscle | 2 | Percentage of lung occupied by linear scar | 2 | Percentage of lung occupied by subpleural line | 2 |
| 7 | Percentage of lung occupied by normal parenchyma | 2 | Axial cross sectional area of pectoralis minor muscle | 2 | Percentage of lung occupied by normal parenchyma | 2 |
| 8 | Coronal cross sectional area of pectoralis minor muscle | 2 | Perpendicular diameter of largest lung nodule | 1 | Percentage of lung occupied by linear scar | 2 |
| 9 | Axial cross sectional area of subcutaneous fat | 2 | Longest diameter of largest lung nodule | 1 | Percentage of lung occupied by centrilobular emphysema | 2 |
| 10 | Axial cross sectional area of pectoralis minor muscle | 2 | Percentage of lung occupied by subpleural line | 2 | Percentage of lung occupied by low attenuation area | 2 |

TABLE 13

Characteristics of the Lung-RADS 1-2 Cohort by Cancer Prediction

| | Subgroup | Cancer Predicted | No Cancer Predicted | p |
|---|---|---|---|---|
| Demographic Characteristics | | | | |
| n | | 294 | 5314 | |
| Age (Years) (mean (SD)) | | 62.5 (5.3) | 61.4 (5.0) | <0.001 |
| Gender (%) | Female | 85 (28.9) | 2242 (42.2) | <0.001 |
| | Male | 209 (71.1) | 3072 (57.8) | |
| Race (%) | American Indian or Alaskan Native | 3 (1.0) | 9 (0.2) | 0.056 |
| | Asian | 8 (2.7) | 128 (2.4) | |
| | Black | 8 (2.7) | 215 (4.1) | |
| | Missing/Unknown | 0 (0.0) | 9 (0.2) | |
| | More than One Race | 4 (1.4) | 72 (1.4) | |
| | Native Hawaiian or Other Pacific Islander | 0 (0.0) | 18 (0.3) | |
| | White | 271 (92.2) | 4847 (91.5) | |
| Current Smoking Status (%) | Current Smoker | 147 (50.0) | 2755 (51.8) | 0.578 |
| | Former Smoker | 147 (50.0) | 2559 (48.2) | |
| Pack Years (mean (SD)) | | 59.1 (26.3) | 55.5 (24.2) | 0.015 |
| Lung Cancer Outcomes | | | | |
| Diagnosis with Lung Cancer over 3 Years of Follow-up (%) | Lung Cancer | 50 (15.4) | 125 (2.1) | <0.001 |
| | No Lung Cancer | 274 (84.6) | 5960 (97.9) | |
| Lung cancer stage (%) | Stage IA | 30 (60.0) | 59 (47.2) | 0.384 |
| | Stage IB | 3 (6.0) | 6 (4.8) | |
| | Stage IIA | 3 (6.0) | 10 (8.0) | |
| | Stage IIB | 2 (4.0) | 1 (0.8) | |
| | Stage IIIA | 3 (6.0) | 11 (8.8) | |
| | Stage IIIB | 0 (0.0) | 8 (6.4) | |
| | Stage IV | 7 (14.0) | 25 (20.0) | |
| | Unknown/Other | 2 (4.0) | 5 (4.0) | |
| Lung cancer type (%) | Adenocarcinoma | 11 (52.4) | 55 (49.1) | 0.973 |
| | Neuroendocrine tumor | 1 (4.8) | 5 (4.5) | |
| | Unknown | 0 (0.0) | 1 (0.9) | |
| | Other | 0 (0.0) | 1 (0.9) | |
| | Squamous cell carcinoma | 5 (23.8) | 20 (17.9) | |
| | Non-small cell carcinoma, NOS | 2 (9.5) | 12 (10.7) | |
| | Small cell carcinoma | 2 (9.5) | 18 (16.1) | |
| Nodule Characteristics | | | | |
| Lung-RADS Score (%) | 1 | 177 (60.2) | 4166 (78.4) | <0.001 |
| | 2 | 117 (39.8) | 1148 (21.6) | |
| Densitometric Measures | | | | |
| Low Attenuation Area (Percent of Lung) (mean (SD)) | | 9.8 (11.1) | 5.7 (8.4) | <0.001 |
| High Attenuation Area (Percent of Lung) (mean (SD)) | | 4.2 (1.4) | 4.7 (1.9) | <0.001 |
| Body Composition | | | | |
| Pectoralis Minor Cross Axial Sectional Area (mean (SD)) | | 1065.8 (247.2) | 1110.4 (351.3) | 0.032 |
| Pectoralis Major Cross Axial Sectional Area (mean (SD)) | | 2965.1 (877.5) | 3115.9 (1176.4) | 0.03 |
| Subcutaneous Fat Axial Cross Sectional Area (mean (SD)) | | 4569.2 (2289.5) | 5804.4 (2946.0) | <0.001 |
| Local Histogram | | | | |
| Normal | | 86.7 (11.3) | 90.0 (8.8) | <0.001 |

TABLE 13-continued

Characteristics of the Lung-RADS 1-2 Cohort by Cancer Prediction

| Subgroup | Cancer Predicted | No Cancer Predicted | p |
|---|---|---|---|
| Parenchyma (Percent of Lung) (mean (SD)) | | | |
| Centrilobular Emphysema (Percent of Lung) (mean (SD)) | 7.7 (11.6) | 3.7 (7.8) | <0.001 |
| Centrilobular Nodule (Percent of Lung) (mean (SD)) | 0.0 (0.0) | 0.0 (0.0) | 0.196 |
| Ground Glass (Percent of Lung) (mean (SD)) | 0.0 (0.0) | 0.0 (0.0) | 0.637 |
| Honeycombing (Percent of Lung) (mean (SD)) | 0.1 (0.1) | 0.1 (0.1) | 0.195 |
| Linear Scar (Percent of Lung) (mean (SD)) | 0.1 (0.1) | 0.1 (0.1) | 0.001 |
| Nodular (Percent of Lung) (mean (SD)) | 0.0 (0.1) | 0.1 (0.2) | <0.001 |
| Reticular (Percent of Lung) (mean (SD)) | 4.9 (3.0) | 5.1 (3.0) | 0.154 |
| Subpleural Line (Percent of Lung) (mean (SD)) | 0.1 (0.1) | 0.2 (0.2) | <0.001 |
| Other Emphysema (Percent of Lung) (mean (SD)) | 0.1 (0.1) | 0.0 (0.1) | <0.001 |
| Cyst (Percent of Lung) (mean (SD)) | 0.0 (0.0) | 0.0 (0.0) | 0.46 |

TABLE 14

Enrichment results of 1 year, 3 year, and 5 year future risk models for Lung-RADS 1-2

| Method | Area Under the Precision Recall Curve | Relative Enrollment Ratio | Relative Enrollment Percentage | Absolute Enrollment Percentage | Cumulative Incidence |
|---|---|---|---|---|---|
| 1 Year | | | | | |
| Null Model | NA | 1 to 1 | 100 | 100 | 0.43 |
| Random Forest | 0.37 | 17 to 1 | 6.03 | 4.77 | 2.37 |
| 3 Year | | | | | |
| Null Model | NA | 1 to 1 | 100 | 100 | 2.37 |
| Random Forest | 0.44 | 19 to 1 | 5.24 | 4.14 | 7.14 |
| 5 Year | | | | | |
| Null Model | NA | 1 to 1 | 100 | 100 | 3.67 |
| Random Forest | 0.46 | 16 to 1 | 6.31 | 4.99 | 7.06 |

[1] The random forest model is tuned random forest model
[2] The relative enrollment ratio and the relative enrollment percentage are based on the ratio of the number of individuals predicted positive by the model to the number of individuals in the tested subgroup, in this case those with Lung-RADS <3
[3] The absolute enrollment percentage is the percent of the total cohort who are predicted positive, i.e. suggested to be enrolled, by the model.
[4] Note that each model is trained independently and so those predicted positive by the 5 year model do not necessarily include all of those predicted positive by the 3 year model.

TABLE 15

Top 10 features for 1 year, 3 year, and 5 year future risk models for Lung-RADS 1. For features categories, a "1" indicates a nodule specific feature whereas a "2" indicates a non-nodule specific feature.

| Feature ranked based on importance | 1 year features | 1 year feature category | 3 year | 3 year feature category | 5 year | 5 year feature category |
|---|---|---|---|---|---|---|
| 1 | Percentage of lung occupied by normal | 2 | Coronal cross sectional area of | 2 | Ratio of low attenuation area in | 2 |

TABLE 15-continued

Top 10 features for 1 year, 3 year, and 5 year future risk models for Lung-RADS 1. For features categories, a "1" indicates a nodule specific feature whereas a "2" indicates a non-nodule specific feature.

| Feature ranked based on importance | 1 year features | 1 year feature category | 3 year | 3 year feature category | 5 year | 5 year feature category |
|---|---|---|---|---|---|---|
| | parenchyma | | subcutaneous fat | | the upper third of the lung to that in the lower third | |
| 2 | Percentage of lung occupied by centrilobular emphysema | 2 | Percentage of lung occupied by low attenuation area | 2 | Percentage of lung occupied by honeycombing | 2 |
| 3 | Axial cross sectional area of subcutaneous fat | 2 | Percentage of lung occupied by centrilobular emphysema | 2 | Axial cross sectional area of pectoralis minor muscle | 2 |
| 4 | Coronal cross sectional area of subcutaneous fat | 2 | Percentage of lung occupied by linear scar | 2 | Percentage of lung occupied by low attenuation area | 2 |
| 5 | Percentage of lung occupied by reticular features | 2 | Axial cross sectional area of pectoralis minor muscle | 2 | Percentage of lung occupied by centrilobular emphysema | 2 |
| 6 | Percentage of lung occupied by subpleural line | 2 | Percentage of lung occupied by emphysematous features | 2 | Axial cross sectional area of pectoralis major muscle | 2 |
| 7 | Sagittal cross sectional area of pectoralis minor muscle | 2 | Percentage of lung occupied by normal parenchyma | 2 | Percentage of lung occupied by linear scar | 2 |
| 8 | Coronal cross sectional area of pectoralis minor muscle | 2 | Axial cross sectional area of subcutaneous fat | 2 | Percentage of lung occupied by normal parenchyma | 2 |
| 9 | Coronal cross sectional area of lean pectoralis minor muscle | 2 | Ratio of low attenuation area in the upper third of the lung to that in the lower third | 2 | Percentage of lung occupied by high attenuation area | 2 |
| 10 | Coronal cross sectional area of lean pectoralis major muscle | 2 | Percentage of lung occupied by honeycombing | 2 | Percentage of lung occupied by subpleural line | 2 |

TABLE 16

Characteristics of the Lung-RADS 1 Cohort by Cancer Prediction

| | Subgroup | Cancer Predicted | No Cancer Predicted | p |
|---|---|---|---|---|
| Demographic Characteristics | | | | |
| n | | 261 | 4077 | |
| Age (Years) (mean (SD)) | | 63.7 (5.5) | 61.1 (4.8) | <0.001 |
| Gender (%) | Female | 35 (13.4) | 1698 (41.6) | <0.001 |
| | Male | 226 (86.6) | 2379 (58.4) | |
| Race (%) | American Indian or Alaskan Native | 1 (0.4) | 10 (0.2) | 0.002 |
| | Asian | 15 (5.8) | 89 (2.2) | |
| | Black | 5 (1.9) | 179 (4.4) | |
| | Missing/Unknown | 0 (0.0) | 10 (0.2) | |
| | More than One Race | 5 (1.9) | 52 (1.3) | |
| | Native Hawaiian or Other Pacific Islander | 2 (0.8) | 11 (0.3) | |
| | White | 232 (89.2) | 3718 (91.4) | |
| Current Smoking Status (%) | Current Smoker | 127 (48.7) | 2108 (51.7) | 0.373 |
| | Former Smoker | 134 (51.3) | 1969 (48.3) | |
| Pack Years (mean (SD)) | | 61.0 (22.8) | 55.3 (23.5) | <0.001 |
| Lung Cancer Outcomes | | | | |
| Diagnosis with Lung Cancer over 3 Years of Follow- up (%) | Lung Cancer | 50 (15.4) | 125 (2.1) | <0.001 |
| | No Lung Cancer | 274 (84.6) | 5960 (97.9) | |
| Lung cancer stage (%) | Stage IA | 30 (60.0) | 59 (47.2) | 0.384 |
| | Stage IB | 3 (6.0) | 6 (4.8) | |
| | Stage IIA | 3 (6.0) | 10 (8.0) | |
| | Stage IIB | 2 (4.0) | 1 (0.8) | |
| | Stage IIIA | 3 (6.0) | 11 (8.8) | |
| | Stage IIIB | 0 (0.0) | 8 (6.4) | |
| | Stage IV | 7 (14.0) | 25 (20.0) | |
| | Unknown/Other | 2 (4.0) | 5 (4.0) | |
| Lung cancer type (%) | Adenocarcinoma | 5 (35.7) | 34 (39.5) | 0.677 |
| | Squamous cell carcinoma | 5 (35.7) | 23 (26.7) | |
| | Non-small cell carcinoma, NOS | 2 (14.3) | 11 (12.8) | |
| | Small cell carcinoma | 1 (7.1) | 9 (10.5) | |
| | Neuroendocrine tumor | 0 (0.0) | 7 (8.1) | |
| | Unknown | 1 (7.1) | 1 (1.2) | |
| | Other | 0 (0.0) | 1 (1.2) | |
| Nodule Characteristics | | | | |
| Lung-RADS Score (%) | 1 | 261 (100) | 4077 (100) | N/A |
| Densitometric Measures | | | | |
| Low Attenuation Area (Percent of Lung) (mean (SD)) | | 16.3 (12.3) | 5.6 (8.6) | <0.001 |
| High Attenuation Area (Percent of Lung) (mean (SD)) | | 3.9 (1.1) | 4.7 (2.0) | <0.001 |
| Body Composition | | | | |
| Pectoralis Minor Cross Axial Sectional Area (mean (SD)) | | 1029.8 (229.1) | 1123.5 (357.5) | <0.001 |
| Pectoralis Major Cross Axial Sectional Area (mean (SD)) | | 2993.4 (697.1) | 3140.3 (1207.9) | 0.052 |
| Subcutaneous Fat Axial Cross Sectional Area (mean (SD)) | | 3850.7 (1643.8) | 5729.3 (2928.9) | <0.001 |
| Local Histogram | | | | |
| Normal | | 80.2 (12.3) | 90.0 (8.7) | <0.001 |

TABLE 16-continued

Characteristics of the Lung-RADS 1 Cohort by Cancer Prediction

| Subgroup | Cancer Predicted | No Cancer Predicted | p |
|---|---|---|---|
| Parenchyma (Percent of Lung) (mean (SD)) | | | |
| Centrilobular Emphysema (Percent of Lung) (mean (SD)) | 14.3 (13.0) | 3.6 (7.7) | <0.001 |
| Centrilobular Nodule (Percent of Lung) (mean (SD)) | 0.0 (0.0) | 0.0 (0.0) | <0.001 |
| Ground Glass (Percent of Lung) (mean (SD)) | 0.0 (0.0) | 0.0 (0.0) | 0.217 |
| Honeycombing (Percent of Lung) (mean (SD)) | 0.1 (0.1) | 0.1 (0.1) | 0.431 |
| Linear Scar (Percent of Lung) (mean (SD)) | 0.1 (0.1) | 0.1 (0.1) | 0.07 |
| Nodular (Percent of Lung) (mean (SD)) | 0.0 (0.0) | 0.1 (0.3) | <0.001 |
| Reticular (Percent of Lung) (mean (SD)) | 4.8 (2.9) | 5.2 (3.0) | 0.039 |
| Subpleural Line (Percent of Lung) (mean (SD)) | 0.1 (0.1) | 0.2 (0.2) | <0.001 |
| Other Emphysema (Percent of Lung) (mean (SD)) | 0.1 (0.2) | 0.0 (0.1) | <0.001 |
| Cyst (Percent of Lung) (mean (SD)) | 0.0 (0.0) | 0.0 (0.0) | 0.854 |

TABLE 17

Enrichment results of 1 year, 3 year, and 5 year future risk models for Lung-RADS 1

| Method | Area Under the Precision Recall Curve | Relative Enrollment Ratio | Relative Enrollment Percentage | Absolute Enrollment Percentage | Cumulative Incidence |
|---|---|---|---|---|---|
| 1 Year | | | | | |
| Null Model | NA | 1 to 1 | 100 | 100 | 0.35 |
| Random Forest | 0.46 | 14 to 1 | 7.10 | 4.34 | 0.32 |
| 3 Year | | | | | |
| Null Model | NA | 1 to 1 | 100 | 100 | 2.31 |
| Random Forest | 0.45 | 17 to 1 | 6.02 | 3.68 | 5.36 |
| 5 Year | | | | | |
| Null Model | NA | 1 to 1 | 100 | 100 | 3.67 |
| Random Forest | 0.47 | 17 to 1 | 5.76 | 3.52 | 6.80 |

[1] The random forest model is tuned random forest model
[2] The relative enrollment ratio and the relative enrollment percentage are based on the ratio of the number of individuals predicted positive by the model to the number of individuals in the tested subgroup, in this case those with Lung-RADS <2
[3] The absolute enrollment percentage is the percent of the total cohort who are predicted positive, i.e. suggested to be enrolled, by the model.
[4] Note that each model is trained independently and so those predicted positive by the 5 year model do not necessarily include all of those predicted positive by the 3 year model.

TABLE 18

Performance of risk prediction models incorporating non-nodule specific features and nodule specific features (radiomic features)

| Time Period (year) | Lung-RADS | Training/Testing | True Positives | True Negatives | False Positives | False Negatives | Sensitivity | Specificity | PPV | NPV | Incidence Rate without Enrichment |
|---|---|---|---|---|---|---|---|---|---|---|---|
| 1 | 1-4B | Training Set | 108 | 6899 | 449 | 27 | 0.8000 | 0.9389 | 0.1939 | 0.9961 | 0.0180 |
| 1 | 1-4B | Testing Set | 76 | 6814 | 548 | 45 | 0.6281 | 0.9256 | 0.1218 | 0.9934 | 0.0162 |
| 1 | 1-4A | Training Set | 35 | 6573 | 426 | 32 | 0.5224 | 0.9391 | 0.0759 | 0.9952 | 0.0095 |

TABLE 18-continued

Performance of risk prediction models incorporating non-nodule specific features and nodule specific features (radiomic features)

| Time Period (year) | Lung-RADS | Training/ Testing | True Positives | True Negatives | False Positives | False Negatives | Sensitivity | Specificity | PPV | NPV | Incidence Rate without Enrichment |
|---|---|---|---|---|---|---|---|---|---|---|---|
| 1 | 1-4A | Testing Set | 18 | 6515 | 423 | 39 | 0.3158 | 0.9390 | 0.0408 | 0.9940 | 0.0081 |
| 1 | 1-3 | Training Set | 41 | 4139 | 1929 | 7 | 0.8542 | 0.6821 | 0.0208 | 0.9983 | 0.0078 |
| 1 | 1-3 | Testing Set | 33 | 4120 | 1893 | 9 | 0.7857 | 0.6852 | 0.0171 | 0.9978 | 0.0069 |
| 1 | 2-4B | Training Set | 84 | 3325 | 153 | 5 | 0.9438 | 0.9560 | 0.3544 | 0.9985 | 0.0250 |
| 1 | 2-4B | Testing Set. | 66 | 3304 | 241 | 17 | 0.7952 | 0.9320 | 0.2150 | 0.9949 | 0.0229 |
| 1 | 4A-4B | Training Set | 79 | 1252 | 28 | 8 | 0.9080 | 0.9781 | 0.7383 | 0.9937 | 0.0636 |
| 1 | 4A-4B | Testing Set | 55 | 1281 | 68 | 24 | 0.6962 | 0.9496 | 0.4472 | 0.9816 | 0.0553 |
| 3 | 1-4B | Training Set | 247 | 6395 | 775 | 66 | 0.7891 | 0.8919 | 0.2417 | 0.9898 | 0.0418 |
| 3 | 1-4B | Testing Set | 155 | 6282 | 896 | 150 | 0.5082 | 0.8752 | 0.1475 | 0.9767 | 0.0408 |
| 3 | 1-4A | Training Set | 167 | 5384 | 1463 | 52 | 0.7626 | 0.7863 | 0.1025 | 0.9904 | 0.0310 |
| 3 | 1-4A | Testing Set | 101 | 5276 | 1508 | 110 | 0.4787 | 0.7777 | 0.0628 | 0.9796 | 0.0302 |
| 3 | 1-3 | Training Set | 104 | 4786 | 1169 | 57 | 0.6460 | 0.8037 | 0.0817 | 0.9882 | 0.0263 |
| 3 | 1-3 | Testing Set | 59 | 4732 | 1180 | 84 | 0.4126 | 0.8004 | 0.0476 | 0.9826 | 0.0236 |
| 3 | 2-4B | Training Set | 199 | 3001 | 355 | 12 | 0.9431 | 0.8942 | 0.3592 | 0.9960 | 0.0592 |
| 3 | 2-4B | Testing Set | 122 | 2951 | 459 | 96 | 0.5596 | 0.8654 | 0.2100 | 0.9685 | 0.0601 |
| 3 | 4A-4B | Training Set | 137 | 1029 | 186 | 15 | 0.9013 | 0.8469 | 0.4241 | 0.9856 | 0.1112 |
| 3 | 4A-4B | Testing Set | 105 | 1000 | 266 | 57 | 0.6481 | 0.7899 | 0.2830 | 0.9461 | 0.1134 |

TABLE 19

Top 10 features for 1 year and 3 year future risk models for Lung-RADS 1-4B subjects using radiomic features. For features categories, a "1" indicates a radiomic feature (e.g., nodule specific feature) whereas a "2" indicates a non-nodule specific feature.

| Feature ranked based on importance | 1 year features | 1 year feature category | 3 year features | 3 year feature category |
|---|---|---|---|---|
| 1 | application of wavelet filter low-high-high neighboring gray tone difference matrix coarseness - edge volume of nodule | 1 | application of wavelet filter low-low-low gray level co-occurrence matrix joint energy - edge volume of nodule | 1 |
| 2 | application of gaussian filter (sigma = 1 mm) 3d neighboring gray tone difference matrix coarseness - edge volume of nodule | 1 | application of gaussian filter (sigma = 1 mm) 3d neighboring gray tone difference matrix coarseness - boundary volume of nodule | 1 |
| 3 | Axial cross sectional area of subcutaneous fat | 2 | original (no filter) neighboring gray tone difference matrix coarseness - boundary volume of nodule | 1 |
| 4 | application of wavelet filter low-low-low gray level co-occurrence matrix joint energy - interior volume of nodule | 1 | application of wavelet filter low-high-low gray level co-occurrence matrix information measure of correlation 1 - edge volume of nodule | 1 |
| 5 | Normal parenchyma - percentage of lung | 2 | Axial cross sectional area of subcutaneous fat | 2 |
| 6 | Emphysematous - percentage of lung | 2 | Upper lower third low attenuation area ratio | 2 |
| 7 | application of wavelet filter high-high-high neighboring gray tone difference matrix coarseness - edge volume of nodule | 1 | application of wavelet filter low-low-high gray level dependence matrix small dependence low gray level emphasis - interior volume of nodule | 1 |
| 8 | application of wavelet filter low-low-high neighboring gray tone difference matrix coarseness - boundary volume of nodule | 1 | Honeycombing - percentage of lung | 2 |
| 9 | application of gaussian filter (sigma = 1 mm) 3d neighboring gray tone difference matrix coarseness - boundary volume of nodule | 1 | Coronal cross sectional area of subcutaneous fat | 2 |
| 10 | application of wavelet filter low-low-high neighboring gray tone difference matrix coarseness - edge volume of nodule | 1 | Lung-RADS | 2 |

TABLE 20

Top 10 features for 1 year and 3 year future risk models for Lung-RADS 1-4A subjects using radiomic features. For features categories, a "1" indicates a radiomic feature (e.g., nodule specific feature) whereas a "2" indicates a non-nodule specific feature.

| Feature ranked based on importance | 1 year features | 1 year feature category | 3 year features | 3 year feature category |
|---|---|---|---|---|
| 1 | Axial cross sectional area of subcutaneous fat | 2 | application of wavelet filter low-high-low neighboring gray tone difference matrix coarseness - boundary volume of nodule | 1 |
| 2 | Coronal cross sectional area of subcutaneous fat | 2 | application of wavelet filter low-high-high neighboring gray tone difference matrix coarseness - edge volume of nodule | 1 |
| 3 | normal parenchyma - percentage of lung | 2 | application of gaussian filter (sigma = 1 mm) 3d neighboring gray tone difference matrix coarseness - edge volume of nodule | 1 |
| 4 | application of wavelet filter high-low-high first order mean - boundary volume of nodule | 1 | original (no filter) gray level co-occurrence matrix information measure of correlation 1 - boundary volume of nodule | 1 |
| 5 | application of wavelet filter low-high-high gray level size zone matrix small area low gray level emphasis - interior volume of nodule | 1 | Coronal cross sectional area of subcutaneous fat | 2 |
| 6 | nodular - percentage of lung | 2 | Axial cross sectional area of subcutaneous fat | 2 |
| 7 | application of wavelet filter high-high-high gray level co-occurrence matrix cluster shade - interior volume of nodule | 1 | application of wavelet filter low-high-low neighboring gray tone difference matrix coarseness - edge volume of nodule | 1 |
| 8 | application of wavelet filter low-low-high first order uniformity - interior volume of nodule | 1 | application of wavelet filter low-low-low gray level run length matrix run variance - boundary volume of nodule | 1 |
| 9 | honeycombing - percentage of lung | 2 | original (no filter) gray level size zone matrix gray level non uniformity normalized - boundary volume of nodule | 1 |
| 10 | application of wavelet filter low-low-low neighboring gray tone difference matrix coarseness - boundary volume of nodule | 1 | application of wavelet filter high-high-high gray level co-occurrence matrix cluster shade - interior volume of nodule | 1 |

TABLE 21

Top 10 features for 1 year and 3 year future risk models for Lung-RADS 1-3 subjects using radiomic features. For features categories, a "1" indicates a radiomic feature (e.g., nodule specific feature) whereas a "2" indicates a non-nodule specific feature.

| Feature ranked based on importance | 1 year features | 1 year feature category | 3 year features | 3 year feature category |
|---|---|---|---|---|
| 1 | Axial cross sectional area of subcutaneous fat | 2 | Axial cross sectional area of subcutaneous fat | 2 |
| 2 | Coronal cross sectional area of subcutaneous fat | 2 | Coronal cross sectional area of subcutaneous fat | 2 |
| 3 | Whole lung normal parenchyma type fraction | 2 | application of wavelet filter low-low-low gray level run length matrix run variance - boundary volume of nodule | 1 |
| 4 | wavelet hlh first order mean boundary | 1 | application of gaussian filter (sigma = 1 mm) 3d gray level co-occurrence matrix information measure of correlation 1 - boundary volume of nodule | 1 |
| 5 | wavelet lhh glszm small area low gray level emphasis interior | 1 | normal parenchyma - percentage of lung | 2 |
| 6 | Whole lung nodular type fraction | 2 | emphysematous - percentage of lung | 2 |
| 7 | wavelet, hhh glcm cluster shade interior | 1 | honeycombing - percentage of lung | 2 |

TABLE 21-continued

Top 10 features for 1 year and 3 year future risk models for Lung-RADS 1-3 subjects using radiomic features. For features categories, a "1" indicates a radiomic feature (e.g., nodule specific feature) whereas a "2" indicates a non-nodule specific feature.

| Feature ranked based on importance | 1 year features | 1 year feature category | 3 year features | 3 year feature category |
|---|---|---|---|---|
| 8 | wavelet llh firstorder uniformity interior | 1 | centrilobular emphysema - percentage of lung | 2 |
| 9 | wholelung honeycombing type fraction | 2 | upper lower third low attenuation area ratio | 2 |
| 10 | wavelet lll ngtdm coarseness boundary | 1 | reticular - percentage of lung | 2 |

TABLE 22

Top 10 features for 1 year and 3 year future risk models for Lung-RADS 2-4B subjects using radiomic features. For features categories, a "1" indicates a radiomic feature (e.g., nodule specific feature) whereas a "2" indicates a non-nodule specific feature.

| Feature ranked based on importance | 1 year features | 1 year feature category | 3 year features | 3 year feature category |
|---|---|---|---|---|
| 1 | application of wavelet filter high-low-low neighboring gray tone difference matrix coarseness - edge volume of nodule | 1 | application of gaussian filter (sigma = 1 mm) 3d neighboring gray tone difference matrix coarseness - boundary volume of nodule | 1 |
| 2 | application of gaussian filter (sigma = 1 mm) 3d neighboring gray tone difference matrix coarseness - edge volume of nodule | 1 | application of wavelet filter low-low-low gray level co-occurrence matrix joint energy - edge volume of nodule | 1 |
| 3 | application of wavelet filter low-low-high neighboring gray tone difference matrix coarseness - boundary volume of nodule | 1 | original (no filter) neighboring gray tone difference matrix coarseness - boundary volume of nodule | 1 |
| 4 | application of wavelet filter low-low-low gray level size zone matrix low gray level zone emphasis - interior volume of nodule | 1 | application of wavelet filter low-high-low gray level co-occurrence matrix information measure of correlation 1 - edge volume of nodule | 1 |
| 5 | application of gaussian filter (sigma = 1 mm) 3d neighboring gray-tone difference matrix coarseness - boundary volume of nodule | 1 | application of wavelet filter high-low-low neighboring gray tone difference matrix coarseness - edge volume of nodule | 1 |
| 6 | application of wavelet filter low-low-high gray level dependence matrix small dependence low gray level emphasis - interior volume of nodule | 1 | application of wavelet filter low-low-high gray level dependence matrix small dependence low gray level emphasis - interior volume of nodule | 1 |
| 7 | application of wavelet filter low-low-high first order uniformity - interior volume of nodule | 1 | original (no filter) gray level co-occurrence matrix information measure of correlation 1 - boundary volume of nodule | 1 |
| 8 | application of wavelet filter low-low-low gray level dependence matrix small dependence low gray level emphasis - interior volume of nodule | 1 | application of wavelet filter high-low-low gray level co-occurrence matrix maximum probability - edge volume of nodule | 1 |
| 9 | application of wavelet filter low-high-high neighboring gray tone difference matrix coarseness - edge volume of nodule | 1 | application of gaussian filter (sigma = 1 mm) 3d gray level co-occurrence matrix information measure of correlation 1 - boundary volume of nodule | 1 |
| 10 | application of wavelet filter high-high-high gray level dependence matrix small dependence low gray level emphasis - interior volume of nodule | 1 | Upper lower third low attenuation area ratio | 2 |

TABLE 23

Top 10 features for 1 year and 3 year future risk models for Lung-RADS 4A-4B subjects using radiomic features. For features categories, a "1" indicates a radiomic feature (e.g., nodule specific feature) whereas a "2" indicates a non-nodule specific feature.

| Feature ranked based on importance | 1 year features | 1 year feature category | 3 year features | 3 year feature category |
|---|---|---|---|---|
| 1 | application of wavelet filter high-low-low neighboring gray tone difference matrix coarseness - edge volume of nodule | 1 | application of wavelet filter low-high-low gray level co-occurrence matrix information measure of correlation 1 - edge volume of nodule | 1 |
| 2 | application of gaussian filter (sigma=1 mm) 3d neighboring gray-tone difference matrix coarseness - edge volume of nodule | 1 | application of wavelet filter low-low-low gray level co-occurrence matrix joint energy - edge volume of nodule | 1 |
| 3 | application of wavelet filter low-high-low gray level co-occurrence matrix information measure of correlation 1 - edge volume of nodule | 1 | original (no filter) neighboring gray tone difference matrix coarseness - boundary-volume of nodule | 1 |
| 4 | application of wavelet filter low-low-high neighboring gray tone difference matrix coarseness - boundary volume of nodule | 1 | application of gaussian filter (sigma = 1 mm) 3d neighboring gray tone difference matrix coarseness - boundary volume of nodule | 1 |
| 5 | application of wavelet filter low-low-high first order uniformity - interior volume of nodule | 1 | application of wavelet filter low-low-high gray level co-occurrence matrix information measure of correlation 1 - edge volume of nodule | 1 |
| 6 | application of gaussian filter (sigma- 1 mm) 3d neighboring gray tone difference matrix coarseness - boundary volume of nodule | 1 | application of wavelet filter low-low-low neighboring gray tone difference matrix coarseness - boundary volume of nodule | 1 |
| 7 | application of wavelet filter low-low-low gray level size zone matrix low gray level zone emphasis - interior volume of nodule | 1 | application of wavelet filter low-low-high gray level dependence matrix small dependence low gray level emphasis - interior volume of nodule | 1 |
| 8 | application of wavelet filter low-low-high gray level dependence matrix small dependence low gray level emphasis - interior volume of nodule | 1 | upper lower third low attenuation area ratio | 2 |
| 9 | application of wavelet filter high-low-low gray level size zone matrix low gray level zone emphasis - interior volume of nodule | 1 | application of wavelet filter high-low-low neighboring gray tone difference matrix coarseness - edge volume of nodule | 1 |
| 10 | application of wavelet filter low-high-high neighboring gray tone difference matrix coarseness - edge volume of nodule | 1 | application of wavelet filter high-low-low gray level co-occurrence matrix maximum probability - edge volume of nodule | 1 |

The invention claimed is:

1. A method for predicting one or more future risks of lung cancer for a subject, the method comprising:
obtaining one or more images captured from the subject;
analyzing, by a neural network, the obtained one or more images to predict one or more future risks of lung cancer for the subject, wherein the neural network is trained with a cohort of individuals in a population, wherein the population comprises over 50% Lung-RADS 1-2 patients;
wherein the analysis comprises processing features of the one or more images comprising at least non-nodule specific features, wherein the non-nodule specific features comprise both lung parenchyma features and body composition features, wherein the body composition features comprise a feature of a muscle or subcutaneous fat of the subject.

2. The method of claim 1, wherein the lung parenchyma features comprise one or more of densitometric measures of the lung parenchyma or local histogram measures of the lung parenchyma.

3. The method of claim 2, wherein the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone.

4. The method of claim 1, wherein the lung parenchyma features comprise one or more percentage(s) of lung occupied by any of normal tissue, centrilobular emphysema, centrilobular nodule, ground glass, honeycombing, linear scar, nodular, reticular, subpleural line, other emphysema, or cyst.

5. The method of claim 1, wherein the feature of the muscle or subcutaneous fat comprises a pectoralis cross-sectional area, pectoralis lean cross-sectional area, or subcutaneous fat cross-sectional area.

6. The method of claim 1, wherein the one or more images comprise thoracic CT images or chest X-ray images.

7. The method of claim 1, wherein the analysis further comprises extracting, by the neural network, the features from the one or more images.

8. A method for predicting one or more future risks of lung cancer for a subject, the method comprising:
obtaining one or more images captured from the subject prior to development of one or more detectable lung nodules;
analyzing, by a trained risk prediction model, the obtained one or more images to predict one or more future risks of lung cancer for the subject, wherein the trained risk prediction model is trained with a cohort of individuals in a population, wherein the population comprises over 50% Lung-RADS 1-2 patients;
wherein the analysis comprises processing features of the one or more images comprising at least non-nodule specific features, wherein the non-nodule specific features comprise both lung parenchyma features and body composition features, wherein the body composition features comprise a feature of a muscle or subcutaneous fat of the subject.

9. The method of claim 8, wherein the subject was previously classified as Lung-RADS 1.

10. The method of claim 8, wherein the lung parenchyma features comprise one or more of densitometric measures of the lung parenchyma or local histogram measures of the lung parenchyma.

11. The method of claim 10, wherein the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone.

12. The method of claim 8, wherein the lung parenchyma features comprise one or more percentage(s) of lung occupied by any of normal tissue, centrilobular emphysema, centrilobular nodule, ground glass, honeycombing, linear scar, nodular, reticular, subpleural line, other emphysema, or cyst.

13. The method of claim 8, wherein the feature of the muscle or subcutaneous fat comprises a pectoralis cross-sectional area, pectoralis lean cross-sectional area, or subcutaneous fat cross-sectional area.

14. The method of claim 8, wherein the lung cancer is either non-small cell lung cancer or small cell lung cancer.

15. A method for predicting one or more future risks of lung cancer for a subject, the method comprising:
obtaining one or more images captured from the subject;
analyzing, by a trained risk prediction model, the obtained one or more images to predict one or more future risks of lung cancer for the subject, wherein the trained risk prediction model is trained with a cohort of individuals in a population, wherein the population comprises over 50% Lung-RADS 1-2 patients;
wherein the analysis comprises processing features of the one or more images comprising at least non-nodule specific features comprising lung parenchyma features, wherein the lung parenchyma features comprise measures of interstitial changes in the lung parenchyma, fibrosis, or pulmonary vascular remodeling.

16. The method of claim 15, wherein the measures of interstitial changes in the lung parenchyma comprise a percentage of the lung occupied by any of emphysema; ground glass, honeycombing, linear scar, nodular, reticular, subpleural line, and $cyst_3$.

17. The method of claim 15, wherein the non-nodule specific features further comprise body composition features comprising a feature of a muscle or subcutaneous fat of the subject.

18. The method of claim 17, wherein the feature of the muscle or subcutaneous fat comprises a pectoralis cross-sectional area, pectoralis lean cross-sectional area, or subcutaneous fat cross-sectional area.

19. The method of claim 15, wherein the lung parenchyma features comprise one or more of densitometric measures of the lung parenchyma or local histogram measures of the lung parenchyma.

20. The method of claim 19, wherein the densitometric measures of the lung parenchyma comprise one or more of: percentage of low attenuation area of the lung, percentage of high attenuation area of the lung, and ratio of low attenuation or high attenuation area in an upper lung zone in comparison to a lower lung zone.

* * * * *